United States Patent
Daugherty et al.

(10) Patent No.: US 12,209,120 B2
(45) Date of Patent: *Jan. 28, 2025

(54) ACTIVATABLE ANTI-VEGF scFv

(71) Applicants: The Regents of the University of California, Oakland, CA (US); CytomX Therapeutics, Inc., South San Francisco, CA (US)

(72) Inventors: Patrick Sean Daugherty, Santa Barbara, CA (US); Nancy Stagliano, Santa Barbara, CA (US); Jerry Thomas, Goleta, CA (US); Kathryn Kamath, Santa Barbara, CA (US); James W. West, Santa Barbara, CA (US); Sanjay Khare, Newbury Park, CA (US); Jason Sagert, Santa Barbara, CA (US)

(73) Assignees: The Regents of the University of California, Oakland, CA (US); CytomX Therapeutics, Inc., South San Francisco, CA (US)

( * ) Notice: Subject to any disclaimer, the term of this patent is extended or adjusted under 35 U.S.C. 154(b) by 521 days.

This patent is subject to a terminal disclaimer.

(21) Appl. No.: 17/245,713

(22) Filed: Apr. 30, 2021

(65) Prior Publication Data

US 2022/0098294 A1 Mar. 31, 2022

Related U.S. Application Data

(63) Continuation of application No. 16/102,531, filed on Aug. 13, 2018, now Pat. No. 11,028,162, which is a continuation of application No. 14/853,840, filed on Sep. 14, 2015, now Pat. No. 10,077,300, which is a continuation of application No. 13/950,174, filed on Jul. 24, 2013, now Pat. No. 9,169,321, which is a continuation of application No. 13/413,447, filed on Mar. 6, 2012, now Pat. No. 8,529,898, which is a continuation of application No. 12/196,269, filed on Aug. 21, 2008, now abandoned.

(60) Provisional application No. 61/052,986, filed on May 13, 2008, provisional application No. 60/957,453, filed on Aug. 22, 2007, provisional application No. 60/957,449, filed on Aug. 22, 2007.

(51) Int. Cl.

| | |
|---|---|
| C07K 16/22 | (2006.01) |
| C07K 16/24 | (2006.01) |
| C07K 16/28 | (2006.01) |
| C07K 16/42 | (2006.01) |
| C12N 15/10 | (2006.01) |

(52) U.S. Cl.
CPC .............. *C07K 16/22* (2013.01); *C07K 16/24* (2013.01); *C07K 16/2818* (2013.01); *C07K 16/2836* (2013.01); *C07K 16/42* (2013.01); *C12N 15/1034* (2013.01); *C12N 15/1044* (2013.01); *C07K 2317/34* (2013.01); *C07K 2317/622* (2013.01); *C07K 2319/00* (2013.01); *C07K 2319/30* (2013.01); *C07K 2319/50* (2013.01)

(58) Field of Classification Search
CPC ................ C07K 16/42; C12N 15/1034; C12N 15/1033; C12N 15/1044
See application file for complete search history.

(56) References Cited

U.S. PATENT DOCUMENTS

| | | |
|---|---|---|
| 3,773,919 A | 11/1973 | Boswell et al. |
| 4,379,145 A | 4/1983 | Masuho et al. |
| 4,671,958 A | 6/1987 | Rodwell et al. |
| 4,816,567 A | 3/1989 | Cabilly et al. |
| 4,867,973 A | 9/1989 | Goers et al. |
| 4,952,394 A | 8/1990 | Senter |
| 4,975,278 A | 12/1990 | Senter et al. |
| 5,010,176 A | 4/1991 | Barton |
| 5,144,012 A | 9/1992 | Johnson et al. |

(Continued)

FOREIGN PATENT DOCUMENTS

| | | |
|---|---|---|
| EP | 0329185 | 8/1989 |
| EP | 0444158 | 5/1990 |

(Continued)

OTHER PUBLICATIONS

Benjamin et al., "Tolerance to rat monoclonal antibodies: Implications for serotherapy", J. Exp. Med. (1986) 163(6):1539-1552.

(Continued)

*Primary Examiner* — Elly-Gerald Stoica
(74) *Attorney, Agent, or Firm* — Edward J. Baba; Bozicevic, Field & Francis LLP

(57) ABSTRACT

The present disclosure provides activatable binding polypeptides (ABPs), which contain a target binding moiety (TBM), a masking moiety (MM), and a cleavable moiety (CM). The present disclosure provides activatable antibody compositions, which contain a TBM containing an antigen binding domain (ABD), a MM and a CM. Furthermore the present disclosure also provides ABPs which contain a first TBM, a second TBM and a CM. The ABPs exhibit an "activatable" conformation such that at least one of the TBMs is less accessible to target when uncleaved than after cleavage of the CM in the presence of a cleaving agent capable of cleaving the CM. The disclosure further provides libraries of candidate ABPs, methods of screening to identify such ABPs, and methods of use. The disclosure further provides ABPs having TBMs that bind VEGF, CTLA-4, or VCAM, ABPs having a first TBM that binds VEGF and a second TBM that binds FGF, as well as compositions and methods of use.

3 Claims, 41 Drawing Sheets

Specification includes a Sequence Listing.

(56) References Cited

U.S. PATENT DOCUMENTS

| | | |
|---|---|---|
| 5,162,218 A | 11/1992 | Schultz |
| 5,223,409 A | 6/1993 | Ladner et al. |
| 5,272,253 A | 12/1993 | Koppel et al. |
| 5,306,731 A | 4/1994 | Epstein |
| 5,403,484 A | 4/1995 | Ladner et al. |
| 5,468,785 A | 11/1995 | Greuel et al. |
| 5,525,491 A | 6/1996 | Huston et al. |
| 5,571,698 A | 11/1996 | Ladner et al. |
| 5,637,288 A | 6/1997 | Goldenburg et al. |
| 5,665,358 A | 9/1997 | Barton et al. |
| 5,679,548 A | 10/1997 | Barbas et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,834,247 A | 11/1998 | Comb et al. |
| 5,837,500 A | 11/1998 | Ladner et al. |
| 5,866,341 A | 2/1999 | Spinella et al. |
| 5,922,845 A | 7/1999 | Deo et al. |
| 5,985,626 A | 11/1999 | Barbas et al. |
| 5,990,286 A | 11/1999 | Khawli et al. |
| 5,994,104 A | 11/1999 | Anderson et al. |
| 6,015,557 A | 1/2000 | Tobinick et al. |
| 6,054,297 A | 4/2000 | Carter et al. |
| 6,066,719 A | 5/2000 | Zapata |
| 6,107,059 A | 8/2000 | Hart et al. |
| 6,165,464 A | 12/2000 | Hudziak et al. |
| 6,217,866 B1 | 4/2001 | Schlessinger et al. |
| 6,235,883 B1 | 5/2001 | Jakobovitis et al. |
| 6,258,562 B1 | 7/2001 | Salfeld et al. |
| 6,265,540 B1 | 7/2001 | Isaacs et al. |
| 6,268,488 B1 | 7/2001 | Barbas et al. |
| 6,342,219 B1 | 1/2002 | Thorpe et al. |
| 6,342,221 B1 | 1/2002 | Thorpe et al. |
| 6,399,063 B1 | 6/2002 | Hudziak et al. |
| 6,407,213 B1 | 6/2002 | Carter et al. |
| 6,534,061 B1 | 3/2003 | Goddard et al. |
| 6,682,736 B1 | 1/2004 | Hansen et al. |
| 6,884,879 B1 | 4/2005 | Baca et al. |
| 6,955,900 B1 | 10/2005 | Barbas et al. |
| 6,979,538 B2 | 12/2005 | Ladner et al. |
| 6,984,720 B1 | 1/2006 | Korman et al. |
| 6,992,174 B2 | 1/2006 | Gillies et al. |
| 7,029,874 B2 | 4/2006 | Baker et al. |
| 7,060,269 B1 | 6/2006 | Baca et al. |
| 7,060,808 B1 | 6/2006 | Goldstein et al. |
| 7,087,409 B2 | 8/2006 | Barbas et al. |
| 7,098,002 B1 | 8/2006 | Rubenstein et al. |
| 7,118,879 B2 | 10/2006 | Ladner et al. |
| 7,157,418 B1 | 1/2007 | McDonald et al. |
| 7,169,901 B2 | 1/2007 | Baca et al. |
| 7,208,293 B2 | 4/2007 | Ladner et al. |
| 7,226,596 B2 | 6/2007 | Bodary et al. |
| 7,297,334 B2 | 11/2007 | Baca et al. |
| 7,304,143 B2 | 12/2007 | Goddard et al. |
| 7,317,091 B2 | 1/2008 | Lazar et al. |
| 7,341,720 B2 | 3/2008 | Stefano et al. |
| 7,365,166 B2 | 4/2008 | Baca et al. |
| 7,375,193 B2 | 5/2008 | Baca et al. |
| 7,452,535 B2 | 11/2008 | Davis et al. |
| 7,465,790 B2 | 12/2008 | Waldmann et al. |
| 7,608,591 B2 | 10/2009 | Liu et al. |
| 7,666,817 B2 | 2/2010 | Daugherty et al. |
| 8,399,219 B2 | 3/2013 | Stagliano et al. |
| 8,513,390 B2 | 8/2013 | Stagliano et al. |
| 8,518,404 B2 | 8/2013 | Daugherty et al. |
| 8,529,898 B2 | 9/2013 | Daugherty et al. |
| 8,541,203 B2 | 9/2013 | Daugherty et al. |
| 8,563,269 B2 | 10/2013 | Stagliano et al. |
| 8,809,504 B2 | 8/2014 | Lauermann |
| 8,993,266 B2 | 3/2015 | Stagliano et al. |
| 9,169,321 B2 | 10/2015 | Daugherty et al. |
| 9,453,078 B2 | 9/2016 | Stagliano et al. |
| 10,059,762 B2 | 8/2018 | Stagliano et al. |
| 10,077,300 B2 | 9/2018 | Daugherty et al. |
| 10,118,961 B2 | 11/2018 | Stagliano et al. |
| 10,875,913 B2 | 12/2020 | Stagliano et al. |
| 2002/0048578 A1 | 4/2002 | Frewin et al. |
| 2002/0168690 A1 | 11/2002 | Miller et al. |
| 2003/0021791 A1 | 1/2003 | Kassis et al. |
| 2003/0134824 A1 | 7/2003 | Breslow et al. |
| 2004/0014652 A1 | 1/2004 | Trouet et al. |
| 2004/0053829 A1 | 3/2004 | Pfizenmaier et al. |
| 2004/0082039 A1 | 4/2004 | Gillies et al. |
| 2004/0146516 A1 | 7/2004 | Roben et al. |
| 2004/0147444 A1 | 7/2004 | Chernajovsky et al. |
| 2004/0185053 A1 | 9/2004 | Govindan |
| 2004/0213797 A1 | 10/2004 | Bodmer et al. |
| 2004/0258677 A1 | 12/2004 | Waldmann et al. |
| 2004/0259768 A1 | 12/2004 | Lauermann |
| 2004/0265274 A1 | 12/2004 | Wei et al. |
| 2005/0042680 A1 | 2/2005 | Fipula et al. |
| 2005/0106100 A1 | 5/2005 | Harris et al. |
| 2005/0136049 A1 | 6/2005 | Ledbetter et al. |
| 2005/0196754 A1 | 9/2005 | Drmanac et al. |
| 2005/0208558 A1 | 9/2005 | Venter et al. |
| 2005/0255042 A1 | 11/2005 | Lam et al. |
| 2005/0255555 A1 | 11/2005 | Johns et al. |
| 2005/0277160 A1 | 12/2005 | Shiba et al. |
| 2005/0287155 A1 | 12/2005 | Santi et al. |
| 2006/0018911 A1 | 1/2006 | Ault-Riche et al. |
| 2006/0078901 A1 | 4/2006 | Buchreiser et al. |
| 2006/0121570 A1 | 6/2006 | Barbas et al. |
| 2006/0228348 A1 | 10/2006 | Stefano |
| 2006/0024606 A1 | 11/2006 | Morgan et al. |
| 2006/0246066 A1 | 11/2006 | Morgan et al. |
| 2006/0252130 A1 | 11/2006 | Boehm et al. |
| 2006/0265274 A1 | 11/2006 | Commins et al. |
| 2007/0041904 A1 | 2/2007 | Jiang et al. |
| 2007/0061916 A1 | 3/2007 | Kovalic et al. |
| 2007/0065878 A1 | 3/2007 | Daugherty et al. |
| 2007/0083334 A1 | 4/2007 | Mintz et al. |
| 2008/0107660 A1 | 5/2008 | Self |
| 2009/0023602 A1 | 1/2009 | Fellouse et al. |
| 2009/0123467 A1 | 5/2009 | Bedi et al. |
| 2009/0304719 A1 | 12/2009 | Daugherty et al. |
| 2010/0168019 A1 | 7/2010 | Gengrinovitch |
| 2010/0189651 A1 | 7/2010 | Stagliano et al. |
| 2010/0189727 A1 | 7/2010 | Rodeck et al. |
| 2010/0221212 A1 | 9/2010 | Stagliano et al. |
| 2011/0178279 A1 | 7/2011 | Williams et al. |
| 2012/0149061 A1 | 6/2012 | Stagliano et al. |
| 2012/0207756 A1 | 8/2012 | Stagliano et al. |
| 2012/0237512 A1 | 9/2012 | Daugherty et al. |
| 2012/0237977 A1 | 9/2012 | Daugherty et al. |
| 2012/0244154 A1 | 9/2012 | Daugherty et al. |
| 2013/0060010 A1 | 3/2013 | Williams et al. |
| 2014/0024810 A1 | 1/2014 | Stagliano et al. |
| 2014/0045195 A1 | 2/2014 | Daugherty et al. |
| 2015/0203559 A1 | 7/2015 | Stagliano et al. |
| 2016/0122425 A1 | 5/2016 | Daugherty et al. |

FOREIGN PATENT DOCUMENTS

| | | |
|---|---|---|
| EP | 0623679 | 6/2003 |
| EP | 1550729 | 6/2003 |
| EP | 1579873 | 9/2005 |
| EP | 1770099 | 4/2007 |
| WO | WO 1995011703 | 5/1995 |
| WO | WO 1996005863 | 2/1996 |
| WO | WO 1996034892 | 11/1996 |
| WO | WO 1997018236 | 5/1997 |
| WO | WO 1997031024 | 8/1997 |
| WO | 1998011126 | 3/1998 |
| WO | WO 2000004192 | 1/2000 |
| WO | WO 2000018962 | 4/2000 |
| WO | WO 2000023472 | 4/2000 |
| WO | WO 2000034519 | 6/2000 |
| WO | WO 2000064946 | 11/2000 |
| WO | WO 2001091798 | 12/2001 |
| WO | WO 2002030460 | 4/2002 |
| WO | WO 2002060488 | 8/2002 |
| WO | WO 2002066058 | 8/2002 |
| WO | WO 2002066656 | 8/2002 |
| WO | WO 2003012105 | 2/2003 |

(56) References Cited

FOREIGN PATENT DOCUMENTS

| WO | WO 2003020212 | 3/2003 |
|---|---|---|
| WO | WO 2003068934 | 8/2003 |
| WO | WO 2004009638 | 1/2004 |
| WO | WO 2004027045 | 4/2004 |
| WO | 2004111192 | 12/2004 |
| WO | WO 2005007198 | 1/2005 |
| WO | WO 2005042034 | 5/2005 |
| WO | WO 2005051315 | 6/2005 |
| WO | WO 2005083431 | 9/2005 |
| WO | WO 2006090813 | 8/2006 |
| WO | WO 2007014744 | 2/2007 |
| WO | WO 2007026972 | 3/2007 |
| WO | 2007064759 | 6/2007 |
| WO | WO 2007066106 | 6/2007 |
| WO | WO 2007099348 | 9/2007 |
| WO | WO 2007105027 | 9/2007 |
| WO | WO 2007106415 | 9/2007 |
| WO | WO 2007109254 | 9/2007 |
| WO | 2008052322 | 5/2008 |
| WO | 2008068637 | 6/2008 |
| WO | WO 2009002846 | 12/2008 |
| WO | WO 2009018500 | 2/2009 |
| WO | WO 2009025846 | 2/2009 |
| WO | WO 2009026274 | 2/2009 |
| WO | WO 2009039409 | 3/2009 |
| WO | WO 2010077643 | 7/2010 |
| WO | WO 2010081173 | 7/2010 |

OTHER PUBLICATIONS

Brinks et al., "Preclinical models Used for Immunogenicity Prediction of Therapeutic Proteins", Pharm. Res. (2013) 30:1719-1728.
Chiller et al. "Cellular events during induction of immunologic unresponsiveness in adult mice", J. Immunol. (1971) 106(6):1647-1653.
Chirinos-Rojas et al, "Use of a solid-phase random peptide library to identify inhibitors of TNF-alpha mediated cytotoxicity in vitro", Cytokine (1997) 9(4):226-232.
Cwirla et al, "Peptides on phage: a vast library of peptides for identifying ligands", Proc. Natl. Acad. Sci. USA (1990) 87(16):6378-6382.
Geysen et al., "A Priori Delineation of a Peptide Which Mimics a Discontinuous Antigenic Determinant", Mol. Immunol. (1986) 23(7):709-715.
Geysen et al., "Strategies for epitope analysis using peptide synthesis", J. Immunol. Meth. (1987) 102(2):259-274.
Golay et al., "Mechanism of action of therapeutic monoclonal antibodies: promises and pitfalls of in vitro and in vivo assays", Arch Biochem Biophys. (2012) 526(2):146-153.
Gravanis et al., "The European Medicines Agency review of ofatumumab (Arzerra®) for the treatment of chronic lymphocytic leukemia in patients refractory to fludarabine and alemtuzumab: summary of the scientific assessment of the European medicines agency committee for medicinal products for human use", Oncologist (2010) 15(12):1335-1343.
Hay et al., "Clinical development success rates for investigational drugs", Nat. Biotech. (2014) 32(1):40-51.
Leitner et al., "A mimotope defined by phage display inhibits IgE binding to the plant panallergen profilin", Eur. J. Immunol. (1998) 28(9):2921-2927.
Lichtenstein, Comprehensive review: antitumor necrosis factor agents in inflammatory bowel disease and factors implicated in treatment Therap. Adv. Gastroenterol. Jul. 2013:6(4):269-932.
Lopez-Olin et al., "Protease degradomics: a new challenge for proteomics", Nat. Rev. Mol. Cell Bio. (2002) 3:509-519.
Mitchison, NA, "The dosage requirements for immunological paralysis by soluble proteins", Immunol. (1968) 15(4):509-530.
Moore et al., "Antibodies to discontinuous or conformationally sensitive epitopes on the gp120 glycoprotein of human immunodeficiency virus type 1 are highly prevalent in sera of infected humans", J. Viral. (1993) 67(2):863-875.
Morris GE, "Epitope Mapping: B-cell Epitopes", Encyclopedia of Life Sciences (2007) p. 1-3.
NEB website http://www.neb.com/neb/products/phd/phd. html "Phage Display Library Kits", "Wayback Machine (Archive)" pp. 1-5, downloaded Jan. 11, 2012.
Roitt et al., "Immunochemical Techniques", Roitt's Essential Immunology (10TH edition), Chapter 6, (2001) pp. 118-120.
Sethu et al., "Immunogenicity to Biologics: Mechanisms, Prediction and Reduction", Arch. Immunol. Ther. Exp. (Warsz) (2012) 60:331-344.
Smith & Petrenko, "Phage Display", Chem. Rev. (1997) 97:391-410.
Albright, et al (2005) "Matrix metalloproteinase-activated doxorubicin prodrugs inhibit HT1080 xenograft growth better than doxorubicin with less toxicity", Mol Cancer Ther. 4(5), pp. 7517-7560.
Van Valckenborgh, et al (2005) "Targeting an MMP-9-activated prodrug to multiple myeloma-diseased bone marrow: a proof of principle in the 5T33MM mouse model", Leukemia 19(9), pp. 1628-1633.
Maeda et al., "Engineering of functional chimeric protein GVargula Luciferase", Anal. Biochem. (1997) 249(2):147-152.
Colman P.M., "Effects of amino acid sequence changes on antibody antigen interactions", Res. Immunol. (1994) 145(1):33-36.
Anderson, et al. Selective Photothermolysis: Precise Microsurgery by Selective Absorption of Pulsed Radiation. Science. Apr. 29, 1983; 220(4596):524-7.
Armentano, et al. Induction of Covalent Binding Antibodies. Immunol Lett. Feb. 28, 2006; 103(1):51-7.
Baron, et al. From Cloning to a Commercial Realization: Human Alpha Interferon. Critical Review in Biotechnology. 1990; 10(3):179-190.
Bartenschlager, et al. Substrate determinants for cleavage in cis and in trans by the hepatitis C virus NS3 proteinase. J Virol. 1995. 69(1):198-205.
Bessette, et al. Construction of designed protein libraries using gene assembly mutagenesis. Methods Mol Biol. 2003; 231:29-37.
Bessette, et al. Rapid Isolation of High-Affinity Protein Binding Peptides Using Bacterial Display. Protein Engineering, Design & Selection 2004, 17(10):731-739.
Boder, et al. Directed evolution of antibody fragments with monovalent femtomolar antigen-binding affinity. Proc Natl Acad Sci U S A. Sep. 26, 2000; 97(20):10701-5.
Boder, et al. Yeast surface display for screening combinatorial polypeptide libraries. Nat Biotechnol. Jun. 1997; 15(6):553-7.
Bupp, et al. Altering retroviral tropism using a random-display envelope library. Mol Ther. Mar. 2002; 5(3):329-35.
Caliceti, et al. Preparation and properties of monomethoxy poly(ethylene glycol) doxorubicin conjugates linked by an amino acid or a peptide as spacer. Farmaco Jul. 1993; 48(7):919-32.
Caron, et al. Murine and humanized constructs of monoclonal antibody M195 (anti-CD33) for the therapy of acute myelogenous leukemia. Cancer. Feb. 1, 1994; 73(3 Suppl):1049-56.
Chang, et al. Intratumoral delivery of IL-18 naked DNA induces T-cell activation and Th1 response in a mouse hepatic cancer model. BMC Cancer. May 23, 2007; 87(7):1-6.
Chari, et al. C242-DM1: A tumor-activated prodrug that shows exceptional activity in human colon tumor xenograft models at non-toxic doses. Proceedings of the American Association for Cancer Research Annual Meeting, Mar. 1998, 39:643 (89th annual meeting).
Chari, et al. Integration of SB-40875 into combination treatments of human colon xenograft models of SCID mice. Proceedings of the American Association for Cancer Research Annual Meeting, Mar. 2000, 41:291 ($91^{st}$ annual meeting of the American Association).
Chari. Targeted Cancer Therapy: Conferring Specificity to Cytotoxic Drugs. Accounts of Chemical Research. Jan. 2008; 41(1):98-107.
Chari. Targeted delivery of chemotherapeutics: Tumor-activated prodrug therapy. Advanced Drug Delivery Reviews Apr. 6, 1998; 31(1-2):89-104.

(56) References Cited

OTHER PUBLICATIONS

Chen, et al. Selection and analysis of an optimized anti-VEGF antibody: crystal structure of an affinity-matured fab in complex with antigen. J Mol Biol. Nov. 5, 1999; 293(4):865-881.

Chmura, et al. Antibodies with infinite affinity. Proc Natl Acad Sci U S A. Jul. 17, 2001; 98(15):8480-4.

Cho, et al. N-terminal processing is essential for release of epithin, a mouse type II membrane serine protease. J Biol Chem. 2001. 276(48):44581-9.

Co, et al. Chimeric and humanized antibodies with specificity for the CD33 antigen. J Immunol. Feb. 15, 1992; 148(4):1149-54.

Cooper, et al. Galactose oxidase from Polyporus circinatus, Fr. J Biol Chem. Mar. 1959; 234(3):445-8.

Daugherty, et al. Flow cytometric screening of cell-based libraries. J Immunol Methods. Sep. 21, 2000; 243(1-2):211-27.

Daugherty, et al. Quantitative analysis of the effect of the mutation frequency on the affinity maturation of single chain Fv antibodies. Proc Natl Acad Sci U S A. Feb. 29, 2000; 97(5):2029-34.

Donaldson, et al. Design and development of masked therapeutic antibodies to limit off-target effects—Application to anti-EGFR antibodies. Cancer Biology & Therapy. Nov. 2009; 8(22):1-6.

Dufner et al. (2006) "Harnessing Phage and Ribosome Display for Antibody Optimisation" *Trends Biotechnol* 24(11):523-529.

European Search Report for European Application No. EP 08795508. 4, dated Feb. 17, 2011.

Facchiano, et al. Identification of a Novel Domain of Fibroblast Growth Factor 2 Controlling Its Angiogenic Properties. The Journal of Biological Chemistry 2003, 278(10):8751-8760.

Ford, et al. Fusion tails for the recovery and purification of recombinant proteins. Protein expression and purification 1991, 2:95-107.

Fricker. MMP-8: a new target for atherosclerosis? Drug Discov Today. Jan. 15, 2002; 7(2):86-88.

Funahashi, et al. A notch1 ectodomain construct inhibits endothelial notch signaling, tumor growth, and angiogenesis. Cancer Res. 2008. 68(12):4727-35.

Georgiou, et al. Display of heterologous proteins on the surface of microorganisms: from the screening of combinatorial libraries to live recombinant vaccines. Nat Biotechnol. Jan. 1997; 15(1):29-34.

Georgiou. Analysis of large libraries of protein mutants using flow cytometry. Adv Protein Chem. 2000; 55:293-315.

Gerspach, et al. Restoration of membrane TNF-like activity by cell surface targeting and matrix metalloproteinase-mediated processing of a TNF prodrug. Cell Death and Differentiation. 2006; 13:273-284.

Gilliland, et al. Rapid and reliable cloning of antibody variable regions and generation of recombinant single chain antibody fragments. Tissue Antigens. Jan. 1996; 47(1):1-20.

Gilliland, et al. Elimination of the Immunogenicity of Therapeutic Antibodies. Journal of Immunology. 1999; 162:3663-3671.

Grussenmeyer, et al. Complexes of polyoma virus medium T antigen and cellular proteins. Proc Natl Acad Sci U S A. Dec. 1985; 82(23):7952-4.

Guay, et al. Potency and selectivity of inhibition of cathepsin K, L and S by their respective propeptides. Eur J Biochem. 2000. 267(20):6311-8.

Hagedorn, et al. A Short Peptide Domain of Platelet Factor 4 Blocks Angiogenic Key Events Induced by FGF-2. The FASEB Journal 2001. 15(3):550-552.

Hale. Synthetic peptide mimotope of the CAMPATH-1 (CD52) antigen, a small glycosylphosphatidylinositol-anchored glycoprotein. Immunotechnology. Dec. 1995; 1(3):175-187.

Harris, et al. Generation of Anti-complement "Prodrugs". The Journal of Biological Chemistry. Sep. 2003; 278(38):36068-36076.

Hillmen, et al. The complement inhibitor eculizumab in paroxysmal nocturnal hemoglobinuria. N Engl J Med. Sep. 21, 2006; 355(12):1233-43.

Holliger et al. (1993) "'Diabodies': Small Bivalent and Bispecific Antibody Fragments" Proc. Natl. Acad. Sci. USA 90(14):6444-6449.

Hopp, et al. A Short Polypeptide Marker Sequence Useful for Recombinant Protein Identification and Purification. Nature Biotechnology 1988 6:1204-1210.

Horton, et al. Engineering hybrid genes without the use of restriction enzymes: gene splicing by overlap extension. Gene. Apr. 15, 1989; 77(1):61-8.

Iiyama, et al. Patterns of Vascular Cell Adhesion Molecule-1 and Intercellular Adhesion Molecule-1 Expression in Rabbit and Mouse Atherosclerotic Lesions and at Sites Predisposed to Lesion Formation. Circulation Research, Am Heart Assoc. 1999; 85:199-207.

Immordino, et al. Stealth liposomes: review of the basic science, rationale, and clinical applications, existing and potential. Int J Nanomedicine. Sep. 2006; 1(3):297-315.

International Search Report for International Application No. PCT/US2008/009974, dated Mar. 23, 2009.

International Search Report for International Application No. PCT/US2006/034096, dated Nov. 13, 2007.

Isaacs, et al. Helplessness as a Strategy for Avoiding Antiglobulin responses to Therapeutic Monoclonal Antibodies. Therapeutic Immunology. Dec. 1994; 1(6):303-312.

Jambunathan, Kalyani et al; "Design of a Serum Stability Tag for Bioactive Peptides"; Protein & Peptide Letters, 21; (2014); pp. 32-38.

Jensen-Jarolim, et al. Peptide mimotopes displayed by phage inhibit antibody binding to bet v 1, the major birch pollen allergen, and induce specific IgG response in mice. FASEB J. Dec. 1998; 12(15):1635-42.

Johnson, et al. Development of a humanized monoclonal antibody (MEDI-493) with potent in vitro and in vivo activity against respiratory syncytial virus. J Infect Dis. Nov. 1997; 176(5):1215-24.

Kam, et al. MUC1 synthetic peptide inhibition of intercellular adhesion molecule-1 and MUC1 binding requires six tandem repeats. Cancer Res. 1998. 58(23):5577-81.

Karush, et al. Interaction of a bivalent ligand with IgM anti-lactose antibody. Biochemistry. May 29, 1979; 18(11):2226-32.

Kline et al. (2004) "Novel antitumor prodrugs designed for activation by matrix metalloproteinases-2 and -9" *Molecular Pharmaceutics* 1(1):9-22.

Knight, et al. Construction and initial characterization of a mouse-human chimeric anti-TNF antibody. Mol Immunol. Nov. 1993; 30(16):1443-53.

La Rocca, et al. Zymographic detection and clinical correlations of MMP-2 and MMP-9 in breast cancer sera. Br J Cancer. Apr. 5, 2004; 90(7):1414-21.

Lambert et al. Pharmacokinetics, in vivo stability, and toxicity of the tumor-activated prodrug. Proceedings of the American Association for Cancer Research Annual Meeting, Mar. 1998, 39:522 (89th annual meeting of the American Association for Cancer Research).

Lamoyi, et al. Preparation of F(ab')2 fragments from mouse IgG of various subclasses. J Immunol Methods. Jan. 28, 1983; 56(2):235-43.

Leger, et al. Humanization of a mouse antibody against human alpha-4 integrin: a potential therapeutic for the treatment of multiple sclerosis. Hum Antibodies. 1997; 8(1):3-16.

Li et al. (2007) "Self-Masking in an Intact ERM-Merlin Protein: An Active Role for the Central Alpha-Helical Domain" *J Mol Biol* 365:1446-1459.

Liu, et al. Overexpression of legumain in tumors is significant for invasion/metastasis and a candidate enzymatic target for prodrug therapy. Cancer Res. Jun. 1, 2003; 63(11):2957-64.

Lowman, et al. Selecting high-affinity binding proteins by monovalent phage display. Biochemistry. Nov. 12, 1991; 30(45):10832-8.

Lozano, et al. Solution Structure and Interaction with Basic and Acidic Fibroblast Growth Factor of a 3-kDa Human Platelet Factor-4 Fragment with Antiangiogenic Activity. The Journal of Biological Chemistry 2001. 276(38):35723-35734.

Mathieu, et al. Substrate specificity of schistosome versus human legumain determined by P1-P3 peptide libraries. Mol Biochem Parasitol. Apr. 30, 2002; 121(1):99-105.

Mattheakis, et al. An in vitro polysome display system for identifying ligands from very large peptide libraries. Proc Natl Acad Sci U S A. Sep. 13, 1994; 91(19):9022-6.

(56) References Cited

OTHER PUBLICATIONS

Melton et al. (1999) "The Use of Prodrugs in Targeted Anticancer Therapies" *S.T.P. Pharma Sciences* 9(1):13-33.

Mhaka et al; "A 5-fluorodeoxyuridine prodrug as targeted therapy for prostate cancer"; Bioorg Med Chem Lett. (2002): 12(17):2459-61.

Mitra, et al. Reagents for the cross-linking of proteins by equilibrium transfer alkylation. J. Am. Chem. Soc., 1979; 101(11):3097-3110.

Müller, et al. Random peptide libraries displayed on adeno-associated virus to select for targeted gene therapy vectors. Nat Biotechnol. Sep. 2003; 21(9):1040-6. Epub Aug. 3, 2003.

Nagahira, et al. Humanization of a mouse neutralizing monoclonal antibody against tumor necrosis factor-α (TNF-α). J Immunol Methods. Jan. 1, 1999; 222(1-2):83-92.

Ngo et al. (1994) "Computational Complexity, Protein Structure Prediction, and the Levinthal Paradox" *The Protein Folding Problem and Tertiary Structure Prediction* Ed. K. Merz Jr. & Le Grand, Birkhäuser Boston, pp. 492-495.

Nicaise, et al. Affinity transfer by CDR grafting on a nonimmunoglobulin scaffold. Protein Sci. 2004. 13(7):1882-91.

Nichifor, et al. Macromolecular Prodrugs of 5-fluorouracil. 2: Enzymatic Degradation. Journal Controlled Release 1996 39(1):79-92.

Nicolaisen-Strouss, et al. Natural feline leukemia virus variant escapes neutralization by a monoclonal antibody via an amino acid change outside the antibody-binding epitope. Journal of Virology. 1987. 61(11):3410-3415.

Nilsson, et al. Expression and purification of recombinant insulin-like growth factors from *Escherichia coli*. Methods Enzymol. 1991; 198:3-16.

Nilsson, et al. Immobilization and purification of enzymes with staphylococcal protein A gene fusion vectors. EMBO J. Apr. 1985; 4(4):1075-80.

Olsen, et al. High-throughput FACS method for directed evolution of substrate specificity. Methods Mol Biol. 2003; 230:329-42.

Palandoken et al. (2005) "Amiloride peptide conjugates: prodrugs for sodium-proton exchange inhibition" *J Pharmacol Exp Ther* 312(3):961-967.

Parham. On the fragmentation of monoclonal IgG1, IgG2a, and IgG2b from BALB/c mice. J Immunol. Dec. 1983; 131(6):2895-902.

Presta, et al. Humanization of an anti-vascular endothelial growth factor monoclonal antibody for the therapy of solid tumors and other disorders. Cancer Res. Oct. 15, 1997; 57(20):4593-9.

Putnam, et al. Complete amino acid sequence of the Mu heavy chain of a human IgM immunoglobulin. Science. Oct. 19, 1973; 182(109):287-91.

Rader, et al. Chemically programmed monoclonal antibodies for cancer therapy: adaptor immunotherapy based on a covalent antibody catalyst. Proc Natl Acad Sci U S A. Apr. 29, 2003; 100(9):5396-400.

Ribas, et al. Tremelimumab (CP-675,206), a Cytotoxic T Lymphocyte-Associated Antigen 4 Blocking Monoclonal Antibody in Clinical Development for Patients with Cancer. Oncologist, Jul. 2007; 12:873-883.

Rice, et al. Bacterial display using circularly permuted outer membrane protein OmpX yields high affinity peptide ligands. Protein Sci. Apr. 2006; 15(4):825-36.

Rodwell, et al. Linker Technology: Antibody-Mediated Delivery Systems. Biotechnology. 1985. 3:889-894.

Samel et al. (2003) "Generation of a FasL-based proapoptotic fusion protein devoid of systemic toxicity due to cell-surface antigen-restricted Activation" *J Biol Chem* 278(34):32077-32082.

Scheraga. Predicting three-dimensional structures of oligopeptides, In: Reviews in Computational Chemistry. vol. III, Lipkowitz and Boyd, eds., New York; 1992:73-142.

Scott, et al. Searching for peptide ligands with an epitope library. Science. Jul. 27, 1990; 249(4967):386-90.

Segerström et al. (2006) "The Anti-VEGF Antibody Bevacizumab Potently Reduces the Growth Rate of High-Risk Neuroblastoma Xenografts" *Pediatr Res* 60(5):576-581.

Self, et al. How specific are therapeutic monoclonal antibodies? www.thelancet.com. Apr. 2006; 367(960):1038-1039.

Self, et al. Light activatable antibodies: Models for remotely activatable proteins. Nature Medicine. Jul. 1996; 2(7):817-820.

Self, et al. Light-Directed Activation of Human T-Cells. ChemMedChem. 2007; 2:1587-1590.

Shusta, et al. Biosynthetic polypeptide libraries. Curr Opin Biotechnol. Apr. 1999; 10(2):117-22.

Sidhu, et al. Exploring protein-protein interactions with phage display. Chembiochem. 2003. 4(1):14-25.

Skolnick et al. (2000) "From Genes to Protein Structure and Function: Novel Applications of Computational Approaches in the Genomic Era" *Trends in Biotech* 18(1):34-39.

Smith, et al. Protein loop grafting to construct a variant of tissue-type plasminogen activator that binds platelet integrin αIIb β3. J Biol Chem. 1995. 270(51):30486-90.

Smith, et al. Single-step purification of polypeptides expressed in *Escherichia coli* as fusions with glutathione S-transferase. Gene. Jul. 15, 1988; 67(1):31-40.

Stanworth, et al. Handbook of experimental immunology, vol. 1, 2nd ed., Weir ed., chapter 10, Blackwell Scientific Publications, London; 1973.

Stryer et al. (1988) "Levels of Structure in Protein Architecture" *Biochemistry* W. H. Freeman and Company, New York, Chapter 2, p. 31-33.

Takagi, et al. A new approach for alteration of protease functions: pro-sequence engineering. Appl Microbiol Biotechnol. 2003. 63(1):1-9.

Thomas et al. "Engineering Enzymatically Activated Targeting Ligands Using Bacterial Peptide Display Libraries" Div of Biochem Tech, The 236th ACS Nat Meeting Aug. 17-21, 2008.

Thompson, et al. The modulation of Protein A-IgG(Fc) binding by the reversible addition of 2-nitrobenzyl groups. Biochemical Society Transactions. May 1995; vol. 23(2): 155S.

Thompson, et al. A Simple Procedure for the Photoregulation of Chymotrypsin Activity. Photochemical & Photobiological Sciences. 2006; 5:326-330.

Thompson, et al. Light Activation of Anti-CD3 in vivo Reduces the Growth of an Aggressive Ovarian Carcinoma. ChemMedChem. 2007; 2:1591-1593.

Thompson, et al. Photocleavable Nitrobenzyl-Protein Conjugates. Biochemical and Biophysical Research Communications. Jun. 1994; 201(3):1213-1219.

Thompson, et al. The construction and in vitro testing of photo-activatable cancer targeting folated anti-CD3 conjugates. Biochemical and Biophysical Research Communication. 2008; 366:526-531.

Thompson, et al. The Construction of a Functional Photoactivatable Cancer Targeting Bispecific Antibody Conjugate. ChemMedChem. 2007; 2:1162-1164.

Trouet, et al. CPI-0004Na: An extracellular tumor-activated prodrug of doxorubicin. Proceedings of the American Association for Cancer Research Annual Meeting, Mar. 2000, 41:522 (91st annual meeting of the American Association for Cancer Research, San Francisco).

Trouet, et al. Extracellularly tumor-activated prodrugs for the selective chemotherapy of cancer: application to doxorubicin and preliminary in vitro and in vivo studies. Cancer Research Apr. 2001 61(7):2843-6.

Tuve, et al. Combination of tumor site-located CTL-associated antigen-4 blockade and systemic regulatory T-cell depletion induces tumor-destructive immune responses. Cancer Res. Jun. 15, 2007; 67(12):5929-39.

United Kingdom Search Report Great Britain Application No. GB0902572.7, dated Jun. 19, 2009.

Vartak, et al. Matrix metalloproteases: Underutilized targets for drug delivery. Journal of Drug Targeting. Jan. 2007; 15(1):1-20.

Watermann, I. et al: "Activation of CD95L fusion protein prodrugs by tumor-associated proteases"; Cell Death Differ. 14(4): (2007); pp. 765-774.

(56) References Cited

OTHER PUBLICATIONS

Weisel, et al. (2001) The Structure and Function of the αC Domains of Fibrinogen. Annals New York Academy of Sciences. 312-327.

Werther, et al. Humanization of an anti-lymphocyte function-associated antigen (LFA)-1 monoclonal antibody and reengineering of the humanized antibody for binding to rhesus LFA-1. J Immunol. Dec. 1, 1996; 157(11):4986-95.

Wiebe, et al. Concepts for the design of anti-HIV nucleoside prodrugs for treating cephalic HIV infection. Advanced Drug Delivery Reviews Oct. 18, 1999; 39(1-3):63-80.

Wilson, et al. The use of mRNA display to select high-affinity protein-binding peptides. Proc Natl Acad Sci U S A. Mar. 27, 2001; 98(7):3750-5. Epub Mar. 13, 2001.

Written Opinion of the International Searching Authority for International Application No. PCT/US2010/025121, dated Nov. 5, 2010.

Wu et al. (1999) "Humanization of a Murine Monoclonal Antibody by Simultaneous Optimization of Framework and CDR Residues" *J Mol Biol* 294(1):151-162.

Wuest et al. (2002) "TNF-Selectokine: A Novel Prodrug Generated for Tumor Targeting and Site-Specific Activation of Tumor Necrosis Factor" *Oncogene* 21(27):4257-4265.

Xie, et al. Identification of the Fibroblast Growth Factor (FGF)-interacting Domain in a Secreted FGF-binding Protein by Phage Display. The Journal of Biological Chemistry 2006. 281(2):1137-1144.

Yang, et al. Ipilimumab (anti-CTLA4 antibody) causes regression of metastatic renal cell cancer associated with enteritis and hypophysitis. J Immunother. Nov.-Dec. 2007; 30(8):825-30.

Yu et al. (2008) "Interaction between Bevacizumab and Murine VEGF-A: A Reassessment" *Invest Ophthalmol Vis Sci* 49(2):522-527.

Zhou, et al. Specific Antibodies to the External Vestibule of Voltage-gated Potassium Channels Block Current. J. Gen. Physiol. 1998. 111:555-563.

Zhu & Witte (1999) "Inhibition of tumor growth and metastasis by targeting tumor-associated angiogenesis with antagonists to the receptors of vascular endothelial growth factor" *Invest. New Drugs* 17(3):195-212.

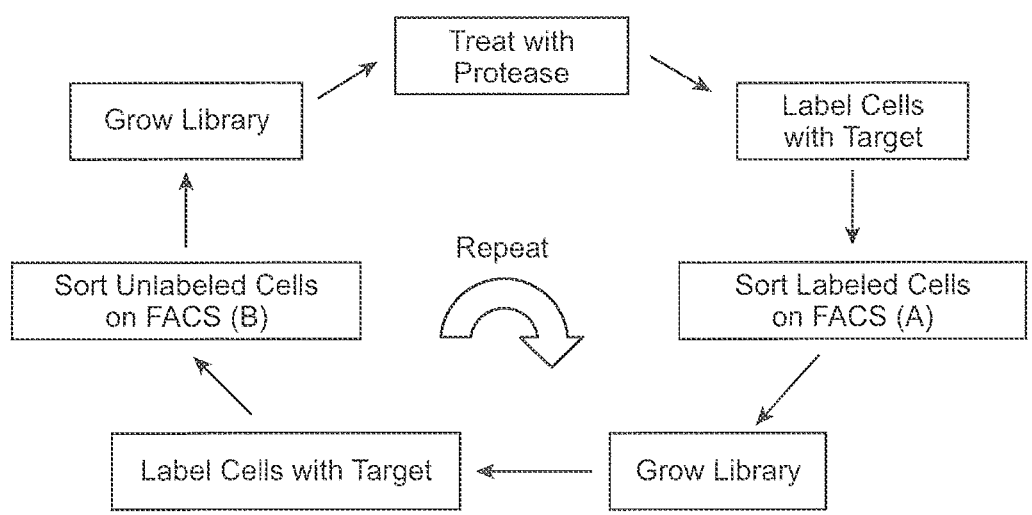
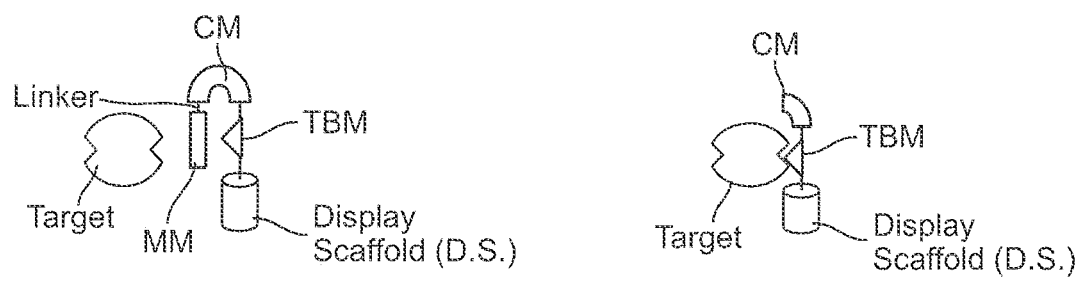
FIG. 2

Creation of libraries for the isolation of improved switches

| N-Terminus | MM Library | CM | | VEGF TBM |
|---|---|---|---|---|
| 1 | GQSGQ | CX$_6$G | PLGLAG | GGSG | NFGYGKWEWDYGKWLEKVGGC |
| 2 | GQSGQ | X$_5$G | PLGLAG | GGSG | NFGYGKWEWDYGKWLEKVGGC |
| 3 | GQSGQ | XCX$_3$ | PLGLAG | GGSG | NFGYGKWEWDYGKWLEKVGGC |
| 4 | GQSGQ | X$_5$G | PLGLAG | GGSG | NFGYGKWEWDYGKWLEKVGGG |

Library 2 develops switch-like behavior after sorting
Unsorted Library #2 — After 1.5 Cycles
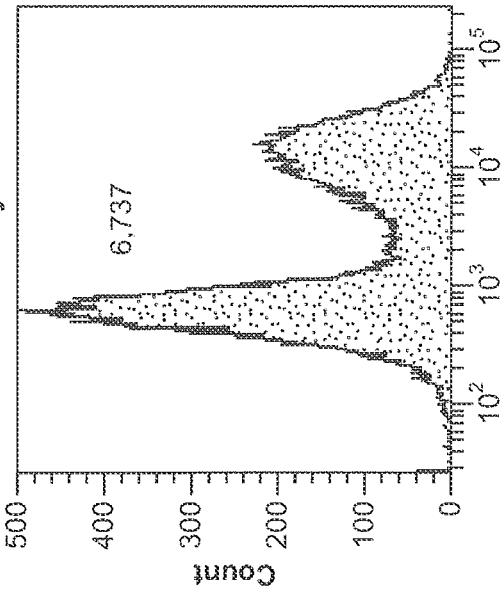
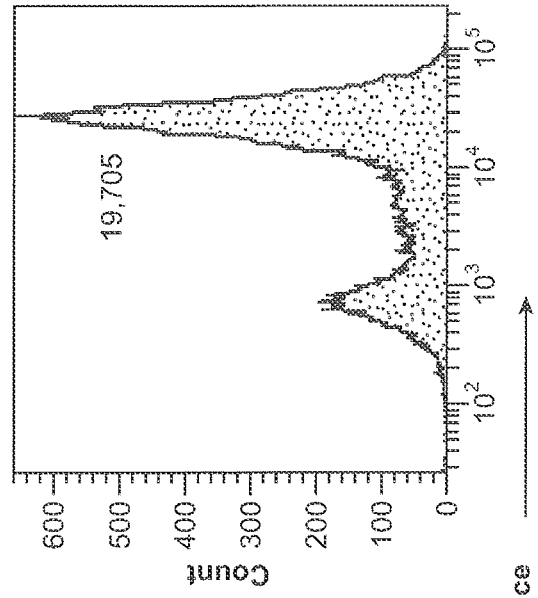
No Enzyme 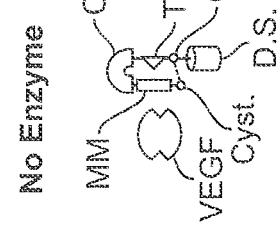
With Enzyme 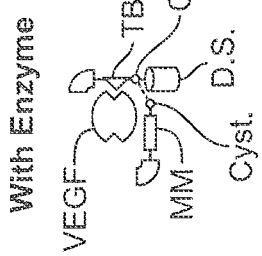
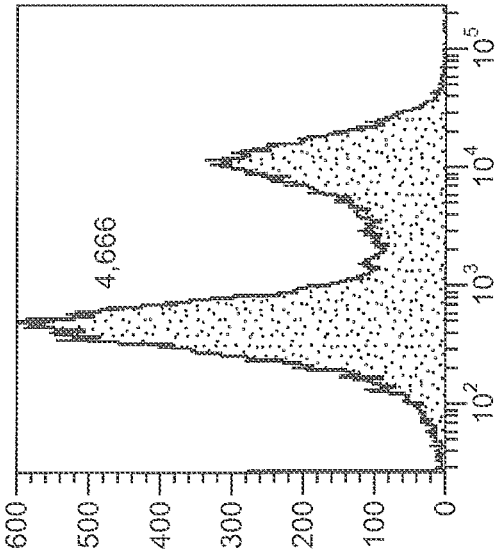
Red Fluorescence
FIG. 8

Sequences of top clones

| | N-Terminus | Library (MM) | (CM) | | VEGF TBM | |
|---|---|---|---|---|---|---|
| 2.2A.3 | GQSGQ | CMAMLG | PLGLAG | GGSG | NFGYGKWEWDYGKWLEKVG | GC |
| 2.2A.4 | GQSGQ | KGGGCG | PLGLAG | GGSG | NFGYGKWEWDYGKWLEKVG | GC |
| 2.2A.5 | GQSGQ | PEWGCG | PLGLAG | GGSG | NFGYGKWEWDYGKWLEKVG | GC |
| 2.2A.8 | GQSGQ | LEGEEG | PLGLAG | GGSG | NFGYGKWEWDYGKWLEKVG | GC |
| 2.2A.19 | GQSGQ | DDMEEG | PLGLAG | GGSG | NFGYGKWEWDYGKWLEKVG | GC |
| 1.2B.2 | GQSGQ | CTGVYLR | PLGLAG | GGSG | NFGYGKWEWDYGKWLEKVG | GC |
| 4.2A.11 | GQSGQ | GEDEEG | PLGLAG | GGSG | NFGYGKWEWDYGKWLEKVG | GG |
| 1.1 | GQSGQ | CSVYGWG | PLGLAG | GGSG | NFGYGKWEWDYGKWLEKVG | GC |
| 1.9 | GQSGQ | CCPKVYG | PLGLAG | GGSG | NFGYGKWEWDYGKWLEKVG | GC |

MM library — VEGF binding sequence

| Clone | Library (MM) |
|---|---|
| 2.2A.3 (2-2A-3) | CMAML<u>G</u> |
| 2.2A.4 (2-2A-4) | KGGGC<u>G</u> |
| 2.2A.5 (2-2A-5) | PEWGC<u>G</u> |
| 2.2A.8 (2-2A-8) | LEGEE<u>G</u> |
| 2.2A.19 (2-2A-19) | DDMEE<u>G</u> |
| 1.2B.2 (1-2B-2) | <u>C</u>TGVYR<u>G</u> |
| 4.2A.11 (4-2A-11) | GEDEE<u>G</u> |
| 1.1 | <u>C</u>SVYGWG<u>G</u> |
| 1.9 | <u>CC</u>PKVYG<u>G</u> |

* Underlined MM library residues indicate residues of fixed identity for a particular MM library.

FIG. 10

Design of a Protease-Activated VEGF Inhibitor

Tumor-specific protease substrate

"Masking Moiety" (MM)

High-affinity VEGF inhibitor (TBM)

IgG binding for serum half-life extension

FIG. 17

Sequences of MM peptides indicate two possible mechanisms of inhibition

| Clone | Library (MM) | Substrate | VEGF TBM |
|---|---|---|---|
| 2-2A-5 | PEWGCG | PLGLAG | NFGYGKWEWDYGKWLEKVGGC |
| 1-2B-2 | CTGVYLRG | | |
| 1-3A-2 | CVRVFRMG | | |
| 1-3A-3 | CFFMPLQG | | |
| 1-3A-4 | CSMYWMRG | | |
| 2-3B-5 | CEYAFG | | |
| 2-3B-8 | GGWCRG | | |
| 2-2A-8 | LEGEEG | | |
| 2-2A-19 | DDMEEG | | |
| 4-2A-11 | GEDEEG | | |
| 2-3B-6 | EYEGEG | | |
| 2-3B-7 | VVSEEG | | |

NFGYGKWEWDYGKWLEKVGGC
NFGYGKWEWDYGKWLEKVGGC
NFGYGKWEWDYGKWLEKVGGC

VEGF Binding Sequence

*Underlined MM library residues indicate residues of fixed identity for a particular MM library.

FIG. 22

Soluble Protein Binding Assays

- C-terminal MBP fusions of VEGF binding clones were constructed

- SPR assays performed on a Biacore 3000
  - VEGF covalently immobilized on the sensor chip surface
  - Up to 15µM peptide was assayed for VEGF binding (Prophetic ABP for cytoplasmic expression as inclusion bodies).

(Prophetic ABP for cytoplasmic expression as inclusion bodies).

(Prophetic ABP for cytoplasmic expression as inclusion bodies).

*anti-VCAM scFV sequence indicated by underlining.

Light and heavy chains of anti-CTLA4 joined via SOE-PCR to generate scFv constructs in both orientations, $V_H V_L$ and $V_L V_H$
1st round PCR
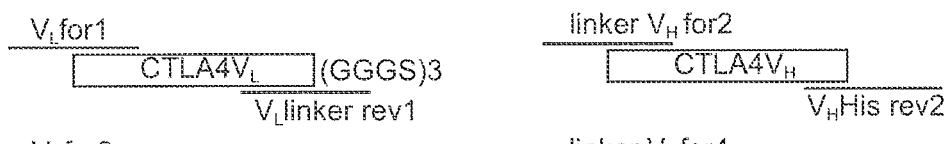
2nd round PCR
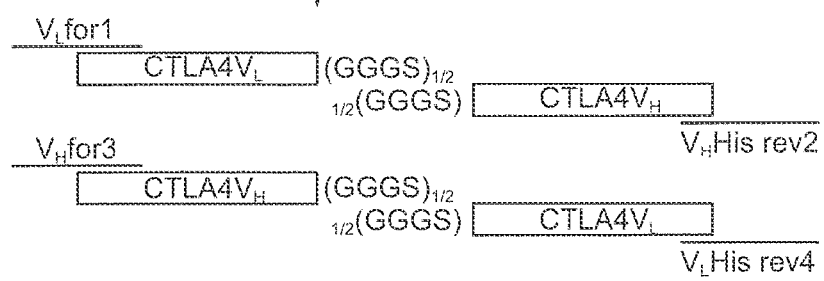
FIG. 43

PCR to add sites for MM cloning, CM cleavage sequence, GGS2 linker on the N-terminus of the anti-CTLA4 scFv $V_HV_L$ and $V_LV_H$ constructs Sequence of MM linker –CM–anti-CTLA4 scFv linker Amino acid sequence:

```
------MM linker------              CM              
G G S G G G S G G S S G Q V H M P L G F L
                                   ------ScFv linker------
                                   G P G G S G G S
```

Nucleotide sequence:
GGCGGTTCTGGTGGCAGCGGTGGCTCGAGCGGCCAAGTGCACATGCCACTGGGCTTCCTGGGTCCGGGTGGAAGCGGCGGCTCA

FIG. 45

```
                        SEQUENCE LISTING

<160> NUMBER OF SEQ ID NOS: 141

<210> SEQ ID NO 1
    <211> LENGTH: 5
    <212> TYPE: PRT
    <213> ORGANISM: Artificial Sequence
    <220> FEATURE:
    <223> OTHER INFORMATION: synthetic peptide

<400> SEQUENCE: 1

Gly Ser Gly Gly Ser
    1               5

<210> SEQ ID NO 2
    <211> LENGTH: 4
    <212> TYPE: PRT
    <213> ORGANISM: Artificial Sequence
    <220> FEATURE:
    <223> OTHER INFORMATION: synthetic peptide

<400> SEQUENCE: 2

Gly Gly Gly Ser
    1

<210> SEQ ID NO 3
    <211> LENGTH: 4
    <212> TYPE: PRT
    <213> ORGANISM: Artificial Sequence
    <220> FEATURE:
    <223> OTHER INFORMATION: synthetic peptide

<400> SEQUENCE: 3

Gly Gly Ser Gly
    1

<210> SEQ ID NO 4
    <211> LENGTH: 5
    <212> TYPE: PRT
    <213> ORGANISM: Artificial Sequence
    <220> FEATURE:
    <223> OTHER INFORMATION: synthetic peptide

<400> SEQUENCE: 4

Gly Gly Ser Gly Gly
    1               5

<210> SEQ ID NO 5
    <211> LENGTH: 5
    <212> TYPE: PRT
```

-continued

```
<213> ORGANISM: Artificial Sequence
<220> FEATURE:
<223> OTHER INFORMATION: synthetic peptide

<400> SEQUENCE: 5

Gly Ser Gly Ser Gly
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic peptide

<400> SEQUENCE: 6

Gly Ser Gly Gly Gly
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic peptide

<400> SEQUENCE: 7

Gly Gly Gly Ser Gly
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic peptide

<400> SEQUENCE: 8

Gly Ser Ser Ser Gly
1               5

<210> SEQ ID NO 9
<211> LENGTH: 6
<212> TYPE: PRT
<213> ORGANISM: Artificial Sequence
<220> FEATURE:
<223> OTHER INFORMATION: synthetic peptide

<400> SEQUENCE: 9

Pro Leu Gly Leu Ala Gly
1               5

<210> SEQ ID NO 10
<211> LENGTH: 21
<212> TYPE: PRT
<213> ORGANISM: Artificial Sequence
<220> FEATURE:
<223> OTHER INFORMATION: synthetic peptide

<400> SEQUENCE: 10

Asn Phe Gly Tyr Gly Lys Trp Glu Trp Asp Tyr Gly Lys Trp Leu Glu
1               5                   10                  15

Lys Val Gly Gly Cys
            20

<210> SEQ ID NO 11
```

```
<211> LENGTH: 6
<212> TYPE: PRT
<213> ORGANISM: Artificial Sequence
<220> FEATURE:
<223> OTHER INFORMATION: synthetic peptide

<400> SEQUENCE: 11

Pro Glu Trp Gly Cys Gly
1               5

<210> SEQ ID NO 12
<211> LENGTH: 48
<212> TYPE: PRT
<213> ORGANISM: Artificial Sequence
<220> FEATURE:
<223> OTHER INFORMATION: synthetic peptide

<400> SEQUENCE: 12

Gly Gln Ser Gly Gln Met Ala Ser Met Thr Gly Gly Gln Gln Met Gly
1               5                   10                  15

Gly Ser Gly Pro Leu Gly Leu Ala Gly Gly Ser Gly Asn Phe Gly
            20                  25                  30

Tyr Gly Lys Trp Glu Trp Asp Tyr Gly Lys Trp Leu Glu Lys Val Gly
        35                  40                  45

<210> SEQ ID NO 13
<211> LENGTH: 41
<212> TYPE: PRT
<213> ORGANISM: Artificial Sequence
<220> FEATURE:
<223> OTHER INFORMATION: synthetic peptide

<400> SEQUENCE: 13

Gly Gln Ser Gly Gln Gly Cys Gly Ser Gly Pro Leu Gly Leu Ala Gly
1               5                   10                  15

Gly Gly Ser Gly Asn Phe Gly Tyr Gly Lys Trp Glu Trp Asp Tyr Gly
            20                  25                  30

Lys Trp Leu Glu Lys Val Gly Gly Cys
        35                  40

<210> SEQ ID NO 14
<211> LENGTH: 51
<212> TYPE: PRT
<213> ORGANISM: Artificial Sequence
<220> FEATURE:
<223> OTHER INFORMATION: synthetic peptide

<400> SEQUENCE: 14

Gly Gln Ser Gly Gln Gly Gly Ser Gly Gly Ser Gly Ser Gly Gly
1               5                   10                  15

Ser Gly Gly Ser Pro Leu Gly Leu Ala Gly Gly Gly Ser Gly Asn Phe
            20                  25                  30

Gly Tyr Gly Lys Trp Glu Trp Asp Tyr Gly Lys Trp Leu Glu Lys Val
        35                  40                  45

Gly Gly Gly
    50

<210> SEQ ID NO 15
<211> LENGTH: 44
<212> TYPE: PRT
<213> ORGANISM: Artificial Sequence
<220> FEATURE:
<223> OTHER INFORMATION: synthetic peptide
<220> FEATURE:
```

```
<221> NAME/KEY: VARIANT
<222> LOCATION: (7)..(12)
<223> OTHER INFORMATION: Xaa = any amino acid

<400> SEQUENCE: 15

Gly Gln Ser Gly Gln Cys Xaa Xaa Xaa Xaa Xaa Xaa Gly Pro Leu Gly
1               5                   10                  15

Leu Ala Gly Gly Gly Ser Gly Asn Phe Gly Tyr Gly Lys Trp Glu Trp
                20                  25                  30

Asp Tyr Gly Lys Trp Leu Glu Lys Val Gly Gly Cys
            35                  40

<210> SEQ ID NO 16
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (6)..(10)
<223> OTHER INFORMATION: Xaa = any amino acid

<400> SEQUENCE: 16

Gly Gln Ser Gly Gln Xaa Xaa Xaa Xaa Xaa Gly Pro Leu Gly Leu Ala
1               5                   10                  15

Gly Gly Gly Ser Gly Asn Phe Gly Tyr Gly Lys Trp Glu Trp Asp Tyr
                20                  25                  30

Gly Lys Trp Leu Glu Lys Val Gly Gly Cys
            35                  40

<210> SEQ ID NO 17
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (6)..(10)
<223> OTHER INFORMATION: Xaa = any amino acid

<400> SEQUENCE: 17

Gly Gln Ser Gly Gln Xaa Cys Xaa Xaa Xaa Pro Leu Gly Leu Ala Gly
1               5                   10                  15

Gly Gly Ser Gly Asn Phe Gly Tyr Gly Lys Trp Glu Trp Asp Tyr Gly
                20                  25                  30

Lys Trp Leu Glu Lys Val Gly Gly Cys
            35                  40

<210> SEQ ID NO 18
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (6)..(10)
<223> OTHER INFORMATION: Xaa = any amino acid

<400> SEQUENCE: 18

Gly Gln Ser Gly Gln Xaa Xaa Xaa Xaa Xaa Gly Pro Leu Gly Leu Ala
1               5                   10                  15

Gly Gly Gly Ser Gly Asn Phe Gly Tyr Gly Lys Trp Glu Trp Asp Tyr
```

```
                    20                  25                  30

Gly Lys Trp Leu Glu Lys Val Gly Gly Gly
        35                  40

<210> SEQ ID NO 19
<211> LENGTH: 6
<212> TYPE: PRT
<213> ORGANISM: Artificial Sequence
<220> FEATURE:
<223> OTHER INFORMATION: synthetic peptide

<400> SEQUENCE: 19

Gly Glu Asp Glu Glu Gly
1               5

<210> SEQ ID NO 20
<211> LENGTH: 6
<212> TYPE: PRT
<213> ORGANISM: Artificial Sequence
<220> FEATURE:
<223> OTHER INFORMATION: synthetic peptide

<400> SEQUENCE: 20

Cys Glu Tyr Ala Phe Gly
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic peptide

<400> SEQUENCE: 21

Cys Ser Met Tyr Trp Met Arg Gly
1               5

<210> SEQ ID NO 22
<211> LENGTH: 6
<212> TYPE: PRT
<213> ORGANISM: Artificial Sequence
<220> FEATURE:
<223> OTHER INFORMATION: synthetic peptide

<400> SEQUENCE: 22

Glu Tyr Glu Gly Glu Gly
1               5

<210> SEQ ID NO 23
<211> LENGTH: 5
<212> TYPE: PRT
<213> ORGANISM: Artificial Sequence
<220> FEATURE:
<223> OTHER INFORMATION: synthetic peptide

<400> SEQUENCE: 23

Gly Glu Asp Glu Glu
1               5

<210> SEQ ID NO 24
<211> LENGTH: 5
<212> TYPE: PRT
<213> ORGANISM: Artificial Sequence
<220> FEATURE:
<223> OTHER INFORMATION: synthetic peptide

<400> SEQUENCE: 24
```

```
Asp Asp Met Glu Glu
1               5

<210> SEQ ID NO 25
<211> LENGTH: 6
<212> TYPE: PRT
<213> ORGANISM: Artificial Sequence
<220> FEATURE:
<223> OTHER INFORMATION: synthetic peptide

<400> SEQUENCE: 25

Asp Asp Met Glu Glu Gly
1               5

<210> SEQ ID NO 26
<211> LENGTH: 15
<212> TYPE: PRT
<213> ORGANISM: Artificial Sequence
<220> FEATURE:
<223> OTHER INFORMATION: synthetic peptide

<400> SEQUENCE: 26

Gly Val Val Leu Thr Thr Met Asn Phe Trp Asp Trp Ile Thr Val
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: synthetic peptide

<400> SEQUENCE: 27

Trp Ala Asp Trp Ala Arg Ser Trp Glu Ala Ile Val Gly Met Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: synthetic peptide

<400> SEQUENCE: 28

Arg Gly Met Asp Met Tyr Trp Ala Glu Ile Ile Tyr Gly Ala Ala
1               5                   10                  15

<210> SEQ ID NO 29
<211> LENGTH: 735
<212> TYPE: DNA
<213> ORGANISM: Artificial Sequence
<220> FEATURE:
<223> OTHER INFORMATION: synthetic oligonucleotide: anti-VEGF scFv TBM

<400> SEQUENCE: 29
gatattcaac tgacccagag cccttcttcc ctgagtgcca gcgtgggtga ccgtgttacg      60
atcacttgct cggccagcca agatatttct aactacctga attggtacca gcagaagcca     120
ggaaaggcac aaaagtcct gatctacttc acaagttcac tgcattccgg cgtaccgtcg      180
cgctttagcg gttctggcag tggtaccgac ttcaccctga ctatctcgag tctgcaacct     240
gaggattttg ctacatatta ctgtcagcaa tattcgaccg tgccgtggac gttcgggcag     300
ggcaccaaag tggagattaa ggggggtgga ggcagcgggg gaggtggctc aggcggtgga     360
gggtctggcg aggtccagct ggtagaaagc ggggggcggac tggtccaacc gggcggatcc     420
```

```
ctgcgtctga gctgcgcggc ctcgggttac gactttactc actacggaat gaactgggtt    480
cgccaagccc ctggtaaagg tctggaatgg gtcggatgga ttaatacata cactggagaa    540
cctacttatg ctgctgattt caaacgtcgc tttactttct ctctggatac aagtaagtca    600
accgccatct gcaaatgaa cagcctgcgt gcagaggaca cggctgtgta ctattgtgcg    660
aaatatcctt attattatgg aacttcccac tggtatttcg atgtatgggg ccagggtact    720
ctggttacag tgtcg                                                      735
```

```
<210> SEQ ID NO 30
<211> LENGTH: 245
<212> TYPE: PRT
<213> ORGANISM: Artificial Sequence
<220> FEATURE:
<223> OTHER INFORMATION: synthetic peptide:  anti-VEGF scFv TBM

<400> SEQUENCE: 30

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val
        115                 120                 125

Glu Ser Gly Gly Gly Leu Val Gln Pro Gly Gly Ser Leu Arg Leu Ser
130                 135                 140

Cys Ala Ala Ser Gly Tyr Asp Phe Thr His Tyr Gly Met Asn Trp Val
145                 150                 155                 160

Arg Gln Ala Pro Gly Lys Gly Leu Glu Trp Val Gly Trp Ile Asn Thr
                165                 170                 175

Tyr Thr Gly Glu Pro Thr Tyr Ala Ala Asp Phe Lys Arg Arg Phe Thr
            180                 185                 190

Phe Ser Leu Asp Thr Ser Lys Ser Thr Ala Tyr Leu Gln Met Asn Ser
        195                 200                 205

Leu Arg Ala Glu Asp Thr Ala Val Tyr Tyr Cys Ala Lys Tyr Pro Tyr
    210                 215                 220

Tyr Tyr Gly Thr Ser His Trp Tyr Phe Asp Val Trp Gly Gln Gly Thr
225                 230                 235                 240

Leu Val Thr Val Ser
                245

<210> SEQ ID NO 31
<211> LENGTH: 17
<212> TYPE: PRT
<213> ORGANISM: Artificial Sequence
<220> FEATURE:
<223> OTHER INFORMATION: synthetic peptide
```

```
<400> SEQUENCE: 31

Ala Thr Ala Val Trp Asn Ser Met Val Lys Gln Ser Cys Tyr Met Gln
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: synthetic peptide

<400> SEQUENCE: 32

Gly His Gly Met Cys Tyr Thr Ile Leu Glu Asp His Cys Asp Arg Val
1               5                   10                  15

Arg

<210> SEQ ID NO 33
<211> LENGTH: 17
<212> TYPE: PRT
<213> ORGANISM: Artificial Sequence
<220> FEATURE:
<223> OTHER INFORMATION: synthetic peptide

<400> SEQUENCE: 33

Pro Cys Ser Glu Trp Gln Ser Met Val Gln Pro Arg Cys Tyr Tyr Gly
1               5                   10                  15

Gly

<210> SEQ ID NO 34
<211> LENGTH: 17
<212> TYPE: PRT
<213> ORGANISM: Artificial Sequence
<220> FEATURE:
<223> OTHER INFORMATION: synthetic peptide

<400> SEQUENCE: 34

Asn Val Glu Cys Cys Gln Asn Tyr Asn Leu Trp Asn Cys Cys Gly Gly
1               5                   10                  15

Arg

<210> SEQ ID NO 35
<211> LENGTH: 15
<212> TYPE: PRT
<213> ORGANISM: Artificial Sequence
<220> FEATURE:
<223> OTHER INFORMATION: synthetic peptide

<400> SEQUENCE: 35

Val His Ala Trp Glu Gln Leu Val Ile Gln Glu Leu Tyr His Cys
1               5                   10                  15

<210> SEQ ID NO 36
<211> LENGTH: 17
<212> TYPE: PRT
<213> ORGANISM: Artificial Sequence
<220> FEATURE:
<223> OTHER INFORMATION: synthetic peptide

<400> SEQUENCE: 36

Gly Val Gly Leu Cys Tyr Thr Ile Leu Glu Gln Trp Cys Glu Met Gly
1               5                   10                  15

Arg
```

```
<210> SEQ ID NO 37
<211> LENGTH: 17
<212> TYPE: PRT
<213> ORGANISM: Artificial Sequence
<220> FEATURE:
<223> OTHER INFORMATION: synthetic peptide

<400> SEQUENCE: 37

Arg Pro Pro Cys Cys Arg Asp Tyr Ser Ile Leu Glu Cys Cys Lys Ser
1               5                   10                  15

Asp

<210> SEQ ID NO 38
<211> LENGTH: 17
<212> TYPE: PRT
<213> ORGANISM: Artificial Sequence
<220> FEATURE:
<223> OTHER INFORMATION: synthetic peptide

<400> SEQUENCE: 38

Gly Ala Met Ala Cys Tyr Asn Ile Phe Glu Tyr Trp Cys Ser Ala Met
1               5                   10                  15

Lys

<210> SEQ ID NO 39
<211> LENGTH: 37
<212> TYPE: DNA
<213> ORGANISM: Artificial Sequence
<220> FEATURE:
<223> OTHER INFORMATION: oligonucleotide

<400> SEQUENCE: 39
gaattcatgg gccatcacca tcaccatcac ggtgggg                         37

<210> SEQ ID NO 40
<211> LENGTH: 43
<212> TYPE: DNA
<213> ORGANISM: Artificial Sequence
<220> FEATURE:
<223> OTHER INFORMATION: oligonucleotide

<400> SEQUENCE: 40
gtgagtaagc ttttattacg acactgtaac cagagtaccc tgg                  43

<210> SEQ ID NO 41
<211> LENGTH: 71
<212> TYPE: DNA
<213> ORGANISM: Artificial Sequence
<220> FEATURE:
<223> OTHER INFORMATION: oligonucleotide

<400> SEQUENCE: 41
gtggcatgtg cacttggcca ccttggccca ctcgagctgg ccagactggc cctgaaaata  60
cagattttcc c                                                      71

<210> SEQ ID NO 42
<211> LENGTH: 81
<212> TYPE: DNA
<213> ORGANISM: Artificial Sequence
<220> FEATURE:
<223> OTHER INFORMATION: oligonucleotide

<400> SEQUENCE: 42
```

```
gagtgggcca aggtggccaa gtgcacatgc cactgggctt cctgggtccg ggcggttctg    60
atattcaact gacccagagc c                                              81
```

<210> SEQ ID NO 43
<211> LENGTH: 40
<212> TYPE: DNA
<213> ORGANISM: Artificial Sequence
<220> FEATURE:
<223> OTHER INFORMATION: oligonucleotide

<400> SEQUENCE: 43

```
ttcgagctcg aacaacaaca acaataacaa taacaacaac                          40
```

<210> SEQ ID NO 44
<211> LENGTH: 40
<212> TYPE: DNA
<213> ORGANISM: Artificial Sequence
<220> FEATURE:
<223> OTHER INFORMATION: oligonucleotide

<400> SEQUENCE: 44

```
gctttcaccg caggtacttc cgtagctggc cagtctggcc                          40
```

<210> SEQ ID NO 45
<211> LENGTH: 40
<212> TYPE: DNA
<213> ORGANISM: Artificial Sequence
<220> FEATURE:
<223> OTHER INFORMATION: oligonucleotide

<400> SEQUENCE: 45

```
cgctccatgg gccaccttgg ccgctgccac cagaaccgcc                          40
```

<210> SEQ ID NO 46
<211> LENGTH: 40
<212> TYPE: DNA
<213> ORGANISM: Artificial Sequence
<220> FEATURE:
<223> OTHER INFORMATION: oligonucleotide

<400> SEQUENCE: 46

```
gcccagccgg ccatggccgg ccagtctggc cagctcgagt                          40
```

<210> SEQ ID NO 47
<211> LENGTH: 62
<212> TYPE: DNA
<213> ORGANISM: Artificial Sequence
<220> FEATURE:
<223> OTHER INFORMATION: oligonucleotide

<400> SEQUENCE: 47

```
ccagtgccaa gcttttagtg gtgatggtga tgatgcgaca ctgtaaccag agtaccctgg    60
cc                                                                   62
```

<210> SEQ ID NO 48
<211> LENGTH: 37
<212> TYPE: DNA
<213> ORGANISM: Artificial Sequence
<220> FEATURE:
<223> OTHER INFORMATION: oligonucleotide

<400> SEQUENCE: 48

```
cttgtcacga attcgggcca gtctggccag ctcgagt                             37
```

```
<210> SEQ ID NO 49
<211> LENGTH: 52
<212> TYPE: DNA
<213> ORGANISM: Artificial Sequence
<220> FEATURE:
<223> OTHER INFORMATION: oligonucleotide

<400> SEQUENCE: 49
cagatctaac catggcgccg ctaccgcccg acactgtaac cagagtaccc tg          52

<210> SEQ ID NO 50
<211> LENGTH: 860
<212> TYPE: DNA
<213> ORGANISM: Artificial Sequence
<220> FEATURE:
<223> OTHER INFORMATION: synthetic oligonucleotide: MBP/MM accepting
      site/MMP-9 CM/Anti-VEGF scFv TBM

<400> SEQUENCE: 50
atgggccatc accatcacca tcacggtggg gaaaatctgt attttcaggg ccagtctggc    60
cagctcgagt gggccaaggt ggccaagtgc acatgccact gggcttcctg ggtccgggcg   120
gttctgatat tcaactgacc cagagccctt cttccctgag tgccagcgtg ggtgaccgtg   180
ttacgatcac ttgctcggcc agccaagata tttctaacta cctgaattgg taccagcaga   240
agccaggaaa ggcaccaaaa gtcctgatct acttcacaag ttcactgcat tccggcgtac   300
cgtcgcgctt tagcggttct ggcagtggta ccgacttcac cctgactatc tcgagtctgc   360
aacctgagga ttttgctaca tattactgtc agcaatattc gaccgtgccg tggacgttcg   420 gcagggcac caaagtggag attaaggggg gtggaggcag cggggaggt ggctcaggcg   480 gtggagggtc tggcgaggtc cagctggtag aaagcggggg cggactggtc caaccgggcg   540
gatccctgcg tctgagctgc gcggcctcgg gttacgactt tactcactac ggaatgaact   600
gggttcgcca agcccctggt aaaggtctgg aatgggtcgg atggattaat acatacactg   660
gagaacctac ttatgctgct gatttcaaac gtcgctttac tttctctctg gatcaagta   720 agtcaaccgc ctatctgcaa atgaacagcc tgcgtgcaga ggacacggct gtgtactatt   780
gtgcgaaata tccttattat tatggaactt cccactggta tttcgatgta tggggccagg   840
gtactctggt tacagtgtcg                                               860

<210> SEQ ID NO 51
<211> LENGTH: 918
<212> TYPE: DNA
<213> ORGANISM: Artificial Sequence
<220> FEATURE:
<223> OTHER INFORMATION: synthetic oligonucleotide: MBP / 306 MM /
      MMP-9 CM / Anti-VEGF scFv TBM

<400> SEQUENCE: 51
atgggccatc accatcacca tcacggtggg gaaaatctgt attttcaggg ccagtctggc    60
cagccgtgtt ctgagtggca gtcgatggtg cagccgcgtt gctattatgg gggcggttct   120
ggtggcagcg gccaaggtgg ccaagtgcac atgccactgg gcttcctggg tccgggcggt   180
tctgatattc aactgaccca gagcccttct ccctgagtg ccagcgtggg tgaccgtgtt   240
acgatcactt gctcggccag ccaagatatt tctaactacc tgaattggta ccagcagaag   300
ccaggaaagg caccaaaagt cctgatctac ttcacaagtt cactgcattc cggcgtaccg   360
tcgcgcttta gcggttctgg cagtggtacc gacttcaccc tgactatctc gagtctgcaa   420
cctgaggatt ttgctacata ttactgtcag caatattcga ccgtgccgtg gacgttcggg   480
```

```
caggcacca aagtggagat taagggggt ggaggcagcg ggggaggtgg ctcaggcggt      540
ggagggtctg gctgaggtcca gctggtagaa agcgggggcg gactggtcca accgggcgga   600
tccctgcgtc tgagctgcgc ggcctcgggt tacgacttta ctcactacgg aatgaactgg    660
gttcgccaag cccctggtaa aggtctggaa tgggtcggat ggattaatac atacactgga    720
gaacctactt atgctgctga tttcaaacgt cgctttactt tctctctgga tacaagtaag    780
tcaaccgcct atctgcaaat gaacagcctg cgtgcagagg acacggctgt gtactattgt    840
gcgaaatatc cttattatta tggaacttcc cactggtatt tcgatgtatg gggccagggt    900
actctggtta cagtgtcg                                                  918
```

<210> SEQ ID NO 52
<211> LENGTH: 306
<212> TYPE: PRT
<213> ORGANISM: Artificial Sequence
<220> FEATURE:
<223> OTHER INFORMATION: synthetic peptide: MBP / 306 MM / MMP-9 CM / Anti-VEGF scFv TBM

<400> SEQUENCE: 52

```
Met Gly His His His His His Gly Gly Glu Asn Leu Tyr Phe Gln
1               5                   10                  15

Gly Gln Ser Gly Gln Pro Cys Ser Glu Trp Gln Ser Met Val Gln Pro
            20                  25                  30

Arg Cys Tyr Tyr Gly Gly Gly Ser Gly Gly Ser Gly Gln Gly Gly Gln
                35                  40                  45

Val His Met Pro Leu Gly Phe Leu Gly Pro Gly Gly Ser Asp Ile Gln
    50                  55                  60

Leu Thr Gln Ser Pro Ser Ser Leu Ser Ala Ser Val Gly Asp Arg Val
65                  70                  75                  80

Thr Ile Thr Cys Ser Ala Ser Gln Asp Ile Ser Asn Tyr Leu Asn Trp
                85                  90                  95

Tyr Gln Gln Lys Pro Gly Lys Ala Pro Lys Val Leu Ile Tyr Phe Thr
            100                 105                 110

Ser Ser Leu His Ser Gly Val Pro Ser Arg Phe Ser Gly Ser Gly Ser
        115                 120                 125

Gly Thr Asp Phe Thr Leu Thr Ile Ser Ser Leu Gln Pro Glu Asp Phe
    130                 135                 140

Ala Thr Tyr Tyr Cys Gln Gln Tyr Ser Thr Val Pro Trp Thr Phe Gly
145                 150                 155                 160

Gln Gly Thr Lys Val Glu Ile Lys Gly Gly Gly Gly Ser Gly Gly Gly
                165                 170                 175

Gly Ser Gly Gly Gly Gly Ser Gly Glu Val Gln Leu Val Glu Ser Gly
        180                 185                 190

Gly Gly Leu Val Gln Pro Gly Gly Ser Leu Arg Leu Ser Cys Ala Ala
    195                 200                 205

Ser Gly Tyr Asp Phe Thr His Tyr Gly Met Asn Trp Val Arg Gln Ala
210                 215                 220

Pro Gly Lys Gly Leu Glu Trp Val Gly Trp Ile Asn Thr Tyr Thr Gly
225                 230                 235                 240

Glu Pro Thr Tyr Ala Ala Asp Phe Lys Arg Arg Phe Thr Phe Ser Leu
                245                 250                 255

Asp Thr Ser Lys Ser Thr Ala Tyr Leu Gln Met Asn Ser Leu Arg Ala
            260                 265                 270

Glu Asp Thr Ala Val Tyr Tyr Cys Ala Lys Tyr Pro Tyr Tyr Tyr Gly
```

-continued

```
                275                 280                 285
Thr Ser His Trp Tyr Phe Asp Val Trp Gly Gln Gly Thr Leu Val Thr
    290                 295                 300

Val Ser
305
```

<210> SEQ ID NO 53
<211> LENGTH: 921
<212> TYPE: DNA
<213> ORGANISM: Artificial Sequence
<220> FEATURE:
<223> OTHER INFORMATION: synthetic oligonucleotide: MBP / 314 MM / MMP-9
      CM / Anti-VEGF scFv TBM

<400> SEQUENCE: 53

```
atgggccatc accatcacca tcacggtggg gaaaatctgt attttcaggg ccagtctggc      60
cagcggccgc cgtgttgccg tgattatagt attttggagt gctgtaagag tgatggcggt     120
tctggtggca gcggccaagg tggccaagtg cacatgccac tgggcttcct gggtccgggc     180
ggttctgata ttcaactgac ccagagccct tcttccctga gtgccagcgt gggtgaccgt     240
gttacgatca cttgctcggc cagccaagat atttctaact acctgaattg gtaccagcag     300
aagccaggaa aggcaccaaa agtcctgatc tacttcacaa gttcactgca ttccggcgta     360
ccgtcgcgct ttagcggttc tggcagtggt accgacttca ccctgactat ctcgagtctg     420
caacctgagg attttgctac atattactgt cagcaatatt cgaccgtgcc gtggacgttc     480
ggcagggca ccaaagtgga gattaagggg ggtggaggca gcggggagg tggctcaggc      540
ggtggagggt ctggcgaggt ccagctggta gaaagcgggg gcggactggt ccaaccgggc     600
ggatccctgc gtctgagctg cgcggcctcg ggttacgact ttactcacta cggaatgaac     660
tgggttcgcc aagcccctgg taaaggtctg gaatgggtcg gatggattaa tacatacact     720
ggagaaccta cttatgctgc tgatttcaaa cgtcgcttta ctttctctct ggatacaagt     780
aagtcaaccg cctatctgca aatgaacagc ctgcgtgcag aggacacggc tgtgtactat     840
tgtgcgaaat atccttatta ttatggaact tcccactggt atttcgatgt atggggccag     900
ggtactctgg ttacagtgtc g                                               921
```

<210> SEQ ID NO 54
<211> LENGTH: 307
<212> TYPE: PRT
<213> ORGANISM: Artificial Sequence
<220> FEATURE:
<223> OTHER INFORMATION: synthetic peptide: MBP / 314 MM / MMP-9 CM /
      Anti-VEGF scFv TBM

<400> SEQUENCE: 54

```
Met Gly His His His His His His Gly Gly Glu Asn Leu Tyr Phe Gln
1               5                   10                  15

Gly Gln Ser Gly Gln Arg Pro Pro Cys Cys Arg Asp Tyr Ser Ile Leu
            20                  25                  30

Glu Cys Cys Lys Ser Asp Gly Gly Ser Gly Gly Ser Gly Gln Gly Gly
        35                  40                  45

Gln Val His Met Pro Leu Gly Phe Leu Gly Pro Gly Gly Ser Asp Ile
    50                  55                  60

Gln Leu Thr Gln Ser Pro Ser Ser Leu Ser Ala Ser Val Gly Asp Arg
65                  70                  75                  80

Val Thr Ile Thr Cys Ser Ala Ser Gln Asp Ile Ser Asn Tyr Leu Asn
                85                  90                  95
```

Trp Tyr Gln Gln Lys Pro Gly Lys Ala Pro Lys Val Leu Ile Tyr Phe
            100                 105                 110

Thr Ser Ser Leu His Ser Gly Val Pro Ser Arg Phe Ser Gly Ser Gly
            115                 120                 125

Ser Gly Thr Asp Phe Thr Leu Thr Ile Ser Ser Leu Gln Pro Glu Asp
        130                 135                 140

Phe Ala Thr Tyr Tyr Cys Gln Gln Tyr Ser Thr Val Pro Trp Thr Phe
145                 150                 155                 160

Gly Gln Gly Thr Lys Val Glu Ile Lys Gly Gly Gly Ser Gly Gly
            165                 170                 175

Gly Gly Ser Gly Gly Gly Ser Gly Glu Val Gln Leu Val Glu Ser
        180                 185                 190

Gly Gly Gly Leu Val Gln Pro Gly Gly Ser Leu Arg Leu Ser Cys Ala
        195                 200                 205

Ala Ser Gly Tyr Asp Phe Thr His Tyr Gly Met Asn Trp Val Arg Gln
210                 215                 220

Ala Pro Gly Lys Gly Leu Glu Trp Val Gly Trp Ile Asn Thr Tyr Thr
225                 230                 235                 240

Gly Glu Pro Thr Tyr Ala Ala Asp Phe Lys Arg Arg Phe Thr Phe Ser
            245                 250                 255

Leu Asp Thr Ser Lys Ser Thr Ala Tyr Leu Gln Met Asn Ser Leu Arg
            260                 265                 270

Ala Glu Asp Thr Ala Val Tyr Tyr Cys Ala Lys Tyr Pro Tyr Tyr Tyr
        275                 280                 285

Gly Thr Ser His Trp Tyr Phe Asp Val Trp Gly Gln Gly Thr Leu Val
        290                 295                 300

Thr Val Ser
305

<210> SEQ ID NO 55
<211> LENGTH: 888
<212> TYPE: DNA
<213> ORGANISM: Artificial Sequence
<220> FEATURE:
<223> OTHER INFORMATION: synthetic oligonucleotide: 306 MM / MMP-9 CM /
      anti-VEGF scFv CHis TBM

<400> SEQUENCE: 55
ggccagtctg gccagccgtg ttctgagtgg cagtcgatgg tgcagccgcg ttgctattat      60
gggggcggtt ctggtggcag cggccaaggt ggccaagtgc acatgccact gggcttcctg     120
ggtccgggcg gttctgatat tcaactgacc cagagccctt cttccctgag tgccagcgtg     180
ggtgaccgtg ttacgatcac ttgctcggcc agcaagata tttctaacta cctgaattgg     240
taccagcaga agccaggaaa ggcaccaaaa gtcctgatct acttcacaag ttcactgcat     300
tccggcgtac cgtcgcgctt tagcggttct ggcagtggta ccgacttcac cctgactatc     360
tcgagtctgc aacctgagga ttttgctaca tattactgtc agcaatattc gaccgtgccg     420
tggacgttcg gcagggcac caaagtggag attaaggggg gtggaggcag cggggggggt     480
ggctcaggcg gtgagggtc tggcgaggtc cagctggtag aaagcgggg cggactggtc     540 caaccgggcg gatccctgcg tctgagctgc gcggcctcgg gttacgactt tactcactac     600
ggaatgaact gggttcgcca agcccctggt aaaggtctgg aatgggtcgg atggattaat     660
acatacactg gagaacctac ttatgctgct gatttcaaac gtcgctttac tttctctctg     720
gatacaagta agtcaaccgc ctatctgcaa atgaacagcc tgcgtgcaga ggacacggct     780

```
gtgtactatt gtgcgaaata tccttattat tatggaactt cccactggta tttcgatgta    840
tggggccagg gtactctggt tacagtgtcg catcatcacc atcaccac                 888
```

<210> SEQ ID NO 56
<211> LENGTH: 296
<212> TYPE: PRT
<213> ORGANISM: Artificial Sequence
<220> FEATURE:
<223> OTHER INFORMATION: synthetic peptide: 306 MM / MMP-9 CM /
      anti-VEGF scFv CHis TBM

<400> SEQUENCE: 56

```
Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
            20                  25                  30

Val His Met Pro Leu Gly Phe Leu Gly Pro Gly Gly Ser Asp Ile Gln
        35                  40                  45

Leu Thr Gln Ser Pro Ser Ser Leu Ser Ala Ser Val Gly Asp Arg Val
    50                  55                  60

Thr Ile Thr Cys Ser Ala Ser Gln Asp Ile Ser Asn Tyr Leu Asn Trp
65                  70                  75                  80

Tyr Gln Gln Lys Pro Gly Lys Ala Pro Lys Val Leu Ile Tyr Phe Thr
                85                  90                  95

Ser Ser Leu His Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
        115                 120                 125

Ala Thr Tyr Tyr Cys Gln Gln Tyr Ser Thr Val Pro Trp Thr Phe Gly
    130                 135                 140

Gln Gly Thr Lys Val Glu Ile Lys Gly Gly Gly Gly Ser Gly Gly Gly
145                 150                 155                 160

Gly Ser Gly Gly Gly Gly Ser Gly Glu Val Gln Leu Val Glu Ser Gly
                165                 170                 175

Gly Gly Leu Val Gln Pro Gly Gly Ser Leu Arg Leu Ser Cys Ala Ala
            180                 185                 190

Ser Gly Tyr Asp Phe Thr His Tyr Gly Met Asn Trp Val Arg Gln Ala
        195                 200                 205

Pro Gly Lys Gly Leu Glu Trp Val Gly Trp Ile Asn Thr Tyr Thr Gly
    210                 215                 220

Glu Pro Thr Tyr Ala Ala Asp Phe Lys Arg Arg Phe Thr Phe Ser Leu
225                 230                 235                 240

Asp Thr Ser Lys Ser Thr Ala Tyr Leu Gln Met Asn Ser Leu Arg Ala
                245                 250                 255

Glu Asp Thr Ala Val Tyr Tyr Cys Ala Lys Tyr Pro Tyr Tyr Tyr Gly
            260                 265                 270

Thr Ser His Trp Tyr Phe Asp Val Trp Gly Gln Gly Thr Leu Val Thr
        275                 280                 285

Val Ser His His His His His His
    290                 295
```

<210> SEQ ID NO 57
<211> LENGTH: 894
<212> TYPE: DNA
<213> ORGANISM: Artificial Sequence
<220> FEATURE:

<223> OTHER INFORMATION: synthetic oligonucleotide: 314 MM / MMP-9 CM /
      anti-VEGF scFv CHis TBM

<400> SEQUENCE: 57

```
ggccagtctg gccagcggcc gccgtgttgc cgtgattata gtattttgga gtgctgtaag      60
agtgatggcg gttctggtgg cagcggccaa ggtggccaag tgcacatgcc actgggcttc     120
ctgggtccgg gcggttctga tattcaactg acccagagcc cttcttccct gagtgccagc     180
gtgggtgacc gtgttacgat cacttgctcg gccagccaag atatttctaa ctacctgaat     240
tggtaccagc agaagccagg aaaggcacca aaagtcctga tctacttcac aagttcactg     300
cattccggcg taccgtcgcg ctttagcggt tctggcagtg gtaccgactt cacccctgact    360
atctcgagtc tgcaacctga ggattttgct acatattact gtcagcaata ttcgaccgtg    420
ccgtggacgt tcgggcaggg caccaaagtg gagattaagg ggggtggagg cagcggggga    480
ggtggctcag gcggtggagg gtctggcgag gtccagctgg tagaaagcgg gggcggactg    540
gtccaaccgg gcggatccct gcgtctgagc tgcgcggcct cgggttacga ctttactcac    600
tacggaatga actgggttcg ccaagcccct ggtaaaggtc tggaatgggt cggatggatt    660
aatacataca ctggagaacc tacttatgct gctgatttca acgtcgctt tactttctct    720
ctggatacaa gtaagtcaac cgcctatctg caaatgaaca gcctgcgtgc agaggacacg    780
gctgtgtact attgtgcgaa atatccttat tattatggaa cttcccactg gtatttcgat    840
gtatggggcc agggtactct ggttacagtg tcgcatcatc accatcacca ctaa          894
```

<210> SEQ ID NO 58
<211> LENGTH: 297
<212> TYPE: PRT
<213> ORGANISM: Artificial Sequence
<220> FEATURE:
<223> OTHER INFORMATION: synthetic peptide: 314 MM / MMP-9 CM /
      anti-VEGF scFv CHis TBM

<400> SEQUENCE: 58

```
Gly Gln Ser Gly Gln Arg Pro Pro Cys Cys Arg Asp Tyr Ser Ile Leu
 1               5                  10                  15

Glu Cys Cys Lys Ser Asp Gly Gly Ser Gly Gly Ser Gly Gln Gly Gly
             20                  25                  30

Gln Val His Met Pro Leu Gly Phe Leu Gly Pro Gly Gly Ser Asp Ile
         35                  40                  45

Gln Leu Thr Gln Ser Pro Ser Ser Leu Ser Ala Ser Val Gly Asp Arg
     50                  55                  60

Val Thr Ile Thr Cys Ser Ala Ser Gln Asp Ile Ser Asn Tyr Leu Asn
 65                  70                  75                  80

Trp Tyr Gln Gln Lys Pro Gly Lys Ala Pro Lys Val Leu Ile Tyr Phe
                 85                  90                  95

Thr Ser Ser Leu His Ser Gly Val Pro Ser Arg Phe Ser Gly Ser Gly
            100                 105                 110

Ser Gly Thr Asp Phe Thr Leu Thr Ile Ser Ser Leu Gln Pro Glu Asp
        115                 120                 125

Phe Ala Thr Tyr Tyr Cys Gln Gln Tyr Ser Thr Val Pro Trp Thr Phe
    130                 135                 140

Gly Gln Gly Thr Lys Val Glu Ile Lys Gly Gly Gly Ser Gly Gly
145                 150                 155                 160

Gly Gly Ser Gly Gly Gly Gly Ser Gly Glu Val Gln Leu Val Glu Ser
                165                 170                 175
```

Gly Gly Gly Leu Val Gln Pro Gly Gly Ser Leu Arg Leu Ser Cys Ala
            180                 185                 190

Ala Ser Gly Tyr Asp Phe Thr His Tyr Gly Met Asn Trp Val Arg Gln
        195                 200                 205

Ala Pro Gly Lys Gly Leu Glu Trp Val Gly Trp Ile Asn Thr Tyr Thr
    210                 215                 220

Gly Glu Pro Thr Tyr Ala Ala Asp Phe Lys Arg Arg Phe Thr Phe Ser
225                 230                 235                 240

Leu Asp Thr Ser Lys Ser Thr Ala Tyr Leu Gln Met Asn Ser Leu Arg
                245                 250                 255

Ala Glu Asp Thr Ala Val Tyr Tyr Cys Ala Lys Tyr Pro Tyr Tyr Tyr
            260                 265                 270

Gly Thr Ser His Trp Tyr Phe Asp Val Trp Gly Gln Gly Thr Leu Val
        275                 280                 285

Thr Val Ser His His His His His His
    290                 295

<210> SEQ ID NO 59
<211> LENGTH: 1578
<212> TYPE: DNA
<213> ORGANISM: Artificial Sequence
<220> FEATURE:
<223> OTHER INFORMATION: synthetic oligonucleotide: 306 MM / MMP-9 CM
      /anti-VEGF scfv-Fc TBM

<400> SEQUENCE: 59
ggccagtctg gccagccgtg ttctgagtgg cagtcgatgg tgcagccgcg ttgctattat        60
gggggcggtt ctggtggcag cggccaaggt ggccaagtgc acatgccact gggcttcctg       120
ggtccgggcg ttctgatat  tcaactgacc cagagccctt cttccctgag tgccagcgtg       180
ggtgaccgtg ttacgatcac ttgctcggcc agccaagata tttctaacta cctgaattgg       240
taccagcaga agccaggaaa ggcaccaaaa gtcctgatct acttcacaag ttcactgcat       300
tccggcgtac cgtcgcgctt tagcggttct ggcagtggta ccgacttcac cctgactatc       360
tcgagtctgc aacctgagga ttttgctaca tattactgtc agcaatattc gaccgtgccg       420
tggacgttcg gcagggcac  caaagtggag attaagggg  gtggaggcag cgggggaggt       480
ggctcaggcg gtgagggtc  tggcgaggtc cagctggtag aaagcggggg cggactggtc       540
caaccgggcg gatccctgcg tctgagctgc gcggcctcgg gttacgactt tactcactac       600
ggaatgaact gggttcgcca agcccctggt aaaggtctgg aatgggtcgg atggattaat       660
acatacactg gagaacctac ttatgctgct gatttcaaac gtcgctttac tttctctctg       720
gatacaagta agtcaaccgc ctatctgcaa atgaacagcc tgcgtgcaga ggacacggct       780
gtgtactatt gtgcgaaata tccttattat tatggaactt cccactggta tttcgatgta       840
tggggccagg gtactctggt tacagtgtcg gcggtagcg  gcgccatggt tagatctgac       900
aaaactcaca catgcccacc gtgcccagca cctgaactcc tggggggacc gtcagtcttc       960
ctcttccccc caaaacccaa ggacaccctc atgatctccc ggacccctga ggtcacatgc      1020
gtggtggtgg acgtgagcca cgaagaccct gaggtcaagt tcaactggta cgtggacggc      1080
gtggaggtgc ataatgccaa gacaaagccg cgggaggagc agtacaacag cacgtaccgt      1140
gtggtcagcg tcctcaccgt cctgcaccag gactggctga atggcaagga gtacaagtgc      1200
aaggtctcca acaaagccct cccagccccc atcgagaaaa ccatctccaa agccaaaggg      1260
cagccccgag aaccacaggt gtacaccctg cccccatccc gggaggagat gaccaagaac      1320

-continued

```
caggtcagcc tgacctgcct ggtcaaaggc ttctatccca gcgacatcgc cgtggagtgg    1380
gagagcaatg ggcagccgga gaacaactac aagaccacgc ctcccgtgct ggactccgac    1440
ggctccttct tcctctacag caagctcacc gtggacaaga gcaggtggca gcaggggaac    1500
gtcttctcat gctccgtgat gcatgagggt ctgcacaacc actacacgca gaagagcctc    1560
tccctgtctc cgggtaaa                                                 1578
```

<210> SEQ ID NO 60
<211> LENGTH: 526
<212> TYPE: PRT
<213> ORGANISM: Artificial Sequence
<220> FEATURE:
<223> OTHER INFORMATION: synthetic peptide: 306 MM / MMP-9 CM /anti-VEGF scfv-Fc TBM

<400> SEQUENCE: 60

```
Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
                20                  25                  30

Val His Met Pro Leu Gly Phe Leu Gly Pro Gly Gly Ser Asp Ile Gln
            35                  40                  45

Leu Thr Gln Ser Pro Ser Ser Leu Ser Ala Ser Val Gly Asp Arg Val
        50                  55                  60

Thr Ile Thr Cys Ser Ala Ser Gln Asp Ile Ser Asn Tyr Leu Asn Trp
65                  70                  75                  80

Tyr Gln Gln Lys Pro Gly Lys Ala Pro Lys Val Leu Ile Tyr Phe Thr
                85                  90                  95

Ser Ser Leu His Ser Gly Val Pro Ser Arg Phe Ser Gly Ser Gly Ser
            100                 105                 110

Gly Thr Asp Phe Thr Leu Thr Ile Ser Ser Leu Gln Pro Glu Asp Phe
        115                 120                 125

Ala Thr Tyr Tyr Cys Gln Gln Tyr Ser Thr Val Pro Trp Thr Phe Gly
    130                 135                 140

Gln Gly Thr Lys Val Glu Ile Lys Gly Gly Gly Gly Ser Gly Gly Gly
145                 150                 155                 160

Gly Ser Gly Gly Gly Gly Ser Gly Glu Val Gln Leu Val Glu Ser Gly
                165                 170                 175

Gly Gly Leu Val Gln Pro Gly Gly Ser Leu Arg Leu Ser Cys Ala Ala
            180                 185                 190

Ser Gly Tyr Asp Phe Thr His Tyr Gly Met Asn Trp Val Arg Gln Ala
        195                 200                 205

Pro Gly Lys Gly Leu Glu Trp Val Gly Trp Ile Asn Thr Tyr Thr Gly
    210                 215                 220

Glu Pro Thr Tyr Ala Ala Asp Phe Lys Arg Arg Phe Thr Phe Ser Leu
225                 230                 235                 240

Asp Thr Ser Lys Ser Thr Ala Tyr Leu Gln Met Asn Ser Leu Arg Ala
                245                 250                 255

Glu Asp Thr Ala Val Tyr Tyr Cys Ala Lys Tyr Pro Tyr Tyr Tyr Gly
            260                 265                 270

Thr Ser His Trp Tyr Phe Asp Val Trp Gly Gln Gly Thr Leu Val Thr
        275                 280                 285

Val Ser Gly Gly Ser Gly Ala Met Val Arg Ser Asp Lys Thr His Thr
    290                 295                 300

Cys Pro Pro Cys Pro Ala Pro Glu Leu Leu Gly Gly Pro Ser Val Phe
```

```
                        305                 310                 315                 320
Leu Phe Pro Pro Lys Pro Lys Asp Thr Leu Met Ile Ser Arg Thr Pro
                    325                 330                 335

Glu Val Thr Cys Val Val Asp Val Ser His Glu Asp Pro Glu Val
                340                 345                 350

Lys Phe Asn Trp Tyr Val Asp Gly Val Glu Val His Asn Ala Lys Thr
                355                 360                 365

Lys Pro Arg Glu Glu Gln Tyr Asn Ser Thr Tyr Arg Val Val Ser Val
            370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ala Pro Ile Glu Lys Thr Ile Ser
                405                 410                 415

Lys Ala Lys Gly Gln Pro Arg Glu Pro Gln Val Tyr Thr Leu Pro Pro
                420                 425                 430

Ser Arg Glu Glu Met Thr Lys Asn Gln Val Ser Leu Thr Cys Leu Val
                435                 440                 445

Lys Gly Phe Tyr Pro Ser Asp Ile Ala Val Glu Trp Glu Ser Asn Gly
                450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495

Gln Gln Gly Asn Val Phe Ser Cys Ser Val Met His Glu Gly Leu His
                500                 505                 510

Asn His Tyr Thr Gln Lys Ser Leu Ser Leu Ser Pro Gly Lys
                515                 520                 525

<210> SEQ ID NO 61
<211> LENGTH: 1581
<212> TYPE: DNA
<213> ORGANISM: Artificial Sequence
<220> FEATURE:
<223> OTHER INFORMATION: synthetic oligonucleotide: 314 MM / MMP-9 CM /
      anti-VEGF scfv-Fc TBM

<400> SEQUENCE: 61
ggccagtctg gccagcggcc gccgtgttgc cgtgattata gtattttgga gtgctgtaag      60
agtgatggcg gttctggtgg cagcggccaa ggtggccaag tgcacatgcc actgggcttc     120
ctgggtccgg gcggttctga tattcaactg acccagagcc cttcttccct gagtgccagc     180
gtgggtgacc gtgttacgat cacttgctcg gccagccaag atatttctaa ctacctgaat     240
tggtaccagc agaagccagg aaaggcacca aaagtcctga tctacttcac aagttcactg     300
cattccggcg taccgtcgcg ctttagcggt tctggcagtg gtaccgactt caccctgact     360
atctcgagtc tgcaacctga ggattttgct acatattact gtcagcaata ttcgaccgtg     420
ccgtggacgt tcgggcaggg caccaaagtg gagattaagg ggggtggagg cagcggggga     480
ggtggctcag gcggtggagg gtctggcgag gtccagctgg tagaaagcgg gggcggactg     540
gtccaaccgg gcggatccct gcgtctgagc tgcgcggcct cgggttacga ctttactcac     600
tacggaatga actgggttcg ccaagcccct ggtaaaggtc tggaatgggt cggatggatt     660
aatacataca ctggagaacc tactatgct gctgatttca acgtcgctt tactttctct      720 ctggatacaa gtaagtcaac cgcctatctg caaatgaaca gcctgcgtgc agaggacacg     780
gctgtgtact attgtgcgaa atatccttat tattatggaa cttcccactg gtatttcgat     840
```

```
gtatggggcc agggtactct ggttacagtg tcgggcggta gcggcgccat ggttagatct    900
gacaaaactc acacatgccc accgtgccca gcacctgaac tcctgggggg accgtcagtc    960
ttcctcttcc ccccaaaacc caaggacacc ctcatgatct cccggacccc tgaggtcaca   1020
tgcgtggtgg tggacgtgag ccacgaagac cctgaggtca agttcaactg gtacgtggac   1080
ggcgtggagg tgcataatgc aagacaaag ccgcgggagg agcagtacaa cagcacgtac    1140
cgtgtggtca gcgtcctcac cgtcctgcac caggactggc tgaatggcaa ggagtacaag   1200
tgcaaggtct ccaacaaagc cctcccagcc cccatcgaga aaaccatctc caaagccaaa   1260
gggcagcccc gagaaccaca ggtgtacacc ctgcccccat cccgggagga tgaccaag     1320
aaccaggtca gcctgacctg cctggtcaaa ggcttctatc ccagcgacat cgccgtggag   1380
tgggagagca atgggcagcc ggagaacaac tacaagacca cgcctcccgt gctggactcc   1440
gacggctcct tcttcctcta cagcaagctc accgtggaca agagcaggtg gcagcagggg   1500
aacgtcttct catgctccgt gatgcatgag ggtctgcaca accactacac gcagaagagc   1560
ctctccctgt ctccgggtaa a                                             1581
```

<210> SEQ ID NO 62
<211> LENGTH: 527
<212> TYPE: PRT
<213> ORGANISM: Artificial Sequence
<220> FEATURE:
<223> OTHER INFORMATION: synthetic peptide: 314 MM / MMP-9 CM / anti-VEGF scfv-Fc TBM

<400> SEQUENCE: 62

```
Gly Gln Ser Gly Gln Arg Pro Pro Cys Cys Arg Asp Tyr Ser Ile Leu
1               5                   10                  15
Glu Cys Cys Lys Ser Asp Gly Gly Ser Gly Gly Ser Gly Gln Gly Gly
            20                  25                  30
Gln Val His Met Pro Leu Gly Phe Leu Gly Pro Gly Gly Ser Asp Ile
        35                  40                  45
Gln Leu Thr Gln Ser Pro Ser Ser Leu Ser Ala Ser Val Gly Asp Arg
    50                  55                  60
Val Thr Ile Thr Cys Ser Ala Ser Gln Asp Ile Ser Asn Tyr Leu Asn
65                  70                  75                  80
Trp Tyr Gln Gln Lys Pro Gly Lys Ala Pro Lys Val Leu Ile Tyr Phe
                85                  90                  95
Thr Ser Ser Leu His Ser Gly Val Pro Ser Arg Phe Ser Gly Ser Gly
            100                 105                 110
Ser Gly Thr Asp Phe Thr Leu Thr Ile Ser Ser Leu Gln Pro Glu Asp
        115                 120                 125
Phe Ala Thr Tyr Tyr Cys Gln Gln Tyr Ser Thr Val Pro Trp Thr Phe
    130                 135                 140
Gly Gln Gly Thr Lys Val Glu Ile Lys Gly Gly Gly Ser Gly Gly
145                 150                 155                 160
Gly Gly Ser Gly Gly Gly Ser Gly Glu Val Gln Leu Val Glu Ser
            165                 170                 175
Gly Gly Gly Leu Val Gln Pro Gly Gly Ser Leu Arg Leu Ser Cys Ala
        180                 185                 190
Ala Ser Gly Tyr Asp Phe Thr His Tyr Gly Met Asn Trp Val Arg Gln
    195                 200                 205
Ala Pro Gly Lys Gly Leu Glu Trp Val Gly Trp Ile Asn Thr Tyr Thr
210                 215                 220
```

-continued

```
Gly Glu Pro Thr Tyr Ala Ala Asp Phe Lys Arg Arg Phe Thr Phe Ser
225                 230                 235                 240

Leu Asp Thr Ser Lys Ser Thr Ala Tyr Leu Gln Met Asn Ser Leu Arg
            245                 250                 255

Ala Glu Asp Thr Ala Val Tyr Tyr Cys Ala Lys Tyr Pro Tyr Tyr Tyr
        260                 265                 270

Gly Thr Ser His Trp Tyr Phe Asp Val Trp Gly Gln Gly Thr Leu Val
    275                 280                 285

Thr Val Ser Gly Gly Ser Gly Ala Met Val Arg Ser Asp Lys Thr His
290                 295                 300

Thr Cys Pro Pro Cys Pro Ala Pro Glu Leu Leu Gly Gly Pro Ser Val
305                 310                 315                 320

Phe Leu Phe Pro Pro Lys Pro Lys Asp Thr Leu Met Ile Ser Arg Thr
            325                 330                 335

Pro Glu Val Thr Cys Val Val Val Asp Val Ser His Glu Asp Pro Glu
        340                 345                 350

Val Lys Phe Asn Trp Tyr Val Asp Gly Val Glu Val His Asn Ala Lys
    355                 360                 365

Thr Lys Pro Arg Glu Glu Gln Tyr Asn Ser Thr Tyr Arg Val Val Ser
370                 375                 380

Val Leu Thr Val Leu His Gln Asp Trp Leu Asn Gly Lys Glu Tyr Lys
385                 390                 395                 400

Cys Lys Val Ser Asn Lys Ala Leu Pro Ala Pro Ile Glu Lys Thr Ile
            405                 410                 415

Ser Lys Ala Lys Gly Gln Pro Arg Glu Pro Gln Val Tyr Thr Leu Pro
        420                 425                 430

Pro Ser Arg Glu Glu Met Thr Lys Asn Gln Val Ser Leu Thr Cys Leu
    435                 440                 445

Val Lys Gly Phe Tyr Pro Ser Asp Ile Ala Val Glu Trp Glu Ser Asn
450                 455                 460

Gly Gln Pro Glu Asn Asn Tyr Lys Thr Thr Pro Pro Val Leu Asp Ser
465                 470                 475                 480

Asp Gly Ser Phe Phe Leu Tyr Ser Lys Leu Thr Val Asp Lys Ser Arg
            485                 490                 495

Trp Gln Gln Gly Asn Val Phe Ser Cys Ser Val Met His Glu Gly Leu
        500                 505                 510

His Asn His Tyr Thr Gln Lys Ser Leu Ser Leu Ser Pro Gly Lys
    515                 520                 525
```

<210> SEQ ID NO 63
<211> LENGTH: 19
<212> TYPE: PRT
<213> ORGANISM: Artificial Sequence
<220> FEATURE:
<223> OTHER INFORMATION: synthetic peptide

<400> SEQUENCE: 63

```
Met Ile Leu Leu Cys Ala Ala Gly Arg Thr Trp Val Glu Ala Cys Ala
1               5                   10                  15

Asn Gly Arg
```

<210> SEQ ID NO 64
<211> LENGTH: 57
<212> TYPE: DNA
<213> ORGANISM: Artificial Sequence
<220> FEATURE:

<223> OTHER INFORMATION: oligonucleotide

<400> SEQUENCE: 64
atgattttgt tgtgcgcggc gggtcggacg tgggtggagg cttgcgctaa tggtagg    57

<210> SEQ ID NO 65
<211> LENGTH: 14
<212> TYPE: PRT
<213> ORGANISM: Artificial Sequence
<220> FEATURE:
<223> OTHER INFORMATION: synthetic peptide

<400> SEQUENCE: 65

Ala Glu Arg Leu Cys Ala Trp Ala Gly Arg Phe Cys Gly Ser
1               5                   10

<210> SEQ ID NO 66
<211> LENGTH: 42
<212> TYPE: DNA
<213> ORGANISM: Artificial Sequence
<220> FEATURE:
<223> OTHER INFORMATION: oligonucleotide

<400> SEQUENCE: 66
gctgagcggt tgtgcgcgtg ggcggggcgg ttctgtggca gc    42

<210> SEQ ID NO 67
<211> LENGTH: 15
<212> TYPE: PRT
<213> ORGANISM: Artificial Sequence
<220> FEATURE:
<223> OTHER INFORMATION: synthetic peptide

<400> SEQUENCE: 67

Trp Ala Asp Val Met Pro Gly Ser Gly Val Leu Pro Trp Thr Ser
1               5                   10                  15

<210> SEQ ID NO 68
<211> LENGTH: 45
<212> TYPE: DNA
<213> ORGANISM: Artificial Sequence
<220> FEATURE:
<223> OTHER INFORMATION: oligonucleotide

<400> SEQUENCE: 68
tgggcggatg ttatgcctgg gtcgggtgtg ttgccgtgga cgtcg    45

<210> SEQ ID NO 69
<211> LENGTH: 20
<212> TYPE: PRT
<213> ORGANISM: Artificial Sequence
<220> FEATURE:
<223> OTHER INFORMATION: synthetic peptide

<400> SEQUENCE: 69

Ser Asp Gly Arg Met Gly Ser Leu Glu Leu Cys Ala Leu Trp Gly Arg
1               5                   10                  15

Phe Cys Gly Ser
            20

<210> SEQ ID NO 70
<211> LENGTH: 60
<212> TYPE: DNA
<213> ORGANISM: Artificial Sequence
<220> FEATURE:
<223> OTHER INFORMATION: oligonucleotide

<400> SEQUENCE: 70
agtgatggtc gtatggggag tttggagctt tgtgcgttgt gggggcggtt ctgtggcagc    60

<210> SEQ ID NO 71
<211> LENGTH: 15
<212> TYPE: PRT
<213> ORGANISM: Artificial Sequence
<220> FEATURE:
<223> OTHER INFORMATION: synthetic peptide

<400> SEQUENCE: 71

Pro Cys Ser Glu Trp Gln Ser Met Val Gln Pro Arg Cys Tyr Tyr
1               5                   10                  15

<210> SEQ ID NO 72
<211> LENGTH: 45
<212> TYPE: DNA
<213> ORGANISM: Artificial Sequence
<220> FEATURE:
<223> OTHER INFORMATION: oligonucleotide

<400> SEQUENCE: 72
gccgtgttct gagtggcagt cgatggtgca gccgcgttgc tatta                   45

<210> SEQ ID NO 73
<211> LENGTH: 55
<212> TYPE: DNA
<213> ORGANISM: Artificial Sequence
<220> FEATURE:
<223> OTHER INFORMATION: oligonucleotide

<400> SEQUENCE: 73
cgtcgatgag ctctagaatt cgcatgtgca agtccgatgg tccccccccc ccccc         55

<210> SEQ ID NO 74
<211> LENGTH: 47
<212> TYPE: DNA
<213> ORGANISM: Artificial Sequence
<220> FEATURE:
<223> OTHER INFORMATION: oligonucleotide
<220> FEATURE:
<221> NAME/KEY: variation
<222> LOCATION: (27)..(33)
<223> OTHER INFORMATION: y = t or c
<220> FEATURE:
<221> NAME/KEY: variation
<222> LOCATION: (36)..(36)
<223> OTHER INFORMATION: n = g or a or t or c
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: variation
<222> LOCATION: (39)..(45)
<223> OTHER INFORMATION: r = a or g
<220> FEATURE:
<221> NAME/KEY: variation
<222> LOCATION: (42)..(42)
<223> OTHER INFORMATION: d = g or a or t

<400> SEQUENCE: 74
cgtcatgtcg acggatccaa gcttacyttc cayttnacrt tdatrtc                  47

<210> SEQ ID NO 75
<211> LENGTH: 48
<212> TYPE: DNA
<213> ORGANISM: Artificial Sequence

```
<220> FEATURE:
<223> OTHER INFORMATION: oligonucleotide
<220> FEATURE:
<221> NAME/KEY: variation
<222> LOCATION: (25)..(25)
<223> OTHER INFORMATION: r = a or g
<220> FEATURE:
<221> NAME/KEY: variation
<222> LOCATION: (28)..(28)
<223> OTHER INFORMATION: n = g or a or t or c
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: variation
<222> LOCATION: (31)..(31)
<223> OTHER INFORMATION: n = g or a or t or c
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: variation
<222> LOCATION: (34)..(34)
<223> OTHER INFORMATION: n = g or a or t or c
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: variation
<222> LOCATION: (37)..(37)
<223> OTHER INFORMATION: n = g or a or t or c
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: variation
<222> LOCATION: (39)..(39)
<223> OTHER INFORMATION: r = a or g
<220> FEATURE:
<221> NAME/KEY: variation
<222> LOCATION: (40)..(40)
<223> OTHER INFORMATION: n = g or a or t or c
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: variation
<222> LOCATION: (43)..(43)
<223> OTHER INFORMATION: r = a or g
<220> FEATURE:
<221> NAME/KEY: variation
<222> LOCATION: (46)..(46)
<223> OTHER INFORMATION: n = g or a or t or c
<220> FEATURE:
<221> NAME/KEY: misc_feature
<222> LOCATION: (46)..(46)
<223> OTHER INFORMATION: n is a, c, g, or t

<400> SEQUENCE: 75
cgtcatgtcg acggatccaa gcttrcangc nggngcnarn ggrtanac        48

<210> SEQ ID NO 76
<211> LENGTH: 131
<212> TYPE: PRT
<213> ORGANISM: Hamster

<400> SEQUENCE: 76

Met Glu Ser His Ile His Val Phe Met Ser Leu Phe Leu Trp Val Ser
1               5                   10                  15

Gly Ser Cys Ala Asp Ile Met Met Thr Gln Ser Pro Ser Ser Leu Ser
```

```
            20                  25                  30
Val Ser Ala Gly Glu Lys Ala Thr Ile Ser Cys Lys Ser Gln Ser
        35                  40                  45

Leu Phe Asn Ser Asn Ala Lys Thr Asn Tyr Leu Asn Trp Tyr Leu Gln
    50                  55                  60

Lys Pro Gly Gln Ser Pro Lys Leu Leu Ile Tyr Tyr Ala Ser Thr Arg
65                  70                  75                  80

His Thr Gly Val Pro Asp Arg Phe Arg Gly Ser Gly Thr Asp Phe Thr
                85                  90                  95

Leu Thr Ile Ser Ser Val Gln Asp Glu Asp Leu Ala Phe Tyr Tyr Cys
            100                 105                 110

Gln Gln Trp Tyr Asp Tyr Pro Tyr Thr Phe Gly Ala Gly Thr Lys Val
        115                 120                 125

Glu Ile Lys
        130
```

<210> SEQ ID NO 77
<211> LENGTH: 399
<212> TYPE: DNA
<213> ORGANISM: Hamster

<400> SEQUENCE: 77

```
atggaatcac atatccatgt cttcatgtcc ttgttccttt gggtgtctgg ttcctgtgca    60
gacatcatga tgacccagtc tccttcatcc ctgagtgtgt cagcgggaga gaaagccact   120
atcagctgca agtccagtca gagtctttc aacagtaacg ccaaaacgaa ctacttgaac    180
tggtatttgc agaaaccagg gcagtctcct aaactgctga tctattatgc atccactagg   240
catactgggg tccctgatcg cttcagaggc agtggatctg ggacggattt cactctcacc   300
atcagcagtg tccaggatga agacctggca ttttattact gtcagcagtg gtatgactac   360
ccatacacgt tcggagctgg gaccaaggtg gaaatcaaa                          399
```

<210> SEQ ID NO 78
<211> LENGTH: 135
<212> TYPE: PRT
<213> ORGANISM: Hamster

<400> SEQUENCE: 78

```
Lys Met Arg Leu Leu Gly Leu Leu Tyr Leu Val Thr Ala Leu Pro Gly
1               5                   10                  15

Val Leu Ser Gln Ile Gln Leu Gln Glu Ser Gly Pro Gly Leu Val Asn
            20                  25                  30

Pro Ser Gln Ser Leu Ser Leu Ser Cys Ser Val Thr Gly Tyr Ser Ile
        35                  40                  45

Thr Ser Gly Tyr Gly Trp Asn Trp Ile Arg Gln Phe Pro Gly Gln Lys
    50                  55                  60

Val Glu Trp Met Gly Phe Ile Tyr Tyr Glu Gly Ser Thr Tyr Tyr Asn
65                  70                  75                  80

Pro Ser Ile Lys Ser Arg Ile Ser Ile Thr Arg Asp Thr Ser Lys Asn
                85                  90                  95

Gln Phe Phe Leu Gln Val Asn Ser Val Thr Thr Glu Asp Thr Ala Thr
            100                 105                 110

Tyr Tyr Cys Ala Arg Gln Thr Gly Tyr Phe Asp Tyr Trp Gly Gln Gly
        115                 120                 125

Thr Met Val Thr Val Ser Ser
        130                 135
```

<210> SEQ ID NO 79
<211> LENGTH: 405
<212> TYPE: DNA
<213> ORGANISM: Hamster

<400> SEQUENCE: 79

```
aagatgagac tgttgggtct tctgtacctg gtgacagccc ttcctggtgt cctgtcccag      60
atccagcttc aggagtcagg acctggcctg gtgaacccct cacaatcact gtccctctct     120
tgctctgtca ctggttactc catcaccagt ggttatggat ggaactggat caggcagttc     180
ccagggcaga aggtggagtg gatgggattc atatattatg agggtagcac ctactacaac     240
ccttccatca agagccgcat ctccatcacc agagacacat cgaagaacca gttcttcctg     300
caggtgaatt ctgtgaccac tgaggacaca gccacatatt actgtgcgag acaaactggg     360
tactttgatt actggggcca aggaaccatg gtcaccgtct cctca                     405
```

<210> SEQ ID NO 80
<211> LENGTH: 39
<212> TYPE: DNA
<213> ORGANISM: Artificial Sequence
<220> FEATURE:
<223> OTHER INFORMATION: oligonucleotide

<400> SEQUENCE: 80

```
caaggaccat agcatatgga catcatgatg acccagtct                             39
```

<210> SEQ ID NO 81
<211> LENGTH: 50
<212> TYPE: DNA
<213> ORGANISM: Artificial Sequence
<220> FEATURE:
<223> OTHER INFORMATION: oligonucleotide

<400> SEQUENCE: 81

```
acttccgcct ccacctgatc caccaccacc tttgatttcc accttggtcc                 50
```

<210> SEQ ID NO 82
<211> LENGTH: 60
<212> TYPE: DNA
<213> ORGANISM: Artificial Sequence
<220> FEATURE:
<223> OTHER INFORMATION: oligonucleotide

<400> SEQUENCE: 82

```
ggatcaggtg gaggcggaag tggaggtggc ggttcccaga tccagcttca ggagtcagga      60
```

<210> SEQ ID NO 83
<211> LENGTH: 61
<212> TYPE: DNA
<213> ORGANISM: Artificial Sequence
<220> FEATURE:
<223> OTHER INFORMATION: oligonucleotide

<400> SEQUENCE: 83

```
ggccggatcc aagcttttag tggtgatggt gatgatgtga ggagacggtg accatggttc      60
c                                                                      61
```

<210> SEQ ID NO 84
<211> LENGTH: 40
<212> TYPE: DNA
<213> ORGANISM: Artificial Sequence
<220> FEATURE:

```
<223> OTHER INFORMATION: oligonucleotide

<400> SEQUENCE: 84
acaaggacca tagcatatgc agatccagct tcaggagtca                              40

<210> SEQ ID NO 85
<211> LENGTH: 54
<212> TYPE: DNA
<213> ORGANISM: Artificial Sequence
<220> FEATURE:
<223> OTHER INFORMATION: oligonucleotide

<400> SEQUENCE: 85
acttccgcct ccacctgatc caccaccacc tgaggagacg gtgaccatgg ttcc              54

<210> SEQ ID NO 86
<211> LENGTH: 63
<212> TYPE: DNA
<213> ORGANISM: Artificial Sequence
<220> FEATURE:
<223> OTHER INFORMATION: oligonucleotide

<400> SEQUENCE: 86
ggtggatcag gtggaggcgg aagtggaggt ggcggttccg acatcatgat gacccagtct        60
cct                                                                      63

<210> SEQ ID NO 87
<211> LENGTH: 62
<212> TYPE: DNA
<213> ORGANISM: Artificial Sequence
<220> FEATURE:
<223> OTHER INFORMATION: oligonucleotide

<400> SEQUENCE: 87
cggccggatc caagctttta gtggtgatgg tgatgatgtt tgatttccac cttggtccca        60
gc                                                                       62

<210> SEQ ID NO 88
<211> LENGTH: 60
<212> TYPE: DNA
<213> ORGANISM: Artificial Sequence
<220> FEATURE:
<223> OTHER INFORMATION: oligonucleotide

<400> SEQUENCE: 88
gccagtctgg ccggtagggc tcgagcggcc aagtgcacat gccactgggc ttcctgggtc        60

<210> SEQ ID NO 89
<211> LENGTH: 60
<212> TYPE: DNA
<213> ORGANISM: Artificial Sequence
<220> FEATURE:
<223> OTHER INFORMATION: oligonucleotide

<400> SEQUENCE: 89
gccactgggc ttcctgggtc cgggtggaag cggcggctca gacatcatga tgacccagtc        60

<210> SEQ ID NO 90
<211> LENGTH: 61
<212> TYPE: DNA
<213> ORGANISM: Artificial Sequence
<220> FEATURE:
<223> OTHER INFORMATION: oligonucleotide

<400> SEQUENCE: 90
```

```
gccactgggc ttcctgggtc cgggtggaag cggcggctca cagatccagc ttcaggagtc    60
a                                                                    61
```

<210> SEQ ID NO 91
<211> LENGTH: 47
<212> TYPE: DNA
<213> ORGANISM: Artificial Sequence
<220> FEATURE:
<223> OTHER INFORMATION: oligonucleotide

<400> SEQUENCE: 91

```
ttcaccaaca aggaccatag catatgggcc agtctggccg gtagggc                  47
```

<210> SEQ ID NO 92
<211> LENGTH: 61
<212> TYPE: DNA
<213> ORGANISM: Artificial Sequence
<220> FEATURE:
<223> OTHER INFORMATION: oligonucleotide

<400> SEQUENCE: 92

```
ggccggatcc aagctttag tggtgatggt gatgatgtga ggagacggtg accatggttc     60
c                                                                    61
```

<210> SEQ ID NO 93
<211> LENGTH: 54
<212> TYPE: DNA
<213> ORGANISM: Artificial Sequence
<220> FEATURE:
<223> OTHER INFORMATION: oligonucleotide

<400> SEQUENCE: 93

```
acttccgcct ccacctgatc caccaccacc tgaggagacg gtgaccatgg ttcc          54
```

<210> SEQ ID NO 94
<211> LENGTH: 28
<212> TYPE: PRT
<213> ORGANISM: Artificial Sequence
<220> FEATURE:
<223> OTHER INFORMATION: synthetic peptide:  MM linker-CM-anti-CTLA4
     scFv linker

<400> SEQUENCE: 94

Gly Gly Ser Gly Gly Ser Gly Gly Ser Ser Gly Gln Val His Met Pro
1               5                   10                  15

Leu Gly Phe Leu Gly Pro Gly Gly Ser Gly Gly Ser
            20                  25

<210> SEQ ID NO 95
<211> LENGTH: 84
<212> TYPE: DNA
<213> ORGANISM: Artificial Sequence
<220> FEATURE:
<223> OTHER INFORMATION: synthetic oligonucleotide:  MM linker-CM-anti-
     CTLA4 scFv linker

<400> SEQUENCE: 95

```
ggcggttctg gtggcagcgg tggctcgagc ggccaagtgc acatgccact gggcttcctg    60
ggtccgggtg gaagcggcgg ctca                                           84
```

<210> SEQ ID NO 96
<211> LENGTH: 291
<212> TYPE: PRT

<213> ORGANISM: Artificial Sequence
<220> FEATURE:
<223> OTHER INFORMATION: synthetic peptide: MM187-anti-CTLA4 ScFv TBM

<400> SEQUENCE: 96

```
Met Ile Leu Leu Cys Ala Ala Gly Arg Thr Trp Val Glu Ala Cys Ala
1               5                   10                  15

Asn Gly Arg Gly Gly Ser Gly Gly Ser Gly Gly Ser Ser Gly Gln Val
            20                  25                  30

His Met Pro Leu Gly Phe Leu Gly Pro Gly Gly Ser Gly Gly Ser Gln
        35                  40                  45

Ile Gln Leu Gln Glu Ser Gly Pro Gly Leu Val Asn Pro Ser Gln Ser
50                  55                  60

Leu Ser Leu Ser Cys Ser Val Thr Gly Tyr Ser Ile Thr Ser Gly Tyr
65                  70                  75                  80

Gly Trp Asn Trp Ile Arg Gln Phe Pro Gly Gln Lys Val Glu Trp Met
                85                  90                  95

Gly Phe Ile Tyr Tyr Glu Gly Ser Thr Tyr Tyr Asn Pro Ser Ile Lys
            100                 105                 110

Ser Arg Ile Ser Ile Thr Arg Asp Thr Ser Lys Asn Gln Phe Phe Leu
        115                 120                 125

Gln Val Asn Ser Val Thr Thr Glu Asp Thr Ala Thr Tyr Tyr Cys Ala
130                 135                 140

Arg Gln Thr Gly Tyr Phe Asp Tyr Trp Gly Gln Gly Thr Met Val Thr
145                 150                 155                 160

Val Ser Ser Gly Gly Gly Gly Ser Gly Gly Gly Gly Ser Gly Gly Gly
                165                 170                 175

Gly Ser Asp Ile Met Met Thr Gln Ser Pro Ser Ser Leu Ser Val Ser
            180                 185                 190

Ala Gly Glu Lys Ala Thr Ile Ser Cys Lys Ser Ser Gln Ser Leu Phe
        195                 200                 205

Asn Ser Asn Ala Lys Thr Asn Tyr Leu Asn Trp Tyr Leu Gln Lys Pro
210                 215                 220

Gly Gln Ser Pro Lys Leu Leu Ile Tyr Tyr Ala Ser Thr Arg His Thr
225                 230                 235                 240

Gly Val Pro Asp Arg Phe Arg Gly Ser Gly Ser Gly Thr Asp Phe Thr
                245                 250                 255

Leu Thr Ile Ser Ser Val Gln Asp Glu Asp Leu Ala Phe Tyr Tyr Cys
            260                 265                 270

Gln Gln Trp Tyr Asp Tyr Pro Tyr Thr Phe Gly Ala Gly Thr Lys Val
        275                 280                 285

Glu Ile Lys
    290
```

<210> SEQ ID NO 97
<211> LENGTH: 894
<212> TYPE: DNA
<213> ORGANISM: Artificial Sequence
<220> FEATURE:
<223> OTHER INFORMATION: synthetic oligonucleotide: MM187-anti-CTLA4
      ScFv TBM

<400> SEQUENCE: 97

```
atgattttgt tgtgcgcggc gggtcggacg tgggtggagg cttgcgctaa tggtaggggc      60
ggttctggtg gcagcggtgg ctcgagcggc caagtgcaca tgccactggg cttcctgggt     120
ccgggtggaa gcggcggctc acagatccag cttcaggagt caggacctgg cctggtgaac     180
```

-continued

```
ccctcacaat cactgtccct ctcttgctct gtcactggtt actccatcac cagtggttat    240
ggatggaact ggatcaggca gttcccaggg cagaaggtgg agtggatggg attcatatat    300
tatgagggta gcacctacta caaccettcc atcaagagcc gcatctccat caccagagac    360
acatcgaaga accagttctt cctgcaggtg aattctgtga ccactgagga cacagccaca    420
tattactgtg cgagacaaac tgggtacttt gattactggg ccaaggaac catggtcacc     480 gtctcctcag gtggtggtgg atcaggtgga ggcggaagtg gaggtggcgg ttccgacatc    540
atgatgaccc agtctccttc atccctgagt gtgtcagcgg gagagaaagc cactatcagc    600
tgcaagtcca gtcagagtct tttcaacagt aacgccaaaa cgaactactt gaactggtat    660
ttgcagaaac cagggcagtc tcctaaactg ctgatctatt atgcatccac taggcatact    720
ggggtccctg atcgcttcag aggcagtgga tctgggacgg atttcactct caccatcagc    780
agtgtccagg atgaagacct ggcattttat tactgtcagc agtggtatga ctacccatac    840
acgttcggag ctgggaccaa ggtggaaatc aaacatcatc accatcacca ctaa           894
```

<210> SEQ ID NO 98
<211> LENGTH: 37
<212> TYPE: DNA
<213> ORGANISM: Artificial Sequence
<220> FEATURE:
<223> OTHER INFORMATION: oligonucleotide

<400> SEQUENCE: 98
tcagatctaa ccatggcttt gatttccacc ttggtcc                              37

<210> SEQ ID NO 99
<211> LENGTH: 37
<212> TYPE: DNA
<213> ORGANISM: Artificial Sequence
<220> FEATURE:
<223> OTHER INFORMATION: oligonucleotide

<400> SEQUENCE: 99
tcagatctaa ccatggctga ggagacggtg accatgg                              37

<210> SEQ ID NO 100
<211> LENGTH: 37
<212> TYPE: DNA
<213> ORGANISM: Artificial Sequence
<220> FEATURE:
<223> OTHER INFORMATION: oligonucleotide

<400> SEQUENCE: 100
cacttgtcac gaattcgatg attttgttgt gcgcggc                              37

<210> SEQ ID NO 101
<211> LENGTH: 36
<212> TYPE: DNA
<213> ORGANISM: Artificial Sequence
<220> FEATURE:
<223> OTHER INFORMATION: oligonucleotide

<400> SEQUENCE: 101
cacttgtcac gaattcgtgg gcggatgtta tgcctg                               36

<210> SEQ ID NO 102
<211> LENGTH: 37
<212> TYPE: DNA
<213> ORGANISM: Artificial Sequence
<220> FEATURE:

```
<223> OTHER INFORMATION: oligonucleotide

<400> SEQUENCE: 102
cacttgtcac gaattcggct gagcggttgt gcgcgtg                              37

<210> SEQ ID NO 103
<211> LENGTH: 37
<212> TYPE: DNA
<213> ORGANISM: Artificial Sequence
<220> FEATURE:
<223> OTHER INFORMATION: oligonucleotide

<400> SEQUENCE: 103
cacttgtcac gaattcgagt gatggtcgta tggggag                              37

<210> SEQ ID NO 104
<211> LENGTH: 38
<212> TYPE: DNA
<213> ORGANISM: Artificial Sequence
<220> FEATURE:
<223> OTHER INFORMATION: oligonucleotide

<400> SEQUENCE: 104
cacttgtcac gaattcgccg tgttctgagt ggcagtcg                             38

<210> SEQ ID NO 105
<211> LENGTH: 20
<212> TYPE: DNA
<213> ORGANISM: Artificial Sequence
<220> FEATURE:
<223> OTHER INFORMATION: oligonucleotide
<220> FEATURE:
<221> NAME/KEY: variation
<222> LOCATION: (3)..(15)
<223> OTHER INFORMATION: y = t or c
<220> FEATURE:
<221> NAME/KEY: variation
<222> LOCATION: (6)..(18)
<223> OTHER INFORMATION: r = a or g
<220> FEATURE:
<221> NAME/KEY: variation
<222> LOCATION: (9)..(12)
<223> OTHER INFORMATION: n = a or g or c or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 105
gtyttrtgng tnacytcrca                                                20

<210> SEQ ID NO 106
<211> LENGTH: 23
<212> TYPE: DNA
<213> ORGANISM: Artificial Sequence
<220> FEATURE:
<223> OTHER INFORMATION: oligonucleotide
<220> FEATURE:
<221> NAME/KEY: variation
<222> LOCATION: (3)..(3)
<223> OTHER INFORMATION: d = g or a or t
<220> FEATURE:
<221> NAME/KEY: variation
<222> LOCATION: (6)..(6)
<223> OTHER INFORMATION: y = t or c
<220> FEATURE:
<221> NAME/KEY: variation
```

```
<222> LOCATION: (9)..(9)
<223> OTHER INFORMATION: y = t or c
<220> FEATURE:
<221> NAME/KEY: variation
<222> LOCATION: (12)..(12)
<223> OTHER INFORMATION: r = a or g
<220> FEATURE:
<221> NAME/KEY: variation
<222> LOCATION: (15)..(15)
<223> OTHER INFORMATION: n = a or t or g or c
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: variation
<222> LOCATION: (18)..(18)
<223> OTHER INFORMATION: y = t or c
<220> FEATURE:
<221> NAME/KEY: variation
<222> LOCATION: (21)..(21)
<223> OTHER INFORMATION: n = a or t or g or c
<220> FEATURE:
<221> NAME/KEY: misc_feature
<222> LOCATION: (21)..(21)
<223> OTHER INFORMATION: n is a, c, g, or t

<400> SEQUENCE: 106
acdatyttyt trtcnacytt ngt                                           23

<210> SEQ ID NO 107
<211> LENGTH: 42
<212> TYPE: PRT
<213> ORGANISM: Artificial Sequence
<220> FEATURE:
<223> OTHER INFORMATION: synthetic peptide

<400> SEQUENCE: 107

Gly Gln Ser Gly Gln Cys Met Ala Met Leu Gly Pro Leu Gly Leu Ala
1               5                   10                  15

Gly Gly Gly Ser Gly Asn Phe Gly Tyr Gly Lys Trp Glu Trp Asp Tyr
            20                  25                  30

Gly Lys Trp Leu Glu Lys Val Gly Gly Cys
        35                  40

<210> SEQ ID NO 108
<211> LENGTH: 42
<212> TYPE: PRT
<213> ORGANISM: Artificial Sequence
<220> FEATURE:
<223> OTHER INFORMATION: synthetic peptide

<400> SEQUENCE: 108

Gly Gln Ser Gly Gln Lys Gly Gly Cys Gly Pro Leu Gly Leu Ala
1               5                   10                  15

Gly Gly Gly Ser Gly Asn Phe Gly Tyr Gly Lys Trp Glu Trp Asp Tyr
            20                  25                  30

Gly Lys Trp Leu Glu Lys Val Gly Gly Cys
        35                  40

<210> SEQ ID NO 109
<211> LENGTH: 42
<212> TYPE: PRT
<213> ORGANISM: Artificial Sequence
<220> FEATURE:
<223> OTHER INFORMATION: synthetic peptide

<400> SEQUENCE: 109
```

```
Gly Gln Ser Gly Gln Pro Glu Trp Gly Cys Gly Pro Leu Gly Leu Ala
1               5                   10                  15

Gly Gly Gly Ser Gly Asn Phe Gly Tyr Gly Lys Trp Glu Trp Asp Tyr
            20                  25                  30

Gly Lys Trp Leu Glu Lys Val Gly Gly Cys
        35                  40
```

<210> SEQ ID NO 110
<211> LENGTH: 42
<212> TYPE: PRT
<213> ORGANISM: Artificial Sequence
<220> FEATURE:
<223> OTHER INFORMATION: synthetic peptide

<400> SEQUENCE: 110

```
Gly Gln Ser Gly Gln Leu Glu Gly Glu Gly Pro Leu Gly Leu Ala
1               5                   10                  15

Gly Gly Gly Ser Gly Asn Phe Gly Tyr Gly Lys Trp Glu Trp Asp Tyr
            20                  25                  30

Gly Lys Trp Leu Glu Lys Val Gly Gly Cys
        35                  40
```

<210> SEQ ID NO 111
<211> LENGTH: 42
<212> TYPE: PRT
<213> ORGANISM: Artificial Sequence
<220> FEATURE:
<223> OTHER INFORMATION: synthetic peptide

<400> SEQUENCE: 111

```
Gly Gln Ser Gly Gln Asp Asp Met Glu Gly Pro Leu Gly Leu Ala
1               5                   10                  15

Gly Gly Gly Ser Gly Asn Phe Gly Tyr Gly Lys Trp Glu Trp Asp Tyr
            20                  25                  30

Gly Lys Trp Leu Glu Lys Val Gly Gly Cys
        35                  40
```

<210> SEQ ID NO 112
<211> LENGTH: 43
<212> TYPE: PRT
<213> ORGANISM: Artificial Sequence
<220> FEATURE:
<223> OTHER INFORMATION: synthetic peptide

<400> SEQUENCE: 112

```
Gly Gln Ser Gly Gln Cys Thr Gly Val Tyr Leu Arg Pro Leu Gly Leu
1               5                   10                  15

Ala Gly Gly Gly Ser Gly Asn Phe Gly Tyr Gly Lys Trp Glu Trp Asp
            20                  25                  30

Tyr Gly Lys Trp Leu Glu Lys Val Gly Gly Cys
        35                  40
```

<210> SEQ ID NO 113
<211> LENGTH: 42
<212> TYPE: PRT
<213> ORGANISM: Artificial Sequence
<220> FEATURE:
<223> OTHER INFORMATION: synthetic peptide

<400> SEQUENCE: 113

```
Gly Gln Ser Gly Gln Gly Glu Asp Glu Glu Gly Pro Leu Gly Leu Ala
1               5                   10                  15
```

Gly Gly Gly Ser Gly Asn Phe Gly Tyr Gly Lys Trp Glu Trp Asp Tyr
            20                  25                  30

Gly Lys Trp Leu Glu Lys Val Gly Gly Gly
        35                  40

<210> SEQ ID NO 114
<211> LENGTH: 44
<212> TYPE: PRT
<213> ORGANISM: Artificial Sequence
<220> FEATURE:
<223> OTHER INFORMATION: synthetic peptide

<400> SEQUENCE: 114

Gly Gln Ser Gly Gln Cys Ser Val Tyr Gly Trp Gly Pro Leu Gly
1               5                   10                  15

Leu Ala Gly Gly Gly Ser Gly Asn Phe Gly Tyr Gly Lys Trp Glu Trp
            20                  25                  30

Asp Tyr Gly Lys Trp Leu Glu Lys Val Gly Gly Cys
            35                  40

<210> SEQ ID NO 115
<211> LENGTH: 44
<212> TYPE: PRT
<213> ORGANISM: Artificial Sequence
<220> FEATURE:
<223> OTHER INFORMATION: synthetic peptide

<400> SEQUENCE: 115

Gly Gln Ser Gly Gln Cys Cys Pro Lys Val Tyr Gly Gly Pro Leu Gly
1               5                   10                  15

Leu Ala Gly Gly Gly Ser Gly Asn Phe Gly Tyr Gly Lys Trp Glu Trp
            20                  25                  30

Asp Tyr Gly Lys Trp Leu Glu Lys Val Gly Gly Cys
            35                  40

<210> SEQ ID NO 116
<211> LENGTH: 6
<212> TYPE: PRT
<213> ORGANISM: Artificial Sequence
<220> FEATURE:
<223> OTHER INFORMATION: synthetic peptide

<400> SEQUENCE: 116

Cys Met Ala Met Leu Gly
1               5

<210> SEQ ID NO 117
<211> LENGTH: 6
<212> TYPE: PRT
<213> ORGANISM: Artificial Sequence
<220> FEATURE:
<223> OTHER INFORMATION: synthetic peptide

<400> SEQUENCE: 117

Lys Gly Gly Gly Cys Gly
1               5

<210> SEQ ID NO 118
<211> LENGTH: 6
<212> TYPE: PRT
<213> ORGANISM: Artificial Sequence
<220> FEATURE:
<223> OTHER INFORMATION: synthetic peptide

<400> SEQUENCE: 118

```
Leu Glu Gly Glu Glu Gly
1               5

<210> SEQ ID NO 119
<211> LENGTH: 8
<212> TYPE: PRT
<213> ORGANISM: Artificial Sequence
<220> FEATURE:
<223> OTHER INFORMATION: synthetic peptide

<400> SEQUENCE: 119

Cys Thr Gly Val Tyr Leu Arg Gly
1               5

<210> SEQ ID NO 120
<211> LENGTH: 8
<212> TYPE: PRT
<213> ORGANISM: Artificial Sequence
<220> FEATURE:
<223> OTHER INFORMATION: synthetic peptide

<400> SEQUENCE: 120

Cys Ser Val Tyr Gly Trp Gly Gly
1               5

<210> SEQ ID NO 121
<211> LENGTH: 8
<212> TYPE: PRT
<213> ORGANISM: Artificial Sequence
<220> FEATURE:
<223> OTHER INFORMATION: synthetic peptide

<400> SEQUENCE: 121

Cys Cys Pro Lys Val Tyr Gly Gly
1               5

<210> SEQ ID NO 122
<211> LENGTH: 43
<212> TYPE: PRT
<213> ORGANISM: Artificial Sequence
<220> FEATURE:
<223> OTHER INFORMATION: synthetic peptide

<400> SEQUENCE: 122

Gly Gln Ser Gly Gln Gly Cys Gly Ser Gly Pro Gln Gly Leu Leu Gly
1               5                   10                  15

Gly Gly Ser Gly Asn Phe Gly Tyr Gly Lys Trp Glu Trp Asp Tyr Gly
            20                  25                  30

Lys Trp Leu Glu Lys Val Gly Gly Cys Gly Gln
        35                  40

<210> SEQ ID NO 123
<211> LENGTH: 37
<212> TYPE: PRT
<213> ORGANISM: Artificial Sequence
<220> FEATURE:
<223> OTHER INFORMATION: synthetic peptide

<400> SEQUENCE: 123

Pro Glu Trp Gly Cys Gly Pro Leu Gly Leu Ala Gly Gly Gly Ser Gly
1               5                   10                  15

Asn Phe Gly Tyr Gly Lys Trp Glu Trp Asp Tyr Gly Lys Trp Leu Glu
            20                  25                  30

Lys Val Gly Gly Cys
```

<210> SEQ ID NO 124
<211> LENGTH: 39
<212> TYPE: PRT
<213> ORGANISM: Artificial Sequence
<220> FEATURE:
<223> OTHER INFORMATION: synthetic peptide

<400> SEQUENCE: 124

Cys Thr Gly Val Tyr Leu Arg Gly Pro Leu Gly Leu Ala Gly Gly Gly
1               5                   10                  15

Ser Gly Asn Phe Gly Tyr Gly Lys Trp Glu Trp Asp Tyr Gly Lys Trp
            20                  25                  30

Leu Glu Lys Val Gly Gly Cys
        35

<210> SEQ ID NO 125
<211> LENGTH: 39
<212> TYPE: PRT
<213> ORGANISM: Artificial Sequence
<220> FEATURE:
<223> OTHER INFORMATION: synthetic peptide

<400> SEQUENCE: 125

Cys Val Arg Val Phe Arg Met Gly Pro Leu Gly Leu Ala Gly Gly Gly
1               5                   10                  15

Ser Gly Asn Phe Gly Tyr Gly Lys Trp Glu Trp Asp Tyr Gly Lys Trp
            20                  25                  30

Leu Glu Lys Val Gly Gly Cys
        35

<210> SEQ ID NO 126
<211> LENGTH: 39
<212> TYPE: PRT
<213> ORGANISM: Artificial Sequence
<220> FEATURE:
<223> OTHER INFORMATION: synthetic peptide

<400> SEQUENCE: 126

Cys Phe Phe Met Pro Leu Gln Gly Pro Leu Gly Leu Ala Gly Gly Gly
1               5                   10                  15

Ser Gly Asn Phe Gly Tyr Gly Lys Trp Glu Trp Asp Tyr Gly Lys Trp
            20                  25                  30

Leu Glu Lys Val Gly Gly Cys
        35

<210> SEQ ID NO 127
<211> LENGTH: 39
<212> TYPE: PRT
<213> ORGANISM: Artificial Sequence
<220> FEATURE:
<223> OTHER INFORMATION: synthetic peptide

<400> SEQUENCE: 127

Cys Ser Met Tyr Trp Met Arg Gly Pro Leu Gly Leu Ala Gly Gly Gly
1               5                   10                  15

Ser Gly Asn Phe Gly Tyr Gly Lys Trp Glu Trp Asp Tyr Gly Lys Trp
            20                  25                  30

Leu Glu Lys Val Gly Gly Cys
        35

```
<210> SEQ ID NO 128
<211> LENGTH: 37
<212> TYPE: PRT
<213> ORGANISM: Artificial Sequence
<220> FEATURE:
<223> OTHER INFORMATION: synthetic peptide

<400> SEQUENCE: 128

Cys Glu Tyr Ala Phe Gly Pro Leu Gly Leu Ala Gly Gly Gly Ser Gly
1               5                   10                  15

Asn Phe Gly Tyr Gly Lys Trp Glu Trp Asp Tyr Gly Lys Trp Leu Glu
            20                  25                  30

Lys Val Gly Gly Cys
        35

<210> SEQ ID NO 129
<211> LENGTH: 37
<212> TYPE: PRT
<213> ORGANISM: Artificial Sequence
<220> FEATURE:
<223> OTHER INFORMATION: synthetic peptide

<400> SEQUENCE: 129

Gly Gly Trp Cys Arg Gly Pro Leu Gly Leu Ala Gly Gly Gly Ser Gly
1               5                   10                  15

Asn Phe Gly Tyr Gly Lys Trp Glu Trp Asp Tyr Gly Lys Trp Leu Glu
            20                  25                  30

Lys Val Gly Gly Cys
        35

<210> SEQ ID NO 130
<211> LENGTH: 37
<212> TYPE: PRT
<213> ORGANISM: Artificial Sequence
<220> FEATURE:
<223> OTHER INFORMATION: synthetic peptide

<400> SEQUENCE: 130

Leu Glu Gly Glu Glu Gly Pro Leu Gly Leu Ala Gly Gly Gly Ser Gly
1               5                   10                  15

Asn Phe Gly Tyr Gly Lys Trp Glu Trp Asp Tyr Gly Lys Trp Leu Glu
            20                  25                  30

Lys Val Gly Gly Cys
        35

<210> SEQ ID NO 131
<211> LENGTH: 37
<212> TYPE: PRT
<213> ORGANISM: Artificial Sequence
<220> FEATURE:
<223> OTHER INFORMATION: synthetic peptide

<400> SEQUENCE: 131

Asp Asp Met Glu Glu Gly Pro Leu Gly Leu Ala Gly Gly Gly Ser Gly
1               5                   10                  15

Asn Phe Gly Tyr Gly Lys Trp Glu Trp Asp Tyr Gly Lys Trp Leu Glu
            20                  25                  30

Lys Val Gly Gly Cys
        35

<210> SEQ ID NO 132
<211> LENGTH: 37
<212> TYPE: PRT
```

```
<213> ORGANISM: Artificial Sequence
<220> FEATURE:
<223> OTHER INFORMATION: synthetic peptide

<400> SEQUENCE: 132

Gly Glu Asp Glu Glu Gly Pro Leu Gly Leu Ala Gly Gly Ser Gly
1               5                   10                  15

Asn Phe Gly Tyr Gly Lys Trp Glu Trp Asp Tyr Gly Lys Trp Leu Glu
                20                  25                  30

Lys Val Gly Gly Gly
        35

<210> SEQ ID NO 133
<211> LENGTH: 37
<212> TYPE: PRT
<213> ORGANISM: Artificial Sequence
<220> FEATURE:
<223> OTHER INFORMATION: synthetic peptide

<400> SEQUENCE: 133

Glu Tyr Glu Gly Glu Gly Pro Leu Gly Leu Ala Gly Gly Ser Gly
1               5                   10                  15

Asn Phe Gly Tyr Gly Lys Trp Glu Trp Asp Tyr Gly Lys Trp Leu Glu
                20                  25                  30

Lys Val Gly Gly Cys
        35

<210> SEQ ID NO 134
<211> LENGTH: 37
<212> TYPE: PRT
<213> ORGANISM: Artificial Sequence
<220> FEATURE:
<223> OTHER INFORMATION: synthetic peptide

<400> SEQUENCE: 134

Val Val Ser Glu Glu Gly Pro Leu Gly Leu Ala Gly Gly Ser Gly
1               5                   10                  15

Asn Phe Gly Tyr Gly Lys Trp Glu Trp Asp Tyr Gly Lys Trp Leu Glu
                20                  25                  30

Lys Val Gly Gly Cys
        35

<210> SEQ ID NO 135
<211> LENGTH: 324
<212> TYPE: PRT
<213> ORGANISM: Artificial Sequence
<220> FEATURE:
<223> OTHER INFORMATION: synthetic peptide

<400> SEQUENCE: 135

Met Lys Lys Thr Ala Ile Ala Ile Ala Val Ala Leu Ala Gly Phe Ala
1               5                   10                  15

Thr Val Ala Gln Ala Asp Tyr Lys Asp Asp Asp Lys Leu His His
                20                  25                  30

His His His His Lys Leu Gly Val Val Leu Thr Thr Met Asn Phe Trp
        35                  40                  45

Asp Trp Ile Thr Val Gly Ser Gly Gly Ser Gly Gly Val Leu Val Pro
        50                  55                  60

Met Ala Met Met Ala Ser Gly Gly Ser Gly Gly Ser Gly Gly Ser Glu
65              70                  75                  80

Val Gln Leu Val Glu Ser Gly Gly Gly Leu Val Gln Pro Gly Arg Ser
```

```
                    85                  90                  95
Leu Lys Leu Ser Cys Ala Ala Ser Gly Phe Thr Phe Asn Asp Tyr Asn
                100                 105                 110

Met Ala Trp Val Arg Gln Ala Pro Lys Arg Gly Leu Glu Trp Val Ala
                115                 120                 125

Thr Ile Ile Tyr Asp Gly Ser Met Thr Tyr Tyr Arg Asp Ser Val Lys
            130                 135                 140

Gly Gln Phe Thr Ile Ser Arg Asp Asn Ala Lys Ser Thr Leu Tyr Leu
145                 150                 155                 160

Gln Met Asp Ser Leu Arg Ser Glu Asp Thr Ala Thr Tyr Tyr Cys Ala
                165                 170                 175

Thr Glu Asp Asn Gly Ser Ser Asn Trp Phe Ala Tyr Trp Gly Gln Gly
                180                 185                 190

Thr Leu Val Thr Val Ser Ser Gly Gly Gly Ser Gly Gly Gly
                195                 200                 205

Ser Gly Gly Gly Gly Ser Asp Ile Gln Met Thr Gln Ser Pro Ala Ser
            210                 215                 220

Leu Ser Ala Ser Pro Glu Glu Ile Val Thr Ile Thr Cys Gln Ala Ser
225                 230                 235                 240

Gln Asp Ile Gly Asn Trp Leu Thr Trp Tyr Gln Lys Pro Gly Lys
                245                 250                 255

Ser Pro Gln Leu Leu Ile Tyr Arg Ala Thr Asn Leu Ala Asp Gly Ile
                260                 265                 270

Pro Ser Arg Phe Ser Gly Arg Ile Ser Gly Thr Gln Tyr Ser Leu Lys
            275                 280                 285

Ile Ser Arg Leu Gln Val Glu Asp Ile Gly Ile Tyr Tyr Cys Leu Gln
        290                 295                 300

Arg Tyr Ser His Pro Trp Thr Phe Gly Gly Gly Thr Lys Leu Glu Leu
305                 310                 315                 320

Lys Arg Leu Glu

<210> SEQ ID NO 136
<211> LENGTH: 324
<212> TYPE: PRT
<213> ORGANISM: Artificial Sequence
<220> FEATURE:
<223> OTHER INFORMATION: synthetic peptide

<400> SEQUENCE: 136

Met Lys Lys Thr Ala Ile Ala Ile Ala Val Ala Leu Ala Gly Phe Ala
1               5                   10                  15

Thr Val Ala Gln Ala Asp Tyr Lys Asp Asp Asp Lys Leu His His
                20                  25                  30

His His His His Lys Leu Trp Ala Asp Trp Ala Arg Ser Trp Glu Ala
            35                  40                  45

Ile Val Gly Met Ala Gly Ser Gly Gly Ser Gly Gly Val Leu Val Pro
        50                  55                  60

Met Ala Met Met Ala Ser Gly Gly Ser Gly Gly Ser Gly Gly Ser Glu
65                  70                  75                  80

Val Gln Leu Val Glu Ser Gly Gly Gly Leu Val Gln Pro Gly Arg Ser
                85                  90                  95

Leu Lys Leu Ser Cys Ala Ala Ser Gly Phe Thr Phe Asn Asp Tyr Asn
                100                 105                 110

Met Ala Trp Val Arg Gln Ala Pro Lys Arg Gly Leu Glu Trp Val Ala
                115                 120                 125
```

Thr Ile Ile Tyr Asp Gly Ser Met Thr Tyr Tyr Arg Asp Ser Val Lys
            130                 135                 140

Gly Gln Phe Thr Ile Ser Arg Asp Asn Ala Lys Ser Thr Leu Tyr Leu
145                 150                 155                 160

Gln Met Asp Ser Leu Arg Ser Glu Asp Thr Ala Thr Tyr Tyr Cys Ala
            165                 170                 175

Thr Glu Asp Asn Gly Ser Ser Asn Trp Phe Ala Tyr Trp Gly Gln Gly
            180                 185                 190

Thr Leu Val Thr Val Ser Ser Gly Gly Gly Ser Gly Gly Gly Gly
            195                 200                 205

Ser Gly Gly Gly Gly Ser Asp Ile Gln Met Thr Gln Ser Pro Ala Ser
            210                 215                 220

Leu Ser Ala Ser Pro Glu Glu Ile Val Thr Ile Thr Cys Gln Ala Ser
225                 230                 235                 240

Gln Asp Ile Gly Asn Trp Leu Thr Trp Tyr Gln Gln Lys Pro Gly Lys
            245                 250                 255

Ser Pro Gln Leu Leu Ile Tyr Arg Ala Thr Asn Leu Ala Asp Gly Ile
            260                 265                 270

Pro Ser Arg Phe Ser Gly Arg Ile Ser Gly Thr Gln Tyr Ser Leu Lys
            275                 280                 285

Ile Ser Arg Leu Gln Val Glu Asp Ile Gly Ile Tyr Tyr Cys Leu Gln
290                 295                 300

Arg Tyr Ser His Pro Trp Thr Phe Gly Gly Gly Thr Lys Leu Glu Leu
305                 310                 315                 320

Lys Arg Leu Glu

<210> SEQ ID NO 137
<211> LENGTH: 324
<212> TYPE: PRT
<213> ORGANISM: Artificial Sequence
<220> FEATURE:
<223> OTHER INFORMATION: synthetic peptide

<400> SEQUENCE: 137

Met Lys Lys Thr Ala Ile Ala Ile Ala Val Ala Leu Ala Gly Phe Ala
1               5                   10                  15

Thr Val Ala Gln Ala Asp Tyr Lys Asp Asp Asp Lys Leu His His
            20                  25                  30

His His His His Lys Leu Arg Gly Met Asp Met Tyr Trp Ala Glu Ile
            35                  40                  45

Ile Tyr Gly Ala Ala Gly Ser Gly Gly Ser Gly Gly Val Leu Val Pro
50                  55                  60

Met Ala Met Met Ala Ser Gly Gly Ser Gly Gly Ser Gly Gly Ser Glu
65                  70                  75                  80

Val Gln Leu Val Glu Ser Gly Gly Gly Leu Val Gln Pro Gly Arg Ser
            85                  90                  95

Leu Lys Leu Ser Cys Ala Ala Ser Gly Phe Thr Phe Asn Asp Tyr Asn
            100                 105                 110

Met Ala Trp Val Arg Gln Ala Pro Lys Arg Gly Leu Glu Trp Val Ala
            115                 120                 125

Thr Ile Ile Tyr Asp Gly Ser Met Thr Tyr Tyr Arg Asp Ser Val Lys
            130                 135                 140

Gly Gln Phe Thr Ile Ser Arg Asp Asn Ala Lys Ser Thr Leu Tyr Leu
145                 150                 155                 160

```
Gln Met Asp Ser Leu Arg Ser Glu Asp Thr Ala Thr Tyr Tyr Cys Ala
            165                 170                 175

Thr Glu Asp Asn Gly Ser Ser Asn Trp Phe Ala Tyr Trp Gly Gln Gly
        180                 185                 190

Thr Leu Val Thr Val Ser Ser Gly Gly Gly Ser Gly Gly Gly Gly
        195                 200                 205

Ser Gly Gly Gly Ser Asp Ile Gln Met Thr Gln Ser Pro Ala Ser
    210                 215                 220

Leu Ser Ala Ser Pro Glu Glu Ile Val Thr Ile Thr Cys Gln Ala Ser
225                 230                 235                 240

Gln Asp Ile Gly Asn Trp Leu Thr Trp Tyr Gln Gln Lys Pro Gly Lys
            245                 250                 255

Ser Pro Gln Leu Leu Ile Tyr Arg Ala Thr Asn Leu Ala Asp Gly Ile
        260                 265                 270

Pro Ser Arg Phe Ser Gly Arg Ile Ser Gly Thr Gln Tyr Ser Leu Lys
        275                 280                 285

Ile Ser Arg Leu Gln Val Glu Asp Ile Gly Ile Tyr Tyr Cys Leu Gln
        290                 295                 300

Arg Tyr Ser His Pro Trp Thr Phe Gly Gly Gly Thr Lys Leu Glu Leu
305                 310                 315                 320

Lys Arg Leu Glu

<210> SEQ ID NO 138
<211> LENGTH: 293
<212> TYPE: PRT
<213> ORGANISM: Artificial Sequence
<220> FEATURE:
<223> OTHER INFORMATION: synthetic peptide

<400> SEQUENCE: 138

Met Gly Val Val Leu Thr Thr Met Asn Phe Trp Asp Trp Ile Thr Val
1               5                   10                  15

Gly Ser Gly Gly Ser Gly Gly Val Leu Val Pro Met Ala Met Met Ala
            20                  25                  30

Ser Gly Gly Ser Gly Gly Ser Gly Gly Ser Glu Val Gln Leu Val Glu
        35                  40                  45

Ser Gly Gly Gly Leu Val Gln Pro Gly Arg Ser Leu Lys Leu Ser Cys
    50                  55                  60

Ala Ala Ser Gly Phe Thr Phe Asn Asp Tyr Asn Met Ala Trp Val Arg
65                  70                  75                  80

Gln Ala Pro Lys Arg Gly Leu Glu Trp Val Ala Thr Ile Ile Tyr Asp
            85                  90                  95

Gly Ser Met Thr Tyr Tyr Arg Asp Ser Val Lys Gly Gln Phe Thr Ile
            100                 105                 110

Ser Arg Asp Asn Ala Lys Ser Thr Leu Tyr Leu Gln Met Asp Ser Leu
        115                 120                 125

Arg Ser Glu Asp Thr Ala Thr Tyr Tyr Cys Ala Thr Glu Asp Asn Gly
    130                 135                 140

Ser Ser Asn Trp Phe Ala Tyr Trp Gly Gln Gly Thr Leu Val Thr Val
145                 150                 155                 160

Ser Ser Gly Gly Gly Gly Ser Gly Gly Gly Gly Ser Gly Gly Gly Gly
            165                 170                 175

Ser Asp Ile Gln Met Thr Gln Ser Pro Ala Ser Leu Ser Ala Ser Pro
        180                 185                 190

Glu Glu Ile Val Thr Ile Thr Cys Gln Ala Ser Gln Asp Ile Gly Asn
```

```
                195                 200                 205
Trp Leu Thr Trp Tyr Gln Gln Lys Pro Gly Lys Ser Pro Gln Leu Leu
    210                 215                 220

Ile Tyr Arg Ala Thr Asn Leu Ala Asp Gly Ile Pro Ser Arg Phe Ser
225                 230                 235                 240

Gly Arg Ile Ser Gly Thr Gln Tyr Ser Leu Lys Ile Ser Arg Leu Gln
                245                 250                 255

Val Glu Asp Ile Gly Ile Tyr Tyr Cys Leu Gln Arg Tyr Ser His Pro
            260                 265                 270

Trp Thr Phe Gly Gly Gly Thr Lys Leu Glu Leu Lys Arg Leu Glu His
        275                 280                 285

His His His His His
        290

<210> SEQ ID NO 139
<211> LENGTH: 293
<212> TYPE: PRT
<213> ORGANISM: Artificial Sequence
<220> FEATURE:
<223> OTHER INFORMATION: synthetic peptide

<400> SEQUENCE: 139

Met Trp Ala Asp Trp Ala Arg Ser Trp Glu Ala Ile Val Gly Met Ala
1               5                   10                  15

Gly Ser Gly Gly Ser Gly Gly Val Leu Val Pro Met Ala Met Met Ala
                20                  25                  30

Ser Gly Gly Ser Gly Gly Ser Gly Gly Ser Glu Val Gln Leu Val Glu
            35                  40                  45

Ser Gly Gly Gly Leu Val Gln Pro Gly Arg Ser Leu Lys Leu Ser Cys
        50                  55                  60

Ala Ala Ser Gly Phe Thr Phe Asn Asp Tyr Asn Met Ala Trp Val Arg
65                  70                  75                  80

Gln Ala Pro Lys Arg Gly Leu Glu Trp Val Ala Thr Ile Ile Tyr Asp
                85                  90                  95

Gly Ser Met Thr Tyr Tyr Arg Asp Ser Val Lys Gly Gln Phe Thr Ile
                100                 105                 110

Ser Arg Asp Asn Ala Lys Ser Thr Leu Tyr Leu Gln Met Asp Ser Leu
            115                 120                 125

Arg Ser Glu Asp Thr Ala Thr Tyr Tyr Cys Ala Thr Glu Asp Asn Gly
        130                 135                 140

Ser Ser Asn Trp Phe Ala Tyr Trp Gly Gln Gly Thr Leu Val Thr Val
145                 150                 155                 160

Ser Ser Gly Gly Gly Gly Ser Gly Gly Gly Ser Gly Gly Gly Gly Gly
                165                 170                 175

Ser Asp Ile Gln Met Thr Gln Ser Pro Ala Ser Leu Ser Ala Ser Pro
                180                 185                 190

Glu Glu Ile Val Thr Ile Thr Cys Gln Ala Ser Gln Asp Ile Gly Asn
            195                 200                 205

Trp Leu Thr Trp Tyr Gln Gln Lys Pro Gly Lys Ser Pro Gln Leu Leu
        210                 215                 220

Ile Tyr Arg Ala Thr Asn Leu Ala Asp Gly Ile Pro Ser Arg Phe Ser
225                 230                 235                 240

Gly Arg Ile Ser Gly Thr Gln Tyr Ser Leu Lys Ile Ser Arg Leu Gln
                245                 250                 255

Val Glu Asp Ile Gly Ile Tyr Tyr Cys Leu Gln Arg Tyr Ser His Pro
```

```
                    260                 265                 270
Trp Thr Phe Gly Gly Gly Thr Lys Leu Glu Leu Lys Arg Leu Glu His
        275                 280                 285

His His His His His
        290

<210> SEQ ID NO 140
<211> LENGTH: 293
<212> TYPE: PRT
<213> ORGANISM: Artificial Sequence
<220> FEATURE:
<223> OTHER INFORMATION: synthetic peptide

<400> SEQUENCE: 140

Met Arg Gly Met Asp Met Tyr Trp Ala Glu Ile Ile Tyr Gly Ala Ala
1               5                   10                  15

Gly Ser Gly Gly Ser Gly Gly Val Leu Val Pro Met Ala Met Met Ala
            20                  25                  30

Ser Gly Gly Ser Gly Gly Ser Gly Gly Ser Glu Val Gln Leu Val Glu
        35                  40                  45

Ser Gly Gly Gly Leu Val Gln Pro Gly Arg Ser Leu Lys Leu Ser Cys
    50                  55                  60

Ala Ala Ser Gly Phe Thr Phe Asn Asp Tyr Asn Met Ala Trp Val Arg
65              70                  75                  80

Gln Ala Pro Lys Arg Gly Leu Glu Trp Val Ala Thr Ile Ile Tyr Asp
            85                  90                  95

Gly Ser Met Thr Tyr Tyr Arg Asp Ser Val Lys Gly Gln Phe Thr Ile
            100                 105                 110

Ser Arg Asp Asn Ala Lys Ser Thr Leu Tyr Leu Gln Met Asp Ser Leu
        115                 120                 125

Arg Ser Glu Asp Thr Ala Thr Tyr Tyr Cys Ala Thr Glu Asp Asn Gly
    130                 135                 140

Ser Ser Asn Trp Phe Ala Tyr Trp Gly Gln Gly Thr Leu Val Thr Val
145                 150                 155                 160

Ser Ser Gly Gly Gly Gly Ser Gly Gly Gly Gly Ser Gly Gly Gly Gly
            165                 170                 175

Ser Asp Ile Gln Met Thr Gln Ser Pro Ala Ser Leu Ser Ala Ser Pro
            180                 185                 190

Glu Glu Ile Val Thr Ile Thr Cys Gln Ala Ser Gln Asp Ile Gly Asn
        195                 200                 205

Trp Leu Thr Trp Tyr Gln Gln Lys Pro Gly Lys Ser Pro Gln Leu Leu
    210                 215                 220

Ile Tyr Arg Ala Thr Asn Leu Ala Asp Gly Ile Pro Ser Arg Phe Ser
225                 230                 235                 240

Gly Arg Ile Ser Gly Thr Gln Tyr Ser Leu Lys Ile Ser Arg Leu Gln
            245                 250                 255

Val Glu Asp Ile Gly Ile Tyr Tyr Cys Leu Gln Arg Tyr Ser His Pro
            260                 265                 270

Trp Thr Phe Gly Gly Gly Thr Lys Leu Glu Leu Lys Arg Leu Glu His
        275                 280                 285

His His His His His
        290

<210> SEQ ID NO 141
<211> LENGTH: 45
<212> TYPE: PRT
```

```
<213> ORGANISM: Artificial Sequence
<220> FEATURE:
<223> OTHER INFORMATION: synthetic peptide

<400> SEQUENCE: 141

Gly Gln Ser Gly Gln Pro Cys Ser Glu Trp Gln Ser Met Val Gln Pro
1               5                   10                  15

Arg Cys Tyr Tyr Gly Gly Gly Ser Gly Gly Ser Gly Gln Gly Gly Gln
            20                  25                  30

Val His Met Pro Leu Gly Phe Leu Gly Pro Gly Gly Ser
            35                  40                  45
```

ACTIVATABLE ANTI-VEGF scFv

CROSS-REFERENCE TO RELATED APPLICATIONS

This application claims the benefit of U.S. Provisional Patent Application Nos. 60/957,449 filed Aug. 22, 2007; 60/957,453, filed Aug. 22, 2007; and 61/052,986, filed May 13, 2008, each of which applications are incorporated herein by reference in their entirety and for all purposes.

STATEMENT REGARDING FEDERALLY SPONSORED RESEARCH

This invention was made with Government support under Federal Grant No. 1 U54 CA119335-01 awarded by the National Institutes of Health. The Government has certain rights in this invention.

BACKGROUND

Protein drugs have changed the face of modern medicine, finding application in a variety of different diseases such a cancer, anemia, and neutropenia. As with any drugs, however, the need and desire for drugs having improved specificity and selectivity for their targets is of great interest, especially in developing second generation of protein drugs having known targets to which they bind.

In the realm of small molecule drugs, strategies have been developed to provide "prodrugs" of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target. An example of this can be seen in many anti-cancer treatments, in which the reduction of adverse effects is always of paramount importance. Drugs used to target hypoxic cancer cells, through the use of redox-activation, utilize the large quantities of reductase enzyme present in the hypoxic cell to convert the drug into its cytotoxic form, essentially activating it. Since the prodrug has low cytotoxicity prior to this activation, there is a markedly decreased risk of damage to non-cancerous cells, thereby providing for reduced side-effects associated with the drug.

There is a need in the field for a strategy for providing features of a prodrug to protein-based therapeutics.

SUMMARY OF THE INVENTION

The present disclosure provides activatable binding polypeptides (ABPs), which contain a target binding moiety (TBM), a masking moiety (MM), and a cleavable moiety (CM). The ABP exhibits an "activatable" conformation such that the such that the TBM is less accessible to target when uncleaved than after cleavage of the CM in the presence of a cleaving agent capable of cleaving the CM. The disclosure further provides libraries of candidate ABPs, methods of screening to identify such ABPs, and methods of use. The disclosure further provides ABPs having a TBM that binds VEGF, as well as compositions and methods of use.

Accordingly, the present disclosure provides an activatable binding polypeptide (ABP) comprising a target binding moiety (TBM); a masking moiety (MM) capable of inhibiting binding of the TBM to a target, wherein said MM does not have an amino acid sequence of a naturally occurring binding partner of said TBM; and a cleavable moiety (CM), wherein said CM is positioned in the activatable binding polypeptide such that in a cleaved state in the presence of a target, the TBM binds the target, and in an uncleaved state in the presence of the target, binding of the TBM to the target is inhibited by the MM.

In related embodiments, the MM is selected from a plurality of candidate polypeptides based on its ability to inhibit binding of the TBM to the target in an uncleaved state and allow binding of the TBM to the target in a cleaved state. In further related embodiments, the MM inhibits binding of the TBM to the target via steric hindrance when the ABP is in an uncleaved state. In other related embodiments, the MM comprises a cysteine residue and steric hindrance is achieved via disulfide bond linkage between said cysteine residue and an additional cysteine residue adjacent to or within the TBM. In additional embodiments the TBM is an extracellular polypeptide.

In further related embodiments, the CM is located between the TBM and the MM in the ABP, and in other embodiments is located within the MM. In certain embodiments, the CM comprises a protease substrate, which can be, for example, a plasmin substrate, a caspase substrate or a matrix metalloprotease (MMP) substrate (e.g., a substrate of MMP-1, MMP-2, MMP-9, or MMP-14). In other embodiments, the CM includes a protease substrate is a substrate for an intracellular protease. In additional embodiments, the CM comprises a cysteine-cysteine disulfide bond.

In another aspect, the disclosure provides methods of screening for an activatable binding polypeptide (ABP), the method comprising contacting a plurality of candidate activatable binding polypeptides (candidate ABPs) with a target capable of binding a target binding moiety of the candidate ABPs and a cleaving agent capable of cleaving a cleavable moiety (CM) of the ABPs; screening a first population of members of said plurality which bind to said target in the presence of the cleaving agent; contacting said first population with the target in the absence of the cleaving agent; and screening a second population of members from said first population by depleting said first population for members that bind the target in the absence of the cleaving agent; wherein said method provides for selection of candidate ABPs which exhibit decreased binding to the target in the absence of the cleaving agent as compared to target binding in the presence of the cleaving agent.

In related embodiments the cleaving agent is a protease or a reducing agent. In further related embodiments, the target comprises a detectable label. In further embodiments, the first population is selected by detection of the detectable label. In further embodiments, the second population is produced by separating from the first population members that are detectably labeled.

In further related embodiments, each of said plurality of candidate activatable binding polypeptides is presented on a surface of a replicable biological entity in a display scaffold.

The disclosure further provides libraries of candidate activatable binding polypeptides (ABPs), the library comprising a plurality of candidate ABPs displayed on the surface of a replicable biological entity. In related embodiments the replicable biological entity is a bacterial, yeast or mammalian cell.

The disclosure also provides compositions comprising a nucleic acid construct comprising a nucleic acid coding for an ABP. In related embodiments, the nucleic acid construct further comprises a nucleic acid coding for a display scaffold wherein the nucleic acid coding for the ABP is operably inserted into the construct to provide for expression of a fusion protein for presentation of the ABP in the display scaffold on the surface of a host cell. An exemplary display scaffold is a circularly permuted outer membrane protein X (CPX). In related embodiments, the ABP is a candidate ABP having a candidate MM.

The disclosure further provides methods of making a library of candidate activatable binding polypeptides, the method comprising introducing into genomes of replicable biological entities a collection of recombinant DNA constructs that encode a plurality of candidate activatable binding polypeptides (ABPs), wherein each member of said plurality comprises a target binding moiety (TBM), a cleavable moiety (CM) and a candidate masking moiety (MM), said introducing producing recombinant replicable biological entities; and culturing said recombinant replicable biological entities under conditions suitable for expression and display of the candidate ABPs.

The disclosure also provides pharmaceutical compositions comprising a therapeutically effective amount of an activatable binding polypeptide (ABP) and a pharmaceutically acceptable excipient. In related embodiments the TBM of the ABP is capable of binding VEGF to effect VEGF inhibition.

The disclosure also provides methods of inhibiting angiogenesis in a subject in need thereof, the method comprising administering to a subject in need thereof a therapeutically effective amount of an ABP, with exemplary ABPs including those having a TBM that binds VEGF to effect inhibition of VEGF activity (e.g., at a tumor site).

In one embodiment, an ABP is disclosed wherein the target of the ABP is any one of VCAM-1, VEGF-A, CTLA-4 or CD40L.

The present disclosure also provides activatable binding polypeptides (ABPs), which contain a first target binding moiety (TBM), a second TBM, and a cleavable moiety (CM). The ABP exhibits an "activatable" conformation such that the such that at least one of the TBMs is less accessible to target when uncleaved than after cleavage of the CM in the presence of a cleaving agent capable of cleaving the CM. The disclosure further provides libraries of candidate ABPs having such a configuration, methods of screening to identify such ABPs, and methods of use. The disclosure further provides ABPs having a TBM that binds VEGF and a TBM that binds FGF to effect inhibition of VEGF and FGF activity, as well as compositions and methods of use.

Accordingly, the disclosure provides an activatable binding polypeptide (ABP) comprising a first target binding moiety (TBM); a second TBM; and a cleavable moiety (CM), wherein said CM is positioned in the activatable binding polypeptide such that in a cleaved state in the presence of a target, the first and second TBMs bind target, and in an uncleaved state the ABP is in a conformation such that the first TBM interferes with target binding by the second TBM.

In related embodiments, the ABP in the uncleaved state is in a conformation such that the first and second TBMs interfere with binding of target to the first and second TBMs. In further related embodiments, the first and second TBMs are capable of binding different targets, e.g., to FGF2 and to VEGF. In further related embodiments, the first TBM is selected from a plurality of candidate polypeptides based on the ability of said first TBM to inhibit binding of said second TBM to a target when the ABP is in an uncleaved state and allow binding of said second TBM to the target when the ABP is in a cleaved state. In another embodiment, the first TBM interferes with target binding by said second TBM via steric hindrance when the ABP is in an uncleaved state. In further related embodiments, the ABP comprises a first cysteine residue within or adjacent to said first TBM and a second cysteine residue within or adjacent to said second TBM, and wherein steric hindrance is achieved via disulfide bond linkage between said first and second cysteine residue. In related embodiments, the target of said first TBM and said second TBM is an extracellular polypeptide. In other embodiments, the CM is located between said first TBM and said second TBM in the ABP, or, where the CM comprises a cysteine-cysteine pair, the CM can be located within either said first TBM or said second TBM. In further related embodiments, the CM comprises a protease substrate, e.g., a matrix metalloprotease (MMP) substrate, e.g., a substrate of MMP-1, MMP-2, MMP-9, or MMP-14. In further related embodiments, the protease substrate is a substrate for an intracellular protease. In another embodiment, the CM comprises a cysteine-cysteine disulfide bond.

The disclosure further provides methods for selecting for a dual target binding activatable binding polypeptide (ABP), said method comprising: contacting a plurality of candidate activatable binding polypeptides (ABPs), wherein each member of said plurality comprises a first target binding moiety (TBM), a second TBM and a cleavable moiety (CM), with a target capable of binding said first TBM and a cleaving agent capable of cleaving the CM; selecting a first population of members of said plurality which bind to said target in the presence of the cleaving agent; contacting said first population with said target in the absence of the cleaving agent; and selecting a second population of members from said first population by depleting said first population for members that bind to said target in the absence of the cleaving agent, wherein said method provides for selection of candidate ABPs which exhibit decreased binding to said target in the absence of the cleaving agent as compared to binding to said target in the presence of the cleaving agent.

In related embodiments, the cleaving agent is a protease or a disulfide bond reducing agent. In further related embodiments, the first target and the second target each comprise a detectable label. In further related embodiments, the first population is selected by detection of the detectable label. In further related embodiments, the second population is produced by separating from the first population members that are detectably labeled. In still other embodiments, the plurality of candidate activatable binding polypeptides is presented on a surface of a replicable biological entity in a display scaffold. In further embodiments, binding of the second TBM to target is assessed by providing the amino acid sequence of the second TBM in a display scaffold and detecting binding of target to the second TBM.

The disclosure further provides libraries of candidate dual target binding activatable binding polypeptides (ABPs), said library comprising a plurality of candidate dual target binding ABPs displayed on the surface of a replicable biological entity. In related embodiments, the replicable biological entity is a bacterial, yeast or mammalian cells.

The disclosure also provides compositions comprising a nucleic acid construct comprising a nucleic acid coding for a dual target binding ABP. In related embodiments, the nucleic acid construct further comprises a nucleic acid coding for a display scaffold wherein the nucleic acid coding for the ABP is operably inserted into the construct to provide for expression of a fusion protein for presentation of the ABP in the display scaffold on the surface of a host cell. In further related embodiments, the display scaffold is a circularly permuted outer membrane protein X (CPX).

The disclosure also provides compositions comprising a nucleic acid construct comprising a nucleic acid encoding a candidate dual target binding activatable binding polypeptide, and further wherein said candidate activatable binding polypeptide comprises: (a) a first target binding moiety (TBM); (b) a cleavable moiety (CM); and (c) a second TBM, wherein the first TBM, CM and second TBM are positioned such that the ability of said first TBM to inhibit binding of said second TBM to a target in an uncleaved state and allow binding of said second TBM to the target in a cleaved state can be determined.

In related embodiments, the nucleic acid construct further comprises a nucleic acid coding for a circularly permuted outer membrane protein X (CPX).

The disclosure further provides methods of making a library of candidate dual target binding activatable binding polypeptides, said method comprising introducing into genomes of replicable biological entities a collection of recombinant DNA constructs that encode a plurality of dual target binding candidate activatable binding polypeptides (ABPs), wherein each member of said plurality comprises a first target binding moiety (TBM), a cleavable moiety (CM) and a second TBM, said introducing producing recombinant replicable biological entities; and culturing said recombinant replicable biological entities under conditions suitable for expression and display of the candidate dual target binding ABPs.

The disclosure also provides pharmaceutical compositions comprising a therapeutically effective amount of a dual target binding activatable binding polypeptide (ABP) and a pharmaceutically acceptable excipient. In related embodiments, the first TBM of the ABP binds VEGF to effect VEGF inhibition and the second TBM binds fibroblast growth factor-2 (FGF2) to effect FGF2 inhibition.

The disclosure also provides methods of inhibiting angiogenesis in a mammalian subject, method comprising administering to a subject in need thereof a therapeutically effective amount of a pharmaceutical composition comprising a dual target binding ABP.

In one aspect, the disclosure provides for a composition comprising an antigen binding domain (ABD) capable of binding a target, wherein said ABD is coupled to at least one masking moiety (MM) wherein said MM interferes with specific binding of the ABD to the target. In one embodiment the composition further comprises a cleavable moiety (CM) wherein said composition comprises two configurations, a first configuration wherein the CM is in an uncleaved state and the MM interferes with specific binding of the ABD to the target and a second configuration wherein the CM is in a cleaved state and the MM does not interfere with specific binding of the ABD to the target.

In another aspect the disclosure provides an activatable binding polypeptide (ABP) comprising at least one antigen binding domain (ABD) capable of binding a target, at least one masking moiety (MM) coupled said ABD capable of interfering with specific binding of the ABD to the target, and, at least one cleavable moiety (CM) coupled to said ABD, wherein said CM is positioned in the ABP such that in an uncleaved state the MM interferes with specific binding of the ABD to the target and in a cleaved state the MM does not interfere with specific binding of the ABD to the target. In certain embodiments the CM is coupled to the C-terminus of the ABD. In other embodiments, the CM is coupled to the N-terminus of the ABD or to the N-terminus of the VL or VH chains of the ABD. In related embodiments the MM is coupled to the C-terminus of the ABD. In other related embodiments, the MM is coupled to the N-terminus of the ABD or to the N-terminus of the VL or VH chains of the ABD. In further embodiments the ABP also contains a linker peptide positioned between the MM and the CM. In related embodiments a linker peptide is positioned between the ABD and the CM. In specific embodiments the ABP comprising an ABD, CM, and MM further comprises a detectable moiety. In certain embodiments the detectable moiety is a diagnostic agent.

In one embodiment the ABP comprising an ABD, CM, and MM contains an ABD that is from a full length antibody, Fab fragment, ScFv, or SCAB. In certain embodiments the target of the ABD is selected from the group consisting of VEGF-A, VEGF-B, VEGF-C, VEGF-D, VEGFR1, VEGFR2, VEGFR3, EGFR, FGF-2, FGFR1, FGFR2, FGFR3, FGFR4, HER2/neu, DLL4, NOTCHR1, IL1B, IL1R, IL2, IL2R, IL4, IL6, IL12, IL13, IL15, IL18, IL23, IGF, IGF1R, ERBB3, VCAM-1, CXCR4, CD3, CD11a, CD19, CD20, CD22, CD25, CD28, CD30, CD33, CD40, CD40L, CD41, CD44, CD52, CD80, CD86, CTLA-4, TNFα, TNFR, TRAIL-R1, TRAIL-R2, IgE, IgE Receptor, PDGF-AA, PDGF-BB, PDGFRα, PDGFRβ, GPIIB/IIIA, CLAUDIN-3, CLAUDIN-4, C5 complement. F protein of RSV, Glyocprotein IIb/IIIa receptor, α4β1 integrin, and α4β7 integrin. In further embodiments the ABP comprising an ABD further comprises a CM which is a substrate for an enzyme selected from the group consisting of MMP1, MMP2, MMP3, MMP8, MMP9, MMP14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In specific embodiments the CM is a substrate for MMP9.

In another aspect, the present disclosure provides a method of modifying a composition containing an antigen binding domain (ABD) capable of binding a target, the method comprising coupling a masking moiety (MM) and a cleavable moiety (CM) to said ABD such that in a uncleaved state the MM interferes with the ABD to specifically bind the target and in a cleaved state the MM does not interfere with the ABD to specifically bind the target. In one embodiment the MM and/or the CM is coupled to the C-terminus of the ABD. In another embodiment MM and/or the CMS is coupled to the N-terminus of the ABD. In some embodiments the CM is a substrate for an enzyme selected from the group consisting of MMP1, MMP2, MMP3, MMP8, MMP9, MMP14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE.

In certain embodiments the target of the ABD is selected from the group consisting of VEGF-A, VEGF-B, VEGF-C, VEGF-D, VEGFR1, VEGFR2, VEGFR3, EGFR, FGF-2, FGFR1, FGFR2, FGFR3, FGFR4, HER2/neu, DLL4, NOTCHR1, IL1B, IL1R, IL2, IL2R, IL4, IL6, IL12, IL13, IL15, IL18, IL23, IGF, IGF1R, ERBB3, VCAM-1, CXCR4, CD3, CD11a, CD19, CD20, CD22, CD25, CD28, CD30, CD33, CD40, CD40L, CD41, CD44, CD52, CD80, CD86, CTLA-4, TNFα, TNFR, TRAIL-R1, TRAIL-R2, IgE, IgE Receptor, PDGF-AA, PDGF-BB, PDGFRα, PDGFRβ, GPIIB/IIIA, CLAUDIN-3, CLAUDIN-4, C5 complement, F protein of RSV, Glyocprotein IIb/IIIa receptor, α4β1 integrin, and α4β7 integrin. In related embodiments, the ABD is from a full length antibody, Fab fragment, ScFv, or SCAB and the ABD is from an antibody or an antibody fragment to a target selected from the group consisting of VEGF, EGFR, CTLA-4, TNFα, Integrinα4, IL2R, Complement C5, CD11a, CD20, CD25, CD33, CD52, Glycoprotein receptor IIb/IIIa, IgE, Her2, and F protein of RSV. In further related embodiments ABD is from an antibody selected from the group consisting of bevacizumab, ranibizumab, trastuzumab, infliximab, adalimumab, efalizumab, gemtuzumab ozogamicin, tositumomab, ibritumomab tiuxetan, eculizumab, alemtuzumab, rituximab, abiciximab, cetuximab, daclizumab, basiliximab, gemtuzumab, panitumumab, eculizumab, natalizumab, omalizumab, ipilimumab, tremelimumab, and palivizumab. In specific embodiments the ABD is from an antibody or an antibody fragment thereof to VEGF. In a related embodiment the ABD is from bevacizumab or ranibizumab. In another specific embodiment, the ABD is from an antibody or an antibody fragment thereof to TNFα. In a related embodiment, the ABD is from infliximab or adalimumab. In another specific embodiment, the ABD is from an antibody or an antibody fragment thereof to CD20. In a related embodiment the ABD is from tositumomab, ibritumomab tiuxetan, or rituximab. In yet another specific embodiment the ABD is from an antibody or an antibody fragment thereof to EGFR. In a related embodiment the ABD is from cetuximab or panitumumab. In yet another specific embodiment the ABD is from an antibody or an antibody fragment thereof to CTLA-4. In a related embodiment the ABD is from ipilimumab or tremelimumab.

The disclosure also provides a method of screening candidate peptides to identify a masking moiety (MM) peptide with specific binding affinity for an antibody or fragment thereof comprising an antigen binding domain (ABD). This method includes providing a library of peptide scaffolds, wherein each peptide scaffolds comprises a transmembrane protein (TM), a candidate peptide and involves contacting the antibody or fragment thereof comprising an ABD with the library and identifying a MM peptide having specific binding affinity for the ABD contained in the antibody or fragment thereof. In some embodiments the library comprises viruses, cells or spores. In a specific embodiment the library comprises *E. coli*. In certain embodiments the peptide scaffold further comprises a detectable moiety.

In certain embodiments the antibody or fragment thereof comprises an ABD to be screened in order to identify MMs is capable of binding a target wherein the target is selected from the group consisting of VEGF-A, VEGF-B, VEGF-C, VEGF-D, VEGFR1, VEGFR2, VEGFR3, EGFR, FGF-2, FGFR1, FGFR2, FGFR3, FGFR4, HER2/neu, DLL4, NOTCHR1, IL1B, IL1R, IL2, IL2R, IL4, IL6, IL12, IL13, IL15, IL18, IL23, IGF, IGF1R, ERBB3, VCAM-1, CXCR4, CD3, CD11a, CD19, CD20, CD22, CD25, CD28, CD30, CD33, CD40, CD40L, CD41, CD44, CD52, CD80, CD86, CTLA-4, TNFα, TNFR, TRAIL-R1, TRAIL-R2, IgE, IgE Receptor, PDGF-AA, PDGF-BB, PDGFRα, PDGFRβ, GPIIB/IIIA, CLAUDIN-3, CLAUDIN-4, C5 complement, F protein of RSV, Glyocprotein IIb/IIIa receptor, α4β1 integrin, and α4β7 integrin. In related embodiments the ABD to be screened to identify MMs is from an antibody selected from the group consisting of bevacizumab, ranibizumab, trastuzumab, infliximab, adalimumab, efalizumab, gemtuzumab ozogamicin, tositumomab, ibritumomab tiuxetan, eculizumab, alemtuzumab, rituximab, abiciximab, cetuximab, daclizumab, basiliximab, gemtuzumab, panitumumab, eculizumab, natalizumab, omalizumab, ipilimumab, tremelimumab, and palivizumab. In specific embodiments the ABD is from an antibody or an antibody fragment to a target selected from the group consisting of VEGF, EGFR, CTLA-4, TNFα, Integrinα4, IL2R, Complement C5, CD11a, CD20, CD25, CD33, CD52, Glycoprotein receptor IIb/IIIa, IgE, Her2, and F protein of RSV. In specific embodiments the ABD is from an antibody or an antibody fragment thereof to VEGF. In a related embodiment the ABD is from bevacizumab or ranibizumab. In another specific embodiment, the ABD is from an antibody or an antibody fragment thereof to TNFα. In a related embodiment, the ABD is from infliximab or adalimumab. In another specific embodiment, the ABD is from an antibody or an antibody fragment thereof to CD20. In a related embodiment the ABD is from tositumomab, ibritumomab tiuxetan, or rituximab. In yet another specific embodiment the ABD is from an antibody or an antibody fragment thereof to EGFR. In a related embodiment the ABD is from cetuximab or panitumumab. In yet another specific embodiment the ABD is from an antibody or an antibody fragment thereof to CTLA-4. In a related embodiment the ABD is from ipilimumab or tremelimumab.

In other aspects the present disclosure provides methods of treating and/or diagnosing a condition in a subject including administering to the subject a composition comprising an antibody or fragment thereof containing an antigen binding domain (ABD) capable of binding a target coupled to a masking moiety (MM) and a cleavable moiety (CM), such that in an uncleaved state the MM interferes with the ABD to specifically bind the target and in a cleaved state the MM does not interfere with the ABD to specifically bind the target. In certain embodiments the ABD is from a full length antibody, a Fab fragment, ScFv, or SCAB. In certain embodiments the ABD is from an antibody selected from the group consisting of bevacizumab, ranibizumab, trastuzumab, infliximab, adalimumab, efalizumab, gemtuzumab ozogamicin, tositumomab, ibritumomab tiuxetan, eculizumab, alemtuzumab, rituximab, abiciximab, cetuximab, daclizumab, basiliximab, gemtuzumab, panitumumab, eculizumab, natalizumab, omalizumab, ipilimumab, tremelimumab, and palivizumab. In related embodiments the target is selected from the group consisting of VEGF-A, VEGF-B, VEGF-C, VEGF-D, VEGFR1, VEGFR2, VEGFR3, EGFR, FGF-2, FGFR1, FGFR2, FGFR3, FGFR4, HER2/neu, DLL4, NOTCHR1, IL1B, IL1R, IL2, IL2R, IL4, IL6, IL12, IL13, IL15, IL18, IL23, IGF, IGF1R, ERBB3, VCAM-1, CXCR4, CD3, CD11a, CD19, CD20, CD22, CD25, CD28, CD30, CD33, CD40, CD40L, CD41, CD44, CD52, CD80, CD86, CTLA-4, TNFα, TNFR, TRAIL-R1, TRAIL-R2, IgE, IgE Receptor, PDGF-AA, PDGF-BB, PDGFRα, PDGFRβ, GPIIB/IIIA, CLAUDIN-3, CLAUDIN-4, C5 complement, F protein of RSV, Glyocprotein IIb/IIIa receptor, α4β1 integrin, and α4β7 integrin. In further related embodiments the ABD is from an antibody or an antibody fragment to a target selected from the group consisting of VEGF, EGFR, CTLA-4, TNFα, Integrinα4, IL2R, Complement C5, CD11a, CD20, CD25, CD33, CD52, Glycoprotein receptor IIb/IIIa, IgE, Her2, and F protein of RSV. In specific embodiments the ABD is from an antibody or an antibody fragment thereof to VEGF. In a related embodiment the ABD is from bevacizumab or ranibizumab. In another specific embodiment, the ABD is from an antibody or an antibody fragment thereof to TNFα. In a related embodiment, the ABD is from infliximab or adalimumab. In another specific embodiment, the ABD is from an antibody or an antibody fragment thereof to CD20. In a related embodiment the ABD is from tositumomab, ibritumomab tiuxetan, or rituximab. In yet another specific embodiment the ABD is from an antibody or an antibody fragment thereof to EGFR. In a related embodiment the ABD is from cetuximab or panitumumab. In yet another specific embodiment the ABD is from an antibody or an antibody fragment thereof to CTLA-4. In a related embodiment the ABD is from ipilimumab or tremelimumab.

In certain specific aspects the disclosure provides for enzyme-activatable antibodies or fragments thereof. In certain embodiments the enzyme selected from the group consisting of MMP1, MMP2, MMP3, MMP8, MMP9, MMP14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE. In related embodiments the antibody fragment is from a full length antibody, or is a scFv, Fab, or SCAB. In one specific aspect the disclosure provides for an enzyme-activatable anti-VEGF-A antibody or fragment thereof. In one specific embodiment the antibody is ranibizumab. In another embodiment the antibody is activated by MMP9. In another aspect the disclosure provides for an enzyme-activatable anti-CTLA-4 antibody or fragment thereof. In one specific embodiment the antibody is ipilimumab or tremelimumab. In another embodiment the antibody is activated by MMP9. In yet another related aspect the disclosure provides for an enzyme-activatable VCAM-1 antibody of fragment thereof. In one specific embodiment the antibody is activated by MMP9.

In one aspect, the disclosure provides a reaction mixture comprising an ABP, a protease capable of cleaving said ABP, and a target of said ABP.

Other aspects and embodiments will be readily apparent upon reading the present disclosure.

BRIEF DESCRIPTION OF THE DRAWINGS

FIG. 2 is a schematic of a library screening procedure which may be used to identify and isolate ABPs.

FIG. 3 also shows cleavage of an MMP-2 substrate (CM) by MMP-2.

FIG. 4 also shows a diagram of the ABP in an inactive (uncleaved state) and an active (cleaved state).

FIG. 8 shows that members of an exemplary library that exhibit switch-like behavior can be identified after sorting constructs according to the screening procedure shown in FIG. 7.

FIG. 10 shows the amino acid sequences of clones isolated from the libraries that demonstrated the most marked "switching" phenotype.

FIG. 17 shows a diagram of an exemplary embodiment of a protease-activatable VEGF inhibitor.

FIG. 22 shows the sequences for various exemplary ABPs having cysteine and non-cysteine containing MMs.

Figure 1:
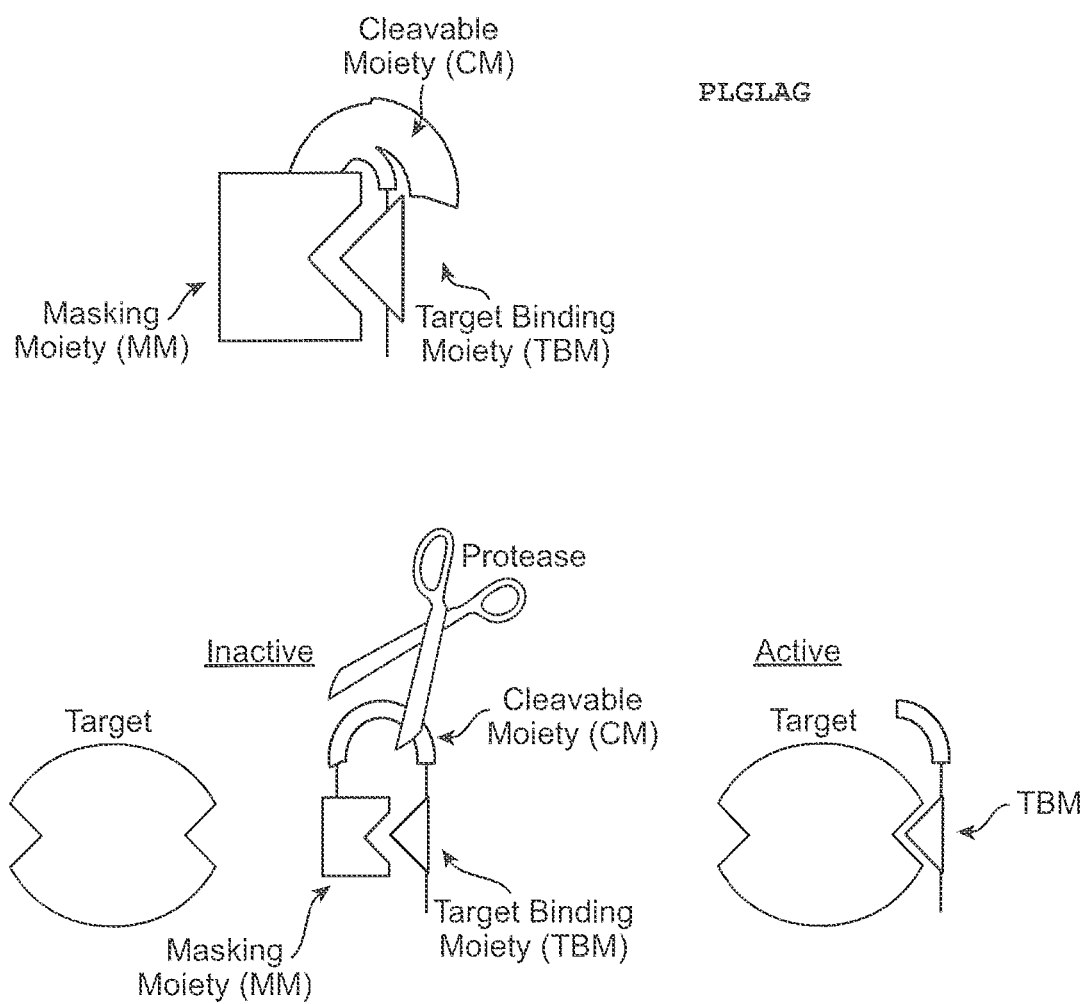
FIG. 1 is a diagram of an ABP which shows the ABP in an inactive (uncleaved state) and an active (cleaved state).

F bind one or more of several targets disclosed herein as well as compositions and methods of use.

Definitions

The term "activatable binding polypeptide" or "ABP" generally refers to a polypeptide that contains a target binding moiety (TBM), a cleavable moiety (CM), and a masking moiety (MM). The TBM generally contains an amino acid sequence that provides for binding to a target protein (e.g., VEGF). In some embodiments the TBM comprises the antigen binding domain (ABD) of an antibody or antibody fragment thereof.

The CM generally includes an amino acid sequence that serves as the substrate for an enzyme and/or a cysteine-cysteine pair capable of forming a reducible disulfide bond. As such, when the terms "cleavage," "cleavable," "cleaved" and the like are used in connection with a CM, the terms encompass enzymatic cleavage, e.g., by a protease, as well as disruption of a disulfide bond between a cysteine-cysteine pair via reduction of the disulfide bond that can result from exposure to a reducing agent.

The MM is an amino acid sequence that, when the CM of the ABP is intact (i.e., uncleaved by a corresponding enzyme, and/or containing an unreduced cysteine-cysteine disulfide bond), the MM interferes with binding of the TBM to its target. The amino acid sequence of the CM may overlap with or be included within the MM. It should be noted that for sake of convenience "ABP" is used herein to refer to an ABP in both its uncleaved (or "native") state, as well as in its cleaved state. It will be apparent to the ordinarily skilled artisan that in some embodiments a cleaved ABP may lack an MM due to cleavage of the CM, e.g, by a protease, resulting in release of at least the MM (e.g., where the MM is not joined to the ABP by a covalent bond (e.g., a disulfide bond between cysteine residues). Exemplary ABPs are described in more detail below.

In an embodiment of particular interest, the ABP comprises two TBMs, wherein at least one of the TBMs acts as a masking moiety (MM) for the other TBM and/or the two TBMs serves as masking moieties for one another, such that in the uncleaved conformation, the ABP exhibits reduced binding to a target for at least one of the TBMs relative to when the ABP is in the cleaved conformation. Thus "activatable binding polypeptide" or "ABP" in this embodiment encompasses a polypeptide that contains a rust target binding moiety (TBM), a second TBM, and a cleavable moiety (CM), wherein the first and second TBMs interact to "mask" binding of at least one of the TBMs to target (i.e., the first and/or second TBMs act as a masking moiety (MM) for target binding). The TBM generally contains an amino acid sequence that provides for binding to a target protein (e.g., VEGF).

In this latter embodiment, when the CM of the ABP is intact (i.e., uncleaved by a corresponding enzyme, and/or containing an unreduced cysteine-cysteine disulfide bond), the interaction of the first and second TBMs interferes with binding of one or both of the TBMs to their corresponding target(s). It should be noted that for sake of convenience "ABP" is used herein to refer to an ABP in both its uncleaved (or "native") state, as well as in its cleaved state. It will be apparent to the ordinarily skilled artisan that in some embodiments a cleaved ABP may no longer contain two TBMs as described above due to cleavage of the CM, e.g, by a protease. Where the ABP includes both a protease-cleavable CM and a CM that includes a disulfide bond, cleavage of the protease cleavable CM may leave the disulfide bond intact, and thus the ABP in the cleaved form may retain two the TBMs, but in an "unmasked" configuration allowing for target binding. Exemplary ABPs are described in more detail below.

As used herein, the term "cleaving agent" refers to an agent capable of cleaving a sequence of the CM. e.g., by enzymatic cleavage, or a reducing agent capable of reducing a disulfide bond between a cysteine-cysteine pair. A "reducing agent" generally refers to a compound or element that serves as an electron-donating compound in a reduction-oxidation reaction with a disulfide bond. Reducing agents of particular interest include cellular reducing agents such as proteins or other agents that are capable of reducing a disulfide bond under physiological conditions, e.g., glutathione, thioredoxin, NADPH, flavins, and ascorbate.

The terms "polypeptide." "peptide." and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "protease", "proteinase" and "enzyme capable of cleaving a polypeptide" are used interchangeably herein to refer to any enzyme, e.g., an endopeptidase or exopeptidase, usually an endopeptidase, that hydrolyzes peptide bonds.

The term "replicable biological entity" refers to self-replicating biological cells, including bacterial, yeast, protozoan, and mammalian cells, as well various viruses and bacteriophage capable of infecting such cells and replicating, and the like.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences that are immunologically identifiable with a polypeptide encoded by the sequence.

"Construct" is used herein to refer to a polypeptide or nucleic acid characterized as a covalently and operably linked elements. For example, an ABP construct can refer to a ABP polypeptide including at least a TBM, an MM, and a CM, which are operably linked to provide a switchable phenotype as described herein, as well as nucleic acid encoding such an ABP polypeptide.

A "vector" is capable of transferring gene sequences to target cells. Typically. "vector construct," "expression vector." and "gene transfer vector," mean any nucleic acid construct capable of directing the expression of a gene of interest in a host cell. Thus, the term includes cloning, and expression vehicles, as well as integrating vectors.

As used herein, "recombinant" has the usual meaning in the art, and refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide.

The term "recombinant" when used with reference to a cell indicates that the cell contains a heterologous nucleic acid, or expresses a peptide or protein encoded by such a heterologous nucleic acid, and usually provides for replication of such heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "heterologous sequence", "heterologous nucleic acid", "heterologous polypeptide" or "heterologous amino acid sequence" as used herein, is one that originates from a source foreign to the particular host cell, or, if from the same source, is modified from its original form. Thus, a heterologous nucleic acid in a host cell includes nucleic acid that, although being endogenous to the particular host cell, has been modified (e.g., so that it encodes an amino acid sequence different from that of a naturally-occurring or parent nucleic acid, to a nucleic acid to provide a sequence not normally found in the host cell, and the like). Modification of the heterologous sequence can be accomplished by a variety of methods. e.g., by treating the DNA with a restriction enzyme to generate a DNA fragment that is capable of being operably linked to the promoter or by operably linking the DNA to a heterologous promoter to provide an expression cassette that is not endogenous to the host cell. Techniques such as site-directed mutagenesis are also useful for modifying a heterologous nucleic acid.

The term "operably linked" refers to functional linkage between molecules to provide a desired function. For example, "operably linked" in the context of nucleic acids refers to a functional linkage between nucleic acids to provide a desired function such as transcription, translation, and the like. e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide. "Operably linked" in the context of a polypeptide refers to a functional linkage between amino acid sequences (e.g., of different domains) to provide for a described activity of the polypeptide (e.g., "masking" of a TBM when an ABP is uncleaved; accessibility to protease to facilitate cleavage and "unmasking" of a TBM of an ABP; and the like).

A "recombinant expression cassette" or simply an "expression cassette" is a nucleic acid construct, generated recombinantly and/or synthetically, that has control elements that are capable of affecting expression of a structural gene that are operably linked to the control elements in hosts compatible with such sequences. Expression cassettes include at least promoters and optionally, transcription termination signals. Typically, the recombinant expression cassette includes at least a nucleic acid to be transcribed and a promoter. Additional factors necessary or helpful in effecting expression can also be used as described herein. For example, transcription termination signals, enhancers, and other nucleic acid sequences that influence gene expression, can also be included in an expression cassette.

"Introducing into a genome" as used herein in the context of making a recombinant replicable biological entity (e.g., host cell, bacteriophage) refers to production of a recombinant replicable biological entity so as to provide for replication and, where desired, expression of an exogenous polypeptide with replication of the replicable biological entity. Where the replicable biological entity is a host cell (e.g., a bacterial, yeast, or mammalian cell) "introducing into a genome" encompasses both genomically introduction by genomic integration (e.g., stable integration) as well as introduction of a episomal element (e.g., plasmid) to provide for stable or transient maintenance of the exogenous nucleic acid in the host cell. The term "transformation" is similarly used to indicate production of a recombinant cell by introduction of exogenous nucleic acid encoding a polypeptide of interest, where the exogenous nucleic acid can be maintained stably or transiently as an episomal element (e.g., such as a plasmid in the context of a bacterial or yeast host cell) or can be stably or transiently genomically integrated.

The term "isolated" refers to separation of an entity (e.g., polypeptide, nucleic acid, etc.) from other entities with which they are naturally associated or may be associated during synthesis (e.g., recombinant, chemical synthesis, etc.). The term "isolated" means an entity is not in a state in which it is found in nature or, where the entity is produced by recombinant or other synthetic means, is separated or enriched relative to other components that may be present. Thus, for example, an "isolated protein" is not as it appears in nature but may be substantially less than 100% pure protein.

"Substantially pure" indicates that an entity (e.g., polypeptide) makes up greater than about 50% of the total content of the composition (e.g., total protein of the composition) and typically, greater than about 60% of the total protein content. More typically, a "substantially pure" refers to compositions in which at least 75%, at least 75%, at least 85%, at least 90% or more of the total composition is the entity of interest (e.g., of the total protein. Preferably, the protein will make up greater than about 90%, and more preferably, greater than about 95% of the total protein in the composition.

"Enriched" indicates a composition is increased in the proportion of an entity of interest relative to a starting composition. For example, a starting or first population in which 10% of the members exhibit a desired attribute (e.g., enzymatically "switchable") can be enriched to provide a second population in which greater than 10% (e.g., 15% or more) of the total members exhibit the desired activity. It should be noted that enrichment can result in a decrease of total different members of the population such that enrichment is accompanied by selection.

"Screen" or "screening", as well as the terms "selection" or "selecting", are used herein to refer to treatment of a population so as to facilitate separation of members in the population having a desired attribute (e.g., enzymatically "switchable") from those that have a less desirable attribute (e.g., no detectable enzymatically switchable phenotype or an enzymatically switchable phenotype that is not of a desired dynamic range). A screen can be effected on a population of members using one or more criterion. Screening can be accomplished by means that maintain the recoverability and/or viability of the separated populations (e.g., by cell sorting using, e.g., FACS) or can be accomplished by reducing viability or recoverability of undesired members of the population.

A screen (or selection) can be a "positive screen" or a "negative screen" (also referred to herein as a "positive selection" or a "negative selection", respectively). In a "positive screen" members exhibiting a desirable attribute are selected according to the presence of a positive signal (e.g., the presence of a detectable signal, growth in the presence of an agent that inhibits growth of members deficient in a desirable attribute, etc.). In "negative screen" members exhibiting a desirable attribute are selected according to a decreased or undetectable signal (e.g., a relatively decreased or undetectable signal; reduced growth in the presence of an agent that inhibits growth of members exhibiting a desirable attribute, etc.)

As used herein, "contacting" has its normal meaning and refers to combining two or more entities (e.g., a target protein, a candidate ABP, an enzyme, etc.). Contacting can occur in, for example, a test tube or other container (e.g., combining of two or more agents [e.g., a cleaving agent (e.g., an enzyme) and a cell expressing a peptide display scaffold]), in a cell-based system (e.g., contacting of a target protein and/or cleaving agent (e.g., enzyme) with an ABP displayed on a cell surface), or in a cell-free system (e.g., combining a cleaving agent (e.g., an enzyme) with a cell membranes, synthetic membrane, or other membranes for presentation of a peptide display scaffold without the need for intact cells).

As used herein, a "ligand" refers to a molecule(s) that binds to a binding partner molecule(s), e.g., a substrate, inhibitor, or allosteric regulator binding to an enzyme, and includes natural and synthetic biomolecules, such as proteins, polypeptides, peptides, nucleic acid molecules, carbohydrates, sugars, lipids, lipoproteins, small molecules, natural and synthetic organic and inorganic materials, synthetic polymers, and the like.

"Binding" as used herein generally refers to a covalent or non-covalent interaction between two molecules (referred to herein as "binding partners", e.g., a substrate and an enzyme), which binding is usually specific.

As used herein. "specifically binds" or "binds specifically" refers to interaction between binding partners such that the binding partners bind to one another, but do not bind other molecules that may be present in the environment (e.g., in a biological sample, in tissue) at a significant or substantial level under a given set of conditions (e.g., physiological conditions).

As used herein, "fluorescent group" refers to a molecule that, when excited with light having a selected wavelength, emits light of a different wavelength. Fluorescent groups may also be referred to as "fluorophores".

As used herein, the term "display scaffold" refers to a polypeptide which when expressed in a host cell is presented on an extracellularly accessible surface of the host cell and provides for presentation of an operably linked heterologous polypeptide. For example, display scaffolds find use in the methods disclosed herein to facilitate screening of candidate ABPs. Display scaffolds can be provided such that a heterologous polypeptide of interest can be readily released from the display scaffold, e.g. by action of a protease that facilitates cleavage of the fusion protein and release of a candidate ABP from the display scaffold.

The term "detecting" or "assessing" includes any form of qualitative or quantitative measurement, and includes determining if an element is present or absent. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "detecting," "determining," "measuring," and "assessing." and "assaying" are used interchangeably and include both quantitative and qualitative determinations.

The term "effective amount" or "therapeutically effective amount" means a dosage sufficient to provide for treatment for the disease state being treated or to otherwise provide the desired effect (e.g., reduction in tumor size, reduction in angiogenesis, etc.). The precise dosage will vary according to a variety of factors such as subject-dependent variables (e.g., age, immune system health, etc.), the disease (e.g., the type of cancer or tumor), and the treatment being effected.

The term "treatment site" is meant to refer to a site at which an ABP is designed to be switchable, as described herein, e.g., a site at which a target for one or both TBMs of an ABP and a cleaving agent capable of cleaving a CM of the ABP are co-localized. Treatment sites include tissues that can be accessed by local administration (e.g., injection, infusion (e.g., by catheter), etc.) or by systemic administration (e.g., administration to a site remote from a treatment site). Treatment sites include those that are relatively biologically confined (e.g., an organ, sac, tumor site, and the like).

Activatable Binding Polypeptides

The present disclosure provides activatable binding polypeptides (ABPs) which exhibit "activatable" binding, also referred to as "switchable" binding, to a target protein. ABPs generally include a target binding moiety ("TBM"), a masking moiety ("MM") and a cleavable moiety ("CM"). In some embodiments, the CM contains an amino acid sequence that serves as a substrate for a protease of interest. In other embodiments, the CM provides a cysteine-cysteine disulfide bond that is cleavable by reduction.

Figure 35:
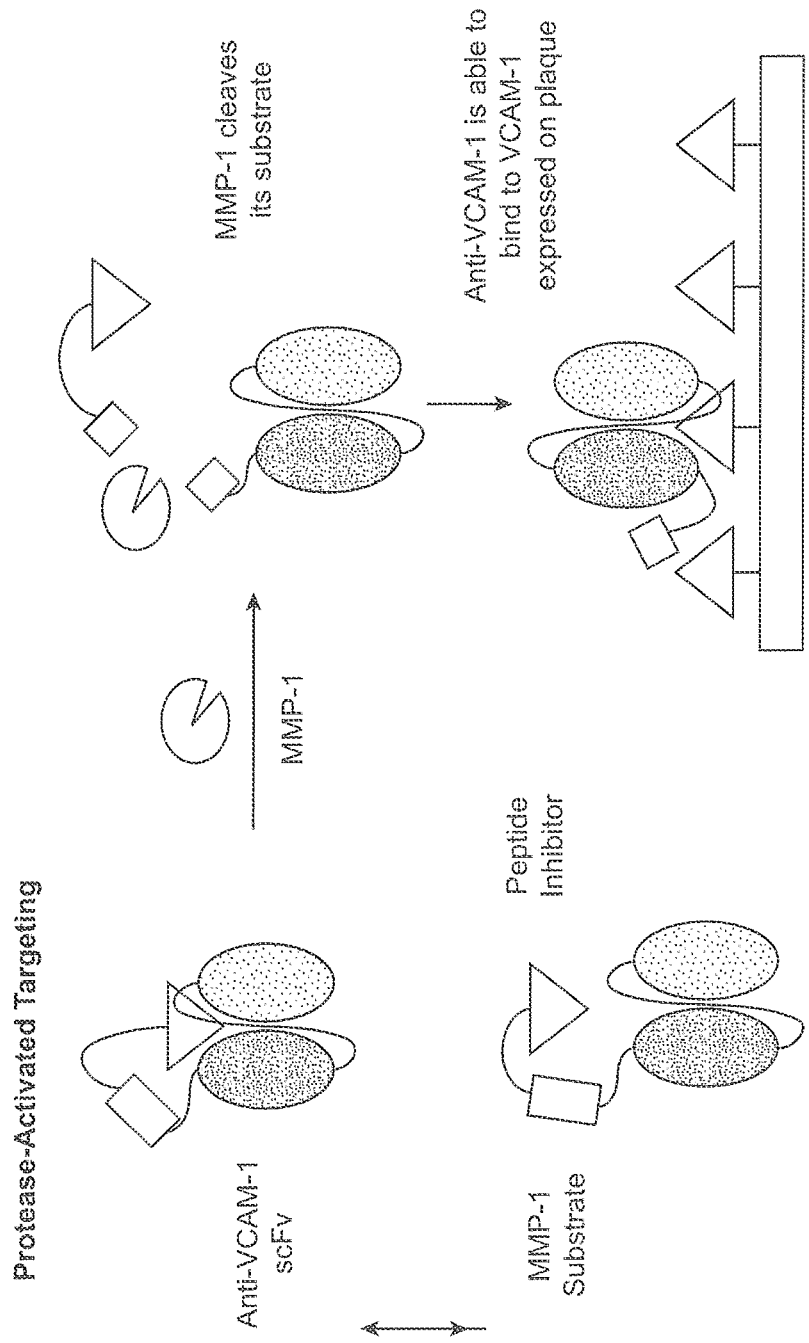
FIG. 35 provides a schematic showing activation and target binding of an ABP with a TBM comprising an anti-VCAM-1 scFV ABD and a CM comprising an MMP-1 substrate.
Figure 36:
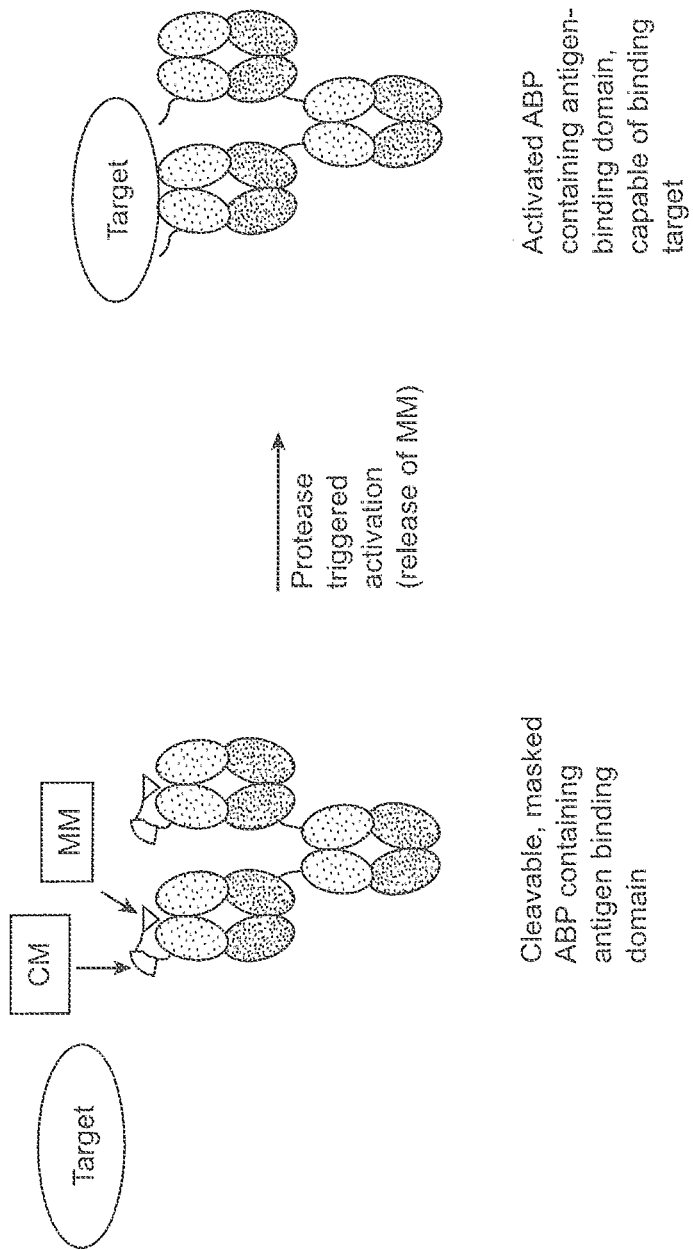
FIG. 36 shows a protease-activated ABP containing an antigen binding domain (ABD).

Schematics of ABPs are provided in FIGS. 1, 35 and 36, the latter two schematically representing the embodiments where the TBM of the ABP contains an antigen-binding domain (ABD). As illustrated in FIGS. 1, 35, and 36 the elements of the ABP are arranged such that the CM is positioned such that in a cleaved state (or relatively "active" state) and in the presence of a target, the TBM binds a target, while in an uncleaved state (or relatively "inactive" state) in the presence of the target, binding of the TBM to the target is inhibited due to the conformation of the ABP, which can involve "masking" of the TBM by the MM. As used herein, the term "cleaved state" refers to the condition of the ABP following cleavage of the CM by a protease and/or reduction of a cysteine-cysteine disulfide bond of the CM. The term "uncleaved state." as used herein, refers to the condition of the ABP in the absence of cleavage of the CM by a protease and/or in the absence reduction of a cysteine-cysteine disulfide bond of the CM. As discussed above, "ABP" is used herein for sake of convenience to refer to ABP in both its uncleaved (or "native") state, as well as in its cleaved state. It will be apparent to the ordinarily skilled artisan that in some embodiments a cleaved ABP may lack an MM due to cleavage of the CM by protease, resulting in release of at least the MM (e.g., where the MM is not joined to the ABP by a covalent bond (e.g., a disulfide bond between cysteine residues).

By "activatable" or "switchable" is meant that the ABP exhibits a first level of binding to a target when in a native or uncleaved state (i.e., a first conformation), and a second level of binding to the target in the cleaved state (i.e., a second conformation), where the second level of target binding is greater than the first level of binding. In general, access of target to the TBM of the ABP is greater in the presence of a cleaving agent capable of cleaving the CM than in the absence of such a cleaving agent. Thus, in the native or uncleaved state the TBM is "masked" from target binding (i.e., the rust conformation is such that it interferes with access of the target to the TBM), and in the cleaved state the TBM is "unmasked" to target binding.

The CM and TBM of the ABP may be selected so that the TBM represents a binding moiety for a target of interest, and the CM represents a substrate for a protease that is co-localized with the target at a treatment site in a subject. Alternatively or in addition, the CM is a cysteine-cysteine disulfide bond that is cleavable as a result of reduction of this disulfide bond. ABPs contain at least one of a protease-cleavable CM or a cysteine-cysteine disulfide bond, and in some embodiments include both kinds of CMs. The ABPs disclosed herein find particular use where, for example, a protease capable of cleaving a site in the CM is present at relatively higher levels in target-containing tissue of a treatment site than in tissue of non-treatment sites.

Stated differently, the CM-TBM pair of the ABPs is designed to exploit the elevated levels of a protease co-localized with a target. Thus. ABP can be designed so that they are predominantly enzymatically activated (and thus exhibit higher levels of target binding) at a treatment site than at non-treatment sites in a subject. ABPs can thus provide for reduced toxicity and/or adverse side effects that can result from binding of the TBM at non-treatment sites. Where the ABP contains a CM that is cleavable by a reducing agent that facilitates reduction of a disulfide bond, the TBMs of such ABPs may selected to exploit activation of a TBM where a target of interest is present at a desired treatment site characterized by elevated levels of a reducing agent, such that the environment is of a higher reduction potential than, for example, an environment of a non-treatment site.

In general, an ABP can be designed by selecting a TBM of interest and constructing the remainder of the ABP so that, when conformationally constrained, the MM provides for masking of the TBM. Structural design criteria to be taken into account to provide for this functional feature. For example, where the ABP includes an MM, a at least one CM, and a linker, the linker is generally selected so that it is at least 1.5 to 2 times, usually at least 2 times, the length representative of the distance from a target binding site of the TBM to a terminus of the TBM to which the remainder of the construct is to be attached.

Dual-target binding ABPs are of particular interest in the present disclosure. Such dual target binding ABPs contain two TBMs, which may bind the same or different target, and wherein at least one TBM serves as dual function of target binding and "masking". As noted above, such dual target binding ABPs generally contain two TBMs, wherein at least one of the TBMs acts as a masking moiety (MM) for the other TBM and/or the two TBMs serves as masking moieties for one another, such that in the uncleaved conformation, the ABP exhibits reduced binding to a target for at least one of the TBMs relative to when the ABP is in the cleaved conformation. Thus "ABP" in this embodiment encompasses a polypeptide that contains a first target binding moiety (TBM), a second TBM, and a cleavable moiety (CM), wherein the first and second TBMs interact to "mask" binding of at least one of the TBMs to target (i.e., the first and/or second TBMs act as a masking moiety (MM) for target binding). The TBMs can include TBMs that bind to different targets (e.g., VEGF and fibroblast growth factor (FGF), e.g., FGF2). Each TBM can be independently selected so that each contains 1 or more actives sites for binding to the target.

Figure 20:
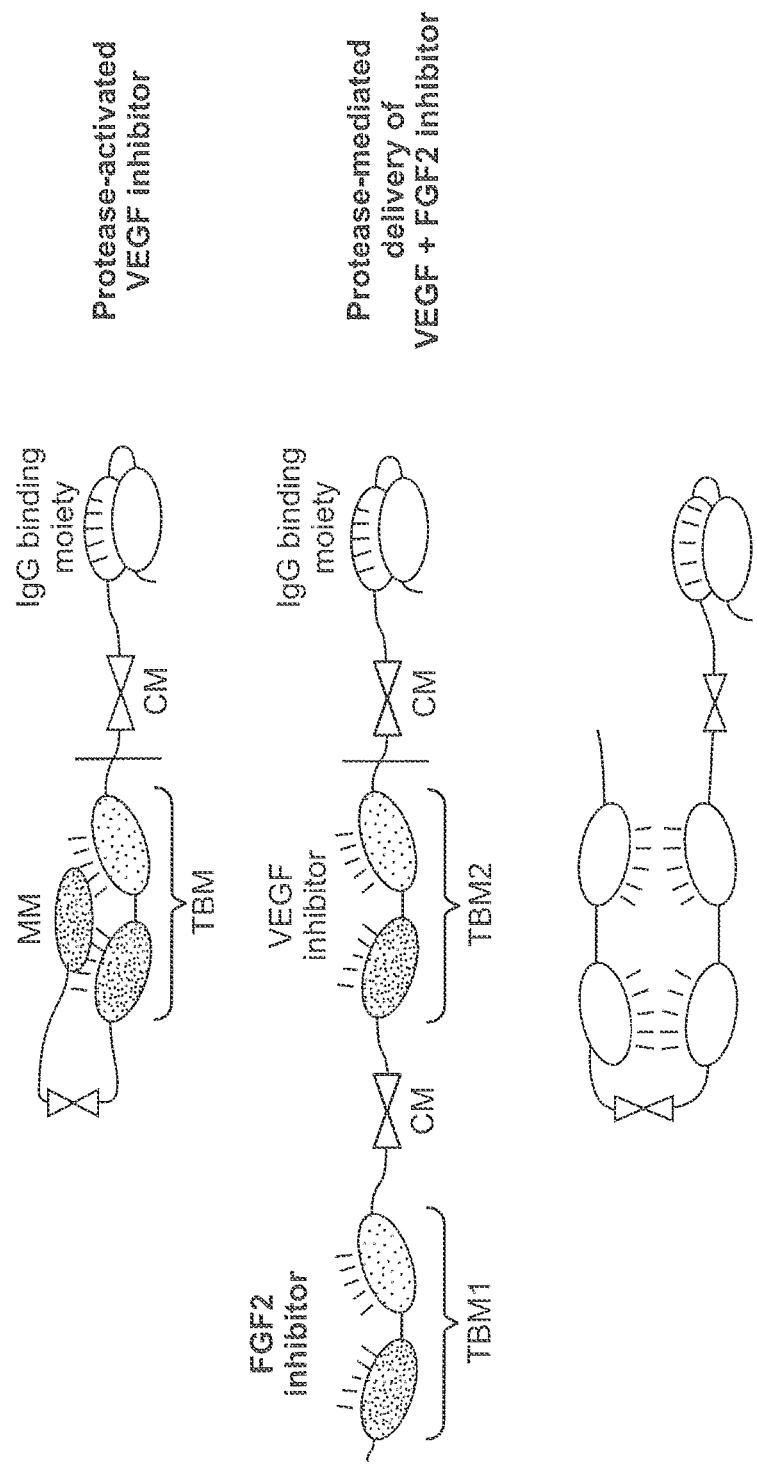
FIG. 20 is a schematic showing exemplary ABPs of the present disclosure.

FIG. 20 is a schematic showing an exemplary ABP of the present disclosure having two TBMs which can serve the dual function of binding their respective targets when the ABP is cleaved and masking the ABP from binding to one or both targets of the TBMs when the ABP is uncleaved. In the upper portion of FIG. 20, an "MM" is shown, where the MM is a first TBM having a single binding site. In the center portion of FIG. 20, an ABP having a first TBM and a second TBM (arbitrarily labeled as TBM1 and TBM2) with a cleavable moiety (CM) positioned between the two TBMs. In a switchable, uncleaved conformation (i.e., when the CM is intact such that it is uncleaved by a corresponding enzyme, and/or containing an unreduced cysteine-cysteine disulfide bond), as illustrated in the lower portion of FIG. 20. TBM1 interacts with TBM2 thus "masking" binding to target to at least TBM1 and in particular embodiments masking target binding to both TBM1 and TBM2. When cleaved, each of the TBMs are "unmasked" and thus are free to bind their respective targets.

Dual target binding TBMs can be designed so as to have a CM cleavable by a cleaving agent that is co-localized in a target tissue with one or both of the targets capable of binding to the TBMs of the ABP. The disclosure further contemplates multiple "units" of TBM1-TBM2 domains, such that cleavage of a single ABP by the cleaving agent results in release of multiple target binding fragments.

As exemplified in FIG. 20, a second CM can be positioned between the "masked" TBMs and a moiety of interest that can provide an additional desired function, such as targeting or serum half-life extension (as exemplified by a serum IgGbinding protein). This second CM can be susceptible to cleavage by the same or different cleaving agents.

It will be apparent to the ordinarily skilled artisan that in some embodiments a cleaved ABP may no longer contain two TBMs as described above due to cleavage of the CM, e.g, by a protease. Where the ABP includes both a protease-cleavable CM and a CM that includes a disulfide bond, cleavage of the protease cleavable CM may leave the disulfide bond intact, and thus the ABP in the cleaved form may retain two the TBMs, but in an "unmasked" configuration allowing for target binding. Exemplary ABPs are described in more detail below.

ABPs exhibiting a switchable phenotype of a desired dynamic range for target binding in a cleaved versus uncleaved conformation are of particular interest. The term "dynamic range" as used herein generally refers to a ratio of (a) a maximum detected level of a parameter under a first set of conditions to (b) a minimum detected value of that parameter under a second set of conditions. For example, in the context of an ABP, the dynamic range refers to the ratio of (a) a maximum detected level of target protein binding to an ABP in the presence of protease capable of cleaving the CM of the ABP to (b) a minimum detected level of target protein binding to an ABP in the absence of the protease. The dynamic range of an ABP can be calculated as the ratio of the equilibrium dissociation constant of an ABP cleaving agent (e.g., enzyme) treatment to the equilibrium dissociation constant of the ABP cleaving agent treatment. The greater the dynamic range of an ABP, the better the "switchable" phenotype of the ABP. ABPs having relatively higher dynamic range values (e.g., greater than 1) exhibit more desirable switching phenotypes such that target protein binding by the ABP occurs to a greater extent (e.g., predominantly occurs) in the presence of a cleaving agent (e.g., enzyme) capable of cleaving the CM of the ABP than in the absence of a cleaving agent.

ABPs can be provided in a variety of structural configurations provided that the TBM, MM and CM are operably positioned in the ABP such that a switchable phenotype is provided. Exemplary formulae for ABPs are provided below. It is specifically contemplated that the N- to C-terminal order of the TBM, MM and CM may be reversed within a ABP. It is also specifically contemplated that the CM and MM may overlap in amino acid sequence, e.g., such that the CM is contained within the MM.

For example, ABPs can be represented by the following formula (in order from an amino ("N") terminal region to carboxyl ("C") terminal region:

(MM)-(CM)-(TBM)

(TBM)-(CM)-(MM)

where MM is a masking moiety, CM is a cleavable moiety, and TBM is a target binding moiety. It should be noted that although MM and CM are indicated as distinct components in the formula above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that may be positioned N-terminal or C-terminal to the ABP elements. In some embodiments, the dual target-binding ABP is such that the MM is a second TBM. It is understood that throughout this disclosure, the formulae provided encompass such dual target-binding ABPs wherein "MM" in the formula is TBM1 and "TBM" is TBM2, where TBM1 and TBM2 are arbitrary designations for first and second TBMs. and where the target capable of binding the TBMs may be the same or different target, or the same or different binding sites of the same target.

It is understood that generally ABPs can exhibit a switchable phenotype as a result of folding of the ABP so that access of target to the TBM is inhibited by at least the MM. Thus, in many embodiments it may be desirable to insert one or more linkers, e.g., flexible linkers, into the ABP construct so as to provide for flexibility at one or more of the MM-CM junction, the CM-TBM junction, or both. For example, the TBM, MM, and/or CM may not contain a sufficient number of residues (e.g., Gly. Ser, Asp. Asn, especially Gly and Ser, particularly Gly) to provide the desired flexibility. As such, the switchable phenotype of such ABP constructs may benefit from introduction of one or more amino acids to provide for a flexible linker. In addition, as described below, where the ABP is provided as a conformationally constrained construct, a flexible linker can be operably inserted to facilitate formation and maintenance of a cyclic structure in the uncleaved ABP.

For example, in certain embodiments an ABP comprises one of the following formulae (where the formula below represent an amino acid sequence in either N- to C-terminal direction or C- to N-terminal direction):

(MM)-$L_1$-(CM)-(TBM)

(MM)-(CM)-$L_1$-(TBM)

(MM)-$L_1$-(CM)-$L_2$-(TBM)

cyclo[$L_1$-(MM)-$L_2$-(CM)-$L_3$-(TBM)]

wherein MM, CM, and TBM are as defined above; wherein $L_1$, $L_2$, and $L_3$ are each independently and optionally present or absent, are the same or different flexible linkers that include at least 1 flexible amino acid (e.g., Gly); and wherein "cyclo" where present the ABP is in the form of a cyclic structure due to the presence of a disulfide bond between a pair of cysteines in the ABP. In addition, the formulae above provide for additional amino acid sequences that may be positioned N-terminal or C-terminal to the ABP elements. It should be understood that in the formula cyclo[$L_1$-(MM)-$L_2$-(CM)-$L_3$-(TBM)], the cysteines responsible for the disulfide bond may be positioned in the ABP to allow for one or two "tails." thereby generating a "lasso" or "omega" structure when the ABP is in a disulfide-bonded structure (and thus conformationally constrained state). The amino acid sequence of the tail(s) can provide for additional ABP features, such as binding to a target receptor to facilitate localization of the ABP, increasing serum half-life of the ABP, and the like. Targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HSA).

As noted above, the formula above encompass dual target-binding ABPs such that "MM" in the formula is TBM1 and "TBM" is TBM2, where TBM1 and TBM2 are arbitrary designations for first and second TBMs. and where the target capable of binding the TBMs may be the same or different target, or the same or different binding sites of the same target. The disclosure further provides that the ABPs can include a second CM, such that the second CM is the same of different and provides for cleavable release of a moiety of interest (e.g., a targeting moiety, a serum half-life extending moiety, a moiety for immobilizing the ABP on a support and the like).

Linkers suitable for use in ABPs are generally ones that provide flexibility of the ABP to facilitate a "masked" conformation. Such linkers are generally referred to as "flexible linkers". Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, (GSGGS: SEQ ID NO: $1)_n$ and (GGGS: SEQ ID NO: $2)_n$, where n is an integer of at least one), glycine-alanine polymers, alanine-serine polymers, and other flexible linkers known in the art. Glycine and glycine-serine polymers are of interest since both of these amino acids are relatively unstructured, and therefore may be able to serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Exemplary flexible linkers include, but are not limited Gly-Gly-Ser-Gly: SEQ ID NO: 3, Gly-Gly-Ser-Gly-Gly: SEQ ID NO: 4, Gly-Ser-Gly-Ser-Gly: SEQ ID NO: 5. Gly-Ser-Gly-Gly-Gly: SEQ ID NO: 6, Gly-Gly-Gly-Ser-Gly: SEQ ID NO: 7. Gly-Ser-Ser-Ser-Gly: SEQ ID NO: 8, and the like. The ordinarily skilled artisan will recognize that design of an ABP can include linkers that are all or partially flexible, such that the linker can include a flexible linker as well as one or more portions that confer less flexible structure to provide for a desired ABP structure.

In addition to the element described above, the ABPs can contain additional elements such as, for example, amino acid sequence N- or C-terminal of the ABP. For example, ABPs can include a targeting moiety to facilitate delivery to a cell or tissue of interest. Moreover, in the context of the ABP libraries discussed further below, the ABP can provided in the context of a scaffold protein to facilitate display of the ABP on a cell surface.

Exemplary basic elements of ABPs are described in more detail below.

Target Binding Moiety (TBM)

The target binding moiety (TBM) of ABPs can include any of a variety of known amino acid sequences that are capable of binding, usually capable of specifically binding, a target, usually a protein target, of interest. For example, the TBM can be selected to include the amino acid sequence of a binding partner of a target protein of interest, where binding of the binding partner and target provides for a desired biological effect, e.g., inhibition of activity of the target protein and/or detection of a target protein.

Exemplary classes of target proteins for which amino acid sequences of binding partners (e.g., inhibitors) are known include, but are not necessarily limited tog cell surface receptors and secreted binding proteins (e.g., growth factors), soluble enzymes, structural proteins (e.g. collagen, fibronectin) and the like. In specifically exemplary embodiments, in no way limiting, the TBM is a binding partner for any target as listed in Table 1 below.

TABLE 1

Exemplary TBM targets

| | | | | |
|---|---|---|---|---|
| VEGF-A | HER2/neu | IGF | CD33 | IgE Receptor |
| VEGF-B | DLL4 | IGF1R | CD40 | PDGF-AA |
| VEGF-C | NOTCHR1 | ERBB3 | CD40L | PDGF-BB |
| VEGF-D | IL1B | VCAM-1 | CD44 | PDGFRα |
| VEGFR1 | IL1R | CXCR4 | CD52 | PDGFRβ |
| VEGFR2 | IL2 | CD3 | CD80 | GPIIB/IIIA |
| VEGFR3 | IL4 | CD11a | CD86 | CLAUDIN-3 |
| EGFR | IL6 | CD19 | CTLA4 | CLAUDIN-4 |
| FGF-2 | IL12 | CD20 | TNFα | C5 complement |
| FGFR1 | IL13 | CD22 | TNFR | α4β1 integrin |
| FGFR2 | IL15 | CD25 | TRAIL-R1 | α4β7 integrin |
| FGFR3 | IL18 | CD28 | TRAIL-R2 | F protein of RSV |
| FGFR4 | IL23 | CD30 | IgE | GP IIb/IIIa receptors |
| IL2R | CD41 | | | |

In some embodiments, the TBM comprises a full length antibody or an antibody fragment containing an antigen binding domain, antigen binding domain fragment or an antigen binding fragment of the antibody (e.g., an antigen binding domain of a single chain) which is capable of binding, especially specific binding, to a target of interest, usually a protein target of interest. In this embodiment the TBM contains an antigen binding domain (ABD). A schematic of an ABP containing a TBM that contains an ABD is provided in FIG. 36. In such embodiments, the ABD can be binding polypeptides such as, but not limited to variable or hypervariable regions of light and/or heavy chains of an antibody (VL, VH), variable fragments (Fv), F(ab') 2 fragments, Fab fragments, single chain antibodies (scAb), single chain variable regions (scFv), complementarity determining regions (CDR), or other polypeptides known in the art containing a ABD capable of binding target proteins or epitopes on target proteins. In further embodiments, the TBM may be a chimera or hybrid combination containing a first TBM that contains a ABD and a second TBM that contains a ABD such that each ABD is capable of binding to the same or different target. In some embodiments, the TBM is a bispecific antibody or fragment thereof, designed to bind two different antigens. In some embodiments there is a first MM and a second MM coupled to the first TBM and the second TBM, respectively, in the activatable form. The origin of the ABD can be a naturally occurring antibody or fragment thereof, a non-naturally occurring antibody or fragment thereof, a synthetic antibody or fragment thereof, a hybrid antibody or fragment thereof, or an engineered antibody or fragment thereof.

Figure 37:
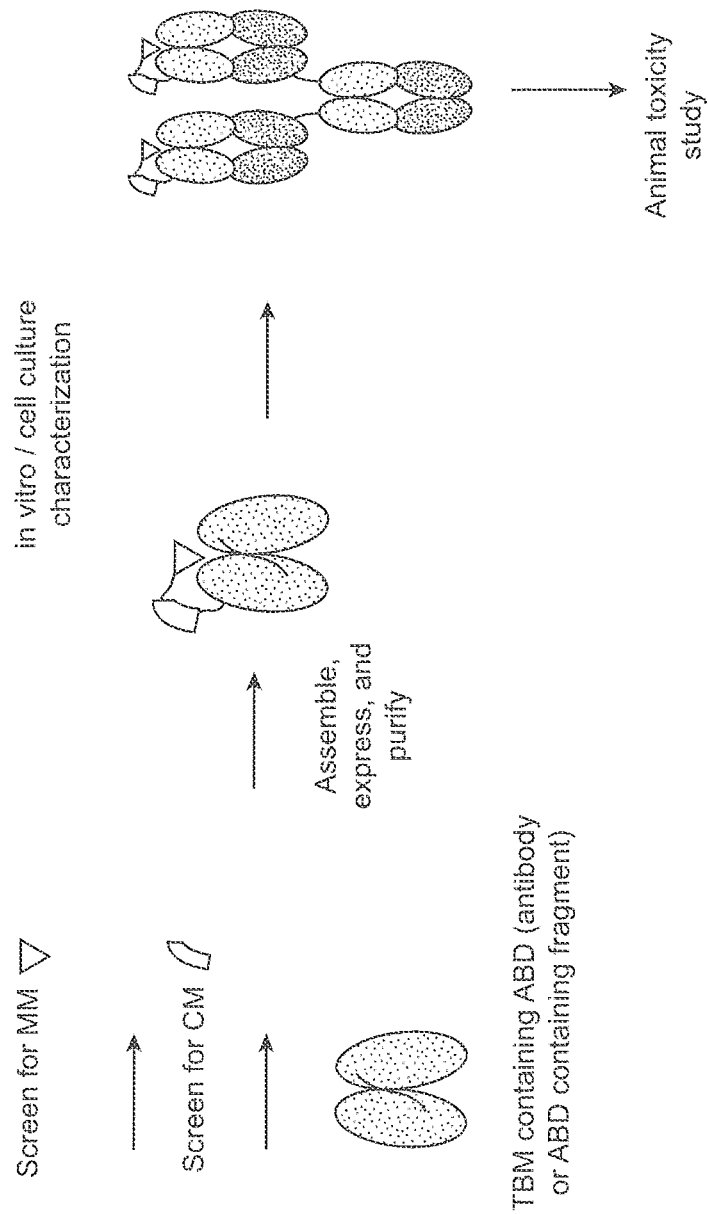
FIG. 37 illustrates a process to produce a protease-activated ABP containing an antigen binding domain (ABD), involving: screening for MMs: screening for CMs; assembling the MM. CM, and TBM containing an ABD; expressing and purifying the assembled construct; and assaying the assembled construct for activity and toxicity in vitro and in vivo.

Methods for generating an antibody for a given target are well known in the art. The structure of antibodies and fragments thereof, variable regions of heavy and light chains of an antibody ($V_H$ and $V_L$), Fv, F(ab')2, Fab fragments, single chain antibodies (scAb), single chain variable regions (scFv), and complementarity determining regions (CDR) are well understood. Methods for generating a polypeptide having a desired antigen-binding domain of a target antigen are known in the art. Methods for modifying antibodies to couple additional polypeptides are also well-known in the art. For instance, peptides such as MMs. CMs or linkers may be coupled to modify antibodies to generate the ABPs and other compositions of the disclosure. ABPs that contain protease-activated ABDs can be developed and produced with standard methods, as described in the schematic in FIG. 37.

Exemplary classes of target proteins for which the TBM contains a ABD include, but are not necessarily limited to, cell surface receptors and secreted binding proteins (e.g growth factors), soluble enzymes, structural proteins (e.g. collagen fibronectin) and the like. The target can be selected from any TBM target as described herein and exemplified but not limited to those in Table 1. In specific exemplary embodiments, in no way limiting, exemplary sources for ABDs are listed in Table 2 below.

TABLE 2

Exemplary sources for ABDs

| Antibody Trade Name (antibody name) | Target |
|---|---|
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Zenapax ™ (daclizumab) | CD25 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Synagis ™ (palivizumab) | F protein of RSV |
| (ipilimumab) | CTLA-4 |
| (tremelimumab) | CTLA4 |

The exemplary sources for ABDs described in Table 2 are discussed in greater detail in the following references which are incorporated by reference herein for their description of one or more of the referenced ABD sources: Remicade™

(infliximab): U.S. Pat. No. 6,015,557, Nagahira K, Fukuda Y, Oyama Y, Kurihara T, Nasu T, Kawashima H, Noguchi C, Oikawa S, Nakanishi T Humanization of a mouse neutralizing monoclonal antibody against tumor necrosis factor-alpha (TNF-alpha). J Immunol Methods. 1999 Jan. 1; 222 (1-2):83-92.) Knight D M, Trinh H, Le J, Siegel S, Shealy D, McDonough M, Scallon B, Moore M A, Vilcek J, Daddona P, et al. Construction and initial characterization of a mouse-human chimeric anti-TNF antibody. Mol Immunol. 1993 November; 30(16):1443-53. Humira™ (adalimumab): Sequence in U.S. Pat. No. 6,258,562. Raptiva™ (efalizumab): Sequence listed in Werther W A, Gonzalez T N, O'Connor S J, McCabe S, Chan B, Hotaling T, Champe M, Fox J A, Jardieu P M, Berman P W, Presta L G. Humanization of an anti-lymphocyte function-associated antigen (LFA)-1 monoclonal antibody and reengineering of the humanized antibody for binding to rhesus LFA-1. J Immunol. 1996 Dec. 1; 157(11):4986-95. Mylotarg™ (gemtuzumab ozogamicin): (Sequence listed in CO MS, Avdalovic N M, Caron P C, Avdalovic M V, Scheinberg D A, Queen C: Chimeric and humanized antibodies with specificity for the CD33 antigen. J Immunol 148:1149, 1991) (Caron P C, Schwartz M A, Co M S, Queen C, Finn R D, Graham M C, Divgi C R, Larson S M, Scheinberg D A. Murine and humanized constructs of monoclonal antibody M195 (anti-CD33) for the therapy of acute myelogenous leukemia. Cancer. 1994 Feb. 1; 73 (3 Suppl):1049-56). Soliris™ (eculizumab): Hillmen P, Young N, Schubert J, Brodsky R, Socié G, Muus P, Röth A, Szer J, Elebute M, Nakamura R, Browne P, Risitano A, Hill A, Schrezenmeier H, Fu C, Maciejewski J, Rollins S, Mojcik C, Rother R, Luzzatto L (2006). "The complement inhibitor eculizumab in paroxysmal nocturnal hemoglobinuria". *N Engl J Med* 355 (12): 1233-43. Tysabri™ (natalizumab): Sequence listed in Leger O J, Yednock T A, Tanner L, Homer H C, Hines D K, Keen S, Saldanha J, Jones S T, Fritz L C, Bendig M M. Humanization of a mouse antibody against human alpha-4 integrin: a potential therapeutic for the treatment of multiple sclerosis. Hum Antibodies. 1997; 8(1):3-16 Synagis™ (palivizumab): Sequence listed in Johnson S, Oliver C, Prince G A, Hemming V G, Pfarr D S, Wang S C, Dormitzer M, O'Grady J, Koenig S, Tamura J K, Woods R, Bansal G, Couchenour D, Tsao E, Hall W C, Young J F. Development of a humanized monoclonal antibody (MEDI-493) with potent in vitro and in vivo activity against respiratory syncytial virus. J Infect Dis. 1997 November; 176(5):1215-24. Ipilimumab: *J. Immunother:* 2007; 30(8): 825-830 Ipilimumab (Anti-CTLA4 Antibody) Causes Regression of Metastatic Renal Cell Cancer Associated With Enteritis and Hypophysitis; James C, Yang, Marybeth Hughes, Udai Kammula, Richard Royal, Richard M. Sherry, Suzanne L, Topalian, Kimberly B, Suri, Catherine Levy, Tamika Allen, Sharon Mavroukakis, Israel Lowy, Donald E. White, and Steven A. Rosenberg Tremelimumab: *Oncologist* 2007; 12; 873-883; Blocking Monoclonal Antibody in Clinical Development for Patients with Cancer; Antoni Ribas, Douglas C, Hanson, Dennis A, Noe, Robert Millham, Deborah J, Guyot, Steven H, Bernstein, Paul C, Canniff, Amarnath Sharma and Jesus Gomez-Navarro.

In some embodiments, the TBM of an ABP (including dual target-binding ABPs) comprises multiple active sites (e.g., 1, 2, 3, or more) for binding a target. These active sites may have the same or different amino acid sequences, and are usually designed to bind to different binding sites on a target of interest such that binding of a first active site of a TBM does not substantially interfere with binding of a second active site of the TBM to the target. In certain embodiments the active sites are separated by an amino acid linker sequence. A TBM comprising multiple active sites is represented schematically in FIGS. 17-19. ABPs can further include multiple TBM-MM "units", which may optionally be separated by additional CMs so that upon exposure to a cleaving agent, the one or more TBMs are unmasked. Dual target-binding ABPs can include multiple TBM1-TBM2 units, which units can be separated by one or more CMs positioned on either "arm" of the dual target-binding ABP, and which may be cleavable by the same or different cleaving agent.

In certain embodiments, the TBM of an ABP can contain more than one ABD. In some embodiments the ABDs can be derived from bispecific antibodies or fragments thereof. In other embodiments the ABP can be synthetically engineered so as to incorporate ABDs derived from two different antibodies or fragments thereof. In such embodiments, the ABDs can be designed to bind two different targets, two different antigens, or two different epitopes on the same target. A TBM containing multiple ABDs capable of binding more than one target site are usually designed to bind to different binding sites on a target or targets of interest such that binding of a first ABD of the TBM does not substantially interfere with binding of a second ABD of the TBM to a target. ABPs containing multiple ABDs can further include multiple ABD-MM "units", which may optionally be separated by additional CMs so that upon exposure to a cleaving agent, the ABDs are unmasked. Dual target-binding ABPs can include multiple ABD1-ABD2 units, which units can be separated by one or more CMs positioned on either "arm" of the dual target-binding ABP, and which may be cleavable by the same or different cleaving agent.

In general, ABPs contemplated by the present disclosure are those having a TBM capable of binding an extracellular target, usually an extracellular protein target. However, ABPs can also be designed such that they are capable of cellular uptake and are designed to be switchable inside a cell.

Masking Moiety (MM)

The masking moiety (MM) of an ABP generally refers to an amino acid sequence positioned in the ABP such that in an uncleaved state, even in the presence of a target for the TBM, the MM interferes with binding of the TBM to the target. However, in the cleaved state of the ABP, the MM's interference with target binding to the TBM is reduced, thereby allowing greater access of the TBM to the target and providing for target binding. Thus, the MM is one that when the ABP is uncleaved provides for "masking" of the TBM from target binding, but does not substantially or significantly interfere or compete for binding for target to the TBM when the ABP is in the cleaved conformation. Thus, the combination of the MM and the CM facilitates the "switchable" phenotype, with the MM decreasing binding of target when the ABP is uncleaved, and cleavage of the CM by protease providing for increased binding of target.

The structural properties of the MM will vary according to a variety of factors such as the minimum amino acid sequence required for interference with TBM binding to target, the target protein-TBM binding pair of interest, the length of the TBM, the length of the CM, whether the CM is positioned within the MM and also serves to "mask" the TBM in the uncleaved ABP, the presence or absence of linkers, the presence or absence of a cysteine within or flanking the TBM that is suitable for providing a CM of a cysteine-cysteine disulfide bond, and the like.

In some embodiments, the MM is coupled to the ABP by covalent binding. In one such embodiment, the coupling is to a C-terminus of the ABP. In another embodiment, the coupling is by cross-linking to an internal amino acid of the ABP. In another embodiment, the ABP composition is masked by binding the MM to an N-terminus of the ABP. In yet another embodiment, the ABP is coupled to the MM by cysteine-cysteine disulfide bridges between the MM and the ABP.

The MM can be provided in a variety of different forms. For example, the MM can be selected to be a known binding partner of the TBM, provided that the MM binds the TBM with less affinity and/or avidity than the target protein to which the TBM is designed to bind following cleavage of the CM so as to reduce interference of MM in target-TBM binding. Stated differently, as discussed above, the MM is one that "masks" the TBM from target binding when the ABP is uncleaved, but does not substantially or significantly interfere or compete for binding for target when the ABP is in the cleaved conformation. In a specific embodiment, the TBM and MM do not contain the amino acid sequences of a naturally-occurring binding partner pair, such that at least one of the TBM and MM does not have the amino acid sequence of a member of a naturally occurring binding partner. In a specific embodiment, the TBM and MM are other than a binding partner pair of TNF-alpha and a complete or partial extracellular domain of TNF receptor, or derivatives thereof, that act as a binding partner for TNF-alpha. In another specific embodiment, the TBM and MM are other than a binding partner pair of TNF-alpha and the viral T2 protein, or derivatives thereof, that act as a binding partner for TNF-alpha. In another specific embodiment, the TBM and MM are other than a binding partner pair of FasL and a complete or partial extracellular domain of a Fas receptor or derivatives thereof, that act as a binding partner for FasL. In another specific embodiment, the TBM and MM are other than a binding partner pair of FasL and a viral protein or derivatives thereof, that act as a binding partner for FasL. In another specific embodiment, the TBM and MM are other than a binding partner pair of FasL and an antibody or fragment thereof having binding affinity for FasL.

For example, the TBM and MM can also be selected so they are not natural binding partners, where the MM may be, for example, a modified binding partner for the TBM which contains amino acid changes that at least slightly decrease affinity and/or avidity of binding to the TBM such that, following cleavage, the MM does not substantially or significantly interfere with TBM-target binding. Because ABPs can be based on known binding partners for which the amino acid sequences that facilitate binding are known, production of such MM-TBM pairs is well within the skill of the ordinarily skilled artisan. For example, the amino acid sequences that facilitate interaction of VEGF and a VEGF inhibitor are well known, and are exemplified herein.

The MM can be identified through a screening procedure from a library of candidates ABPs having variable MMs. For example, a TBM and CM can be selected to provide for a desired enzyme/target combination, and the amino acid sequence of the MM can be identified by the screening procedure described below to identify an MM that provides for a switchable phenotype. For example, a random peptide library (e.g., from about 4 to about 40 amino acids or more) may be used in the screening methods disclosed herein to identify a suitable MM. A random peptide library may also be utilized in connection with the targeted introduction of cysteine residues to favor disulfide bond formation and facilitate formation of a conformationally constrained, "cyclic" ABP structure.

In other embodiments. MMs with specific binding affinity for an antigen binding domain (ABD) can be identified through a screening procedure that includes providing a library of peptide scaffolds consisting of candidate MMs wherein each scaffold is made up of a transmembrane protein and the candidate MM. The library is then contacted with an entire or portion of TBM such as a full length antibody, a naturally occurring antibody fragment, or a non-naturally occurring fragment containing an antigen binding domain (also capable of binding the target of interest), and identifying one or more candidate MMs having detectably bound ABD. Screening can include one more rounds of magnetic-activated sorting (MACS) or fluorescence-activated sorting (FACS).

In this manner, ABPs having an MM that inhibits binding of the TBM to the target in an uncleaved state and allows binding of the TBM to the target in a cleaved state can be identified, and can further provide for selection of an ABP having an optimal dynamic range for the switchable phenotype. Methods for identifying ABPs having a desirable switching phenotype are described in more detail below.

Alternatively, the MM may not specifically bind the TBM, but rather interfere with TBM-target binding through non-specific interactions such as steric hindrance. For example, the MM may be positioned in the uncleaved ABP such that the folded ABP allows the MM to "mask" the TBM through charge-based interaction, thereby holding the MM in place to interfere with target access to the TBM.

ABPs can also be provided in a conformationally constrained structure, such as a cyclic structure, to facilitate the switchable phenotype. This can be accomplished by including a pair of cysteines in the ABP construct so that formation of a disulfide bond between the cysteine pairs places the ABP in a loop or cyclic structure. Thus the ABP remains cleavable by the desired protease while providing for inhibition of target binding to the TBM. Upon cleavage of the CM, the cyclic structure is "opened", allowing access of target to the TBM. FIG. 6 provides a schematic of an uncleaved ABP which is conformationally constrained by a disulfide bond (represented by a dashed line) between cysteine residues positioned in a region at or near the ends of a ABP (where the "ends" refers to the ABP in the linear form prior to disulfide bond formation). Such cyclic ABPs can be designed or be optimized (e.g., using the screening methods described below) such that in the uncleaved ABP accessibility of the CM to its corresponding protease is greater than accessibility of the TBM to target protein binding. It should be noted that target access to the TBM may also occur following reduction of the disulfide bond.

The cysteine pairs can be positioned in the ABP at any position that provides for a conformationally constrained ABP, but that, following CM cleavage, does not substantially or significantly interfere with target biding to the TBM. For example, the cysteine residues of the cysteine pair are positioned in the MM and a linker flanked by the MM and TBM, within a linker flanked by the MM and TBM, or other suitable configurations. For example, the MM or a linker flanking an MM can include one or more cysteine residues, which cysteine residue forms a disulfide bridge with a cysteine residue positioned opposite the MM when the ABP is in a folded state. It is generally desirable that the cysteine residues of the cysteine pair be positioned outside the TBM so as to avoid interference with target binding following cleavage of the ABP. Where a cysteine of the cysteine pair to be disulfide bonded is positioned within the TBM, it is desirable that it be positioned to as to avoid interference with TBM-target binding following exposure to a cleaving agent, e.g., after exposure to a reducing agent.

Exemplary ABPs capable of forming a cyclic structure by disulfide bonds between cysteines can be of the general formula (which may be from either N- to C-terminal or from C- to N-terminal direction):

$X_{n1}$-($Cys_1$)-$X_m$-CM-TBM-($Cys_2$)-$X_{n2}$ $X_{n1}$-cyclo[($Cys_1$)-$X_m$-CM-TBM-($Cys_2$)]-$X_{n2}$ wherein

- $X_{n1}$ and $X_{n2}$ are independently, optionally present or absent and, when present, independently represent any amino acid, and can optionally include an amino acid sequence of a flexible linker (e.g., at least one Gly, Ser, Asn, Asp, usually at least one Gly or Ser, usually at least one Gly), and $n_1$ and $n_2$ are independently selected from s zero or any integer, usually nor more than 1, 2, 3, 4, 5, 6, 7, 8, 9 or 10;
- $Cys_1$ and $Cys_2$ represent first and second cysteines of a pair capable of forming a disulfide bond;
- $X_m$ represents amino acids of a masking motif (MM), where X is any amino acid, wherein $X_m$ can optionally include a flexible linker (e.g., at least one Gly, Ser, Asn, Asp, usually at least one Gly or Ser, usually at least one Gly); and where m is an integer greater than 1, usually 2, 3, 4, 5, 6, 7, 8, 9, 10 or more (as described above);
- CM represents a cleavable moiety (as described herein); and
- TBM represents a target binding moiety (as described herein).

As used in the formula above, “cyclo” indicates a disulfide bond in the ABP that provides for a cyclic structure of the ABP. Furthermore, the formula above contemplate dual target-binding ABPs wherein “MM” refers to a TBM1 and “TBM” refers to TBM2, where TBM1 and TBM2 are arbitrary designations for first and second TBMs, and where the target capable of binding the TBMs may be the same or different target, or the same or different binding sites of the same target. In such embodiments, the TBM1 and/or TBM2 acts as a masking moiety to interfere with target binding to an uncleaved dual target-binding ABP.

As illustrated above, the cysteines can thus be positioned in the ABP allow for one or two “tails” (represented by $X_{n1}$ and $X_{n2}$ above), thereby generating a “lasso” or “omega” structure when the ABP is in a disulfide-bonded structure (and thus conformationally constrained state). The amino acid sequence of the tail(s) can provide for additional ABP features, such as binding to a target receptor to facilitate localization of the ABP.

For example, in an ABP containing an exemplary VEGF binder as a TBM, the TBM can comprise the amino acid sequence NFGYGKWEWDYGKWLEKVGGC: SEQ ID NO: 10, and a corresponding MM comprises the amino acid sequence PEWGCG: SEQ ID NO: 11. Further specific examples are provided in the Examples section below.

In certain specific embodiments, the MM does not inhibit cellular entry of the ABP.

Cleavable Moiety (CM)

The cleavable moiety (CM) of the ABP may include an amino acid sequence that can serve as a substrate for a protease, usually an extracellular protease (i.e., other than an intracellular protease). Optionally, the CM comprises a cysteine-cysteine pair capable of forming a disulfide bond, which can be cleaved by action of a reducing agent. The CM is positioned in the ABP such that when the CM is cleaved by a cleaving agent (e.g., a protease substrate of a CM is cleaved by the protease and/or the cysteine-cysteine disulfide bond is disrupted via reduction by exposure to a reducing agent), in the presence of a target, resulting in a cleaved state, the TBM binds the target, and in an uncleaved state, in the presence of the target, binding of the TBM to the target is inhibited by the MM. It should be noted that the amino acid sequence of the CM may overlap with or be included within the MM, such that all or a portion of the CM facilitates “masking” of the TBM when the ABP is in the uncleaved conformation.

As discussed above, the CM may be selected based on a protease that is co-localized in tissue with the desired target of the TBM of the ABP. A variety of different conditions are known in which a target of interest is co-localized with a protease, where the substrate of the protease is known in the art. For example, the target tissue can be a cancerous tissue, particularly cancerous tissue of a solid tumor. There are many reports in the literature of increased levels of proteases having known substrates in a number of cancers, e.g., solid tumors. See. e.g., La Rocca et al. (2004) British J. of Cancer 90(7): 1414-1421. Furthermore, anti-angiogenic targets, such as VEGF, are known. As such, where the TBM of an ABP is selected such that it is capable of binding an anti-angiogenic target such as VEGF, a suitable CM will be one which comprises a peptide substrate that is cleavable by a protease that is present at the cancerous treatment site, particularly that is present at elevated levels at the cancerous treatment site as compared to non-cancerous tissues. For example, the TBM of an ABP can be a polypeptide, peptide, or antigen binding domain (ABD) that binds VEGF and the CM can be a matrix metalloprotease (MMP) substrate, and thus is cleavable by an MMP.

Exemplary substrates can include but are not limited to substrates cleavable by one or more of the following enzymes: MMP-1, MMP-2, MMP-3, MMP-8, MMP-9, MMP-14, PLASMIN, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE.

Alternatively or in addition, the TBM of an ABP can be one that binds VEGF and the CM can involve a disulfide bond of a cysteine pair, which is thus cleavable by a reducing agent such as, for example, a cellular reducing agent such as glutathione (GSH), thioredoxins, NADPH, flavins, ascorbate, and the like, which can be present in large amounts in tissue of or surrounding a solid tumor.

Exemplary ABPs

In certain embodiments the ABP is an activatable antibody or activatable antibody fragment that includes a TBM, a CM, and a MM. In such embodiments the TBM comprises an ABD or ABD fragment. Non limiting exemplary activatable antibody compositions include a MMP-9 activatable, masked anti-VEGF scFv, a MMP-9 activatable, masked anti-VCAM scFv, and a MMP-9 activatable masked anti-CTLA4. These are provided by way of example only and such enzyme activatable masked antibody ABPs could be designed to any target as listed in but not limited to those in Table 1 and by using any antibody as listed in but not limited to those in Table 2.

Methods and Compositions for Identifying and/or Optimizing ABPs

Methods for identifying and/or optimizing ABPs, as well as compositions useful in such methods, are described below.

Libraries of ABPs or Candidate ABPs Displayed on Replicable Biological Entities

In general, the screening methods to identify an ABP and/or to optimize an ABP for a switchable phenotype involve production of a library of replicable biological entities (as exemplified by cells) that display on their surface a plurality of different candidate ABPs. These libraries can then be subjected to screening methods to identify candidate ABPs having one or more desired characteristics of an ABP.

The candidate ABP libraries can contain candidate ABPs that differ by one or more of the MM, linker (which may be part of the MM), CM (which may be part of the MM), and TBM. As discussed above, ABPs are may be designed to target a known protease-target pair of a condition of interest. Thus, generally the candidate ABPs in the library are variable for the MM and/or the linker, with the TBM and CM being preselected. Where the ABP is to include pairs of cysteine residues to provide a disulfide bond in the ABP, the relative position of the cysteines in the ABP can be varied.

The library for screening is generally provided as a library of replicable biological entities which display on their surface different candidate ABPs. For example, a library of candidate ABPs can include a plurality of candidate ABPs displayed on the surface of population of a replicable biological entities, wherein each member of said plurality of candidate activatable binding polypeptides comprises: (a) a target binding moiety (TBM); (b) a cleavable moiety (CM); and (c) a candidate masking moiety (candidate MM), wherein the TBM, CM and candidate MM are positioned such that the ability of the candidate MM to inhibit binding of the TBM to a target in an uncleaved state and allow binding of the TBM to the target in a cleaved state can be determined.

Suitable replicable biological entities include cells (e.g., bacteria (e.g., *E. coli*), yeast (e.g., *S. cerevisiae*), mammalian cells), bacteriophage, and viruses. Bacterial host cells and bacteriophage, particularly bacterial host cells, are of interest.

Display of Candidate ABPs on the Surface of Replicable Biological Entities

A variety of display technologies using replicable biological entities are known in the art. These methods and entities include, but are not limited to, display methodologies such as mRNA and ribosome display, eukaryotic virus display, and bacterial, yeast, and mammalian cell surface display. See Wilson, D. S., et al. 2001 *PNAS USA* 98(7): 3750-3755; Muller, O. J., et al. (2003) *Nat. Biotechnol.* 3:312; Bupp, K. and M. J. Roth (2002) *Mol. Ther.* 5(3):329 3513; Georgiou, G., et al., (1997) *Nat. Biotechnol.* 15(1):29 3414; and Boder, E. T. and K. D. Wittrup (1997) *Nature Biotech.* 15(6):553 557. Surface display methods are attractive since they enable application of fluorescence-activated cell sorting (FACS) for library analysis and screening. See Daugherty, P. S., et al. (2000) *J. Immunol. Methods* 243(1 2):211 2716: Georgiou, G. (2000) *Adv. Protein Chem.* 55:293 315; Daugherty, P. S., et al. (2000) *PNAS USA* 97(5):2029 3418; Olsen, M. J., et al. (2003) *Methods Mol. Biol.* 230:329 342; Boder, E. T. et al. (2000) *PNAS USA* 97(20):10701 10705; Mattheakis, L. C., et al. (1994) *PNAS USA* 91(19): 9022 9026; and Shusta, E. V., et al. (1999) *Curr. Opin. Biotech.* 10(2):117 122. Additional display methodologies which may be used to identify a peptide capable of binding to a biological target of interest are described in U.S. Pat. No. 7,256,038, the disclosure of which is incorporated herein by reference.

Phage display involves the localization of peptides as terminal fusions to the coat proteins. e.g., pIII, pIV of bacteriophage particles. See Scott, J. K. and G. P. Smith (1990) *Science* 249(4967):386 390; and Lowman, H. B., et al. (1991) *Biochem.* 30(45):10832 10838. Generally, polypeptides with a specific function of binding are isolated by incubating with a target, washing away non-binding phage, eluting the bound phage, and then re-amplifying the phage population by infecting a fresh culture of bacteria.

Exemplary phage display and cell display compositions and methods are described in U.S. Pat. Nos. 5,223,409; 5,403,484; 7,118,879; 6,979,538; 7,208,293; 5,571,698; and 5,837,500.

Additional exemplary display scaffolds and methods include those described in U.S. Patent Application Publication No: 2007/0065878, published Mar. 22, 2007.

Optionally, the display scaffold can include a protease cleavage site (different from the protease cleavage site of the CM) to allow for cleavage of an ABP or candidate ABP from a surface of a host cell.

In one, where the replicable biological entity is a bacterial cell, suitable display scaffolds include circularly permuted *Escherichia coli* outer membrane protein OmpX (CPX) described by Rice et al. *Protein Sci.* (2006) 15: 825-836. See also, U.S. Pat. No. 7,256,038, issued Aug. 14, 2007.

Constructs Encoding ABPs and Candidate ABPs

The disclosure further provides nucleic acid constructs which include sequences coding for ABPs and/or candidate ABPs. Suitable nucleic acid constructs include, but are not limited to, constructs which are capable of expression in a prokaryotic or eukaryotic cell. Expression constructs are generally selected so as to be compatible with the host cell in which they are to be used.

For example, non-viral and/or viral constructs vectors may be prepared and used, including plasmids, which provide for replication of ABP- or candidate ABP-encoding DNA and/or expression in a host cell. The choice of vector will depend on the type of cell in which propagation is desired and the purpose of propagation. Certain constructs are useful for amplifying and making large amounts of the desired DNA sequence. Other vectors are suitable for expression in cells in culture. The choice of appropriate vector is well within the skill of the art. Many such vectors are available commercially. Methods for generating constructs can be accomplished using methods well known in the art.

In order to effect expression in a host cell, the polynucleotide encoding an ABP or candidate ABP is operably linked to a regulatory sequence as appropriate to facilitate the desired expression properties. These regulatory sequences can include promoters, enhancers, terminators, operators, repressors, and inducers. Expression constructs generally also provide a transcriptional and translational initiation region as may be needed or desired, which may be inducible or constitutive, where the coding region is operably linked under the transcriptional control of the transcriptional initiation region, and a transcriptional and translational termination region. These control regions may be native to the species from which the nucleic acid is obtained, or may be derived from exogenous sources.

Promoters may be either constitutive or regulatable. In some situations it may be desirable to use conditionally active promoters, such as inducible promoters, e.g., temperature-sensitive promoters. Inducible elements are DNA sequence elements that act in conjunction with promoters and may bind either repressors (e.g. lacO/LAC Iq repressor system in *E. coli*) or inducers (e.g. gall/GAL4 inducer system in yeast). In such cases, transcription is virtually "shut off" until the promoter is derepressed or induced, at which point transcription is "turned-on."

Constructs, including expression constructs, can also include a selectable marker operative in the host to facilitate, for example, growth of host cells containing the construct of interest. Such selectable marker genes can provide a phenotypic trait for selection of transformed host cells such as dihydrofolate reductase or neomycin resistance for eukaryotic cell culture.

Expression constructs can include convenient restriction sites to provide for the insertion and removal of nucleic acid sequences encoding the ABP and/or candidate ABP. Alternatively or in addition, the expression constructs can include flanking sequences that can serve as the basis for primers to facilitate nucleic acid amplification (e.g., PCR-based amplification) of an ABP-coding sequence of interest.

The above described expression systems may be employed with prokaryotes or eukaryotes in accordance with conventional ways, depending upon the purpose for expression. In some embodiments, a unicellular organism, such as E. coli, B. subtilis, S. cerevisiae, insect cells in combination with baculovirus vectors, or cells of a higher organism such as vertebrates, e.g. COS 7 cells, HEK 293, CHO, Xenopus Oocytes, etc., may be used as the expression host cells. Expression systems for each of these classes and types of host cells are known in the art.

Methods of Making Libraries of ABPs or Candidate ABPS Displayed on Replicable Biological Entities The present disclosure contemplates methods of making the libraries of ABPs and/or candidate ABPs described herein.

In one embodiment, a method of making an ABP library and/or candidate ABP library comprises: (a) constructing a set of recombinant DNA vectors as described herein that encode a plurality of ABPs and/or candidate ABPs; (b) transforming host cells with the vectors of step (a); and (c) culturing the host cells transformed in step (b) under conditions suitable for expression and display of the fusion polypeptides.

Production of Nucleic Acid Sequences Encoding Candidate ABPs

Production of candidate ABPs for use in the screening methods can be accomplished using methods known in the art. Polypeptide display, single chain antibody display, antibody display and antibody fragment display are methods well know in the art. In general, an element of an ABP e.g., MM, to be varied in the candidate ABP library is selected for randomization. The candidate ABPs in the library can be fully randomized or biased in their randomization. e.g. in nucleotide/residue frequency generally or in position of amino acid(s) within an element. By "randomized" is meant that any genetically-encodable amino acid can be provided at any given position within a randomized amino acid sequence. An amino acid sequence of an element of an ABP that is to be optimized can also be partially randomized. For example, the ABP element (e.g., candidate MM) can be partially randomized so as to provide for only a subset of amino acids at a selected position (e.g., to provide for a flexible linker at a selected position in the amino acid sequence, to provide for an amino acid residue of a desired characteristic (e.g., hydrophobic, polar, positively charged, negatively charged, etc.). In another example, the ABP element (e.g., candidate MM) can be partially randomized so that one or more residues within the otherwise randomized amino acid sequence is selected and held as invariable among a population or subpopulation of ABP library members (e.g., so as to provide a cysteine at a desired position within the candidate MM).

Where the ABP is a dual target-binding ABP, a first TBM may be "fixed" and the second TBM having a known target binding activity can be provided in its unmodified form (e.g., a native amino acid sequence having a known target binding activity) or can be modified (e.g., by directed or random mutagenesis) and screened for activity in providing a "switchable" phenotype. TBMs that are identified through the screening methods can subsequently be evaluated for activity in binding the target of interest, e.g., to determine that the "masking" TBM retains a desired level of target binding.

Using such methods candidate ABPs having a variety of different possible combinations of amino acid sequence over the length of the amino acid sequence of an element(s) to be varied can be generated, thus providing a library of randomized candidate ABPs. As such, in some embodiments, the library of candidate ABPs can be fully randomized, with no sequence preferences or constants at any position of an element(s) to be optimized. In other embodiments, the library of candidate peptides is biased. That is, some positions within the sequence are either held constant, or are selected from a limited number of possibilities. For example, in one embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

Methods of Screening for Activatable Binding Polypeptides

The present disclosure provides methods of identifying ABPs, which can be enzymatically activated ABPs, reducing agent-susceptible ABPs. or an ABP that is activatable by either or both of enzymatic activation or reducing agent-based activation. Generally, the methods include contacting a plurality of candidate ABPs with a target capable of binding a TBM of the ABPs and a protease capable of cleaving a CM of the ABPs, selecting a first population of members of said plurality which bind to the target when exposed to protease, contacting said rust population with the target in the absence of the protease, and selecting a second population of members from said first population by depleting from said first population members that bind the target in the absence of the protease, wherein said method provides for selection of candidate ABPs which exhibit decreased binding to the target in the absence of the protease as compared to target binding in the presence of the protease.

In general, the method for screening for candidate ABPs having a desired switchable phenotype is accomplished through a positive screening step (to identify members that bind target following exposure to protease) and a negative screening step (to identify members that do not bind target when not exposed to protease). The negative screening step can be accomplished by, for example, depleting from the population members that bind the target in the absence of the protease. It should be noted that the library screening methods described herein can be initiated by conducting the negative screening first to select for candidates that do not bind labeled target in the absence of enzyme treatment (i.e., do not bind labeled target when not cleaved), and then conducting the positive screening (i.e., treating with enzyme and selecting for members which bind labeled target in the cleaved state). However, for convenience, the screening method is described below with the positive selection as a first step.

Figure 18:
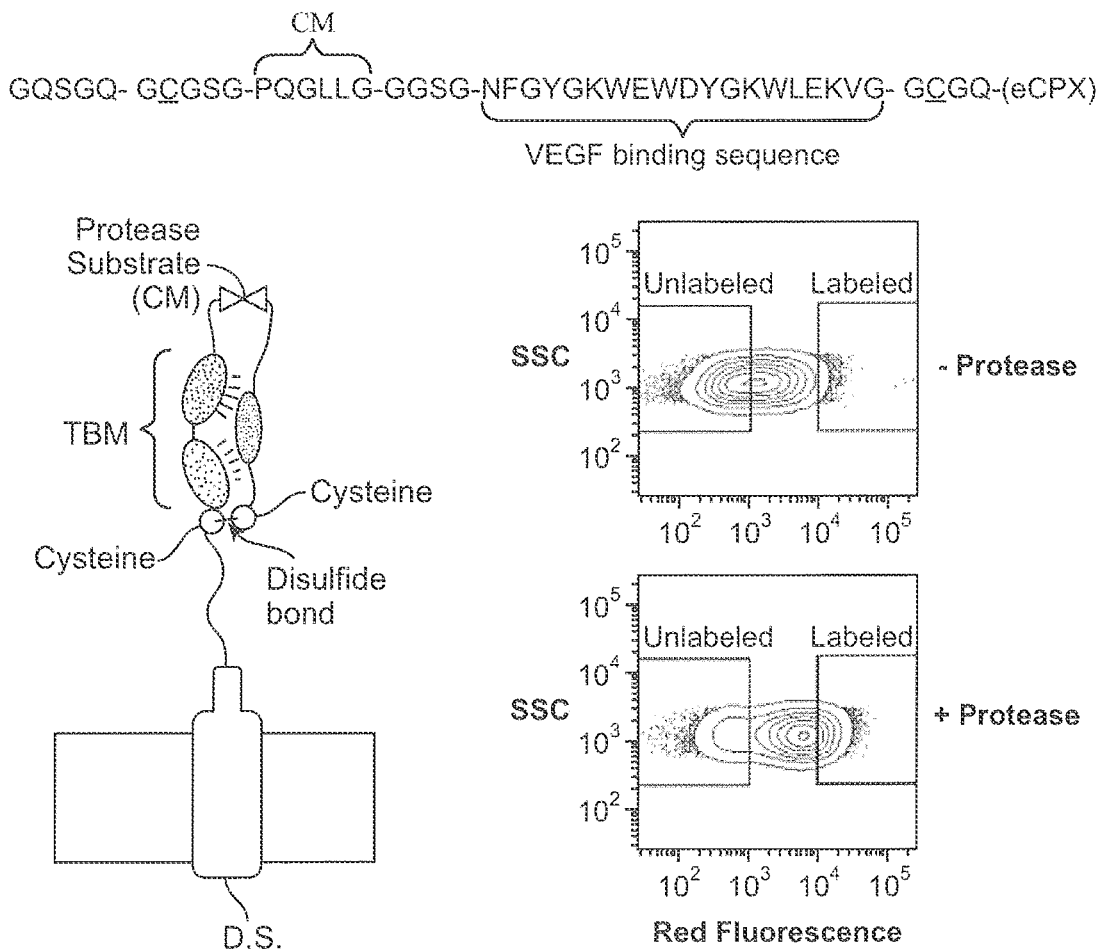
FIG. 18 shows the amino acid sequence of an exemplary ABP identified through a screen of a candidate ABP library.

The positive and negative screening steps can be conveniently conducted using flow cytometry to sort candidate ABPs based on binding of a detectably labeled target. For example, as illustrated in the schematic of FIG. 18, candidate ABPs having a CM susceptible to cleavage by a protease (such as the one exemplified in FIG. 18) can be expressed in a host cell (e.g., *E. coli*) in a display scaffold (exemplified by CPX). Host cells displaying the candidate ABP are exposed to a protease capable of cleaving the CM and to a detectably labeled target that is capable of binding the TBM. As illustrated in the lower panel of the right side of FIG. 18, the cells are sorted by FACS for intensity of detectable signal (exemplified by red fluorescence) of the detectably labeled target. The cells that are detectably labeled include those displaying a candidate ABP that was present on the cell surface, contained a CM cleavable by the protease, and that bound to detectably labeled target. The unlabeled subpopulation (or population having relative lower detectable signal) represents host cells that fail to bind target at a desirable level. The "labeled" subpopulation can then be collected and subjected to a negative screen in which the candidate ABPs are exposed to detectably labeled target in the absence of protease. As exemplified in the upper panel on the right side of FIG. 18, those cells that are unlabeled include those that present on their surface a candidate ABP that has relatively lower or no detectable binding of detectably labeled target relative to other members of the population. Cells that are detectably labeled include those displaying a candidate ABP that binds target in the absence of cleavage. The "unlabeled" subpopulation can then be collected and, if desired, subjected to further rounds or screening.

One "round" or "cycle" of the screening procedure involves both a positive selection step and a negative selection step. The methods may be repeated for a library such that multiple cycles (including complete and partial cycles. e.g., 1.5 cycles. 2.5 cycles, etc.) are performed. In this manner, members of the plurality of candidate ABPs that exhibit the switching characteristics of an ABP may be enriched in the resulting population.

In general, the screening methods are conducted by first generating a nucleic acid library encoding a plurality of candidate ABPs in a display scaffold, which is in turn introduced into a display scaffold for expression on the surface of a replicable biological entity. As used herein, a "plurality of candidate activatable binding polypeptides," or a "plurality of candidate ABPs" refers to a plurality of polypeptides having amino acid sequences encoding candidate ABPs, where members of the plurality are variable with respect to the amino acid sequence of at least one of the components of an ABP, e.g., the plurality is variable with respect to the amino acid sequence of the MM, the CM or the TBM, usually the MM.

Figure 19:
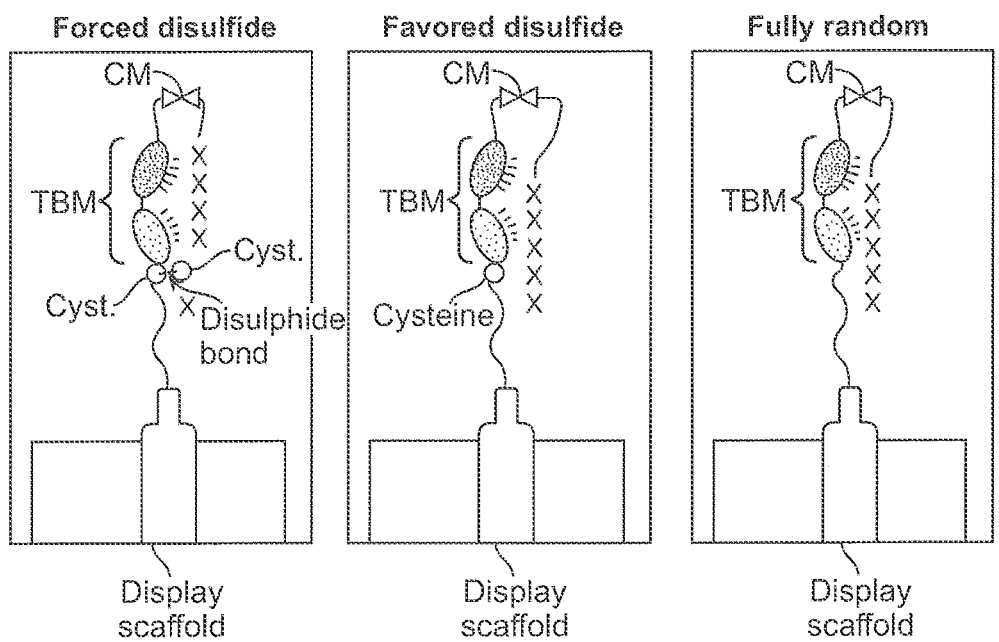
FIG. 19 shows a diagram of candidate ABP libraries with candidate masking moieties suitable for the identification of protease-activatable VEGF inhibitors.

For example, the TBM and CM of the candidate ABPs are held "fixed" and the candidate ABPs in the library are variable with respect to the amino acid sequence of the MM. The variable amino acid sequence of the MM is referred to hereinafter as a candidate masking moiety (candidate MM). As illustrated in FIG. 19, libraries can be generated having different MMs, which can include, for example, candidate ABPs having an MM that is designed to position a cysteine residue to "force" formation of a disulfide bond with another cysteine present in the candidate ABP (with other residues selected to provide an MM having an amino acid sequence that is otherwise fully or at least partially randomized). In another example, a library can be generated to include candidate ABPs having an MM that is designed to position a cysteine residue such that disulfide bond formation with another cysteine in the candidate ABP is favored (with other residues selected to provide an MM having an amino acid sequence that is otherwise fully or at least partially randomized). In another example, a library can be generated to include candidate ABPs in which the MM includes a fully randomized amino acid sequence. Such libraries can contain candidate ABPs designed by one or more of these criterion. By screening members of said plurality according to the methods described herein, members having candidate MMs that provide a desired switchable phenotype can be identified.

The term "candidate", as used in the context of, for example. "candidate ABP" or "candidate MM" (or other element of an ABP that is to be screened), refers to a polypeptide that is to be screened to determine whether it exhibits desired structural and/or functional characteristics. For example, a "candidate ABP" refers to a polypeptide that is designed to resemble the structure of an ABP as described herein, except that at least one of the MM. CM, TBM, and linker(s) are variable with respect to their amino acid sequences, wherein the candidate ABP is to be screened for a desired switchable phenotype. A "candidate MM", for example, refers to an amino acid sequence of an ABP which is to be screened for its function as a masking moiety in the context of an ABP.

In one embodiment of the methods, each member of the plurality of candidate ABPs is displayed on the surface of a replicable biological entity (exemplified here by bacterial cells). The members of the plurality are exposed to a protease capable of cleaving the CM of the candidate ABPs and contacted with a target which is a binding partner of the TBM of the candidate ABPs. Bacterial cells displaying members comprising TBMs which bind the target after exposure to the protease are identified and/or separated via detection of target binding (e.g., detection of a target-TBM complex). Members comprising TBMs which bind the target after protease exposure (which can lead to cleavage of the CM) are then contacted with the target in the absence of the protease. Bacterial cells displaying members comprising TBMs which exhibit decreased or undetectable binding to the target in the absence of cleavage are identified and/or separated via detection of cells lacking bound target. In this manner, members of the plurality of candidate ABPs which bind target in a cleaved state and exhibit decreased or undetectable target binding in an uncleaved state are identified and/or selected.

As noted above, candidate ABP libraries can be constructed so as to screen for one or more aspects of the ABP constructs, e.g., to provide for optimization of a switchable phenotype for one or more of the MM, the CM, and the TBM. One or more other elements of the ABP can be varied to facilitate optimization. For example: vary the MM, including varying the number or position of cysteines or other residues that can provide for different conformational characteristics of the ABP in the absence of cleaving agent (e.g., enzyme): vary the CM to identify a substrate that is optimized for one or more desired characteristics (e.g., specificity of enzyme cleavage, and the like); and/or vary the TBM to provide for optimization of "switchable" target binding.

In general, the elements of the candidate ABP libraries are selected according to a target protein of interest, where the ABP is to be activated to provide for enhanced binding of the target in the presence of a cleaving agent (e.g., enzyme) that cleaves the CM. For example, where the CM and TBM are held "fixed" among the library members, the CM is selected such that it is cleavable by a cleaving agent (e.g., enzyme) that is co-localized with a target of interest, where the target of interest is a binding partner of the TBM. In this manner, an ABP can be selected such that it is selectively activated under the appropriate biological conditions, and thus at an appropriate biological location. For example, where it is desired to develop an ABP to be used as an anti-angiogenic compound and exhibit a switchable phenotype for VEGF binding, the CM of the candidate ABP is selected to be a substrate for an enzyme and/or a reducing agent that is colocalized with VEGF (e.g., a CM cleavable by a matrix-metalloprotease).

As discussed above, a TBM is generally selected according to a target of interest. Many targets are known in the art. Biological targets of interest include protein targets that have been identified as playing a role in disease. Such targets include but are not limited to cell surface receptors and secreted binding proteins (e.g., growth factors), soluble enzymes, structural proteins (e.g. collagen, fibronectin) and the like. Exemplary non-limiting targets are presented in Table 1, but other suitable targets will be readily identifiable by those of ordinary skill in the art. In addition, many proteases are known in the art which co-localize with targets of interest. As such, persons of ordinary skill in the art will be able to readily identify appropriate enzymes and enzyme substrates for use in the above methods.

Optional Enrichment for Cell Surface Display Prior to ABP Screening

Prior to the screening method, it may be desirable to enrich for cells expressing an appropriate peptide display scaffold on the cell surface. The optional enrichment allows for removal of cells from the cell library that (1) do not express peptide display scaffolds on the cell outer membrane or (2) express non-functional peptide display scaffolds on the cell outer membrane. By "non-functional" is meant that the peptide display scaffold does not properly display a candidate ABP. e.g., as a result of a stop codon or a deletion mutation.

Enrichment for cells can be accomplished by growing the cell population and inducing expression of the peptide display scaffolds. The cells are then sorted based on, for example, detection of a detectable signal or moiety incorporated into the scaffold or by use of a detectably-labeled antibody that binds to a shared portion of the display scaffold or the ABP. These methods are described in greater detail in U.S. Patent Application Publication No: 2007/0065878, published Mar. 22, 2007.

Screening for Target Binding by Cleaved ABPs

Prior to screening, the candidate ABP library can be expanded (e.g., by growth in a suitable medium in culture under suitable conditions). Subsequent to the optional expansion, or as an initial step, the library is subjected to a first screen to identify candidate ABPs that bind target following exposure to protease. Accordingly, this step is often referred to herein as the "positive" selection step.

In order to identify members that bind target following protease cleavage, the candidate ABP library is contacted with a protease capable of cleaving the CM of the displayed candidate ABPs for an amount of time sufficient and under conditions suitable to provide for cleavage of the protease substrate of the CM. A variety of protease-CM combinations will be readily ascertainable by those of ordinary skill in the art, where the protease is one which is capable of cleaving the CM and one which co-localizes in vivo with a target of interest (which is a binding partner of the TBM). For example, where the target of interest is a solid tumor associated target (e.g. VEGF), suitable enzymes include, for example, Matrix-Metalloproteases (e.g., MMP-2). A Disintegrin and Metalloprotease(s) (ADAMs)/ADAM with thrombospondin-like motifs (ADAMTS). Cathepsins and Kallikreins. The amino acid sequences of substrates useful as CMs in the ABPs described herein are known in the art and, where desired, can be screened to identify optimal sequences suitable for use as a CM by adaptation of the methods described herein. Exemplary substrates can include but are not limited to substrates cleavable by one or more of the following enzymes: MMP-1, MMP-2, MMP-3, MMP-8, MMP-9, MMP-14, PLASMIN, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, and TACE.

The candidate ABP library is also exposed to target for an amount of time sufficient and under conditions suitable for target binding, which conditions can be selected according to conditions under which target binding to the TBM would be expected. The candidate ABP library can be exposed to the protease prior to exposure to target (e.g., to provide a population of candidate ABPs which include cleaved ABPs) or in combination with exposure to target, usually the latter so as to best model the expected in vivo situation in which both protease and target will be present in the same environmental milieu. Following exposure to both protease and target, the library is then screened to select members having bound target, which include candidate ABPs in a target-TBM complex.

Detection of target-bound candidate ABPs can be accomplished in a variety of ways. For example, the target may be detectably labeled and the first population of target-bound candidate ABPs may be selected by detection of the detectable label to generate a second population having bound target (e.g., a positive selection for target-bound candidate ABPs).

Screening for Candidate ABPs that do not Bind Target in the Absence of Protease Cleavage The population of candidate ABPs selected for target binding following exposure to protease can then be expanded (e.g., by growth in a suitable medium in culture under suitable conditions), and the expanded library subjected to a second screen to identify members exhibiting decreased or no detectable binding to target in the absence of protease exposure. The population resulting from this second screen will include candidate ABPs that, when uncleaved, do not bind target significantly or to a detectable level. Accordingly, this step is often referred to herein as the "negative" selection step.

The population that resulted from the first screen is contacted with target in the absence of the protease for a time sufficient and under conditions suitable for target binding, which conditions can be selected according to conditions under which target binding to the TBM would be expected. A negative selection can then be performed to identify candidate ABPs that are relatively decreased for target binding, including those which exhibit no detectably target binding. This selection can be accomplished by, for example, use of a detectably labeled target, and subjecting the target-exposed population to flow cytometry analysis to sort into separate subpopulation those cells that display a candidate ABP that exhibits no detectable target binding and/or which exhibit a relatively lower detectable signal. This subpopulation is thus enriched for cells having a candidate ABP that exhibit decreased or undetectable binding to target in the absence of cleavage.

Detectable Labels

As used herein, the terms "label", "detectable label" and "detectable moiety" are used interchangeably to refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens) and the like. The term "fluorescer" refers to a substance or a portion thereof which is capable of exhibiting fluorescence in the detectable range. Exemplary detectable moieties suitable for use as target labels include, affinity tags and fluorescent proteins.

The term "affinity tag" is used herein to denote a peptide segment that can be attached to a target that can be detected using a molecule that binds the affinity tag and provides a detectable signal (e.g., a fluorescent compound or protein). In principal, any peptide or protein for which an antibody or other specific binding agent is available can be used as an affinity tag. Exemplary affinity tags suitable for use include, but are not limited to, a monocytic adaptor protein (MONA) binding peptide, a T7 binding peptide, a streptavidin binding peptide, a polyhistidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), or other antigenic epitope or binding domain. See, in general. Ford et al., Protein Expression and Purification 2:95 (1991). DNA molecules encoding affinity tags are available from commercial suppliers (e.g., Pharmacia Biotech, Piscataway, N.J.).

Any fluorescent polypeptide (also referred to herein as a fluorescent label) well known in the art is suitable for use as a detectable moiety or with an affinity tag of the peptide display scaffolds described herein. A suitable fluorescent polypeptide will be one that can be expressed in a desired host cell, such as a bacterial cell or a mammalian cell, and will readily provide a detectable signal that can be assessed qualitatively (positive/negative) and quantitatively (comparative degree of fluorescence). Exemplary fluorescent polypeptides include, but are not limited to, yellow fluorescent protein (YFP), cyan fluorescent protein (CFP), GFP, mRFP, RFP (tdimer2), HCRED, etc., or any mutant (e.g., fluorescent proteins modified to provide for enhanced fluorescence or a shifted emission spectrum), analog, or derivative thereof. Further suitable fluorescent polypeptides, as well as specific examples of those listed herein, are provided in the art and are well known.

Biotin-based labels also find use in the methods disclosed herein. Biotinylation of target molecules and substrates is well known, for example, a large number of biotinylation agents are known, including amine-reactive and thiol-reactive agents, for the biotinylation of proteins, nucleic acids, carbohydrates, carboxylic acids; see, e.g., chapter 4, Molecular Probes Catalog, Haugland, 6th Ed. 1996, hereby incorporated by reference. A biotinylated substrate can be detected by binding of a detectably labeled biotin binding partner, such as avidin or streptavidin. Similarly, a large number of haptenylation reagents are also known.

Screening Methods

Any suitable method that provides for separation and recovery of ABPs of interest may be utilized. For example, a cell displaying an ABP of interest may be separated by FACS, immunochromatography or, where the detectable label is magnetic, by magnetic separation. As a result of the separation, the population is enriched for cells that exhibit the desired characteristic, e.g., exhibit binding to target following cleavage or have decreased or no detectable binding to target in the absence of cleavage.

For example, selection of candidate ABPs having bound detectably labeled target can be accomplished using a variety of techniques known in the art. For example, flow cytometry (e.g., FACS®) methods can be used to sort detectably labeled candidate ABPs from unlabeled candidate ABPs. Flow cytometry methods can be implemented to provide for more or less stringent requirements in separation of the population of candidate ABPs, e.g., by modification of gating to allow for "dimmer" or to require "brighter" cell populations in order to be separated into the second population for further screening.

In another example, immunoaffinity chromatography can be used to separate target-bound candidate ABPs from those that do not bind target. For example, a support (e.g., column, magnetic beads) having bound anti-target antibody can be contacted with the candidate ABPs that have been exposed to protease and to target. Candidate ABPs having bound target bind to the anti-target antibody, thus facilitating separation from candidate ABPs lacking bound target. Where the screening step is to provide for a population enriched for uncleaved candidate ABPs that have relatively decreased target binding or no detectable target binding (e.g., relative to other candidate ABPs), the subpopulation of interest is those members that lack or have a relatively decreased detectably signal for bound target. For example, where an immunoaffinity technique is used in such negative selection for bound target, the subpopulation of interest is that which is not bound by the anti-target support.

Screening for Dual Target-Binding ABPs

Methods for screening disclosed herein can be readily adapted to identify dual target-binding ABPs having a desired switchable phenotype due to interaction between two TBMs. In general, rather than a candidate MM in the example above, a TBM having a known binding activity is presented in the candidate ABP in place of the MM. In general, the method thus involves a library containing a plurality of candidate ABPs, wherein each member of said plurality comprises a first TBM, a second TBM and a CM. The library is contacted with target capable of binding at least the first TBM and a cleaving agent capable of cleaving the CM. A first population of members of the library is selected for binding the target in the presence of the cleaving agent (e.g., protease for the CM). This selected population is then subjected to the negative screen above, in which binding of target to the library members in the absence of the cleaving agent is assessed. A second population of members is then generated by depleting the subpopulation of members that bind to said target in the absence of the cleaving agent. This can be accomplished by, for example, sorting members that are not bound to target away from those that are bound to target, as determined by detection of a detectably labeled target. This method thus provides for selection of candidate ABPs which exhibit decreased binding to the target in the absence of the cleaving agent as compared to binding to said target in the presence of the cleaving agent.

This method can be repeated for both targets, although target binding to a TBM that is not associated with a display scaffold following cleavage must be assessed by evaluating the presence or absence (and/or relative levels) of target complexed with TBM-containing ABP fragments in solution.

In one example, a library containing a plurality of candidate ABPs is generated, wherein each member comprises a first TBM, a second TBM and a CM, where the CM is positioned between the first and second TBMs, and where the first TBM is immobilized on the surface of a replicable biological entity via a display scaffold. The library is then subjected to the positive and negative screening steps above with a target that is capable of binding the second TBM. For example, the library is contacted with a target capable of binding the first TBM and a cleaving agent capable of cleaving the CM, then selecting a first population of members of said plurality which bind to said target in the presence of the cleaving agent. The selected first population is then contacted with target capable of binding the first TBM in the absence of the cleaving agent, and a second population of members selected that bind to said target in the absence of the cleaving agent.

As above, any element of a dual target binding ABP can be varied within the library. For example, a first TBM may be "fixed" and the second TBM having a known target binding activity can be provided in its unmodified form (e.g., a native amino acid sequence having a known target binding activity) or can be modified (e.g., by directed or random mutagenesis) and screened for activity in providing a "switchable" phenotype. TBMs that are identified through the screening methods as exhibiting "masking" activity can subsequently be evaluated for activity in binding the target of interest, e.g., to determine that the "masking" TBM retains a desired level of target binding. For example, a construct encoding a display scaffold and a TBM-MM dual function element of a dual target-binding ABP can be inserted for expression and display on a replicable biological entity surface. Binding of the TBM-MM can then be evaluated according to methods in the art.

Exemplary Variations of the Screening Methods to Select for Candidate ABPs

The above method may be modified to select for populations and library members that demonstrate desired switching characteristics.

Iterative Screens to Identify and/or Optimize ABP Elements

The methods and candidate ABP libraries described herein can be readily adapted to provide for identification and/or optimization of one or more elements of an ABP. For example, candidate ABPs that vary with respect to any one or more of TBM. CM, linkers, and the like can be produced and subjected to the screening methods described herein.

Reducing Agent-Activatable ABPs

While the methods above describe screening methods for identifying ABPS, it should be understood that an ABP or candidate ABP with a CM that can facilitate formation of a cysteine-cysteine disulfide bond in an ABP can also be subjected to the screening methods disclosed herein. Such ABPs may or may not further include a CM (which may be the same or different CM) that may or may not comprise a protease substrate. In these embodiments, the positive screen described above may be conducted by exposing an ABP or candidate ABP to a reducing agent (e.g., to reducing conditions) capable of cleaving the disulfide bond of the cysteine-cysteine pair of the ABP. The negative screen can then be conducted in the absence of the reducing conditions. As such, a library produced having may be enriched for ABPs which are activatable by exposure to disulfide bond reducing conditions.

Number of Cycles and Scaffold Free Screening of ABPs

By increasing the number of cycles of the above methods, populations and library members that demonstrate improved switching characteristics can be identified, as exemplified in FIG. 8. Any number of cycles of screening can be performed.

In addition, individual clones of candidate ABPs can be isolated and subjected to screening so as to determine the dynamic range of the candidate ABP. Candidate ABPs can also be tested for a desired switchable phenotype separate from the scaffold, i.e., the candidate ABP can be expressed or otherwise generated separate from the display scaffold, and the switchable phenotype of the candidate ABP assessed in the absence of the scaffold and, where desired, in a cell-free system (e.g., using solubilized ABP).

It may be desirable to provide an ABP expression construct which includes a secretion signal to provide for extracellular secretion of the ABP, thereby facilitating production and recovery of an ABP of interest. Secretion signals suitable for use in bacterial and mammalian systems are well known in the art.

Optimization of ABP Components and Switching Activity

The above methods may be modified to optimize the performance of an ABP, e.g., an ABP identified in the screening method described herein. For example, where it is desirable to optimize the performance of the masking moiety, e.g., to provide for improved inhibition of target binding of the TBM in the uncleaved state, the amino acid sequences of the TBM and the CM may be "fixed" in a candidate ABP library, and the MM varied such that members of a library have variable MMs relative to each other. The MM may be optimized in a variety of ways including alteration in the number and or type of amino acids that make up the MM. For example, each member of the plurality of candidate ABPs may comprise a candidate MM, wherein the candidate MM comprises at least one cysteine amino acid residue and the remaining amino acid residues are variable between the members of the plurality. In a further example, each member of the plurality of candidate ABPs may comprise a candidate MM, wherein the candidate MM comprises a cysteine amino acid residue and a random sequence of amino acid residues, e.g., a random sequence of 5 amino acids.

Selection for Expanded Dynamic Range

As noted above, ABPs having a desired dynamic range with respect to target binding in the cleaved versus uncleaved state are of particular interest. Such ABPs are those that, for example, have no detectable binding in the presence of target at physiological levels found at treatment and non-treatment sites in a subject but which, once cleaved by protease, exhibit high affinity and/or high avidity binding to target. The greater the dynamic range of an ABP, the better the "switchable" phenotype of the ABP. Thus ABPs can be optimized to select for those having an "expanded" dynamic range for target binding in the presence and absence of a cleaving agent.

The screening methods described herein can be modified so as to enhance selection of ABPs having a desired and/or optimized dynamic range. In general, this can be accomplished by altering the concentrations of target utilized in the positive selection and negative selection steps of the method such that screening for target binding of ABPs exposed to protease (i.e., the screening population that includes cleaved ABPs) is performed using a relatively lower target concentration than when screening for target binding of uncleaved ABPs. Accordingly, the target concentration is varied between the steps so as to provide a "selective pressure" toward a switchable phenotype. Where desired, the difference in target concentrations used at the positive and negative selection steps can be increased with increasing cycle number.

Use of a relatively lower concentration of target in the positive selection step can serve to drive selection of those ABP members that have improved target binding when in the cleaved state. For example, the screen involving protease-exposed ABPs can be performed at a target concentration that is from about 2 to about 100 fold lower, about 2 to 50 fold lower, about 2 to 20 fold lower, about 2 to 10-fold lower, or about 2 to 5-folder lower than the Kd of the TBM-target interaction. As a result, after selection of the population for target-bound ABPs, the selected population will be enriched for ABPs that exhibit higher affinity and/or avidity binding relative to other ABPs in the population.

Use of a relatively higher concentration of target in the negative selection step can serve to drive selection of those ABP members that have decreased or no detectable target binding when in the uncleaved state. For example, the screen involving ABPs that have not been exposed to protease (in the negative selection step) can be performed at a target concentration that is from about 2 to about 100 fold higher, about 2 to 50 fold higher, about 2 to 20 fold higher, about 2 to 10-fold higher, or about 2 to 5-folder higher, than the Kd of the TBM-target interaction. As a result, after selection of the population for ABPs that do not detectably bind target, the selected population will be enriched for ABPs that exhibit lower binding for target when in the uncleaved state relative to other uncleaved ABPs in the population. Stated differently, after selection of the population for ABPs that do not detectably bind target, the selected population will be enriched for ABPs for which target binding to TBM is inhibited. e.g., due to "masking" of the TBM from target binding.

Where the ABP is a dual target-binding ABP, the screening method described above can be adapted to provide for ABPs having a desired dynamic range for a first target that is capable of binding a first TBM and for a second target that is capable of binding a second TBM. Target binding to a TBM that is located on a portion of the ABP that is "cleaved away" from the ABP presented on a display scaffold can be evaluated by assessing formation of target-TBM complexes in solution (e.g., in the culture medium). e.g., immunochromatography having an anti-ABP fragment antibody to capture cleaved fragment, then detecting bound, detectably labeled target captured on the column.

Testing of Soluble ABPs

Candidate ABPs can be tested for their ability to maintain a "switchable" phenotype while in soluble form. One such method involves the immobilization of target to support (e.g., an array, e.g., a Biacore™ CM5 sensor chip surface). Immobilization of a target of interest can be accomplished using any suitable techniques (e.g., standard amine coupling). The surface of the support can be blocked to reduce non-specific binding. Optionally, the method can involve use of a control (e.g., a support that does not contain immobilized target (e.g., to assess background binding to the support) and/or contains a compound that serves as a negative control (e.g., to assess specificity of binding of the candidate ABP to target versus non-target).

After the target is covalently immobilized, the candidate ABP is contacted with the support under conditions suitable to allow for specific binding to immobilized target. The candidate ABP can be contacted with the support-immobilized target in the presence and in the absence of a suitable cleavage agent in order to assess the "switchable" phenotype. Assessment of binding of the candidate ABP in the presence of cleavage agent as compared to in the absence of cleavage agent and, optionally, compared to binding in a negative control provides a binding response, which in turn is indicative of the "switchable" phenotype.

Screening for Individual Moieties for Use in Candidate ABPs

It may be desirable to screen separately for one or more of the moieties of a candidate ABP, e.g., a TBM. MM or CM, prior to testing the candidate ABP for a "switchable" phenotype. For example, known methods of identifying peptide substrates cleavable by specific proteases can be utilized to identify cleavable moieties for use in ABPs designed for activation by such proteases. In addition a variety of methods are available for identifying peptide sequences which bind to a target of interest. These methods can be used, for example, to identify TBMs which binds to a particular target or to identify a MM which binds to a particular TBM.

The above methods include, for example, methods in which a moiety of a candidate ABP. e.g., a TBM. MM or CM, is displayed using a replicable biological entity.

As discussed previously herein, a variety of display technologies using replicable biological entities are known in the art. These methods and entities include, but are not limited to, display methodologies such as mRNA and ribosome display, eukaryotic virus display, and bacterial, yeast, and mammalian cell surface display. See Wilson, D. S., et al. 2001 PNAS USA 98(7):3750-3755; Muller, O. J., et al. (2003) Nat. Biotechnol. 3:312; Bupp, K. and M. J. Roth (2002) Mol. Ther. 5(3):329 3513; Georgiou, G., et al., (1997) Nat. Biotechnol. 15(1):29 3414; and Boder, E. T. and K. D. Wittrup (1997) Nature Biotech. 15(6):553 557. Surface display methods are attractive since they enable application of fluorescence-activated cell sorting (FACS) for library analysis and screening. See Daugherty, P. S., et al. (2000) J. Immunol. Methods 243(1 2):211 2716; Georgiou, G. (2000) Adv. Protein Chem. 55:293 315; Daugherty, P. S., et al. (2000) PNAS USA 97(5):2029 3418; Olsen, M. J., et al. (2003) Methods Mol. Biol. 230:329 342; Boder, E. T. et al. (2000) PNAS USA 97(20):10701 10705; Mattheakis, L. C., et al. (1994) PNAS USA 91(19): 9022 9026; and Shusta, E. V., et al. (1999) Curr. Opin. Biotech. 10(2):117 122. Additional display methodologies which may be used to identify a peptide capable of binding to a biological target of interest are described in U.S. Pat. No. 7,256,038, the disclosure of which is incorporated herein by reference.

Phage display involves the localization of peptides as terminal fusions to the coat proteins, e.g., pIII. pIIV of bacteriophage particles. See Scott. J. K. and G. P. Smith (1990) Science 249(4967):386 390; and Lowman, H. B., et al. (1991) Biochem. 30(45):10832 10838. Generally, polypeptides with a specific function of binding are isolated by incubating with a target, washing away non-binding phage, eluting the bound phage, and then re-amplifying the phage population by infecting a fresh culture of bacteria.

Exemplary phage display and cell display compositions and methods are described in U.S. Pat. Nos. 5,223,409; 5,403,484; 7,118,879; 6,979,538; 7,208,293; 5,571,698; and 5,837,500.

Additional exemplary display scaffolds and methods include those described in U.S. Patent Application Publication No: 2007/0065878, published Mar. 22, 2007.

Optionally, the display scaffold can include a protease cleavage site (different from the protease cleavage site of the CM) to allow for cleavage of an ABP or candidate ABP from a surface of a host cell.

In one, where the replicable biological entity is a bacterial cell, suitable display scaffolds include circularly permuted *Escherichia coli* outer membrane protein OmpX (CPX) described by Rice et al. Protein Sci. (2006) 15: 825-836. See also, U.S. Pat. No. 7,256,038, issued Aug. 14, 2007.

Automated Screening Methods

The screening methods described herein may be automated to provide convenient, real time, high volume methods of screening a library of ABPs for a desired switchable activity. Automated methods can be designed to provide for iterative rounds of positive and negative selection, with the selected populations being separated and automatically subjected to the next screen for a desired number of cycles.

Analysis points to assess of candidate ABPs in a population may be over time following completion of a positive selection step, a negative selection step, or both. In addition, information regarding the average dynamic range of a population of candidate ABPs at selected target concentrations in the positive and negative selection steps can be monitored and stored for later analysis, e.g. so as to assess the effect of selective pressure of the different target concentrations.

A computer program product can control operation of the detection and/or measuring means and can perform numerical operations relating to the above-described steps, and generate a desired output (e.g., flow cytometry analysis, etc.). Computer program product comprises a computer readable storage medium having computer-readable program code means embodied in the medium. Hardware suitable for use in such automated apparatus will be apparent to those of skill in the art, and may include computer controllers, automated sample handlers, fluorescence measurement tools, printers and optical displays. The measurement tool may contain one or more photodetectors for measuring the fluorescence signals from samples where fluorescently detectable molecules are utilized. The measurement tool may also contain a computer-controlled stepper motor so that each control and/or test sample can be arranged as an array of samples and automatically and repeatedly positioned opposite a photodetector during the step of measuring fluorescence intensity.

The measurement tool (e.g., a fluorescence activated cell sorter) can be operatively coupled to a general purpose or application specific computer controller. The controller can comprise a computer program produce for controlling operation of the measurement tool and performing numerical operations relating to the above-described steps. The controller may accept set-up and other related data via a file, disk input or data bus. A display and printer may also be provided to visually display the operations performed by the controller. It will be understood by those having skill in the art that the functions performed by the controller may be realized in whole or in part as software modules running on a general purpose computer system. Alternatively, a dedicated stand-alone system with application specific integrated circuits for performing the above described functions and operations may be provided.

Methods of Use of ABPs in Therapy

ABPs can be incorporated into pharmaceutical compositions containing, for example, a therapeutically effective amount of an ABP of interest and a carrier pharmaceutically acceptable excipient (also referred to as a pharmaceutically acceptable carrier). Many pharmaceutically acceptable excipients are known in the art, are generally selected according to the route of administration, the condition to be treated, and other such variables that are well understood in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc. Pharmaceutical compositions can also include other components such as pH adjusting and buffering agents, tonicity adjusting agents, stabilizers, wetting agents and the like. In some embodiments, nanoparticles or liposomes carry a pharmaceutical composition comprising an ABP.

Suitable components for pharmaceutical compositions of ABPs can be guided by pharmaceutical compositions that may be available for a TBM of the ABP. For example, where the, the ABP include a VEGF binder (i.e., VEGF inhibitor), such ABPs can be formulated in a pharmaceutical formulation according to methods and compositions suitable for use with the VEGF binder. In embodiments where the ABP comprises a full length antibody or an antigen binding fragment thereof, the composition can be formulated in a pharmaceutical formulation according to methods and compositions suitable for use with antibodies and antigen binding fragments.

In general, pharmaceutical formulations of one or more ABPs are prepared for storage by mixing the ABP having a desired degree of purity with optional physiologically acceptable carriers, excipients or stabilizers (Remington's Pharmaceutical Sciences 16th edition, Osol. A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations to be used for in vivo administration must be sterile. This is readily accomplished by filtration through sterile filtration membranes. Pharmaceutical formulations may also contain more than one active compound as necessary for the particular indication being treated, where the additional active compounds generally are those with activities complementary to an ABP. Such compounds are suitably present in combination in amounts that are effective for the purpose intended.

The pharmaceutical formulation can be provided in a variety of dosage forms such as a systemically or local injectable preparation. The components can be provided in a carrier such as a microcapsule, e.g., such as that prepared by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nanoparticles and nanocapsules) or in macroemulsions. Such techniques are disclosed in Remington's Pharmaceutical Sciences 16th edition. Osol. A. Ed. (1980).

Sustained-release preparations are also within the scope of ABP-containing formulations. Exemplary sustained-release preparations can include semipermeable matrices of solid hydrophobic polymers containing the antibody, which matrices are in the form of shaped articles. e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

When encapsulated ABPs remain in the body for a long time, they may denature or aggregate as a result of exposure to moisture at 37 degrees C., resulting in decreased biological activity and possible changes in immunogenicity. Rational strategies can be devised for stabilization depending on the mechanism involved. For example, if the aggregation mechanism is discovered to be undesirable intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

ABPs can be conjugated to delivery vehicles for targeted delivery of an active agent that serves a therapeutic purpose. For example, ABPs can be conjugated to nanoparticles or liposomes having drugs encapsulated therein or associated therewith. In this manner, specific, targeted delivery of the drug can be achieved. Methods of linking polypeptides to liposomes are well known in the art and such methods can be applied to link ABPs to liposomes for targeted and or selective delivery of liposome contents. By way of example, polypeptides can be covalently linked to liposomes through thioether bonds. PEGylated gelatin nanoparticles and PEGylated liposomes have also been used as a support for the attachment of polypeptides, e.g., single chain antibodies. See, e.g., Immordino et al. (2006) *Int J Nanomedicine*. September, 1(3): 297-315, incorporated by reference herein for its disclosure of methods of conjugating polypeptides, e.g., antibody fragments, to liposomes.

Methods of Treatment

ABPs described herein can be selected for use in methods of treatment of suitable subjects according to the CM-TBM combination provided in the ABP. Examples based on the VEGF-inhibiting ABP are provided below.

The ABP can be administered by any suitable means, including parenteral, subcutaneous, intraperitoneal, intrapulmonary, and intranasal, and, if desired for local injection (e.g., at the site of a solid tumor). Parenteral administration routes include intramuscular, intravenous, intraarterial, intraperitoneal, or subcutaneous administration.

The appropriate dosage of ABP will depend on the type of disease to be treated, the severity and course of the disease, the patient's clinical history and response to the ABP, and the discretion of the attending physician. ABPs can suitably be administered to the patient at one time or over a series of treatments.

Depending on the type and severity of the disease, about 1 μg/kg to 15 mg/kg (e.g., 0.1-20 mg/kg) of ABP can serve as an initial candidate dosage for administration to the patient, whether, for example, by one or more separate administrations, or by continuous infusion. A typical daily dosage might range from about 1 μg/kg to 100 mg/kg or more, depending on factors such as those mentioned herein. For repeated administrations over several days or longer, depending on the condition, the treatment is sustained until a desired suppression of disease symptoms occurs. However, other dosage regimens may be useful.

The ABP composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the ABP, the method of administration, the scheduling of administration, and other factors known to medical practitioners. The "therapeutically effective amount" of an ABP to be administered will be governed by such considerations, and is the minimum amount necessary to prevent, ameliorate, or treat a disease or disorder.

Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this invention can be used to prevent the onset or reoccurrence of the disease or disorder in a subject or mammal.

ABPs can be used in combination (e.g., in the same formulation or in separate formulations) with one or more additional therapeutic agents or treatment methods ("combination therapy"). An ABP can be administered in admixture with another therapeutic agent or can be administered in a separate formulation. Therapeutic agents and/or treatment methods that can be administered in combination with an ABP, and which are selected according to the condition to be treated, include surgery (e.g., surgical removal of cancerous tissue), radiation therapy, bone marrow transplantation, chemotherapeutic treatment, certain combinations of the foregoing, and the like.

Use of ABPs that Inhibit VEGF in Anti-Angiogenic Therapies

Where the ABP contains a TBM that is a VEGF inhibitor, the ABP finds use in treatment of conditions in which inhibition of angiogenesis is desired, particularly those conditions in which inhibition of VEGF is of interest. VEGF-inhibiting ABPs can include dual target binding ABPs having a TBM that binds to VEGF as well as a TBM that binds to a second growth factor, such as a fibroblast growth factor (e.g., FGF-2), and inhibits FGF activity. Such dual target binding ABPs thus can be designed to provide for inhibition of two angiogenesis-promoting factors, and which are activatable by a cleaving agent (e.g., enzyme, such as a MMP or other enzyme as discussed herein) which co-localizes at a site of aberrant angiogenesis.

Angiogenesis-inhibiting ABPs find use in treatment of solid tumors in a subject (e.g., human), particularly those solid tumors that have an associated vascular bed that feeds the tumor such that inhibition of angiogenesis can provide for inhibition or tumor growth. Anti-VEGF-based anti-angiogenesis ABPs also find use in other conditions having one or more symptoms amenable to therapy by inhibition of abnormal angiogenesis.

In general, abnormal angiogenesis occurs when new blood vessels either grow excessively, insufficiently or inappropriately (e.g., the location, timing or onset of the angiogenesis being undesired from a medical standpoint) in a diseased state or such that it causes a diseased state. Excessive, inappropriate or uncontrolled angiogenesis occurs when there is new blood vessel growth that contributes to the worsening of the diseased state or causes a diseased state, such as in cancer, especially vascularized solid tumors and metastatic tumors (including colon, lung cancer (especially small-cell lung cancer), or prostate cancer), diseases caused by ocular neovascularisation, especially diabetic blindness, retinopathies, primarily diabetic retinopathy or age-induced macular degeneration and rubeosis; psoriasis, psoriatic arthritis, haemangioblastoma such as haemangioma; inflammatory renal diseases, such as glomerulonephritis, especially mesangioproliferative glomerulonephritis, haemolytic uremic syndrome, diabetic nephropathy or hypertensive neplirosclerosis; various inflammatory diseases, such as arthritis, especially rheumatoid arthritis, inflammatory bowel disease, psoriasis, sarcoidosis, arterial arteriosclerosis and diseases occurring after transplants, endometriosis or chronic asthma and other conditions that will be readily recognized by the ordinarily skilled artisan. The new blood vessels can feed the diseased tissues, destroy normal tissues, and in the case of cancer, the new vessels can allow tumor cells to escape into the circulation and lodge in other organs (tumor metastases).

ABP-based anti-angiogenesis therapies can also find use in treatment of graft rejection, lung inflammation, nephrotic syndrome, preeclampsia, pericardial effusion, such as that associated with pericarditis, and pleural effusion, diseases and disorders characterized by undesirable vascular permeability, e.g., edema associated with brain tumors, ascites associated with malignancies, Meigs' syndrome, lung inflammation, nephrotic syndrome, pericardial effusion, pleural effusion, permeability associated with cardiovascular diseases such as the condition following myocardial infarctions and strokes and the like.

Other angiogenesis-dependent diseases that may be treated using anti-angiogenic ABPs as described herein include angiofibroma (abnormal blood of vessels which are prone to bleeding), neovascular glaucoma (growth of blood vessels in the eye), arteriovenous malformations (abnormal communication between arteries and veins), nonunion fractures (fractures that will not heal), atherosclerotic plaques (hardening of the arteries), pyogenic granuloma (common skin lesion composed of blood vessels), scleroderma (a form of connective tissue disease), hemangioma (tumor composed of blood vessels), trachoma (leading cause of blindness in the third world), hemophilic joints, vascular adhesions and hypertrophic scars (abnormal scar formation).

Amounts of ABP for administration to provide a desired therapeutic effect will vary according to a number of factors such as those discussed above. In general, in the context of cancer therapy, a therapeutically effective amount of an ABP is an amount that that is effective to inhibit angiogenesis, and thereby facilitate reduction of, for example, tumor load, atherosclerosis, in a subject by at least about 5%, at least about 10%, at least about 20%, at least about 25%, at least about 50%, at least about 75%, at least about 85%, or at least about 90%, up to total eradication of the tumor, when compared to a suitable control. In an experimental animal system, a suitable control may be a genetically identical animal not treated with the agent. In non-experimental systems, a suitable control may be the tumor load present before administering the agent. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen) to determine the number of cells bearing a given tumor antigen; computed tomography scanning, magnetic resonance imaging, and/or x-ray imaging of the tumor to estimate and/or monitor tumor size; measuring the amount of tumor-associated antigen in a biological sample, e.g., blood or serum; and the like.

In some embodiments, the methods are effective to reduce the growth rate of a tumor by at least about 5%, at least about 10%, at least about 20%, at least about 25%, at least about 50%, at least about 75%, at least about 85%, or at least about 90%, up to total inhibition of growth of the tumor, when compared to a suitable control. Thus, in these embodiments, "effective amounts" of an ABP are amounts that are sufficient to reduce tumor growth rate by at least about 5%, at least about 10%, at least about 20%, at least about 25%, at least about 50%, at least about 75%, at least about 85%, or at least about 90%, up to total inhibition of tumor growth, when compared to a suitable control. In an experimental animal system, a suitable control may be tumor growth rate in a genetically identical animal not treated with the agent. In non-experimental systems, a suitable control may be the tumor load or tumor growth rate present before administering the agent. Other suitable controls may be a placebo control.

Whether growth of a tumor is inhibited can be determined using any known method, including, but not limited to, an in vivo assay for tumor growth; an in vitro proliferation assay; a $^3$H-thymidine uptake assay; and the like.

Non-Therapeutic Methods of Using ABPs

ABPs can also be used in diagnostic and/or imaging methods. For example, ABPs having an enzymatically cleavable CM can be used to detect the presence or absence of an enzyme that is capable of cleaving the CM. Such ABPs can be used in diagnostics, which can include in vivo detection (e.g., qualitative or quantitative) of enzyme activity (or, in some embodiments, an environment of increased reduction potential such as that which can provide for reduction of a disulfide bond) accompanied by presence of a target of interest through measured accumulation of activated ABPs in a given tissue of a given host organism.

For example, the CM can be selected to be a protease substrate for a protease found at the site of a tumor, at the site of a viral or bacterial infection at a biologically confined site (e.g., such as in an abscess, in an organ, and the like), and the like. The TBM can be one that binds a target antigen. Using methods familiar to one skilled in the art, a detectable label (e.g., a fluorescent label) can be conjugated to a TBM or other region of an ABP. Suitable detectable labels are discussed in the context of the above screening methods and additional specific examples are provided below. Using a TBM specific to a protein or peptide of the disease state, along with a protease whose activity is elevated in the disease tissue of interest, ABPs will exhibit increased rate of binding to disease tissue relative to tissues where the CM specific enzyme is not present at a detectable level or is present at a lower level than in disease tissue. Since small proteins and peptides are rapidly cleared from the blood by the renal filtration system, and because the enzyme specific for the CM is not present at a detectable level (or is present at lower levels in non-diseased tissues), accumulation of activated ABP in the diseased tissue is enhanced relative to non-disease tissues.

In another example, ABPs can be used in to detect the presence or absence of a cleaving agent in a sample. For example, where the ABP contains a CM susceptible to cleavage by an enzyme, the ABP can be used to detect (either qualitatively or quantitatively) the presence of an enzyme in the sample. In another example, where the ABP contains a CM susceptible to cleavage by reducing agent, the ABP can be used to detect (either qualitatively or quantitatively) the presence of reducing conditions in a sample. To facilitate analysis in these methods, the ABP can be detectably labeled, and can be bound to a support (e.g., a solid support, such as a slide or bead). The detectable label can be positioned on a portion of the ABP that is released following cleavage. The assay can be conducted by, for example, contacting the immobilized, detectably labeled ABP with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the ABP prior to contacting with the sample (e.g., a reduction in detectable signal due to cleavage of the ABP by the cleaving agent in the sample and the removal of an ABP fragment to which the detectable label is attached as a result of such cleavage.

Such detection methods can be adapted to also provide for detection of the presence or absence of a target that is capable of binding the TBM of the ABP. Thus, the in vitro assays can be adapted to assess the presence or absence of a cleaving agent and the presence or absence of a target of interest. The presence or absence of the cleaving agent can be detected by a decrease in detectable label of the ABP as described above, and the presence or absence of the target can be detected by detection of a target-TBM complex, e.g., by use of a detectably labeled anti-target antibody.

As discussed above, the ABPs disclosed herein can comprise a detectable label. In one embodiment, the ABP comprises a detectable label which can be used as a diagnostic agent. Non-limiting examples of detectable labels that can be used as diagnostic agents include imaging agents containing radioisotopes such as indium or technetium; contrasting agents for MRI and other applications containing iodine, gadolinium or iron oxide; enzymes such as horse radish peroxidase, alkaline phosphatase, or β-galactosidase; fluorescent substances and fluorophores such as GFP, europium derivatives; luminescent substances such as N-methylacrydium derivatives or the like.

The rupture of vulnerable plaque and the subsequent formation of a blood clot are believed to cause the vast majority of heart attacks. Effective targeting of vulnerable plaques can enable the delivery of stabilizing therapeutics to reduce the likelihood of rupture.

VCAM-1 is upregulated both in regions prone to atherosclerosis as well as at the borders of established lesions. Iiyama, et al. (1999) *Circulation Research, Am Heart Assoc.* 85: 199-207. Collagenases, such as MMP-1, MMP-8 and MMP-13, are overexpressed in human atheroma which may contribute to the rupture of atheromatous plaques. Fricker, J. (2002) *Drug Discov Today* 7(2): 86-88.

In one example, ABPs disclosed herein find use in diagnostic and/or imaging methods designed to detect and/or label atherosclerotic plaques, e.g., vulnerable atherosclerotic plaques. By targeting proteins associated with atherosclerotic plaques, ABPs can be used to detect and/or label such plaques. For example, ABPs comprising an anti-VCAM-1 ABD and a detectable label find use in methods designed to detect and/or label atherosclerotic plaques. These ABPs can be tested in animal models, such as ApoE mice.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius. and pressure is at or near atmospheric. Standard abbreviations may be used, e.g., bp, base pair(s); kb, kilobase(s); pl, picoliter(s); s or sec, second(s); min, minute(s); h or hr, hours); aa, amino acid(s); kb, kilobase(s); bp, base pair(s); nt, nucleotide(s); i.m., intramuscular(ly); i.p., intraperitoneal (ly); s.c., subcutaneous(ly); and the like.

Methods and Materials

The following methods and materials were used in Examples 1-5 below.

Cloning and expression experiments were performed using *E. coli* strain MC1061. Cells were grown overnight at 37° C. in LB medium and chloramphenicol. Cultures were then diluted 1:50 into LB medium containing chloramphenicol, grown for 2 hours at 37° C., and substrate expression was induced with 0.2% L-(+)-arabinose at 37° C. for 2 hours. Approximately $2 \times 10^8$ cells were centrifuged at 5000 rpm for 5 minutes, washed once with 50 mM Tris-Cl (pH 7.5) supplemented with 20 mM NaCl/2 mM $CaCl_2$)/100 μM $ZnCl_2$, and resuspended in 10 uL of Tris-Cl buffer.

In experiments involving addition of enzyme. 30 nM MMP-2 was included in the Tris-Cl buffer (no enzyme added to the control reaction), and the reaction mixture was incubated at room temperature for 2 hours. Cells were then removed and diluted 1:100 in PBS (pH 7.4) to stop the reaction, pelleted by centrifugation, and resuspended in 30 microliters of refrigerated PBS containing 25 nM biotinylated VEGF. After incubation in the refrigerator on a rotary shaker for 45 minutes, cells were pelleted at 4° C. and resuspended in refrigerated PBS containing 50 nM Streptavidin-Phycoerythrin fluorescent conjugate. After incubation in the refrigerator on a rotary shaker for 45 minutes, cells were pelleted at 4° C. and resuspended in PBS and red fluorescence was measured for analysis or sorting on a FACSAria cell sorter. The fluorescence of cells treated with enzyme was compared to control samples to determine the increase in VEGF binding.

All switch constructs and libraries were displayed on the surface of *E. coli* bacteria using the N-terminus of the circularly permuted outer membrane protein X (CPX).

It should be noted that in describing the clones identified in the experiments below, the following naming conventions are used interchangeably: #-#X-# and #.#X.#, where # is a numerical identifier and X is a alphabetical identifier.

Figure 3:
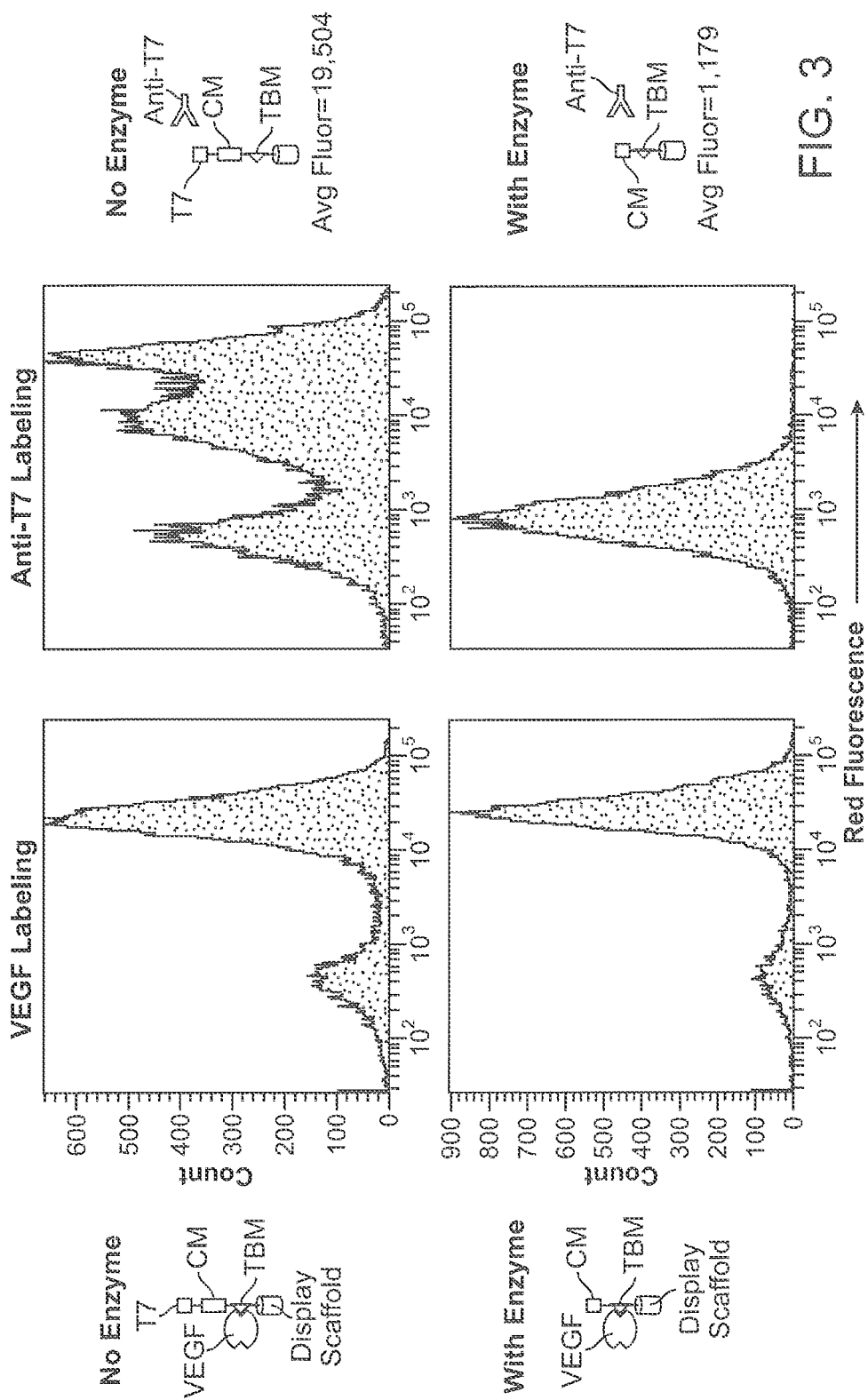
FIG. 3 shows the amino acid sequence of a T7 control construct and shows that the VEGF binds the control construct in both the presence and absence of enzyme.

Example 1: Construction of Polypeptides Having a VEGF Binding Moiety and a Moiety Cleavable by an Enzyme As discussed above, the activatable binding polypeptides (ABPs) include a target binding moiety (TBM) and a cleavable moiety (CM), where the CM contains a substrate for a protease. As a first step in the production of ABPs, constructs for display on a bacterial cell surface were generated containing a VEGF binding sequence (to act as the TBM) and an amino acid sequence that is cleavable by matrix metalloprotease-2 (MMP-2). The amino acid sequence of T7 antigen was included at the N-terminus as an immunodetectable tag to facilitate detection of uncleaved product. Specifically binding of a detectably labeled anti-T7 antibody was indicative of uncleaved ABP. The amino acid sequence of this construct without the cell surface anchoring sequences is provided below as SEQ ID NO: 12. FIG. 3 provides a schematic of the construct in the presence and absence of enzyme (see upper right panel for details).

TABLE 3

SEQ ID NO: 12:

| N-Terminus | T 7 | Substrate | | VEGF Binder |
|---|---|---|---|---|
| GQSGQ | MASMTGGQQMGGSG | PLGLAG | GGSG | NFGYGKWEWD YGKWLEKVG |

The ability of the construct to bind labeled VEGF in the presence or absence of MMP-2 was tested. Bacteria displaying the construct on its surface were incubated in the presence of labeled VEGF either in the presence or absence of MMP-2 (FIG. 3, left panels). Cleavage of the construct by the protease was confirmed by incubating the cells either in the presence or absence of a detectably-labeled anti-T7 antigen antibody (FIG. 3, right panels). Binding of either labeled VEGF or labeled anti-T7 antibody was assessed by FACS. As shown in FIG. 3, when the construct is contacted with labeled VEGF in either the presence or absence of MMP-2, the labeled VEGF is able to bind the VEGF binder sequence, indicating that the presence of the enzyme substrate does not substantially interfere with VEGF binding to the TBM of the construct. FIG. 3 also confirms that MMP-2 cleaved the PLGLAG substrate of the construct, as indicated by an approximately 16.5 fold decrease in average fluorescence of the construct in the presence of the enzyme.

These data illustrate that VEGF binding is not substantially impaired by the presence of the MMP-2 substrate and that the MMP-2 substrate utilized in the T7 control polypeptide is a candidate enzyme substrate for use as a CM in an ABP.

Example 2: ABP Having a Cysteine-Constrained Loop

One strategy for "masking" a target binding moiety (TBM) in an ABP is to provide the ABP in a "loop" that sterically hinders access of target to the TBM. In this strategy, cysteines are positioned at or near the N-terminus and C-terminus of the ABP, such that upon formation of a disulfide bond between the cysteines, the TBM is masked.

Figure 4:
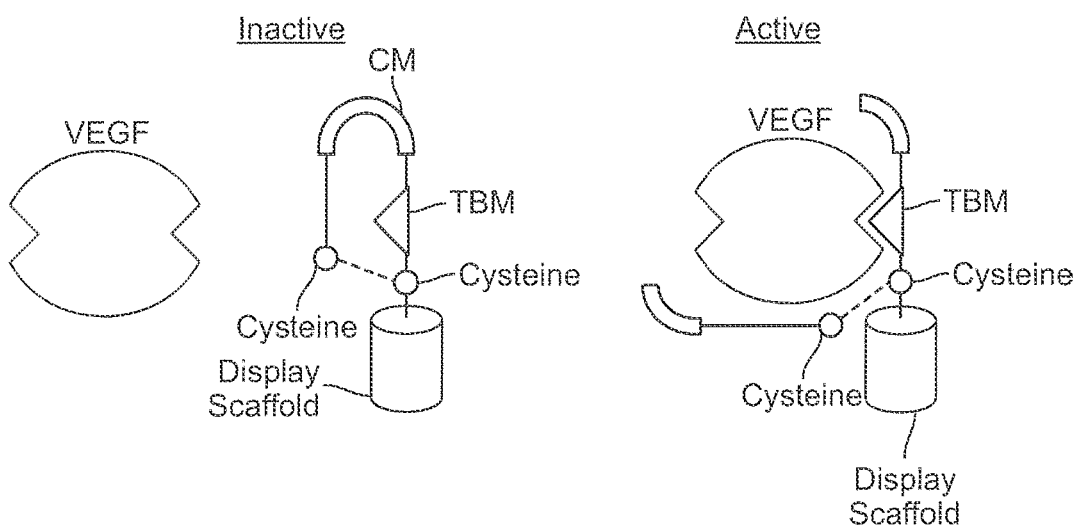
FIG. 4 shows the amino acid sequences of a cysteine constrained loop ABP and a GS control construct.

An exemplary ABP is illustrated in FIG. 4. This ABP includes a cysteine-containing flexible linker sequence positioned N-terminal of a MMP-2 substrate (the cleavable moiety (CM), indicated as "substrate" below), which in turn was N-terminal of a VEGF binder as the TBM. A flexible linker was positioned between the CM and TBM. The sequence is provided below as SEQ ID NO: 13.

TABLE 4

SEQ ID NO: 13:

| N-Terminus | Cysteine | Substrate | Linker | VEGF Binder |
|---|---|---|---|---|
| GQSGQ | GeGSG | PLGLAG | GGSG | NFGYGKWEWD YGKWLEKVGGC |

A control ("GS Control") that lacked the cysteine-cysteine disulfide bond was also constructed. The sequence of the GS control is provided below in SEQ ID NO: 14.

TABLE 5

SEQ ID NO: 14:

| N-Terminus | Insert | Substrate | | VEGF Binder |
|---|---|---|---|---|
| GQSGQ | (GGS)$_5$ | PLGLAG | GGSG | NFGYGKWEWD YGKWLEKVGGG |

These constructs were then tested for the ability to bind labeled VEGF in the presence or in the absence of MMP-2 as described above.

Figure 5:
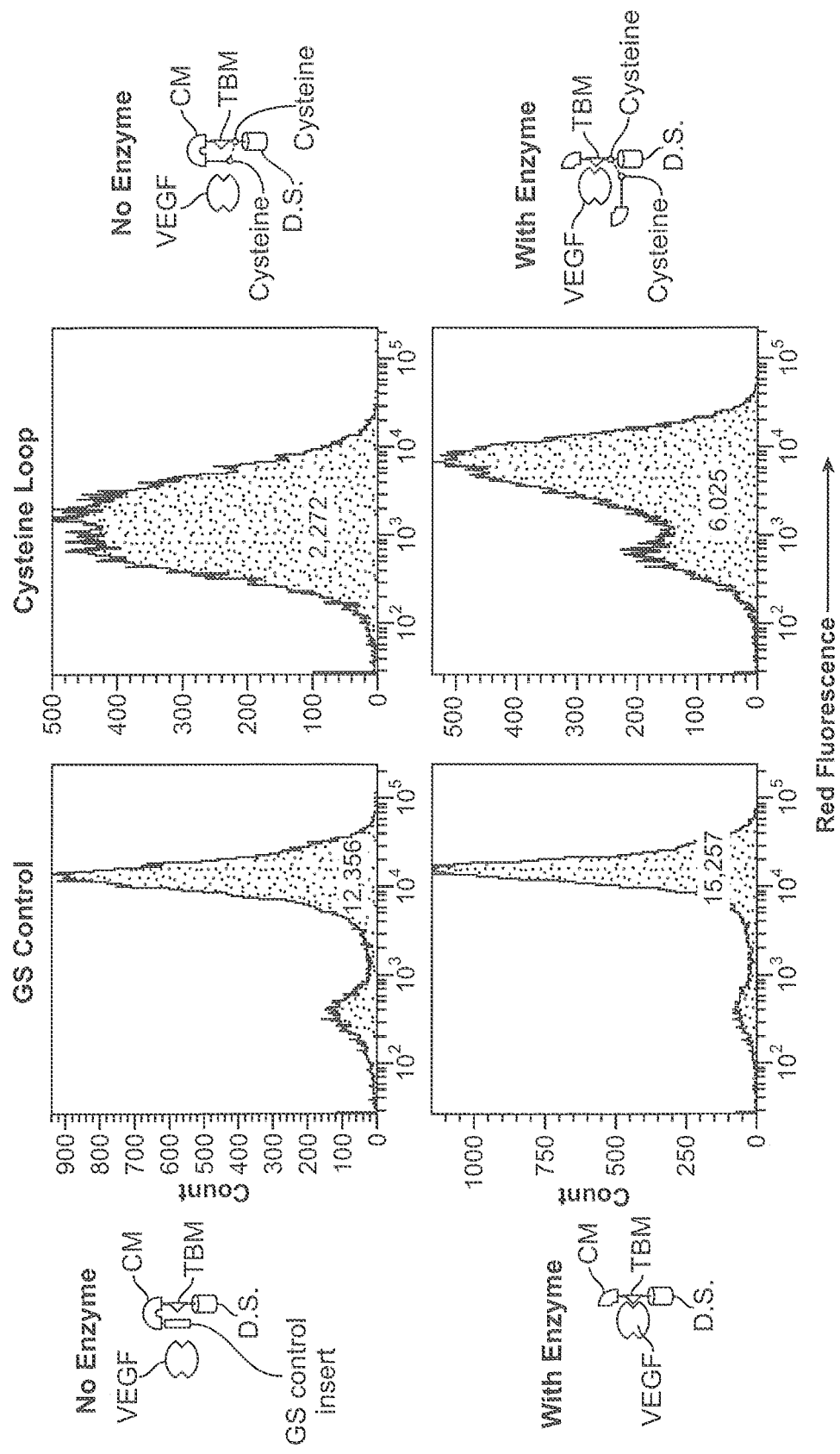
FIG. 5 shows the results of binding experiments which indicate that the formation of a cysteine constrained loop in an ABP interferes with VEGF binding. Diagrams of the GS control and the ABP, in both cleaved and uncleaved states, are also shown.

The ABP of FIG. 4 was displayed on the surface of a bacterial cell and contacted with labeled VEGF in presence and absence of MMP-2 enzyme. FACS analysis to detect VEGF-labeled cells was performed to determine whether the ABP demonstrated switching behavior as compared to the control polypeptide lacking the cysteine-cysteine disulfide bond. As illustrated in FIG. 5, binding of labeled VEGF was increased in the presence of enzyme compared to in the absence of enzyme, as evidenced by an approximately 2.6 fold increase in fluorescence after MMP-2 treatment (FIG. 5, right panels). A similar increase in VEGF binding was not seen in the GS control polypeptide.

These data illustrate that cleavage of the substrate by MMP-2 provided for enhanced binding of VEGF to the ABP as compared to the binding of VEGF to the ABP in the absence of MMP-2. In addition, the cysteine loop-containing ABP exhibited a more enhanced "switchable" VEGF-binding phenotype as compared to the GS control. The level of VEGF binding to cleaved cysteine loop-containing ABP relative to uncleaved cysteine loop-containing ABP was greater than the level of VEGF binding to cleaved GS control relative to uncleaved GS control.

Example 3: Screening of ABP Libraries

In order to identify further ABPs having desired "switching" characteristics (i.e., decreased target binding when in an uncleaved conformation relative to target binding when in a cleaved conformation), libraries of candidate ABPs having different variable amino acid sequences in the masking moieties (MMs) and varying positions of the cysteine in the MM were generated. The amino acid sequences of exemplary libraries are provided below as SEQ ID NOs. 15-18 in Table 6. "X" represents a randomized amino acid sequence. Glycine was included in order to impart flexibility to the MM.

TABLE 6

| | N-TerminusLibrary | Substrate | Linker | VEGF Binder |
|---|---|---|---|---|
| 1 (SEQ ID NO: 15) | GQSGQ | C̲X$_6$G | PLGLAG | GGSG | NFGYGKWEWDYGKWLEKVGGC̲ |
| 2 (SEQ ID NO: if) | GQSGQ | X$_5$G | PLGLAG | GGSG | NFGYGKWEWDYGKWLEKVGGC̲ |
| 3 (SEQ ID NO: 17) | GQSGQ | XC̲X$_3$ | PLGLAG | GGSG | NFGYGKWEWDYGKWLEKVGGC̲ |
| 4 (SEQ ID NO: 18) | GQSGQ | X$_5$G | PLGLAG | GGSG | NFGYGKWEWDYGKWLEKVGGG |

X = any amino acid

Figure 6:
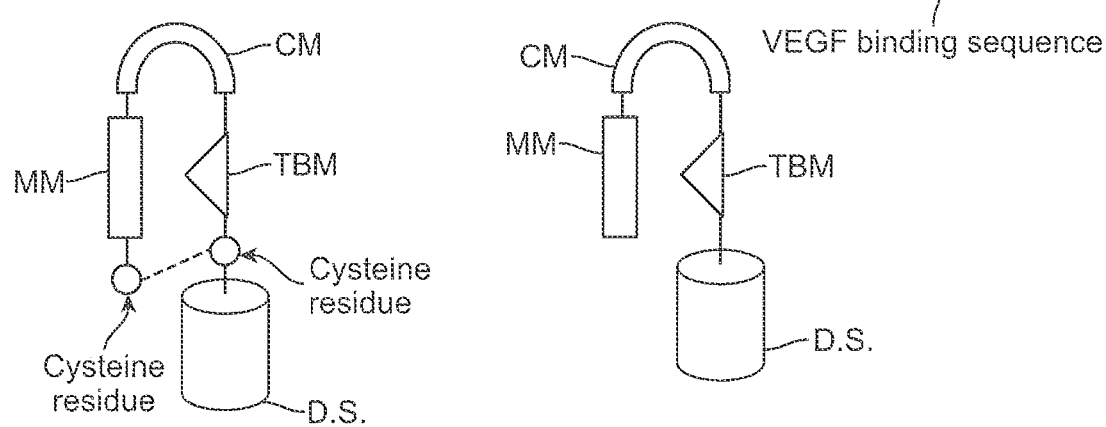
FIG. 6 shows the amino acid sequences of 4 exemplary construct libraries and shows diagrams representing the displayed constructs of the libraries.

FIG. 6 provides a schematic of the library constructs, and illustrates the construct design to provide cysteines of the construct (underlined residues) which can form a disulfide bridge, thereby constraining the conformation of the construct in the uncleaved state.

Figure 7:
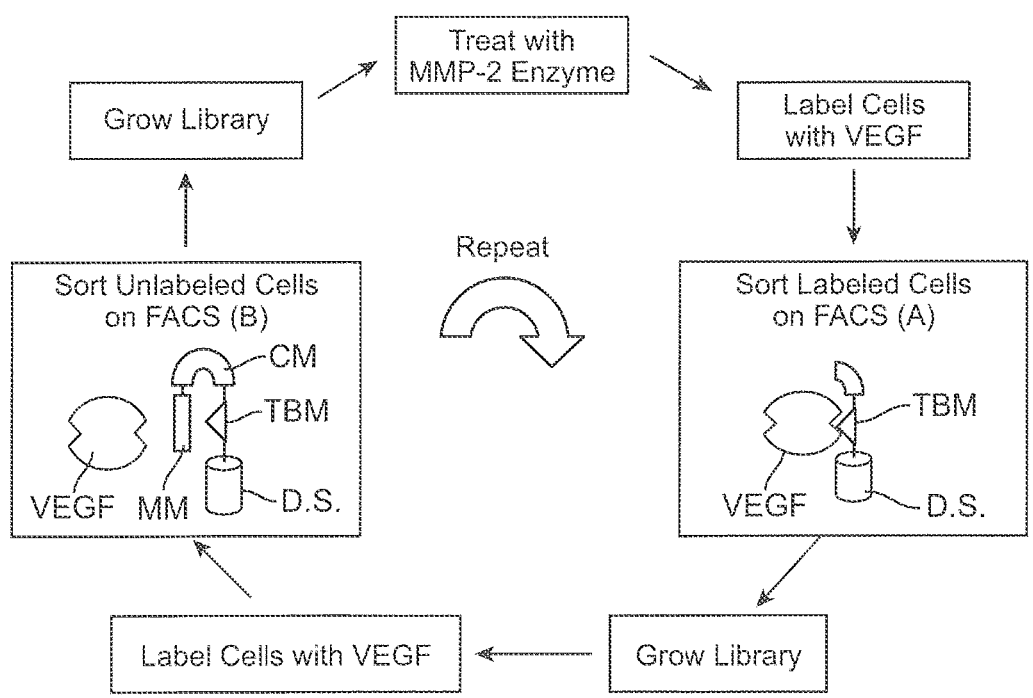
FIG. 7 is a schematic of the screening procedure applied to the construct libraries shown in FIG. 6.

FIG. 7 provides a schematic illustrating the screening/sorting method used to identify candidates that display the switchable phenotype. The libraries were introduced via expression vectors resulting in display of the ABP polypeptides on the surface of the bacterial cells. The resulting display library contained more than 3×10$^8$ transformants. After expansion of the libraries by culture ("Grow Library"), cells displaying the ABP polypeptides were then treated with MMP-2 enzyme to provide for cleavage of the cleavable substrate moiety. MMP-2 treated cells were then contacted with fluorescently labeled VEGF and the cells were sorted by FACS to isolate cells displaying ABPs which bound VEGF after cleavage with MMP-2. The cells that displayed VEGF-binding constructs were then expanded by growth in culture ("Grow Library"). The cells were then contacted with labeled VEGF and sorted by FACS to isolate cells displaying ABPs which failed to bind labeled VEGF in the absence of MMP-2. These steps represented one "cycle" of the screening procedure. The cells can then be subjected to additional cycles by expansion by growth in culture ("Grow Library"), and again subjecting the culture to all or part of the screening steps.

It should be noted that library screening and sorting could also be initiated by first selecting for candidates that do not bind labeled VEGF in the absence of enzyme treatment (i.e., do not bind VEGF when not cleaved).

Exemplary data for one of the libraries is provided in FIG. 8. After 1.5 cycles of selection (i.e., one complete cycle of enzyme treatment, sorting, VEGF-binding, sorting; followed by a half-cycle of enzyme treatment and sorting), libraries exhibited a marked improvement in the "switchable" phenotype, with binding of labeled VEGF in the absence of enzyme (FIG. 8, top right panel) being significantly less than in the presence of enzyme (FIG. 8, bottom right panel). In addition, as illustrated in FIG. 8, left panels, the unsorted library exhibited a less significant switchable phenotype, confirming that the selection/sorting method is effective in enrichment of the library for cells displaying an ABP having a desired switchable phenotype.

Figure 9:
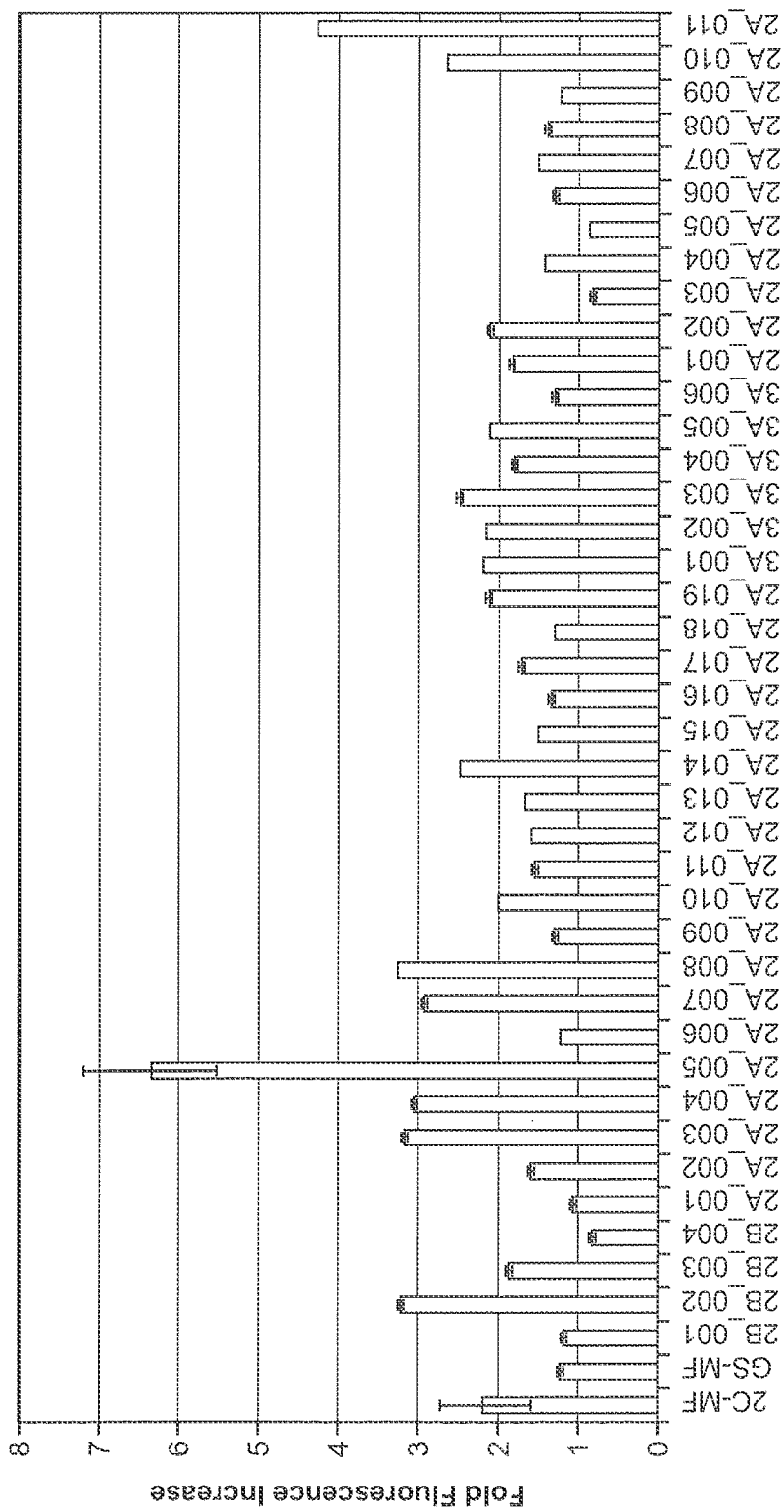
FIG. 9 shows that selected library clones demonstrate improved switching activity over cysteine constrained controls.

In addition, selected clones demonstrated improved "switching" activity compared to cysteine-constrained controls. FIG. 9 shows fold fluorescence increase after cleavage with MMP-2 for selected library clones identified from each of libraries 1-4. The selected clones of FIG. 9, identified after screening the libraries identified in FIG. 6, showed a modest improvement when compared with clones derived from a screen of a random library. For example, of the 40 clones identified in FIG. 9, six demonstrated a 3-fold increase in fluorescence. The average fluorescence increase for the 40 clones was approximately 2 fold. For clones derived from the random library. 2 of 23 clones demonstrated a 3-fold increase in fluorescence. The average fluorescence increase for the random library of clones was approximately 1.5 fold.

The amino acid sequences of clones exhibiting the most marked "switching" phenotype (also referred to as an enzymatically "activatable" phenotype) are provided in FIG. 10.

Figure 24:
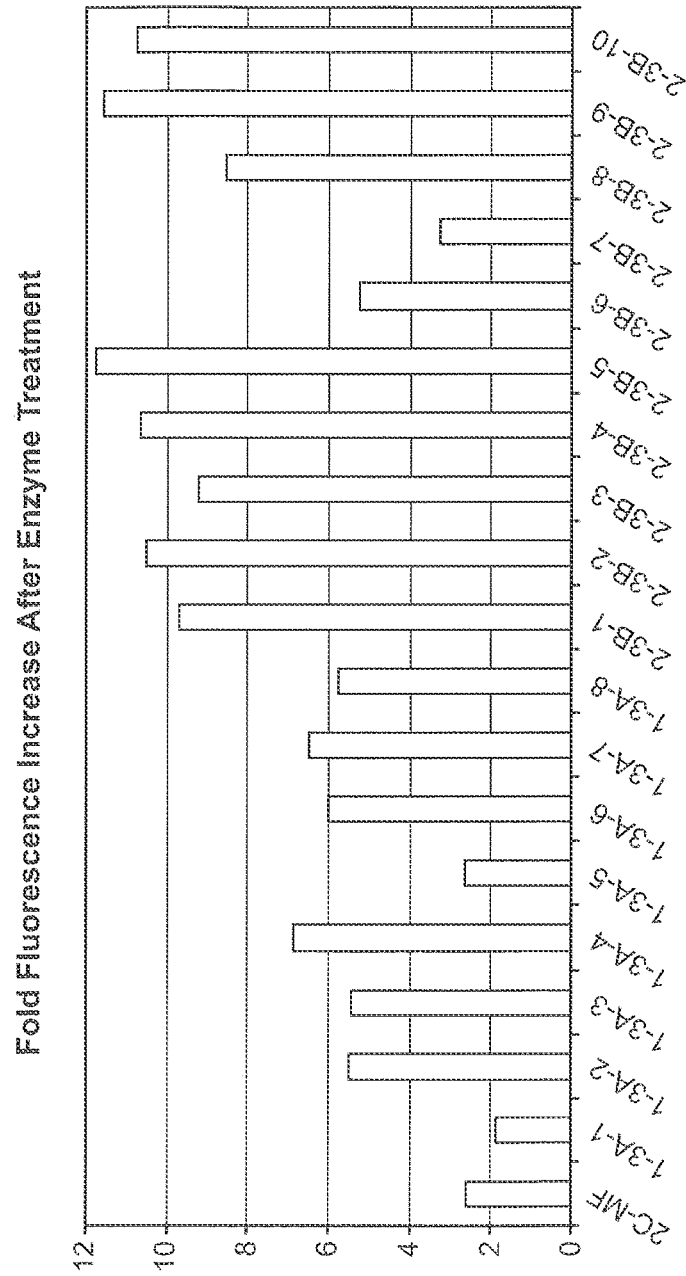
FIG. 24 shows fold fluorescence increase after enzyme treatment for various ABP library clones.

In a further screen, several additional clones were identified which exhibited a marked "switching" phenotype. The fold fluorescence increase after enzyme treatment for these clones is shown in FIG. 24.

Figure 25:
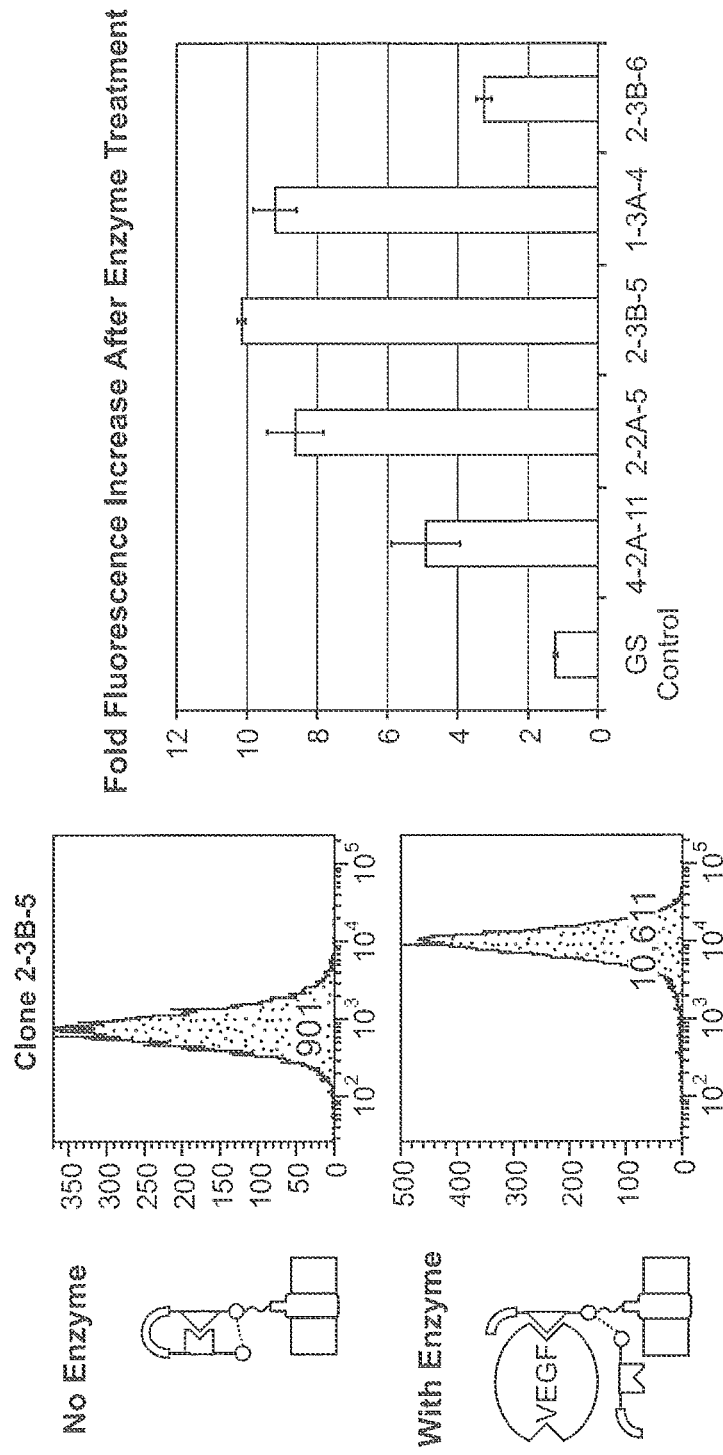
FIG. 25 shows switching activity for selected ABP library clones.
Figure 26:
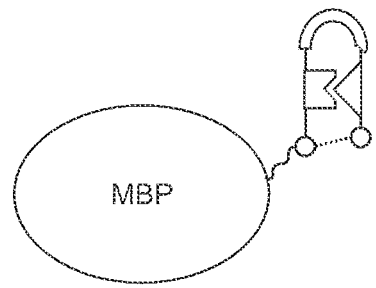
FIG. 26 shows a diagram of a maltose-binding protein (MBP)-ABP fusion utilized in soluble protein binding assays.

FIG. 25 shows switching activity for selected clones based on fold fluorescence increase after enzyme cleavage. Each of clones 4-2A-11 (GEDEEG: SEQ ID NO: 19 including fixed G residue). 2-2A-5 (PEWGCG: SEQ ID NO: 11 including fixed G residue), 2-3B-5 (CEYAFG: SEQ ID NO: 20 including fixed G residue). 1-3A-4 (CSMYWMRG: SEQ ID NO: 21 including fixed C and G residues), and 2-3B-6 (EYEGEG: SEQ ID NO: 22 including fixed G residue) exhibit improved switching activity relative to control, with clone 2-3B-5 exhibiting an approximate 10-fold increase in fluorescence relative to an increase in fluorescence of less than approximately 2-fold for the GS control.

Example 4: The Switchable Phenotype is Attributable to Cleavage of the Cleavable Moiety In general, the switchable phenotype is due to a change in conformation of the ABP that allows for more or less access of the target to the target binding moiety (TBM). Where the ABP contains cysteines capable of forming a disulfide bridge, the switchable phenotype could be a result of at least two different mechanisms: 1) cleavage of the ABP at the enzyme cleavage site; or 2) reduction of the disulfide bond between cysteines positioned near the N- and C-termini of the ABP.

Figure 11:
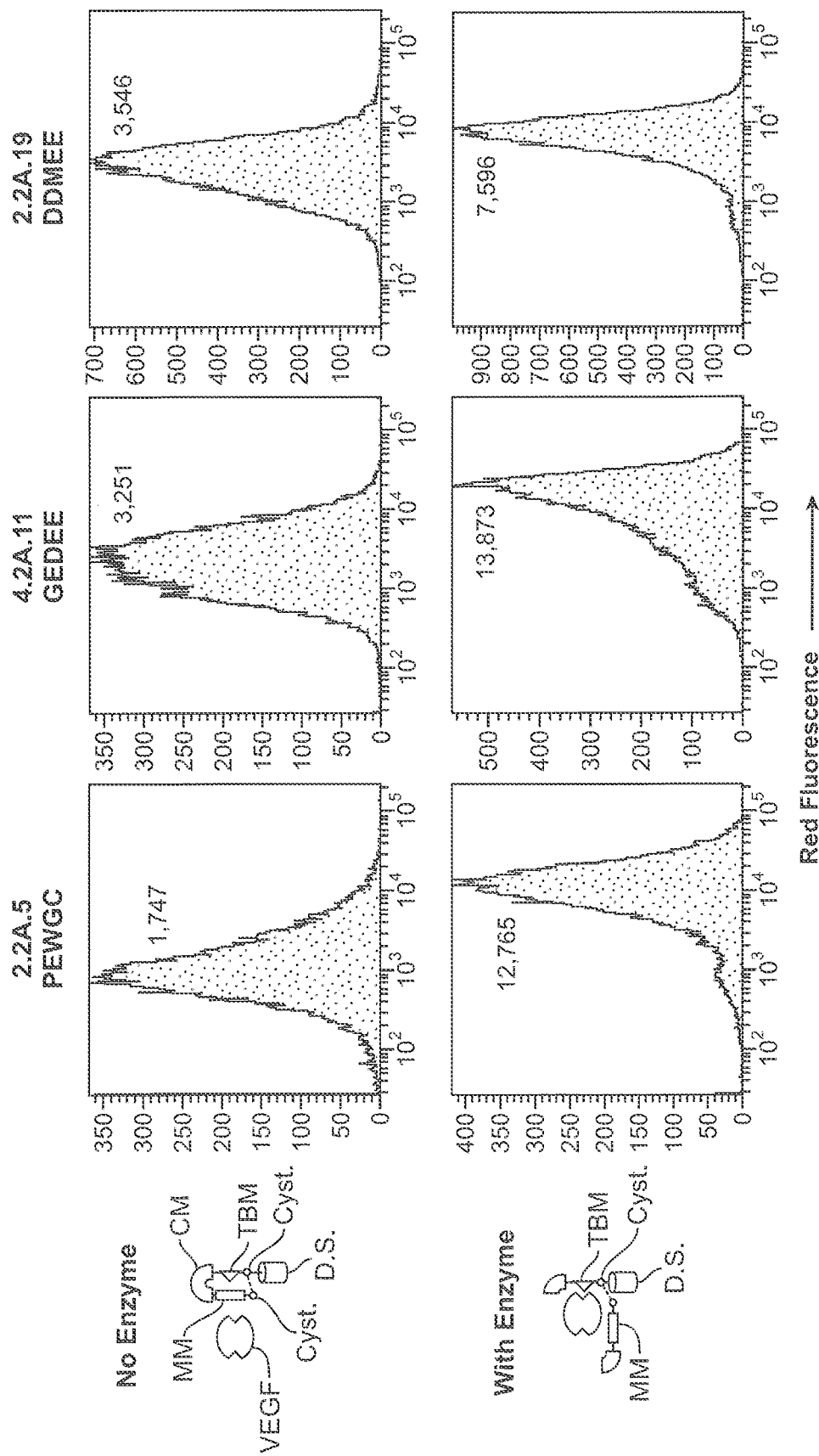
FIG. 11 shows the results of binding experiments that demonstrate switching activity for clones having cysteine residues in the MM as well for clones lacking cysteine residues in the MM.

For example, switching behavior was observed in ABPs that contained a MM that lacked a cysteine. Three clones, each with a different 5 amino acid MM library sequence, were tested for the ability to bind labeled VEGF in the presence and absence of MMP-2. As seen in FIG. 11, clones with MM library amino acid sequences of GEDEE: SEQ ID NO: 23 (GEDEEG: SEQ ID NO: 19 including fixed G residue) and DDMEE: SEQ ID NO: 24 (DDMEEG: SEQ ID NO: 25 including fixed G residue) showed improved binding in the presence of MMP-2 despite the lack of cysteine residues in the MM. This result indicates that the disulfide bond linkage is not necessarily required in order for an ABP to demonstrate the desired switching activity.

Additional cysteine and non-cysteine containing MM sequences identified according to the screening methods described herein are shown in FIG. 22.

Figure 12:
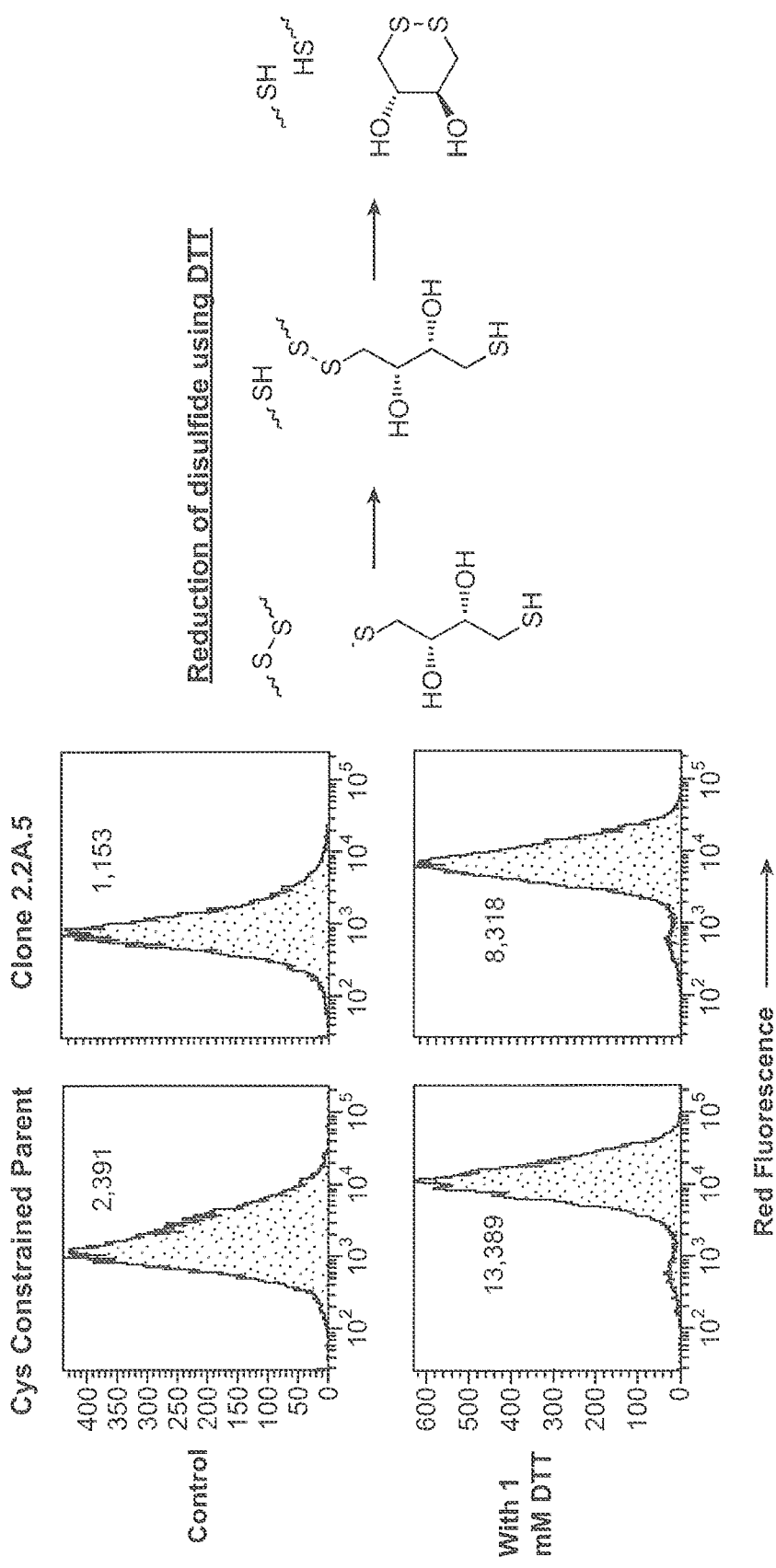
FIG. 12 shows the results of experiments demonstrating that reduction of disulfide bonds in both a cysteine constrained parent and a library clone having a cysteine in the MM results in increased binding of VEGF to the TBM of the constructs.

As indicated above, the switchable phenotype could potentially result from the disruption of the disulfide bond linkage between a cysteine residue in the MM and a cysteine residue adjacent the TBM. This possibility was verified by testing clones in the presence and absence of disulfide bond reducing conditions. As indicated in FIG. 12, clone 2.2A.5 (a clone that was the product of the screening procedure above) and a cysteine constrained parent (i.e., a design or "trial" sequence that shows 2-fold switching activity, sequence given in FIG. 4) that was not the product of the screening procedure were each tested for the ability to bind labeled VEGF in the presence and absence DTT reducing conditions. Both the cysteine constrained parent and clone 2.2A.5 showed increased binding of labeled VEGF after reduction of the disulfide bond with DTT.

Figure 13:
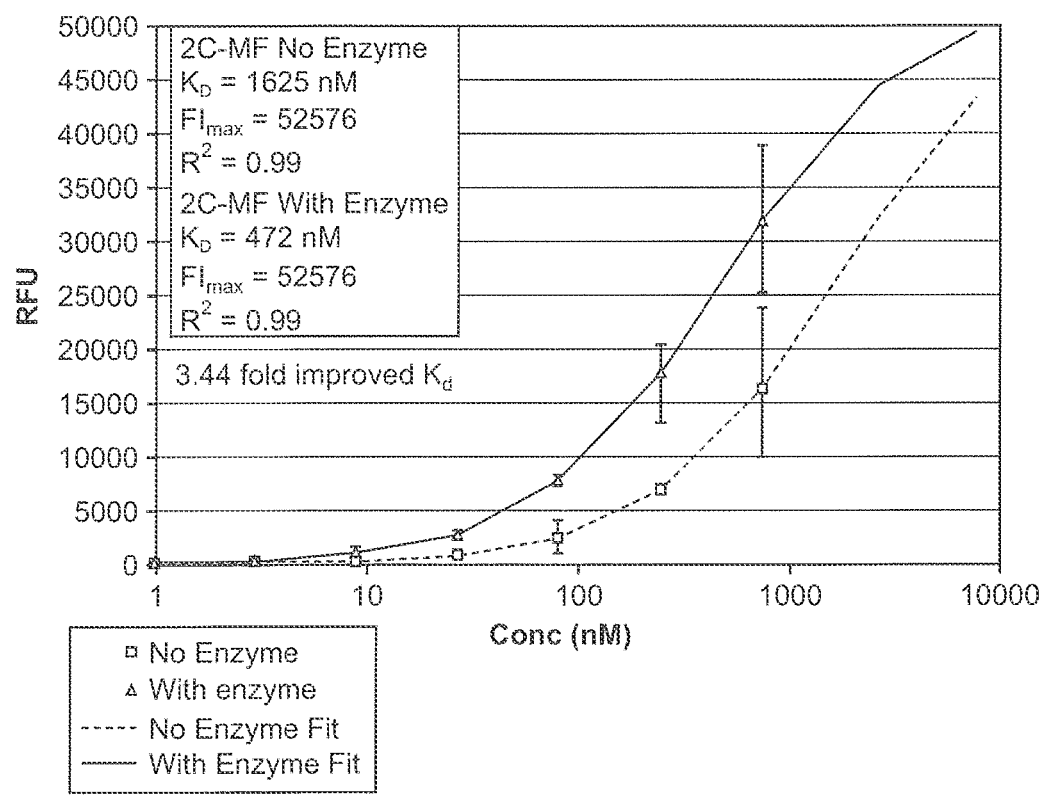
FIG. 13 shows a graphical representation of the improvement in $K_d$ that occurred when a cysteine constrained parent construct was contacted with VEGF and treated with MMP-2, as compared with the $K_d$ in the absence of MMP-2 treatment.
Figure 14:
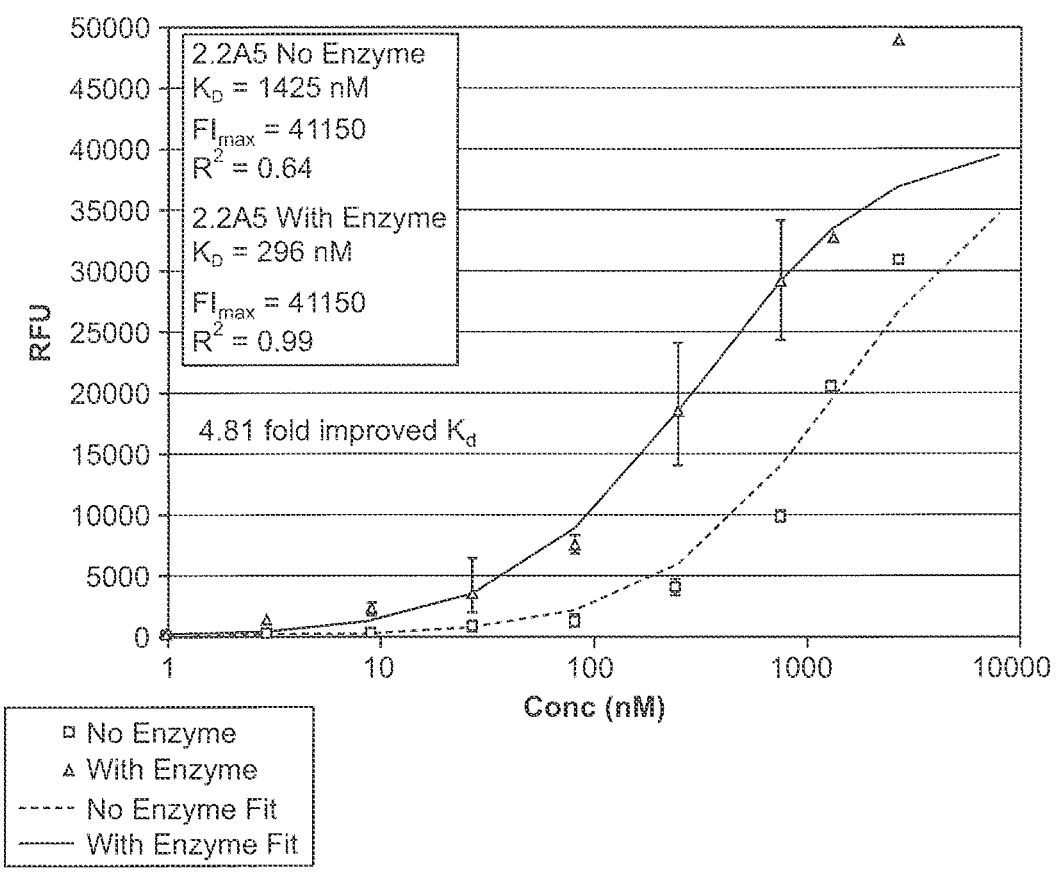
FIG. 14 shows a graphical representation of the improvement in $K_d$ that occurred when library clone 2.2A.5 was contacted with VEGF and treated with MMP-2, as compared with the $K_d$ in the absence of MMP-2 treatment.

However, the screening procedure of the Example above provides for an enhanced switching phenotype over that associated with conformation change as a result of reduction of disulfide bonds. This is evidenced by the results of analysis of the switching phenotype of the cysteine-constrained parent construct and clone 2.2A.5. The $K_{d,app}$ values for VEGF binding by the cysteine constrained parent were determined in the presence and absence of MMP-2 and compared with $K_{d,app}$ values for VEGF binding by the library clone 2.2A.5 in the presence and absence of MMP-2. Clone 2.2A.5 showed an approximately 4.8 fold improvement in $K_d$ in the presence of enzyme (FIG. 14) as compared with an approximately 3.4 fold improvement in $K_d$ in the presence of enzyme for the cysteine constrained parent (FIG. 13).

Figure 23:
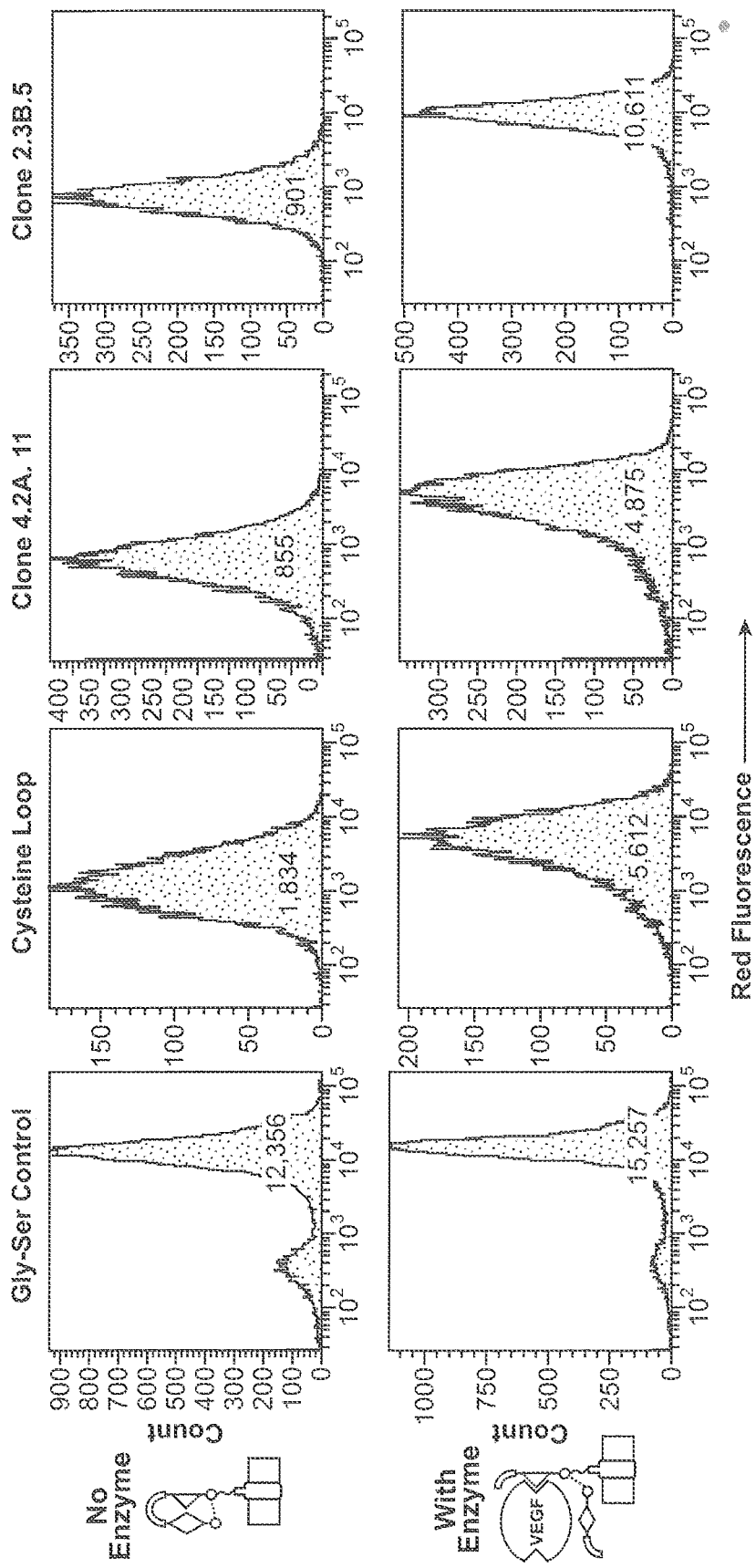
FIG. 23 shows fluorescence values for a cysteine constrained loop structure in the presence and absence of MMP-2 compared with the fluorescence values for library clones 4.2A.11 (a.k.a. 4-2A-11) and 2.3B.5 (a.k.a. 2-3B-5) in the presence and absence of MMP-2.

In an additional experiment, the fluorescence values for a cysteine constrained loop structure were determined in the presence and absence of MMP-2 and compared with the fluorescence values for library clones 4.2A.11 (a.k.a. 4-2A-11) and 2.3B.5 (a.k.a. 2-3B-5) in the presence and absence of MMP-2. Clone 4.2A.11 showed an approximate 5.7 fold increase in fluorescence in the presence of enzyme (FIG. 23) and clone 2.3B.5 showed an approximate 11.8 fold increase in fluorescence in the presence of enzyme as compared with an approximately 3 fold increase in fluorescence in the presence of enzyme for the cysteine constrained loop structure (FIG. 23).

These results indicate that optimization of a cysteine constrained ABP to provide for an enhanced switchable phenotype can be achieved by screening an ABP library containing MMs with variable amino acid sequences.

Example 5: Screening for Desired Dynamic Range

Figure 15:
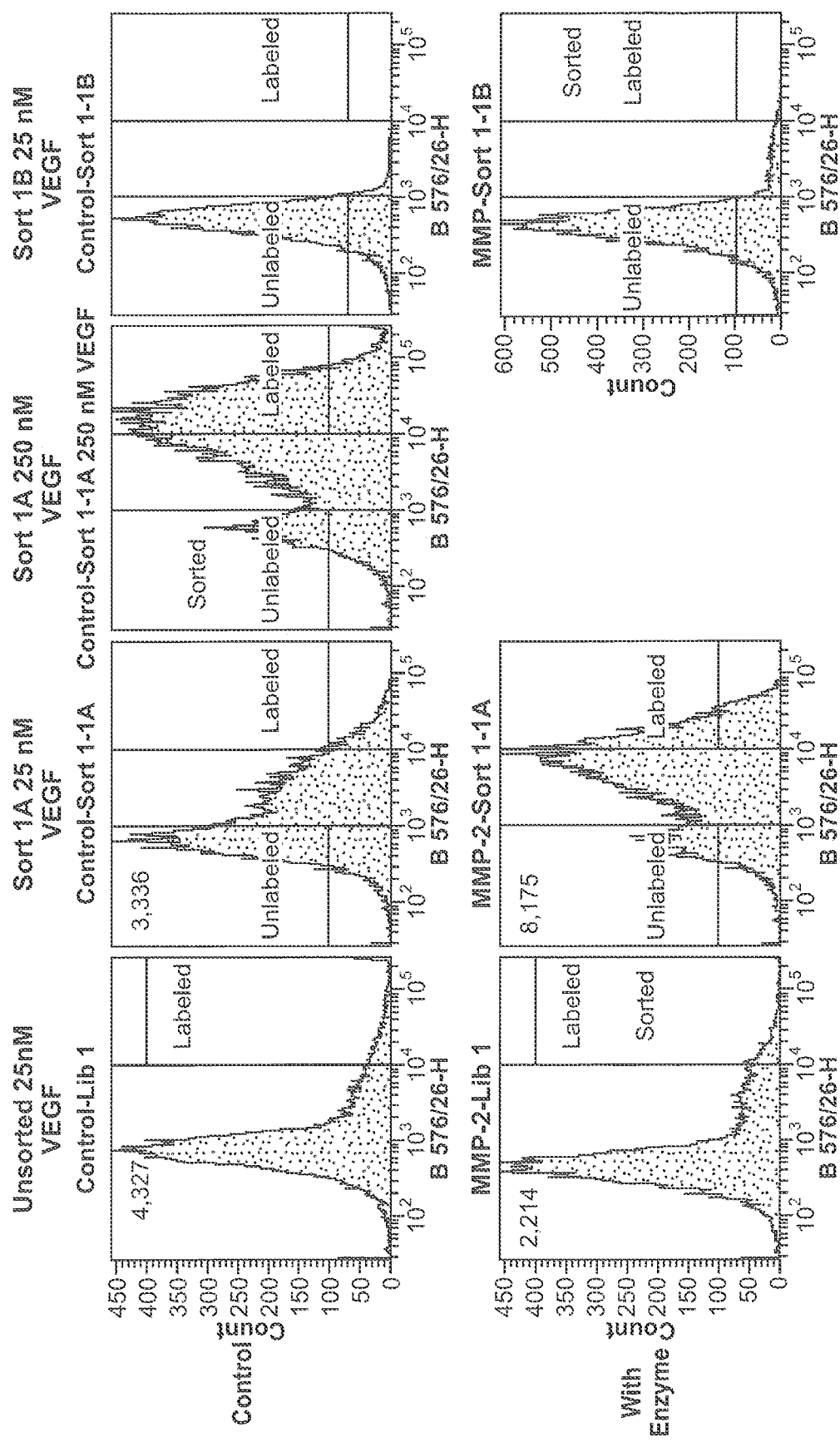
FIG. 15 shows the results of sorting of masking moiety Library 1 for expanded dynamic range by adjusting the concentration of labeled target.
Figure 16:
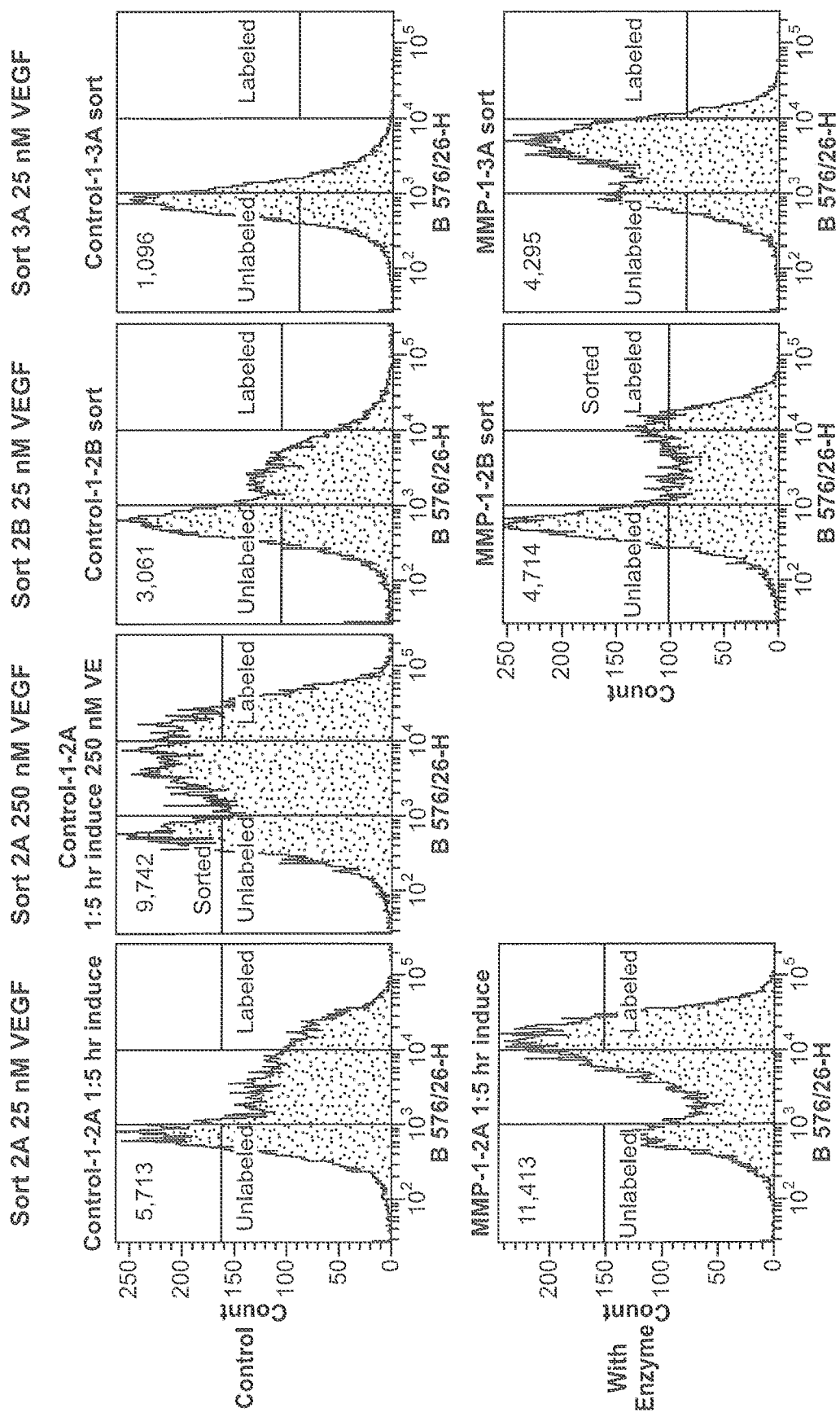
FIG. 16 shows the results of sorting of masking moiety Library 1 for expanded dynamic range by adjusting the concentration of labeled target and identifies an average 4 fold dynamic range for a Library 1 ABP pool. Note that for FIG. 16, the term EABP refers to an ABP as described herein.
Figure 21:
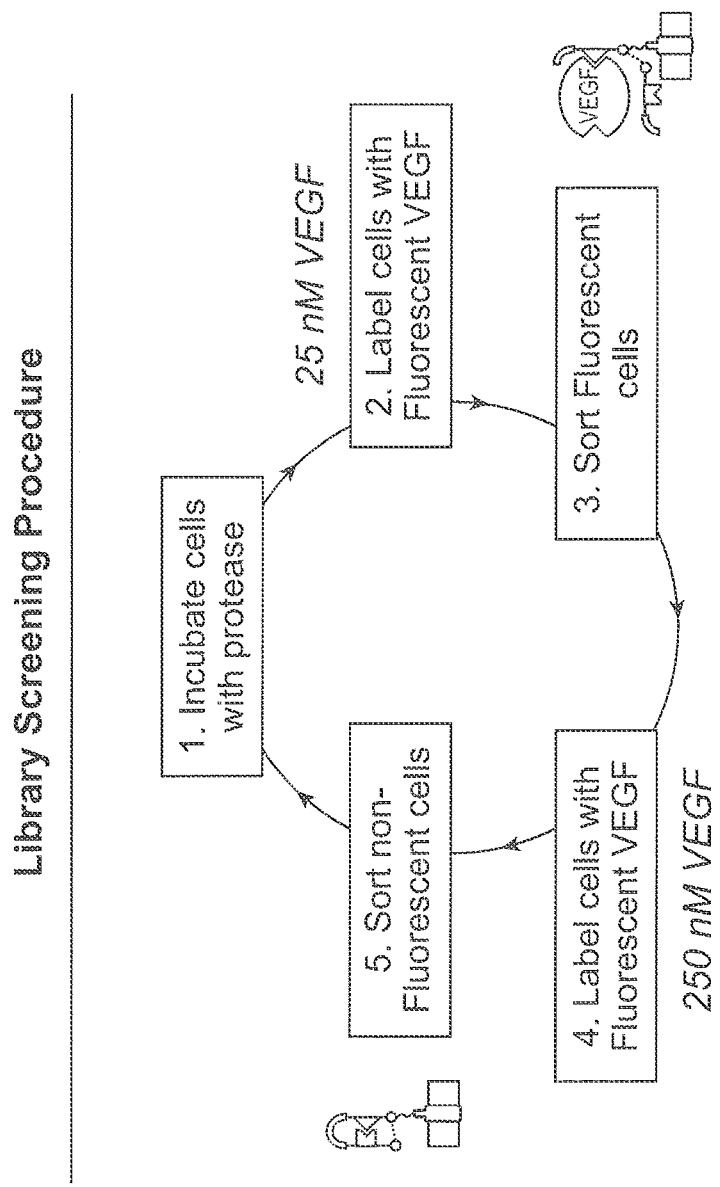
FIG. 21 shows an embodiment of the library screening procedure shown in FIG. 2.

Dynamic range can be enhanced by at least two mechanisms; 1) the switch off state can be improved by improving the MM to prevent binding between the target and TBM, and 2) the affinity of the TBM can be improved after substrate cleavage that results in the MM motif acting as cooperative target binding element (FIGS. 4 and 5). Screening for expanded dynamic range can, in certain embodiments, be effectively accomplished by using alternating separations, (e.g. using FACS) that use different concentrations of the target protein for the "A" and "B" steps represented in FIG. 2. To identify in separation "A" binders that may have improved affinity relative to the TBM when used alone (i.e. outside of the switch context), a target concentration of 10 nM was used that is approximately 10-fold below the expected dissociation constant (100 nM) of the TBM. Cells exhibiting the highest level of fluorescence were then collected using FACS, and amplified by overnight growth. Then, to improve the off-state (i.e. ability to bind the target in the absence of the protease), the cell population was incubated with 1 µM VEGF (a concentration significantly above the KD of the TBM), and cells exhibiting low levels of fluorescence were collected. This process resulted in a pool of ABPs with a greater dynamic range, than a process using the same concentration of the target in both A and B sorts. An additional embodiment of a screening method using different target concentrations for steps "A" and "B" is depicted in FIG. 21, wherein a 25 nM VEGF concentration is used for the "A" sort and a 250 nM VEGF concentration is used for the "B" sort. The enriched cell populations resulting from selection using FACS are shown in FIGS. 15 and 16 for sorts 1A, 1B, 2A, 2B, and 3A where A and B are positive and negative selections, respectively. Enrichment of the library for ABPs can be determined by comparing the unsorted library populations' fluorescence distribution change from protease treatment, to that of the round 3A population before and after protease treatment. The later enriched pool shows an average dynamic range of approximately four-fold as indicated by the four fold increase in cell fluorescence after enzyme treatment (FIG. 16. Right-hand panel "Sort 3A 25 nM VEGF").

Example 6: Soluble Protein Fusions Demonstrate Enzyme Mediated Binding

In order to demonstrate the activity of ABPs in soluble form. C-terminal maltose-binding protein (MBP) fusions of VEGF binding clones and VEGF binding ABPs were constructed and tested.

Methods and Materials

VEGF was immobilized to the Biacore™ CM5 sensor chip surface using the standard amine coupling kit. An NHS/EDC mixture was injected first to activate the surface using the surface preparation wizard in the Biacore™ software. Then. 25 ug/mL concentration of VEGF was injected until the desired immobilization amount was reached (typically ~5000 response units). The surface is then blocked with ethanolamine. A control reaction was performed on another surface with NHS/EDC then Ethanolamine.

After the VEGF is covalently immobilized, the maltose-binding protein (MBP) fusions of VEGF binding or VEGF binding ABP clones were injected over both the VEGF surface and the control surface. Injections were typically for 1 minute, with a few minutes of dissociation time after each injection. The clones were injected both with and without 30 nM MMP-2 enzyme. For analysis, the signal on the VEGF surface minus the signal on the control surface is the binding response (in RU). Clones were compared in triplicate, with and without enzyme, at clone concentrations of up to 15 micromolar.

Results

Figure 27:
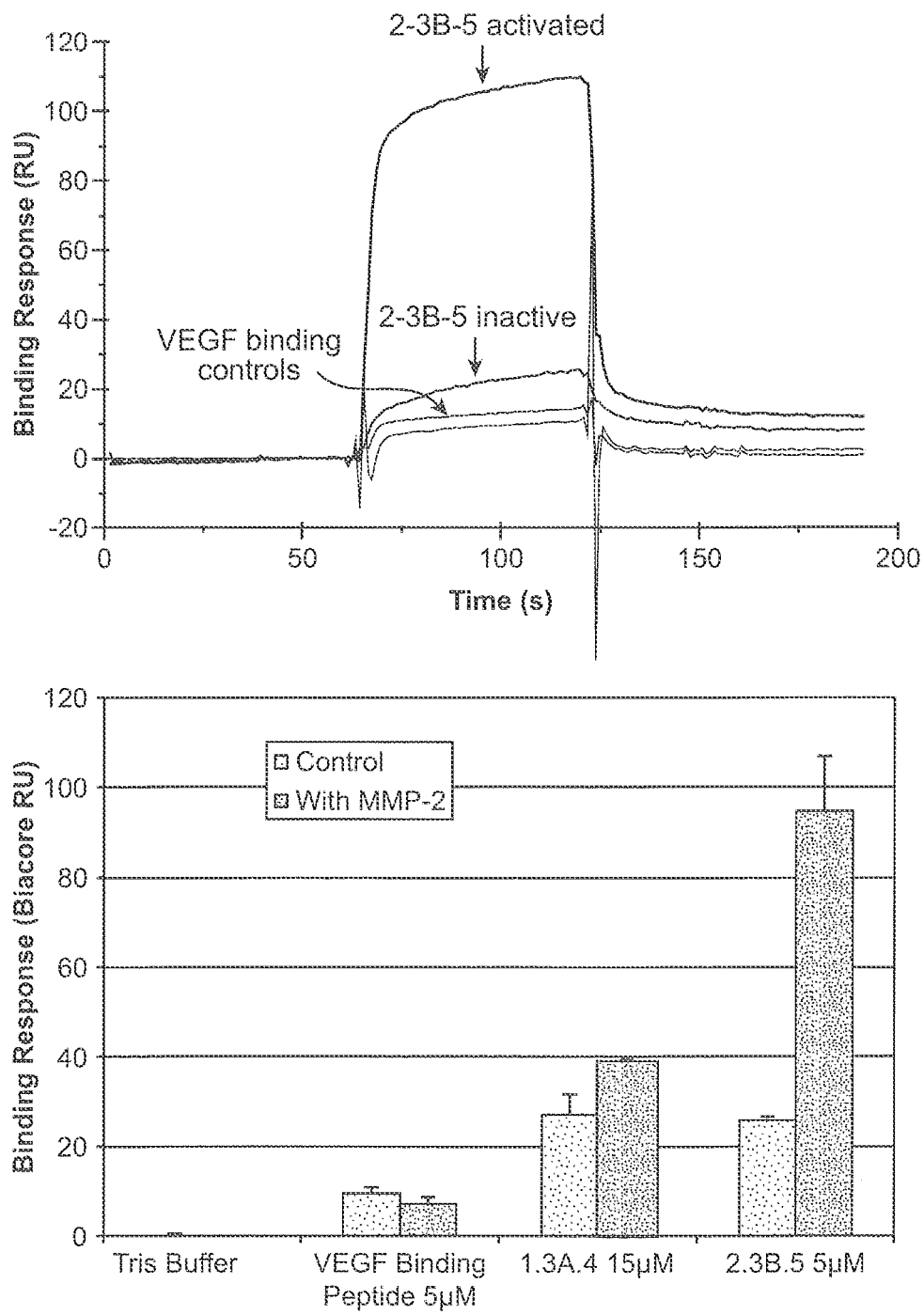
FIG. 27 provides graphs showing Biacore™ assay results demonstrating that soluble ABP fusions retain enzyme mediated binding properties.
Figure 28:
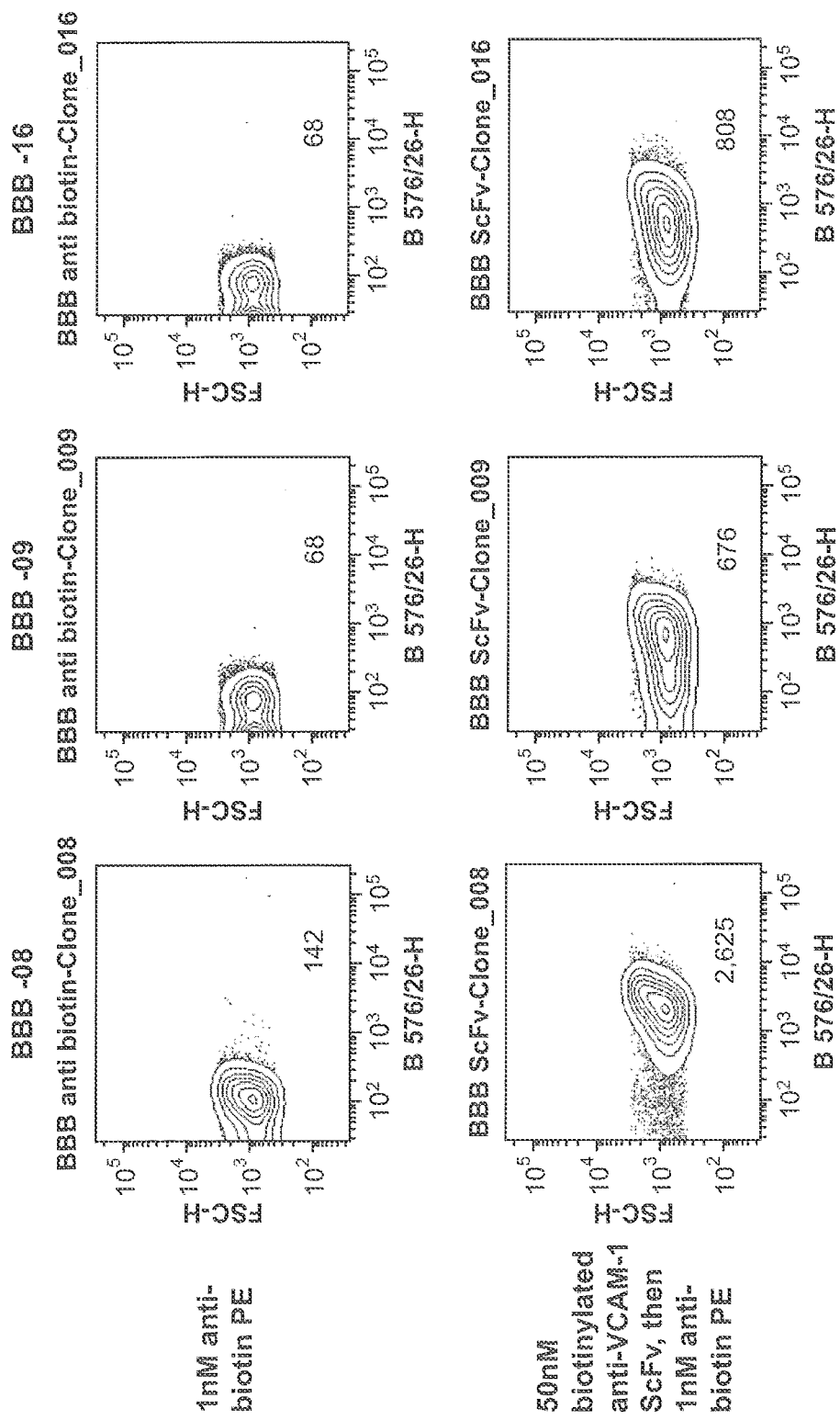
FIG. 28 provides the results of FACS analysis showing binding of selected candidate MM peptides to anti-VCAM-1 scFV.
Figure 29:
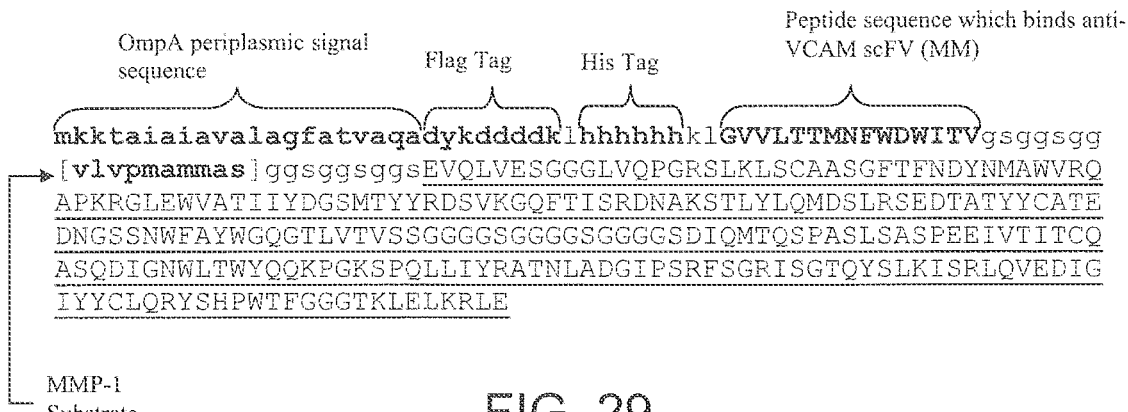
FIGS. 29, 30 and 31 each provide an amino acid sequence of a prophetic ABP comprising an anti-VCAM-1 scFV.
Figure 30:
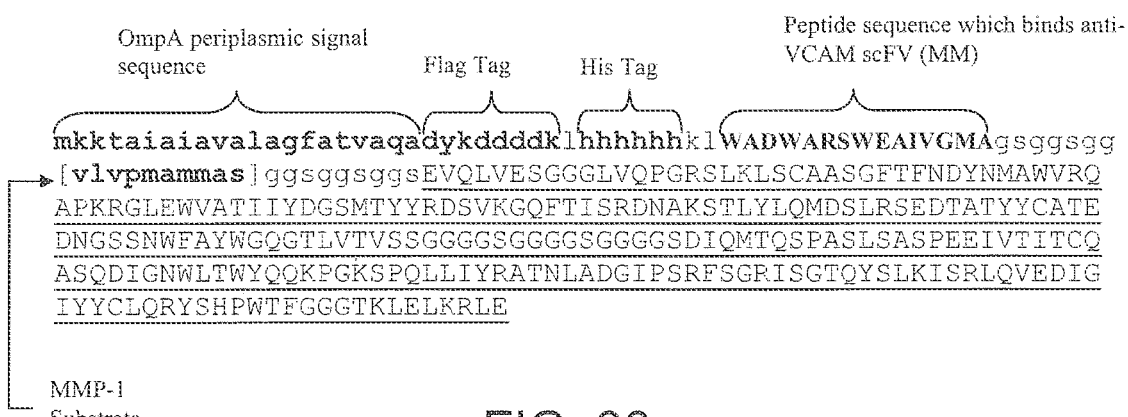
Figure 31:
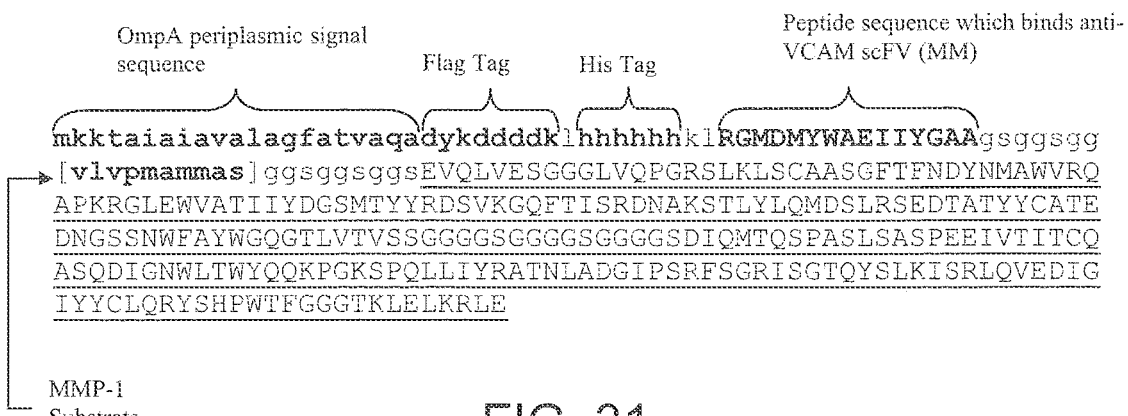
Figure 32:
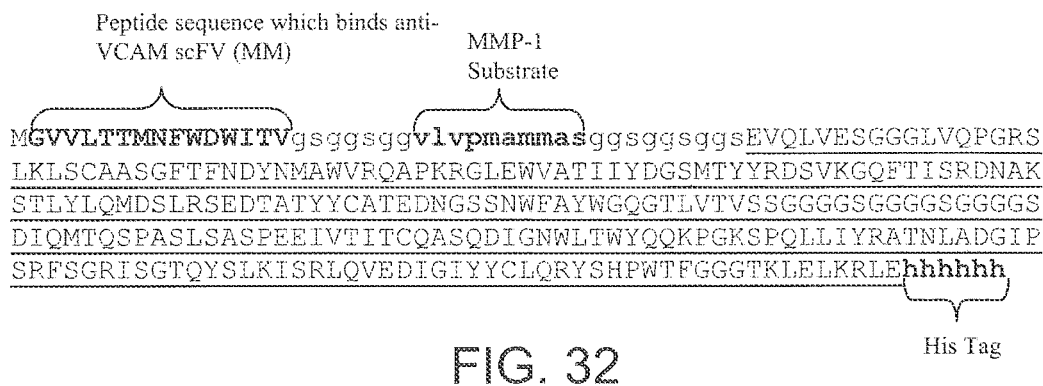
FIGS. 32, 33 and 34 each provide an amino acid sequence of a prophetic ABP comprising an anti-VCAM-1 scFV, wherein the ABPs are designed for cytoplasmic expression as inclusion bodies.
Figure 33:
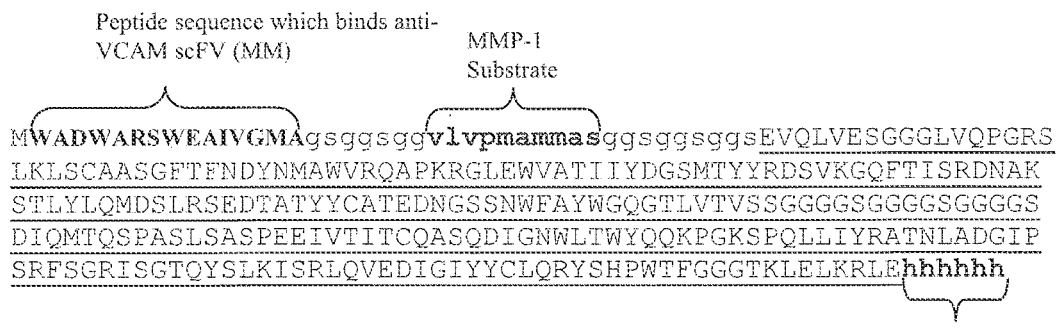
Figure 34:
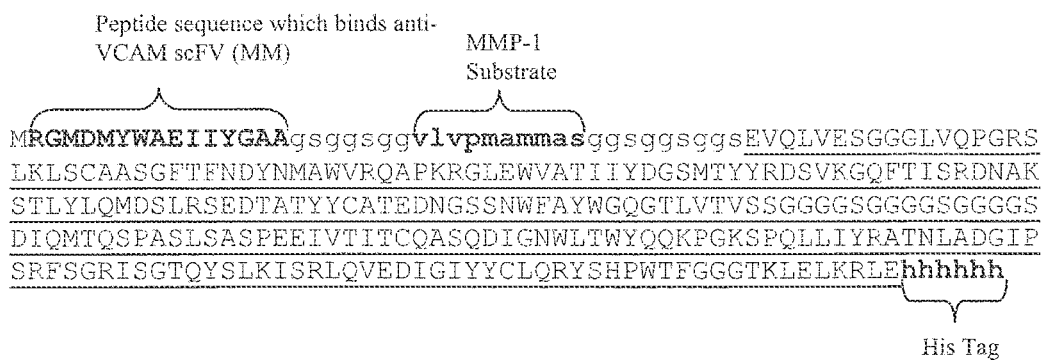

As indicated in FIG. 27, exemplary MBP-ABP fusions retained their enzyme mediated VEGF binding properties, with the 2.3B.5 (2-3B-5) fusion exhibiting an approximate 4-fold increase in binding response in the presence of MMP-2 enzyme. A similar increase in binding response in the presence of enzyme was not seen for the VEGF binding peptide controls. These results demonstrate retained "switching activity" for soluble ABPs.

Example 7: Identification of Peptide Sequences for Use as MMs in an Anti-VCAM-1 ABP The following materials and methods were utilized to identify peptide sequences for use as masking moieties (MM) in ABPs wherein the target binding moiety (TBM) comprises an antigen binding domain (ABD) of an anti-VCAM-1 scFv.

Methods and Materials

Magnetic-Activated Cell Sorting (MACS) (one round) and Fluorescence Activated Cell Sorting (FACS) (three rounds) were utilized to enrich for clones exhibiting strong binding to anti-VCAM-1 scFv.

Bacterial cells displaying selected peptide sequences were sorted by FACS after contacting with 1 nM anti-biotin phycoerythrin (PE) or 50 nM biotinylated anti-VCAM scFv followed by 1 nM anti-biotin PE.

Results

The following peptide sequences were identified as a result of the referenced MACS and FACS analysis:

TABLE 7

| Clone | Amino Acid Sequence |
|---|---|
| BBB-08 | GVVLTTMNFWDWITV (SEQ ID NO: 26) |
| BBB-09 | WADWARSWEAIVGMA (SEQ ID NO: 27) |
| BBB-16 | RGMDMYWAEIIYGAA (SEQ ID NO: 28) |

As demonstrated by FACS analysis in FIG. 28, each of clones BBB-08, BBB-09 and BBB-16 showed significant binding to anti-VCAM-1 scFV. Of the three clones. BBB-08 showed the highest level of binding to anti-VCAM-1 scFV with an average fluorescence value of 2,625 following incubation with anti-VCAM-1 scFV as compared to an average fluorescence value of 142 in the absence of anti-VCAM-1 scFV. As such, these peptides are likely candidates for functional MMs in ABPs comprising an antigen binding domain (ABD) of an anti-VCAM-1 scFv as a TBM.

Example 8: Prophetic ABPs Comprising an Anti-VCAM-1 Antigen Binding Domain

Prophetic examples of ABPs comprising an anti-VCAM-1 scFv (MK271) are described herein. These ABPS will be inactive under normal conditions due to an attached MM. When the scFv reaches the site of plaque, however, matrix metalloproteinase-1 will cleave a substrate linker connecting the peptide inhibitor to the scFv allowing it to bind to VCAM-1. A representation of this process is set forth in FIG. 35. Bacterial cell surface display was used as described in Example 7 to find suitable MMs for the antibody. In the prophetic ABPs, selected MMs are combined with an enzyme substrate to be used as a trigger to create a scFv construct that becomes competent for targeted binding after protease activation.

Prophetic ABPs utilizing the peptide sequences identified in Example 7 and comprising an antigen binding domain (ABD) of an anti-VCAM-1 scFv are provided in FIGS. 29, 30 and 31. These prophetic ABP sequences comprises an OmpA periplasmic signal sequence, a Flag tag, a His tag, a peptide sequence which binds anti-VCAM scFV, an MMP-1 substrate and an anti-VCAM scFV sequence. Lower-case, non-bold letters indicate linker sequences. The sequence of the anti-VCAM scFV is indicated by underlining and all caps. The MM sequence is indicated in bold and all caps.

Construction of Protease Activated Antibody

Genes encoding ABPs comprising a VCAM-1 antibody in single-chain form are produced by overlap extension PCR or total gene synthesis with flanking SfiI restriction enzyme sites, digested with SfiI and ligated into a similarly digested expression plasmid pBAD33, or any other suitable bacterial, yeast, or mammalian expression vector familiar to one skilled in the art. Full length antibodies could alternatively be produced using commercially available expression vectors incorporating half-life extending moieties (e.g. the Fc region of an IgG, serum albumin, or transferrin) and methods familiar to one skilled in the art. The expression plasmid is then transformed or transfected into an appropriate expression host such as BL21 for *E. coli* or HEK293t cells. Single chain antibodies are harvested from overnight cultures using a Periplasmic fraction extraction kit (Pierce), and purified by immobilized metal ion affinity chromatography, and by size exclusion chromatography.

In some instances, it may be desirable to produce ABPs comprising antibodies as insoluble aggregates in the cytoplasm. In such cases, the signal sequence can be removed, and an appropriate affinity tag (6×His) can be introduced at the C-terminus to aid purification. Prophetic ABP sequences for cytoplasmic expression (as inclusion bodies) are provided in FIGS. 32, 33 and 34. Lower-case, non-bold letters indicate linker sequences. The sequence of the anti-VCAM scFV is indicated by underlining and all caps. The MM sequence is indicated in bold and all caps.

Assay for Antibody Switching Activity In Vitro

Aliquots of protease-activated antibodies, at a concentration of 1 pM-1 μM) are incubated in a buffered aqueous solution separately with 0 and 50 nM MMP-1 for 3 hrs. The reaction mixtures are then assayed for binding using ELISA or surface Plasmon resonance with immobilized antigen VCAM-1. An increase in binding activity for the ABP after protease treatment is indicated by an increase in resonance units when using BIAcore™ SPR instrumentation. The change in apparent dissociation constant (Kdiss) as a result of MMP cleavage can then be calculated according the instrument manufacturer's instructions (BIAcore, GE Healthcare).

Example 9: Cloning of the Anti-VEGF scFv TBM

In certain embodiments, the ABP includes a TBM that contains an ABD, a MM, and a CM. In this and following examples an ABP containing a masked MMP-9 cleavable anti-VEGF scFv (target=VEGF; TBM=anti-VEGF single chain Fv) was constructed. As a first step in the production of such an ABP, constructs containing an anti-VEGF scFv were generated (the TBM). An anti-VEGF scFv TBM ($V_L$-linker L-$V_H$) was designed from the published sequence of ranibizumab (Genetech. Chen, Y., Wiesmann, C., Fuh, G., Li, B., Christinger, H., McKay, P., de Vos, A. M., Lowman, H. B. (1999) Selection and Analysis of an Optimized Anti-VEGF Antibody: Crystal Structure of an Affinity-matured Fab in Complex with Antigen *J. Mol. Biol.* 293, 865-881) and synthesized by Codon Devices (Cambridge, MA).

Ranibizumab is a monoclonal antibody Fab fragment derived from the same parent murine antibody as bevacizumab (Presta L G, Chen H, O'Connor S J, et al Humanization of an anti-vascular endothelial growth factor monoclonal antibody for the therapy of solid tumors and other disorders. Cancer Res, 57: 4593-9, 1997). It is much smaller than the parent molecule and has been affinity matured to provide stronger binding to VEGF-A. Ranibizumab binds to and inhibits all subtypes of vascular endothelial growth factor A (VEGF-A). A His6 tag at the N-terminus and a TEV protease cleavage site were included in the design. The TEV protease is a protease isolated from tobacco etch virus, is very specific, and is used to separate fusion proteins following purification. The anti-VEGF scFv nucleotide and amino acid sequences are provided below in SEQ ID NOs: 29 and 30 respectively.

TABLE 8

SEQ ID NO: 29:
anti-VEGF scFv TBM nucleotide sequence gatattcaactgacccagagcccttcttccctgagtgccagcgtgggtga ccgtgttacgatcacttgctcggccagccaagatatttctaactacctga attggtaccagcagaagccaggaaaggcaccaaaagtcctgatctacttc acaagttcactgcattccggcgtaccgtcgcgctttagcggttctggcag tggtaccgacttcaccctgactatctcgagtctgcaacctgaggattttg ctacatattactgtcagcaatattcgaccgtgccgtggacgttcgggcag ggcaccaaagtggagattaaggggggtggaggcagcggggaggtggctc aggcggtggagggtctggcgaggtccagctggtagaaagcggggcggac tggtccaaccgggcggatccctgcgtctgagctgcgcggcctcgggttac gactttactcactacggaatgaactgggttcgccaagcccctggtaaagg tctggaatgggtcggatggattaatacatacactggagaacctacttatg ctgctgatttcaaacgtcgctttactttctctctggatacaagtaagtca accgcctatctgcaaatgaacagcctgcgtgcagaggacacggctgtgta ctattgtgcgaaatatccttattattatggaacttcccactggtatttcg atgtatgggccagggtactctggttacagtgtcg

TABLE 9

SEQ ID NO: 30:
anti-VEGF scFv TBM amino acid sequence

DIQLTQSPSSLSASVGDRVTITCSASQDISNYLBWYQQKPGKAPKVLIYF

TSSLHSGVPSRFSGSGSGTDFTLTISSLQPEDFATYYCQQYSTVPWTFGQ

GTKVEIKGGGGSGGGGSGGGGSGEVQLVESGGGLVQPGGSLRLSCAASGY

DFTHYGMNWVRQAPGKGLEWVGWINTYTGEPTYAADFKRRFTFSLDTSKS

TAYLQMNSLRAEDTAVYYCAKYPYYYGTSHWYFDVWGQGTLVTVS

Example 10: Screening and Identification of MMs for Anti-VEGF scFv

Ranibizumab was used to screen a pooled random peptide library, consisting of peptides that are $X_{15}$ ($8.3 \times 10^9$), $X_4CX_7CX_4$ ($3.6 \times 10^9$), or $X_{12}CX_3$ ($1.1 \times 10^9$), where X is any amino acid and the number represents the total diversity of the library. The total diversity of the pooled library was $1.3 \times 10^{10}$. The screening consisted of one round of MACS and two rounds of FACS sorting. In the first round MACS screen, $1 \times 10^{11}$ cells were probed with 150 nM biotinylated-ranibizumab, and $5.5 \times 10^7$ binding cells were isolated. In the first FACS screen, positive cells isolated in the MACS screen were probed with 500 nM biotinylated-ranibizumab, and visualized with neutrAvidin-PE (Molecular Probes, Eugene, OR). The second and third rounds of FACS selections were done with 500 nM and then 100 nM Alexa-labeled ranibizumab in the presence of 20 uM IgG. Individual clones were sequenced and subsequently verified for their ability to bind anti-VEGF scfv by FACS analysis. Amino acid sequences of MMs for anti-VEGF scFv are provided in Table 10 below. (These sequences will hereafter be referred to as 283MM, 292MM, 306MM, etc.)

TABLE 10

| MMs for anti-VEGF scFv | |
|---|---|
| JS283 | ATAVWNSMVKQSCYMQG (SEQ ID NO: 31) |
| JS292 | GHGMCYTILEDHCDRVR (SEQ ID NO: 32) |
| JS306 | PCSEWQSMVQPRCYYGG (SEQ ID NO: 33) |
| JS308 | NVECCQNYNLWNCCGGR (SEQ ID NO: 34) |
| JS311 | VHAWEQLVIQELYHC (SEQ ID NO: 35) |
| JS313 | GVGLCYTILEQWCEMGR (SEQ ID NO: 36) |
| JS314 | RPPCCRDYSILECCKSD (SEQ ID NO: 37) |
| JS315 | GAMACYNIFEYWCSAMK (SEQ ID NO: 38) |

Figure 38:
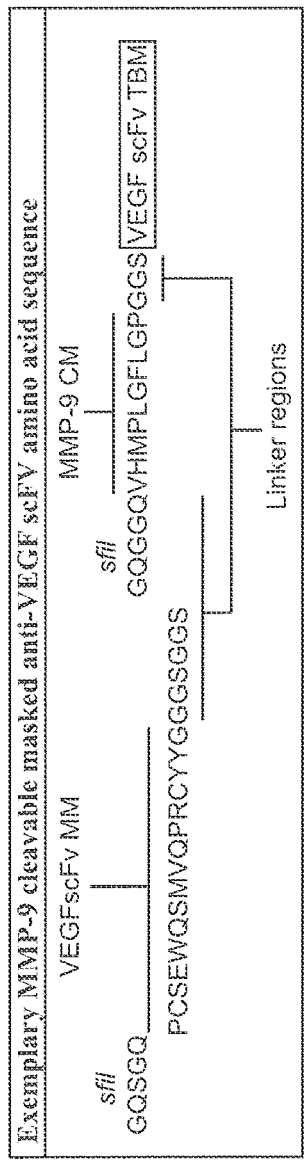

Example 10: Construction of the ABP: MMP-9 Cleavable, Masked-Anti-VEGF scFv Vectors A CM (substrate for MMP-9) was fused to the masked anti-VEGF scFv construct to provide a cleavable, masked ABP. An exemplary construct is provided in FIG. 38. Several exemplary ABP constructs and sequences containing different CMs are described in great detail below. Primers utilized for construction of the exemplary constructs are represented in Table 11 below.

TABLE 11

Primers utilized for construction of MMP-9 cleavable, masked- anti-VEGF scFv

CX0233 5'gaattcatgggccatcaccatcaccatcacggtgggg3' (SEQ ID NO: 39)

CX0249 5'gtgagtaagcttttattacgacactgtaaccagagtaccctgg3' (SEQ ID NO: 40)

CX0270 5'gtggcatgtgcacttggccaccttggcccactcgagctggccagactggccctgaaaatacgatttttccc3' (SEQ ID NO: 41)

CX0271 5'gagtgggccaaggtggccaagtgcacatgccactgggcttcctgggtccggcggttctgatattcaactgacccagagcc3' (SEQ ID NO: 42)

CX0288 5' ttcgagctcgaacaacaacaacaataacaataacaacaac3' (SEQ ID NO: 43)

CX0289 5' gctttcaccgcaggtacttccgtagctggccagtctggcc3' (SEQ ID NO: 44)

TABLE 11-continued

Primers utilized for construction of MMP-9 cleavable, masked- anti-VEGF scFv

CX0290 5' cgctccatgggccaccttggccgctgccaccagaaccgcc3' (SEQ ID NO: 45)

CX0308 5' gcccatgccggccatggccggccagtctggccagctcgagt3' (SEQ ID NO: 46)

CX0310 5' ccagtgccaagctttagtggtgatggtgatgatgcgacactgtaaccagagtaccctggcc3' (SEQ ID NO: 47)

CX0312 5'cttgtcacgaattcgggccagtctggccagctcgagt3' (SEQ ID NO: 48)

CX0314 5'cagatctaaccatggcgccgctaccgcccgacactgtaaccagagtaccctg3' (SEQ ID NO: 49)

Cloning and Expression of the ABP: A MMP-9 Cleavable, Masked Anti-VEGF scFv as a MBP Fusion Cloning: A MBP:anti-VEGF scFv TBM fusion was cloned. The MBP (maltose binding protein) expresses well in E. coli, as a fusion protein, and can be purified on a maltose column, a method well known in the art to make fusion proteins. In this example, the MBP was used to separate the masked scFv. The His6 tagged Anti-VEGF scFv TBM was cloned into the pMal-c4x vector (NEB) as a C-terminal fusion with MBP using the EcoRI and HindIII restriction sites in the multiple cloning site (MCS). The primers CX0233 and CX0249 (Table 11) were used to amplify the Anti-VEGF scFv TBM and introduce the EcoRI and HindIII sites, respectively.

The accepting vector for the ABP (the peptide MM, the anti-VEGF scFv TBM and the MMP-9 CM) was synthesized using polymerase chain reaction (PCR) with the overlapping primers CX0271 and CX0270 which placed the cloning site for the peptide MM's, linker sequences, and MMP-9 CM protease site between the TEV protease site and the anti-VEGF scFv TBM. The primers CX0271 and CX0249 (Table 11) were used to amplify the C-terminal portion of the construct, while the primers CX0270 and CX0288 (Table 11) were used to amplify the N-terminal portion. Products from both the above reactions were combined for a final PCR reaction using the outside primers, CX0249 and CX0288 (Table 11), and cloned into the pMal vector as an MBP fusion using the Sac and HindII restriction sites (SEQ ID NO: 50)

TABLE 12

SEQ ID NO: 50: MBP/MM accepting site/MMP-9 CM/Anti-VEGF scFv TBM vector nucleotide sequence
atgggccatcaccatcaccatcacggtggggaaaatctgtattttcagggccagtctggccagctcgagtg
ggccaaggtggccaagtgcacatgccactgggcttcctgggtccgggcggttctgatattcaactgaccca
gagcccttcttccctgagtgccagcgtgggtgaccgtgttacgatcacttgctcggccagccaagatattt
ctaactacctgaattggtaccagcagaagccaggaaaggcaccaaaagtcctgatctacttcacaagttca
ctgcattccggcgtaccgtcgcgctttagcggttctggcagtggtaccgacttcaccctgactatctcgag
tctgcaacctgaggattttgctacatattactgtcagcaatattcgaccgtgccgtggacgttcgggcagg
gcaccaaagtggagattaaggggggtggaggcagcggggaggtggctcaggcggtggagggtctggcgag
gtccagctggtagaaagcggggcggactggtccaaccgggcggatccctgcgtctgagctgcgcggcctc
ggggttacgactttactcactacggaatgaactgggttcgccaagcccctggtaaaggtctggaatgggtcg
gatggattaatacatacactggagaacctacttatgctgctgatttcaaacgtcgctttactttctctctg
gatacaagtaagtcaaccgcctatctgcaaatgaacagcctgcgtgcagaggacacggctgtgtactattg
tgcgaaatatccttattattatggaacttcccactggtatttcgatgtatggggccagggtactctggtta
cagtgtcg The 306MM and 314MM (Table 10) were amplified from the ecpX display vector using the primers CX0289 and CX0290 (Table 11), and directionally cloned into the N-terminally masked vector using the SfiI restriction sites. The corresponding nucleotide and amino acid sequences are provided in Table 13 below.

TABLE 13

SEQ ID NO: 51: MBP/306 MM/MMP-9 CM/Anti-VEGF scFv TBM nucleotide sequence
atgggccatcaccatcaccatcacggtggggaaaatctgtattttcagggccagtctggccagc
cgtgttctgagtggcagtcgatggtgcagccgcgttgctattatgggggcggttctggtggcag
cggccaaggtggccaagtgcacatgccactgggcttcctgggtccgggcggttctgatattcaa
ctgacccagagcccttcttccctgagtgccagcgtgggtgaccgtgttacgatcacttgctcgg
ccagccaagatatttctaactacctgaattggtaccagcagaagccaggaaaggcaccaaaagt
cctgatctacttcacaagttcactgcattccggcgtaccgtcgcgctttagcggttctggcagt
ggtaccgacttcaccctgactatctcgagtctgcaacctgaggattttgctacatattactgtc
agcaatattcgaccgtgccgtggacgttcgggcagggcaccaaagtggagattaaggggggtgg
aggcagcggggaggtggctcaggcggtggagggtctggcgaggtccagctggtagaaagcgggg
gcggactggtccaaccgggcggatccctgcgtctgagctgcgcggcctcggggttacgactta
ctcactacggaatgaactgggttcgccaagcccctggtaaaggtctggaatgggtcggatggat
taatacatacactggagaacctacttatgctgctgatttcaaacgtcgctttactttctctctg
gatacaagtaagtcaaccgcctatctgcaaatgaacagcctgcgtgcagaggacacggctgtgt
actattgtgcgaaatatccttattattatggaacttcccactggtatttcgatgtatggggcca

TABLE 13-continued

```
gggtactctggttacagtgtcg
```

SEQ ID NO: 52: MBP/306 MM/MMP-9 CM/Anti-VEGF scFv TBM amino acid sequence
MGHHHHHHGGENLYFQGQSGQPCSEWQSMVQPRCYYGGGSGGSGQGGQVHMPLGFLGPGG
SDIQLTQSPSSLSASVGDRVTITCSASQDISNYLNWYQQKPGKAPKVLIYFTSSLHSGVP
SRFSGSGSGTDFTLTISSLQPEDFATYYCQQYSTVPWTFGQGTKVEIKGGGGSGGGGSGG
GGSGEVQLVESGGGLVQPGGSLRLSCAASGYDFTHYGMNWVRQAPGKGLEWVGWIMTYTG
EPTYAADFKRRFTFSLDTSKSTAYLQMNSLRAEDTAVYYCAKYPYYYGTSHWYFDVWGQG
TLVTVS SEQ ID NO: 53: MBP/314 MM/MMP-9 CM/Anti-VEGF scFv TBM nucleotide sequence
```
atgggccatcaccatcaccatcacggtggggaaaatctgtattttcagggccagtctggccagc
ggccgccgtgttgccgtgattatagtattttggagtgctgtaagagtgatggcggttctggtgg
cagcggccaaggtggccaagtgcacatgccactgggcttcctgggtccgggcggttctgatatt
caactgacccagagcccttcttccctgagtgccagcgtgggtgaccgtgttacgatcacttgct
cggccagccaagatatttctaactacctgaattggtaccagcagaagccaggaaaggcaccaaa
agtcctgatctacttcacaagttcactgcattccggcgtaccgtcgcgctttagcggttctggc
agtggtaccgacttcaccctgactatctcgagtctgcaacctgaggattttgctacatattact
gtcagcaatattcgaccgtgccgtggacgttcgggcagggcaccaaagtggagattaagggggg
tggaggcagcggggaggtggctcaggcggtggagggtctggcgaggtccagctggtagaaagc
ggggcggactggtccaaccgggcggatccctgcgtctgagctgcgcggcctcgggttacgact
ttactcactacggaatgaactgggttcgccaagcccctggtaaaggtctggaatgggtcggatg
gattaatacatacactggagaacctacttatgctgctaatttcaaacgtcgctttactttctct
ctggatacaagtaagtcaaccgcctatctgcaaatgaacagcctgcgtgcagaggacacggctg
tgbactattgtgcgaaatatccttattattatggaacttcccactggtatttcgatgtatgggg
ccagggtactctggttacagtgtcg
```

SEQ ID NO: 54: MBP/314 MM/MMP-9 CM/Anti-VEGF scFv TBM amino acid sequence
MGHHHHHHGGENLYFQGQSGQRPFCCRDYSILECCKSDGGSGGSGQGGQVHMPLGFLGPG
GSDIQLTQSPSSLSASVGDRVTITGSASQDISNYLNWYQQKPGKAPKVLIYFTSSLHSGV
PSRFSGSGSGTDFTLTISSLQPEDFATYYCQQYSTVPWTFGQGTKVEIKGGGGSGGGGSG
GGGSGEVQLVESGGGLVQPGGSLRLSCAASGYDFTHYGMNWVRQAPGKGLEWVGWINTYT
GEPTYAADFKRRFTFSLDTSKSTAYLQMNSLRAEDTAVYYCAKYPYYYGTSHWYFDVWGQ
GTLVTVS Expression: Expression of the MBP:ABP fusions were conducted in a K12 TB1 strain of *E. coli*. An ampicillin-resistant colony containing the desired construct was used to inoculate a 5 ml overnight culture containing LB medium supplemented with 50 µg/mL Ampicillin. The entire overnight culture was used to inoculate 500 mL of fresh LB medium supplemented with 50 µg/mL ampicillin and 0.2% Glucose and allowed to grow at 37° C. shaking at 250 rpm until an O.D. of 0.5 was reached. Isopropylthio-β-D-galactosidase was then added to a final concentration of 0.3 mM and the culture was allowed to grow for a further 3 hrs under the same conditions after which the cells were harvested by centrifugation at 3000×g. Inclusion bodies were purified using standard methods. Briefly, 10 mls of BPER II cell lysis reagent (Pierce). Insoluble material was collected by centrifugation at 14,000×g and the soluble proteins were discarded. The insoluble materials were resuspended in 5 mls BPER II supplemented with 1 mg/mL lysozyme and incubated on ice for 10 minutes after which 5 mls of BPER II diluted in water 1:20 was added and the samples were spun at 14.000×g. The supernatant was removed and the pellets were wash twice in 1:20 BPERII. The purified inclusion bodies were solubilized in PBS 8 M Urea, 10 mM BME, pH 7.4.

The MBP fusion proteins were diluted to a concentration of approximately 1 mg/mL and refolded using a stepwise dialysis in PBS pH 7.4 from 8 to 0 M urea through 6, 4, 2, 0.5, and 0 M urea. At the 4, 2, and 0.5 M Urea steps 0.2 M Arginine, 2 mM reduced Glutathione, and 0.5 mM oxidized glutathione was added. The OM Urea dialysis included 0.2 M Arginine. After removal of the urea, the proteins were dialyzed against 0.05 M Arginine followed by and extensive dialysis against PBS pH 7.4. All dialysis were conducted at 4° C. overnight. To remove aggregates, each protein was subjected to size exclusion chromatography on a sephacryl S-200 column. Fractions containing the correctly folded proteins were concentrated using an Amicon Ultra centrifugal filter.

Cloning and Expression of the ABP: A MMP-9 Cleavable, Masked Anti-VEGF scFv CHis Tag Cloning: The primers CX0308 and CX0310 (Table 11) were used to amplify and add a NcoI restriction site to the 5' end and a HindIII restriction site and His6 tag to the 3' end, respectively, of the (MM accepting site/MMP-9 CM/VEGFscFv TBM) vector which was subsequently cloned into a vector containing the pelB signal peptide. Anti-VEGF scFv MMs were cloned as previously described. The corresponding nucleotide and amino acid sequences are provided in Table 14 below.

TABLE 14

SEQ ID NO: 55: 306 MM/MMR-9 CM/anti-VEGF scFv CHis TBM nucleotide sequence
```
ggccagtctggccagccgtgttctgagtggcagtcgatggtgcagccgcgttgctattatggggcggtt
ctggtagcagcggccaaggtggccaagtgcacatgccactgggcttcctgggtccgggcggttctgatat
tcaactgacccagagcccttcttccctgagtgccagcgtgggtgaccgtgttacgatcacttgctcggcc
agccaagatatttctaactacctgaattggtaccagcagaagccaggaaaggcaccaaaagtcctgatct
acttcacaagttcactgcattccggcgtaccgtcgcgctttagcggttctggcagtggtaccgacttcac
cctgactatctcgagtctgcaacctgaggattttgctacatattactgtcagcaatattcgaccgtgccg
tggacgttcgggcagggcaccaaagtggagattaagggggtggaggcagcggggaggtggctcaggcg
gtggagggtctggcgaggtccagctggtagaaagcggggcggactggtccaaccgggcggatccctgcg
```

TABLE 14-continued tctgagctgcgcggcctcgggttacgactttactcactacggaatgaactgggttcgccaagcccctggt
aaaggtctggaatgggtcggatggattaatacatacactggagaacctacttatgctgctgatttcaaac
gtcgctttactttctctctggatacaagtaagtcaaccgcctatctgcaaatgaacagcctgcgtgcaga
ggacacggctgtgtactattgtgcgaaatatccttattattatggaacttcccactggtatttcgatgta
tggggccagggtactctggttacagtgtcgcatcatcaccatcaccac SEQ ID NO: 56: 306 MM/MMP-9 CM/anti-VEGF scFv CHis TBM amino acid sequence
GQSGQPCSEWQSMVQPRCYYGGGSGGSGQGGQVHMPLGFLGFGGSDIQLTQSPSSLSASV
GDRVTITCSASQDISNYLNWYQQKPGKAPKVLIYFTSSLHSGVPSRFSGSGSGTDFTLTI
SSLQPEDFATYYCQQYSTVPWTFGQGTKVEIKGGGGSGGGGSGGGGSGEVQLVESGGGLV
QPGGSLRLSCAASGYDFTHYGMNWVRQAPGKGLEWVGWINTYTGEPTYAADFKRRFTFSL
DTSKSTAYLQMNSLRAEDTAVYYCAKYPYYYGTSHWYFDVWGQGTLVTVSHHHHHH SEQ ID NO: 57: 314 MM/MMP-9 CM/anti-VEGF scFv CHis TBM nucleotide sequence
ggccagtctggccagcggccgccgtgttgccgtgattatagtattttggagtgctgtaagagtg
atggcggttctggtggcagcggccaaggtggccaagtgcacatgccactgggcttcctgggtcc
gggcggttctgatattcaactgacccagagcccttcttccctgagtgccagcgtgggtgaccgt
gttacgatcacttactcggccagccaagatatttctaactacctgaattggtaccagcagaagc
caggaaaggcaccaaaagtcctgatctacttcacaagttcactgcattccggcgtaccgtcgcg
ctttagcggttctggcagtggtaccgacttcaccctgactatctcgagtctgcaacctgaggat
tttgctacatattactgtcagcaatattcgaccgtgccgtggacgttcgggcagggcaccaaag
tggagattaagggggggtggaggcagcgggggaggtggctcaggcggtggagggtctggcgaggt
ccagctggtagaaagcgggggcggactggtccaaccgggcggatccctgcgtctgagctgcgcg
gcctcgggttacgactttactcactacggaatgaactgggttcgccaagcccctggtaaaggtc
tggaatgggtcggatggattaatacatacactggagaacctacttatgctgctgatttcaaacg
tcgctttactttctccctggatacaagtaagtcaaccgcctatctgcaaatgaacagcctgcgt
gcagaggacacggctgtgtactattgtgcgaaatatccttattattatggaacttcccactggt
atttcgatgtatggggccagggtactctggttacagtgtcgcatcatcaccatcaccactaa SEQ ID NO: 58:314 MM/MMP-9 CM/anti-VEGF scFv CHis TBM amino acid sequence
GQSGQRPPCCRDYSILECCKSDGGSGGSGQGGQVHMPLGFLGPGGSDIQLTQSPSSLSAS
VGDRVTITCSASQDISNYLNWYQQKPGKAPKVLIYFTSSLHSGVPSRFSGSGSGTDFTLT
ISSLQPEDFATYYCQQYSTVPWTFGQGTKVEIKGGGGSGGGGSGGGGSGEVQLVESGGGL
VQPGGSLRLSCAASGYDFTHYGMNWVRQAPGKGLEWVGWINTYTGEPTYAADFKRRFTFS
LDTSKSTAYLQMNSLRAEDTAVYYCAKYPYYYGTSHWYFDVWGQGTLVTVSHHHHHH Expression: Expression of the Anti-VEGF scFv His ABPs was conducted in a K12 TB1 strain of *E. coli*. An ampicillin-resistant colony containing the desired construct was used to inoculate a 5 ml overnight culture containing LB medium supplemented with 50 μg/mL Ampicillin. 2.5 ml of overnight culture was used to inoculate 250 mL of fresh LB medium supplemented with 50 μg/mL ampicillin and 0.2% Glucose and allowed to grow at 37° C. shaking at 250 rpm until an O.D. of 1.0 was reached. Isopropylthio-s-D-galactosides was then added to a final concentration of 0.3 mM and the culture was allowed to grow for a further 5 hrs at 30° C. after which the cells were harvested by centrifugation at 3000×g. The periplasmic fraction was immediately purified using the lysozyme/osmotic shock method. Briefly, the cell pellet was resuspended in 3 mLs of 50 mM Tris, 200 mM NaCl, 10 mM EDTA, 20% Sucrose, pH 7.4 and 2 uL/mL ready-use lysozyme solution was added. After a 15 min. incubation on ice, 1.5 volumes of water (4.5 mLs) was added and the cells were incubated for another 15 min. on ice. The soluble periplasmic fraction was recovered by centrifugation at 14,000×g.

The Anti-VEGF scFv His proteins were partially purified using Ni-NTA resin. Crude periplasmic extracts were loaded onto 0.5 ml of Ni-NTA resin and washed with 50 mM phosphate, 300 mM NaCl, pH 7.4. His tagged proteins were eluted with 50 mM phosphate, 300 mM NaCl, 200 mM Imidizale, pH 6.0. Proteins were concentrated to approximately 600 μL and buffer exchanged into PBS using Amicon Ultra centrifugal concentrators.

Cloning and Expression of the ABP: A MMP-9 Cleavable, Masked Anti-VEGF scFv as Human Fc Fusion Cloning: The primers CX0312 and CXO314 (Table 11) were used to amplify the sequence encoding MMP-9 CM/Anti-VEGF scFv. The primers also included sequences for a 5' EcoRI restriction site and a 3' NcoI restriction site and linker sequence. Cutting the PCR amplified sequence with EcoRI and NcoI and subsequent cloning into the pFUSE-hIgG1-Fc2 vector generated vectors for the expression of Fc fusion proteins. Anti-VEGF scFv TBM MMs were inserted into these vectors as previously described. Constructs containing 306MM, 313MM, 314MM, 315MM, a non-binding MM (100MM), as well as no MM were constructed and sequences verified. The corresponding nucleotide and amino acid sequences are provided below in Table 15.

TABLE 15

SEQ ID NO: 59: 306 MM/MMP-9 CM/anti-VEGF scfv-Fc TBM nucleotide sequence
ggccagtctggccagccgtgttctgagtggcagtcgatggtgcagccgcgttgctattatgggg
gcggttctggtggcagcggccaaggtggccaagtgcacatgccactgggcttcctgggtccggg
cggttctgatattcaactgacccagagcccttcttccctgagtgccagcgtgggtgaccgtgtt
acgatcacttgctcggccagccaagatatttctaactacctgaattggtaccagcagaagccag
gaaaggcaccaaaagtcctgatctacttcacaagttcactgcattccggcgtaccgtcgcgctt
tagcggttctggcagtggtaccgacttcaccctgactatctcgagtctgcaacctgaggatttt
gctacatattactgtcagcaatattcgaccgtgccgtggacgttcgggcagggcaccaaagtgg
agattaagggggggtggaggcagcgggggaggtggctcaggcggtggagggtctggcgaggtcca
gctggtagaaagcgggggcggactggtccaaccgggcggatccctgcgtctgagctgcgcggcc
tcgggttacgactttactcactacggaatgaactgggttcgccaagcccctggtaaaggtctgg TABLE 15-continued

```
aatgggtcggatggattaatacatacactggagaacctacttatgctgctgatttcaaacgtcg
ctttactttctctctggatacaagtaagtcaaccgcctatctgcaaatgaacagcctgcgtgca
gaggacacggctgtgtactattgtgcgaaatatccttattattatggaacttcccactggtatt
tcgatgtatggggccagggtactctggttacagtgtcgggcggtagcggcgccatggttagatc
tgacaaaactcacacatgcccaccgtgcccagcacctgaactcctgggggggaccgtcagtcttc
ctcttcccccaaaacccaaggacaccctcatgatctcccggaccectgaggtcacatgcgtgg
tggtggacgtgagccacgaagaccctgaggtcaagttcaactggtacgtggacggcgtggaggt
gcataatgccaagacaaagccgcgggaggagcagtacaacagcacgtaccgtgtggtcagcgtc
ctcaccgtcctgcaccaggactggctgaatggcaaggagtacaagtgcaaggtctccaacaag
ccctcccagcccccatcgagaaaaccatctccaaagccaaagggcagccccgagaaccacaggt
gtacaccctgcccccatcccgggaggagatgaccaagaaccaggtcagcctgacctgcctggtc
aaaggcttctatcccagcgacatcgccgtggagtgggagagcaatgggcagccggagaacaact
acaagaccacgcctcccgtgctggactccgacggctccttcttcctctacagcaagctcaccgt
ggacaagagcaggtggcagcaggggaacgtcttctcatgctccgtgatgcatgagggtctgcac
aaccactacacgcagaagagcctctccctgtctccgggtaaa
```

SEQ ID NO: 60: 306 MM/MMP-9 CM/anti-VEGF scFv-Fc TBM amino acid sequence
GQSGQPCSEWQSMVQPRCYYGGGSGGSGQGGQVHMPLGFLGPGGSDIQLTQSPSSLSASV
GDRVTITCSASQDISNYLNWYQQKPGKAPKVLIYFTSSLHSGVPSRFSGSGSGTDFTLTI
SSLQPEDFATYYCQQYSTVPWTFGQGTKVEIKGGGGSGGGGSGGGGSGEVQLVESGGGLV
QPGGSLRLSCAASGYDFTHYGMNWVRQAPGKGLEWVGWINTYTGEPTYAADFKRRFTFSL
DTSKSTAYLQMNSLRAEDTAVYYCAKYPYYYGTSHWYFDVWGQGTLVTVSGGSGAMVRSD
KTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKG
QPREPQVYTLPPSREEMTKNQVSLTCLVKGFYPSDIAVEWESNGQPENNYKTTPPVLDSD
GSFFLYSKLTVDKSRWQQGNVFSCSVMHEGLHNHYTQKSLSLSPGK SEQ ID NO: 61: 314 MM/MMP-9 CM/anti-VEGF scfv-Fc TBM nucleotide sequence
```
ggccagtctggccagcggccgccgtgttgccgtgattatagtatttggagtgctgtaagagtg
atggcggttctggtggcagcggccaaggtggccaagtgccactgggcttcctgggtcc
gggcggttctgatattcaactgacccagagccettcctcectgagtgccagcgtgggtgaccgt
gttacgatcacttgctcggccagccaagatatttctaactacctgaattggtaccagcagaagc
caggaaaggcaccaaaagtcctgatctacttcacaagttcactgcattccggcgtaccgtcgcg
ctttagcggttctggcagtggtaccgacttcaccctgactatctcgatctgcaacctgaggat
tttgctacatattactgtcagcaatattcgaccgtgccgtggacgttcgggcagggcaccaaag
tggagattaaggggggtggaggcagcggggaggtggctcaggcggtggagggtctggcgaggt
ccagctggtagaaagcggggcggactggtccaacegggcggatcctgcgtctgagctgcgcg
gcctcgggttacgactttactcactacggaatgaactgggttcgccaagcecctggtaaaggtc
tggaatgggtcggatggattaatacatacactggagaacctacttatgctgctgatttcaaacg
tcgctttactttctctctggatacaagtaagtcaaccgcctatctgcaaatgaacagcctgcgt
gcagaggacacggctgtgtactattgtgcgaaatatccttattattatggaacttcccactggt
atttcgatgtatggggccagggtactctggttacagtgtcgggcggtagcggcgccatggttag
atctgacaaaactcacacatgcccaccgtgcccagcacctgaactcctgggggaccgtcagtc
ttcctcttcccccaaaacccaaggacaccctcatgatctcccggaccectgaggtcacatgcg
tggtggtggacgtgagccacgaagaccctgaggtcaagttcaactggtacgtggacggcgtgga
ggtgcataatgccaagacaaagccgcgggaggagcagtacaacagcacgtaccgtgtggtcagc
gtcctcaccgtcctgcaccaggactggctgaatggcaaggagtacaagtgcaaggtctccaaca
aagcectcccagcccccatcgagaaaaccatctccaaagccaaagggcagccccgagaaccaca
ggtgtacaccctgcccccatcccgggaggagatgaccaagaaccaggtcagcctgacctgcctg
gtcaaaggcttctatcccagcgacatcgccgtggagtgggagagcaatgggcagccggagaaca
actacaagaccacgcctcccgtgctggactccgacggctccttcttcctctacagcaagctcac
cgtggacaagagcaggtggcagcaggggaacgtcttctcatgctccgtgatgcatgagggtctg
cacaaccactacacgcagaagagcctctccctgtctccgggtaaa
```

SEQ ID NO: 62: 314 MM/MMP-9 CM/anti-VEGF scFv-Fc TBM amino acid sequence
GQSGQRPPCCRDYSILECCKSDGGSGGSGQGGQVHMPLGFLGPGGSDTQLTQSPSSLSAS
VGDRVTITCSASQDISNYLNWYQQKPGKAPKVLIYFTSSLHSGVPSRFSGSGSGTDFTLT
ISSLQPEDFATYYCQQYSTVPWTFGQGTKVEIKGGGGSGGGGSGGGGSGEVQLVESGGGL
VQPGGSLRLSCAASGYDFTHYGMNWVRQAPGKGLEWVGWINTYTGEPTYAADFKRRFTFS
LDTSKSTAYLQMNSLRAEDTAVYYCAKYPYYYGTSHWYFDVWGQGTLVTVSGGSGAMVRS
DKTHTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDS
DGSFFLYSKLTVDKSRWQQGNVFSCSVMHEGLHNHYTQKSLSLSPGK Expression: 10 μg of expression vectors for 306 MM/MMP-9 CM/anti-VEGFscFv-Fc, 314 MM/MMP-9 CM/anti-VEGFscFv-Fc or anti-VEGFscFv-Fc were introduced into $10^7$ HEK-293 freestyle cells (Invitrogen, CA) by transfection using transfectamine 2000 as per manufacturer's protocol (Invitrogen, CA). The transfected cells were incubated for an additional 72 hours. After incubation, the conditioned media was harvested and cleared of cells and debris by centrifugation. The conditioned media was assayed for activity by ELISA.

Example 11: Testing of a ABP

To measure the activation of the masked MMP-9 cleavable anti-VEGF ABPs by MMP-9, 100 W of a 2 μg/ml PBS solution of VEGF was added to microwells (96 Well Easy Wash; Corning) and incubated overnight at 4° C. Wells were then blocked for 3×15 minute with 300 uL Superblock (Pierce). One hundred microliters of ABP (see below for details pertaining to each construct), treated or untreated with MMP-9, were then added to wells in PBST, 10% Superlock and incubated at room temperature (RT) for 1 hr. All wash steps were done three times and performed with 300 ul PBST. One hundred microliters of secondary detection reagent were then added and allowed to incubate at RT for 1 hr. Detection of HRP was completed using 100 ul of TMB one (Pierce) solution. The reaction was stopped with 100 μL of 1N HCL and the absorbance was measured at 450 nM.

ELISA Assay of ABP Construct Containing: MBP/MM/MMP-9 CM/Anti-VEGF scFv TBM

Figure 39:
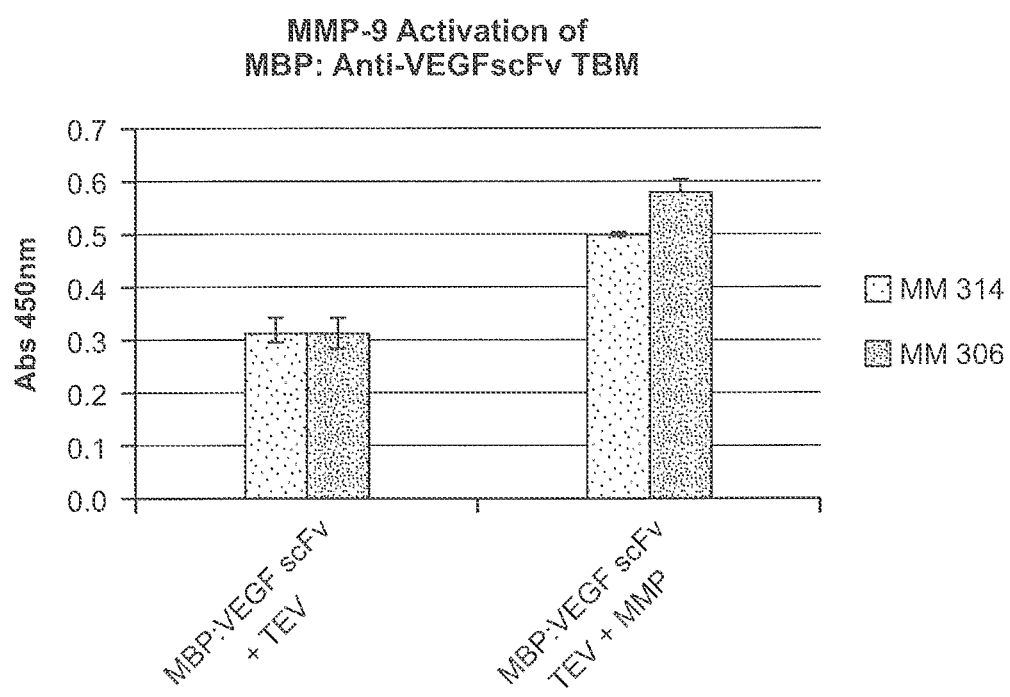

Two hundred microliters of biotinylated ABP in MMP-9 digestion buffer (50 mM Tris, 2 mM CaCl$_2$), 20 mM NaCl, 100 μM ZnCl$_2$, pH 6.8) at a concentration of 200 nM was digested with 20 U TEV protease overnight at 4° C. to remove the MBP fusion partner. Samples were then incubated for 3 hrs with or without ~3 U of MMP-9 at 37° C. diluted 1:1 to a final concentration of 100 nM in PBST, 10% Superblock, and added to the ELISA wells. Detection of the ABP was achieved with an Avidin-HRP conjugate at a dilution of 1:7500. MMP-9 activation of MMP-9 cleavable masked MBP:anti-VEGF scFv ABP is presented in FIG. 39.

ELISA Assay of ABP Construct Containing: MM/MMP-9 CM/Anti-VEGF scFv His

Figure 40:
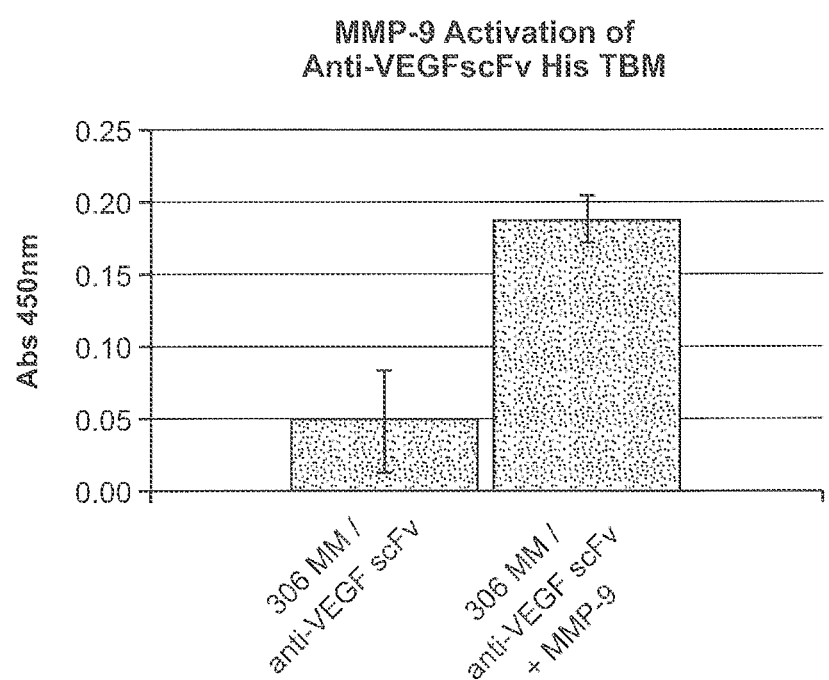

Crude periplasmic extracts dialyzed in MMP-9 digestion buffer (150 μL) were incubated with or without ~3 U of MMP-9 for 3 hrs at 37° C. Samples were then diluted to 400 μL with PBST, 10% Superblock and added to the ELISA wells. Detection of the ABP was achieved using an Anti-His6-HRP conjugate at a dilution of 1:5000. MMP-9 activation of MMP-9 cleavable masked anti-VEGF scFv His ABP is presented in FIG. 40.

ELISA Assay of ABP Construct Containing: MM/MMP-9 CM/Anti-VEGF scFv-Fc

Figure 41:
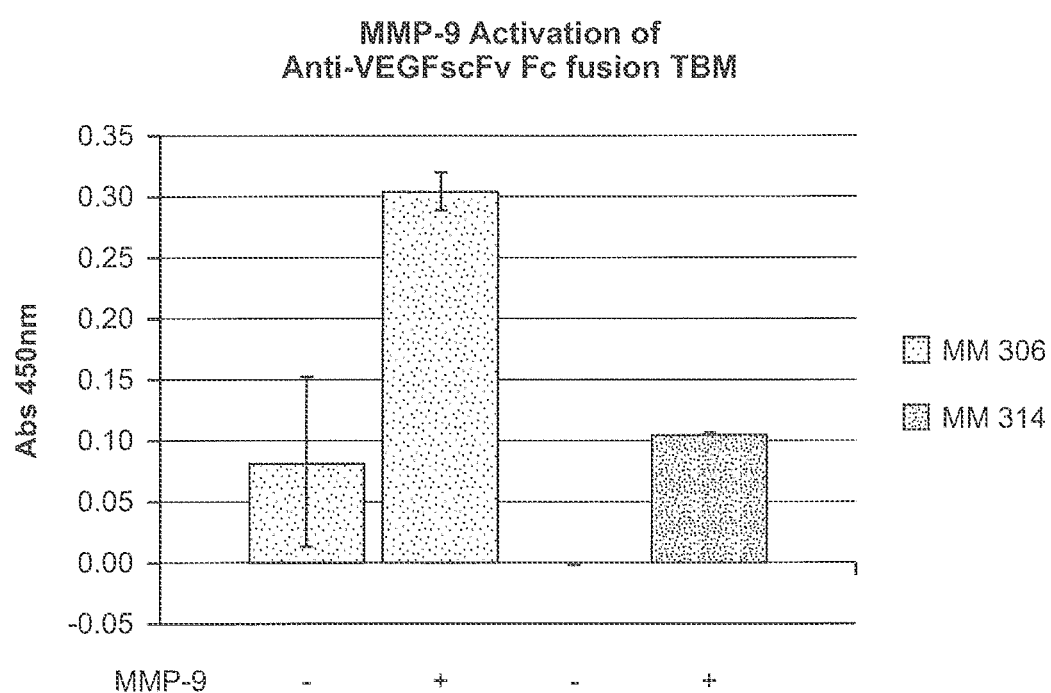

Fifty microliters of HEK cell supernatant was added to 200 μL MMP-9 digestion buffer and incubated with or without ~19 U MMP-9 for 2 hrs at 37° C. Samples were then diluted 1:1 in PBST, 10% Superblock and 100 μL were added to the ELISA wells. Detection of the ABP was achieved using Anti-human Fc-HRP conjugate at a dilution of 1:2500. MMP-9 activation of MMP-9 cleavable masked anti-VEGF scFv-Fc is presented in FIG. 41.

Figure 42:
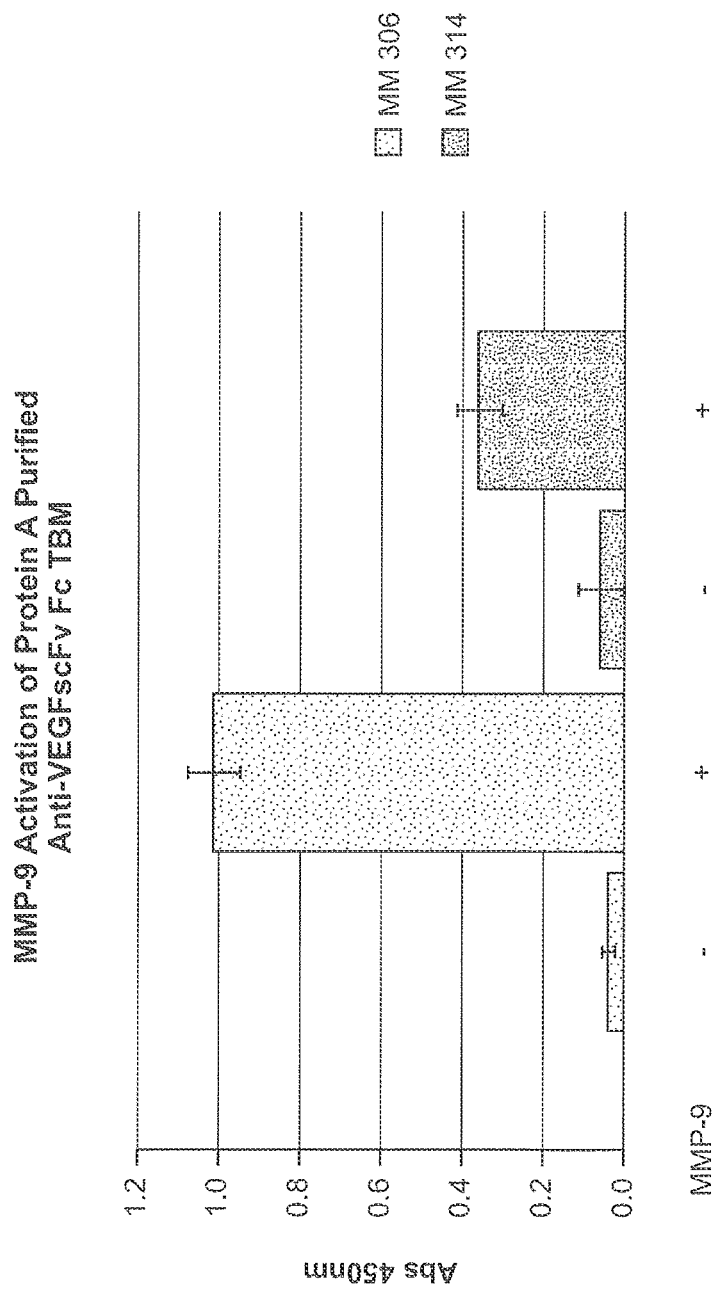

Purification and Assay of ABP Construct Containing: MM/MMP-9 CM/Anti-VEGF scFv-Fc Anti-VEGF scFv Fc ABPs were purified using a Protein A column chromatography. Briefly. 10 mLs of HEK cell supernatants were diluted 1:1 with PBS and added to 0.5 mL Protein A resin pre-equilibrated in PBS. Columns were washed with 10 column volumes of PBS before eluting bound protein with 170 mM acetate. 300 mL NaCl pH. 2.5 and immediately neutralized 1 mL fractions with 200 μL of 2 M Tris pH 8.0. Fractions containing protein were then concentrated using Amicon Ultra centrifugal concentrators. ELISA was conducted as with HEK cell supernatants. ELISA data showing the MMP-9 dependent VEGF binding of Anti-VEGFscFv Fc ABP constructs with the MMs 306 and 314 that were purified using a Protein A column are presented in FIG. 42.

Example 12: Library Screening and Isolation of Anti-CTLA4 MMs

CTLA4 antibody masking moieties (MMs) were isolated from a combinatorial library of $10^{10}$ random 15mer peptides displayed on the surface of *E. coli* according to the method of Bessette et al (Bessette, P. H., Rice, J. J and Daugherty, P. S. Rapid isolation of high-affinity protein binding peptides using bacterial display. Protein Eng. Design & Selection. 17:10, 731-739, 2004). Biotinylated mouse anti-CTLA4 antibody (clone UC4F10-11, 25 nM) was incubated with the library and antibody-bound bacteria expressing putative binding peptides were magnetically sorted from non-binders using streptavidin-coated magnetic nanobeads. Subsequent rounds of enrichment were carried out using FACS. For the initial round of FACS, bacteria were sorted using biotinylated target (5 nM) and secondary labeling step with streptavidin phycoerythrin. In subsequent rounds of FACS, sorting was performed with Dylight labeled antibody and the concentration of target was reduced (I nM, then 0.1 nM) to avoid the avidity effects of the secondary labeling step and select for the highest affinity binders. One round of MACS and three rounds of FACS resulted in a pool of binders from which individual clones were sequenced. Relative affinity and off-rate screening of individual clones were performed using a ficin digested Dylight-labeled Fab antibody fragment to reduce avidity effects of the bivalent antibody due to the expression of multiple peptides on the bacterial surface. As an additional test of target specificity, individual clones were screened for binding in the presence of 20 uM *E. Coli* depleted IgG as a competitor. Amino acid and nucleotide sequences of the 4 clones chosen for MM optimization are shown in Table 16. These sequences will interchangeably referred to as 187MM, 184MM, 182MM, and 175MM. MM candidates with a range of off-rates were chosen, to determine the effects of off-rates on MM dissociation after cleavage. An MM that did not bind anti-CTLA4 was used as a negative control.

TABLE 16

| Amino acid and nucleotide sequences for MMs that mask anti-CTLA4 |
|---|
| KK187 MM |
| M I L L C A A G R T W E A C A N G R (SEQ ID NO: 63) |
| ATGATTTTGTTGTGCGCGGCGGGTCGGACGTGGGTGGAGGCTTGCGCTAA TGGTAGG (SEQ ID NO: 64) |
| KK184 MM |
| A E R L C A W A G R F C G S (SEQ ID NO: 65) |
| GCTGAGCGGTTGTGCGCGTGGGCGGGGCGGTTCTGTGGCAGC (SEQ ID NO: 66) |
| KK182 MM |
| W A D V M P G S G V L P W T S (SEQ ID NO: 67) |
| TGGGCGGATGTTATGCCTGGGTCGGGTGTGTTGCCGTGGACGTCG (SEQ ID NO: 68) |
| KK175 MM |
| S D G R M G S L E L C A L W G R F C G S (SEQ ID NO: 69) |
| AGTGATGGTCGTATGGGGAGTTTGGAGCTTTGTGCGTTGTGGGGGCGGTTCTGTGGCAGC (SEQ ID NO: 70) |

TABLE 16-continued Amino acid and nucleotide sequences for MMs that mask anti-CTLA4

Negative control (does not bind anti-CTLA

Example 14: Construction of the Anti-CTLA4 scFv with MMs and CMs

To determine the optimal orientation of the anti-CTLA4 scFv for expression and function, primers were designed to PCR amplify the variable light and heavy chains individually, with half of a (GGGS)$_3$ linker at either the N- or C-terminus for a subsequent 'splicing by overlapping extension' PCR (SOE-PCR; Horton, R. M., Hunt, H. D., Ho. S. N., Pullen, J. K. and Pease, L. R. (1989) Engineering hybrid genes without the use of restriction enzymes: gene splicing by overlap extension. Gene 77, 61-68) with either V$_H$ or V$_L$ at the N-terminus. An NdeI restriction site was engineered at the N-terminus to generate a start codon in frame at the beginning of the nucleotide sequence and a His tag and stop codon were added to the C-terminus. Light and heavy chains were then joined via sewing PCR using the outer primers to generate ScFvs in both V$_H$V$_L$ and V$_L$V$_H$ (FIG. 43). Primers are shown below in Table 19.

TABLE 19

Primers to generate scFvs V$_H$V$_L$ and V$_L$V$_H$

| | |
|---|---|
| VL for1 | caaggaccatagcatatggacatcatgatgacccagtct (SEQ ID NO: 80) |
| VL linker rev1 | acttccgcctccacctgatccaccaccacctttgatttccaccttggtcc (SEQ ID NO: 81) |
| linker VH for2 | ggatcaggtggaggcggaagtggaggtggcggttcccagatccagcttcaggagtcagga (SEQ ID NO: 82) |
| VH his rev2 | ggccggatccaagcttttagtggtgatggtgatgatgtgaggagacggtgaccatggttcc (SEQ ID NO: 83) |
| VH for3 | acaaggaccatagcatatgcagatccagcttcaggagtca (SEQ ID NO: 84) |
| VH linker rev3 | acttccgcctccacctgatccaccaccacctgaggagacggtgaccatggttcc (SEQ ID NO: 85) |
| linker VL for4 | ggtggatcaggtggaggcggaagtggaggtggcggttccgacatcatgatgacccagtctcct (SEQ ID NO: 86) |
| VL his rev4 | cggccggatccaagcttttagtggtgatggtgatgatgtttgatttccaccttggtcccagc (SEQ ID NO: 87) |

Figure 44:
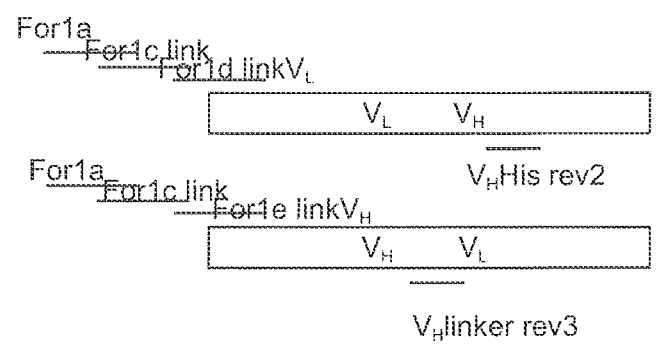

Next, a set of overlapping primers were designed to add sfi and xho1 sites for MM cloning followed by the MMP-9 cleavage sequence and (GGS)$_2$ linker on the N-terminus of the ScFv constructs. These primers are presented in Table 20 and shown schematically in FIG. 44.

TABLE 20

Primers MM and CM cloning

| | |
|---|---|
| for 1c linker | gccagtctggccggtagggctcgagcggccaagtgcacatgccactgggcttcctgggtc (SEQ ID NO: 88) |
| for 1d linker VL | gccactgggcttcctgggtccgggtggaagcggcggctcagacatcatgatgacccagtc (SEQ ID NO: 89) |
| for 1e linker VH | gccactgggcttcctgggtccgggtggaagcggcggctcacagatccagcttcaggagtca (SEQ ID NO: 90) |
| for 1a | ttcaccaacaaggaccatagcatatgggccagtctggccggtagggcggge (SEQ ID NO: 91) |
| VH his rev2 | ggccggatccaagcttttagtggtgatggtgatgatgtgaggagacggtgaccatggttcc (SEQ ID NO: 92) |
| VH linker rev3 | acttccgcctccacctgatccaccaccacctgaggagacggtgacccatggttcc (SEQ ID NO: 93) |

Linker containing ScFvs were PCR amplified, digested with Nde1 and EcoR1 (an internal restriction site in V$_H$) and gel purified. The PCR fragments were ligated into the vectors and transformed into *E. Coli*. The nucleotide and amino acid sequences are presented in Table 21 and illustrated in FIG. 45.

TABLE 21

Sequence of MM linker-CM-anti-CTLA4 scFv linker

Amino acid sequence:
G G S G G S G G S S G Q V H M P L G F L
G P G G S G G S (SEQ ID NO: 94)

Nucleotide sequence:
GGCGGTTCTGGTGGCAGCGGTGGCTCGAGCGGCCAAGTGCACATGCCAC
TGGGCTTCCTGGGTCCGGGTGGAAGCGGCGGCTCA
(SEQ ID NO: 95)

MM sequences were PCR amplified, digested at sfi1 and xho1 sites, ligated into linker anti-CTLA4 scFv constructs, transformed into *E. coli* and sequenced. The complete nucleotide and amino acid sequences of the MM187-CM-TBM are shown below in Tables 22 and 23 as SEQ ID NOs: 96 and 97 respectively.

TABLE 22

Amino acid sequence of MM187-anti-CTLA4 ScFv TBM:

M I L L C A A G R T W V E A C A N G R G G S G G S G G S S G Q
V H M P L G F L G P G G S G G S Q I Q L Q E S G P G L V N P S Q
S L S L S C S V T G Y S I T S G Y G W N W I R Q F P G Q K V E W
M G F I Y Y E G S T Y Y N P S I K S R I S I T R D T S K N Q F F L
Q V N S V T T E D T A T Y Y C A R Q T G Y F D Y W G Q G T M V
T V S S G G G G S G G G G S G G G G S D I M M T Q S P S S L S V
S A G E K A T I S C K S S Q S L F N S N A K T N Y L N W Y L Q
K P G Q S P K L L I Y Y A S T R H T G V P D R F R G S G S G T D
F T L T I S S V Q D E D L A F Y Y C Q Q W Y D Y P Y T F G A G T
K V E I K (SEQ ID NO: 96)

TABLE 23

Nucleotide sequence of MM187-anti-CTLA4 ScFv TBM:

atgattttgttgtgcgcggcgggtcggacgtgggtggaggcttgcgctaatggtaggggcggttctggtggcagcggtggctcgagcggccaa
gtgcacatgccactgggcttcctgggtccgggtggaagcggcggctcacagatccagctcaggagtcaggacctggcctggtgaaccctca
caatcactgtccctctcttgctctgtcactggttactccatcaccagtggttatggatggaactggatcaggcagttcccagggcagaaggtg
gagtggatgggattcatatattatgagggtagcacctactacaaccctttccatcaagagccgcatctccatcaccagagacacatcgaagaac
cagttcttcctgcaggtgaattctgtgaccactgaggacacagccacatattactgtgcgagacaaactgggtactttgattactggggccaa
ggaaccatggtcaccgtctcctcaggtggtggtggatcaggtggaggcggaagtggcggttccgacatcatgatgacccagtctcct
tcatccctgagtgtgtcagcgggagagaaagccactatcagctgcaagtccagtcagagtcttttcaacagtaacgccaaaacgaactacttg
aactggtatttgcagaaaccagggcagtctcctaaactgctgatctattatgcatccactaggcatactggggtccctgatcgcttcagaggc
agtggatctgggacggatttcactctcaccatcagcagtgtccaggatgaagacctggcattttattactgtcagcagtggtatgactaccca
tacacgttcggagctgggaccaaggtggaaatcaaacatcatcaccatcaccactaa (SEQ ID NO: 97)

To generate MM-CM-anti-CTLA4 scFV-Fc fusions, the following primers listed in Table 24 were designed to PCR amplify the constructs for cloning into the pfuse Fc vector via the in fusion system (Clontech). Plasmids were transformed into *E. coli*, and the sequence of individual clones was verified.

Example 15: Expression and Assay of Masked/MMP-9/Anti-CTLA scFv-Fc in HEK-293 Cells 10 ug of expression vectors for p175CTLA4pfuse, p182CTLA4pfuse, p184CTLA4pfuse, p187CTLA4pfuse, or pnegCTLA4pfuse were introduced into $10^7$ HEK-293 freestyle cells (Invitrogen) by transfection using transfectamine 2000 as per manufacturer's protocol (Invitrogen). The transfected cells were incubated for an additional 72 hours. After incubation the conditioned media was harvested and cleared of cells and debris by centrifugation. The conditioned media was assayed for activity by ELISA as described below.

Fifty microliters of conditioned media from HEK-293 expressing MM175-anti-CTLA4 scFv, MM182-anti-CTLA4 scFv, MM184-anti-CTLA4 scFv, MM187-anti-CTLA4 scFv. or MMneg-anti-CTLA4 scFv was added to 200 μL MMP-9 digestion buffer and incubated with or without ~19 U MMP-9 for 2 hrs at 37° C. Samples were then diluted 1:1 in PBS, 4% non fat dry milk (NFDM) and assayed for binding activity by competition ELISA.

TABLE 24

Primers to generate MM-CM-anti-CTLA4 scFV-Fc fusions

| | |
|---|---|
| HLCTLA4ScFv pFuse reverse | tcagatctaaccatggctttgatttccaccttggtcc (SEQ ID NO: 98) |
| LHCTLA4ScFv pFuse reverse | tcagatctaaccatggctgaggagacggtgaccatgg (SEQ ID NO: 99) |
| p187CTLA4 pfuse forward | cacttgtcacgaattcgatgattttgttgtgcgcggc (SEQ ID NO: 100) |
| p182CTLA4 pfuse forward | cacttgtcacgaattcgtgggcggatgttatgcctg (SEQ ID NO: 101) |
| p184CTLA4 pfuse forward | cacttgtcacgaattcggctgagcggttgtgcgcgtg (SEQ ID NO: 102) |
| p175CTLA4 pfuse forward | cacttgtcacgaattcgagtgatggtcgtatgggag (SEQ ID NO: 103) |
| pnegCTLA4 pfuse forward | cacttgtcacgaattcgccgtgttctgagtggcagtcg (SEQ ID NO: 104) |

100 ul of 0.5 mg/ml solution of murine CTLA4-Fc fusion protein (R & D systems) in PBS was added to wells of 96 well Easy Wash plate (Corning) and incubated overnight at 4° C. Wells were then blocked for one hour at room temperature (RT) with 100 ul of 2% non-fat dry milk (NFDM) in PBS and then washed 3× with PBS; 0.05% Tween-20 (PBST). 50 ul of conditioned media from cultures of transfected HEK-293 cells expressing MM175-anti-CTLA4 scFv. MM182-anti-CTLA4 scFv. MM184-anti-CTLA4 scFv. MM187-anti-CTLA4 scFv, or MMneg-anti-CTLA4 scFv that had previously been untreated or treated with MMP-9, were added to wells and incubated RT for 15 minutes. Following incubation, 50 ul of PBS containing 0.5 ug/ml biotinylated murine B71-Fc (R & D systems) was added to each well. Following a further incubation at RT of 30 minutes the wells were washed 5× with 150 ul PBST. 100 ul of PBS containing 1:3000 dilution of avidin-HRP was added and the plate incubated at RT for 45 minutes and then washed 7× with 150 ul PBST. The ELISA was developed with 100 ul of TMB (Pierce), stopped with 100 uL of 1N HCL and the absorbance was measured at 450 nM.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An activatable binding polypeptide (ABP), comprising an amino acid sequence selected from the group consisting of SEQ ID NOs: 52, 54, 56, 58, 60, and 62.

2. An isolated nucleic acid molecule encoding the ABP of claim 1.

3. A method of producing the ABP of claim 1 by culturing a cell under conditions that lead to expression of the ABP, wherein the cell comprises a vector comprising the isolated nucleic acid molecule of claim 2.

* * * * *

UNITED STATES PATENT AND TRADEMARK OFFICE
CERTIFICATE OF CORRECTION

| | |
|---|---|
| PATENT NO. | : 12,209,120 B2 |
| APPLICATION NO. | : 17/245713 |
| DATED | : January 28, 2025 |
| INVENTOR(S) | : Patrick Sean Daugherty et al. |

Page 1 of 5

It is certified that error appears in the above-identified patent and that said Letters Patent is hereby corrected as shown below:

In the Specification

In Column 1, Line 16, before "awarded" insert -- and NIH:R43 CA132498-01A1 --.

In Column 1, Line 23, delete "a" and insert -- as --.

In Column 1, Line 55, after "the" delete "such that the".

In Column 3, Line 36, after "the" delete "such that".

In Column 4, Line 31, delete "agent," and insert -- agent; --.

In Column 6, Line 20, delete "complement." and insert -- complement, --.

In Column 6, Line 21, delete "Glyocprotein" and insert -- Glycoprotein --.

In Column 6, Line 62, delete "Glyocprotein" and insert -- Glycoprotein --.

In Column 7, Line 7, delete "abiciximab," and insert -- abciximab, --.

In Column 7, Line 54, delete "Glyocprotein" and insert -- Glycoprotein --.

In Column 7, Line 60, delete "abiciximab," and insert -- abciximab, --.

In Column 8, Line 33, delete "abiciximab," and insert -- abciximab, --.

In Column 8, Line 48, delete "Glyocprotein" and insert -- Glycoprotein --.

In Column 9, Line 24, delete "of" and insert -- or --.

Signed and Sealed this
Twenty-seventh Day of May, 2025

Coke Morgan Stewart
*Acting Director of the United States Patent and Trademark Office*

CERTIFICATE OF CORRECTION (continued)

U.S. Pat. No. 12,209,120 B2

In Column 11, Line 9, delete "MMs:" and insert -- MMs; --.

In Column 11, Line 10, delete "MM." and insert -- MM, --.

In Column 11, Line 36, delete "cloning." and insert -- cloning, --.

In Column 12, Line 14, delete ""solely."" and insert -- "solely," --.

In Column 14, Line 6, delete "CM." and insert -- CM, --.

In Column 14, Line 16, delete ""polypeptide." "peptide."" and insert -- "polypeptide," "peptide," --.

In Column 14, Line 34, after "well" insert -- as --.

In Column 14, Line 66, delete "Typically." and insert -- Typically, --.

In Column 14, Lines 66-67, delete "vector."" and insert -- vector," --.

In Column 15, Line 37, delete "methods." and insert -- methods, --.

In Column 15, Line 49, delete "like." and insert -- like, --.

In Column 17, Line 44, delete "herein." and insert -- herein, --.

In Column 18, Line 8, delete ""assessing."" and insert -- "assessing," --.

In Column 18, Line 54, delete "state."" and insert -- state," --.

In Column 18, Line 56, after "absence" insert -- of --.

In Column 19, Line 27, delete "Thus." and insert -- Thus, --.

In Column 21, Line 38, delete "TBMs." and insert -- TBMs, --.

In Column 21, Line 48, delete "Gly." and insert -- Gly, --.

In Column 21, Line 48, delete "Asp." and insert -- Asp, --.

In Column 22, Line 13, delete ""tails."" and insert -- "tails," --.

In Column 22, Line 28, delete "TBMs." and insert -- TBMs, --.

In Column 22, Line 63, delete "5." and insert -- 5, --.

In Column 22, Line 64, delete "7." and insert -- 7, --.

CERTIFICATE OF CORRECTION (continued)
U.S. Pat. No. 12,209,120 B2

In Column 23, Line 9, after "can" insert -- be --.

In Column 23, Line 26, delete "tog" and insert -- to, --.

In Column 24, Line 23, delete "MMs." and insert -- MMs, --.

In Column 24, Line 55, delete "Myelotarg" and insert -- Mylotarg --.

In Column 24, Line 58, delete "(abiciximab)" and insert -- (abciximab) --.

In Column 25, Line 50, delete "C," and insert -- C. --.

In Column 25, Line 51, delete "L," and insert -- L. --.

In Column 25, Line 52, delete "B," and insert -- B. --.

In Column 25, Line 56, delete "C," and insert -- C. --.

In Column 25, Line 57, delete "A," and insert -- A. --.

In Column 25, Line 57, delete "J," and insert -- J. --.

In Column 25, Line 58, delete "H," and insert -- H. --.

In Column 25, Line 58, delete "C," and insert -- C. --.

In Column 28, Line 1, delete "embodiments." and insert -- embodiments, --.

In Column 28, Line 12, after "one" insert -- or --.

In Column 28, Line 54, delete "biding" and insert -- binding --.

In Column 28, Line 67, delete "to as to" and insert -- to --.

In Column 30, Line 21, delete "See." and insert -- See, --.

In Column 31, Line 13, after "ABPs" delete "are".

In Column 31, Line 55, delete "2716:" and insert -- 2716; --.

In Column 31, Line 67, delete "proteins." and insert -- proteins, --.

In Column 32, Line 66, delete "gall" and insert -- gal1 --.

In Column 33, Line 48, delete "know" and insert -- known --.

CERTIFICATE OF CORRECTION (continued)
U.S. Pat. No. 12,209,120 B2

In Column 33, Line 51, delete "randomization." and insert -- randomization, --.

In Column 34, Line 35, delete "ABPs." and insert -- ABPs, --.

In Column 34, Line 42, delete "rust" and insert -- first --.

In Column 35, Line 37, delete "cycles." and insert -- cycles, --.

In Column 35, Line 37, delete "cycles." and insert -- cycles, --.

In Column 36, Line 14, delete "example." and insert -- example, --.

In Column 36, Line 20, delete "MM." and insert -- MM, --.

In Column 37, Line 37, delete "ABP." and insert -- ABP, --.

In Column 39, Line 8, delete "strepavidin" and insert -- streptavidin --.

In Column 39, Line 30, delete "general." and insert -- general, --.

In Column 41, Line 43, delete "TBM." and insert -- TBM, --.

In Column 43, Line 28, delete "inhibited." and insert -- inhibited, --.

In Column 43, Line 39, delete "medium)." and insert -- medium), --.

In Column 44, Line 4, delete "TBM." and insert -- TBM, --.

In Column 44, Line 15, delete "ABP." and insert -- ABP, --.

In Column 44, Line 15, delete "TBM." and insert -- TBM, --.

In Column 44, Line 44, delete "pIII." and insert -- pIII, --.

In Column 44, Line 45, delete "Scott." and insert -- Scott, --.

In Column 46, Line 12, after "where" delete "the,".

In Column 46, Line 62, delete "-(methylmethacylate)" and insert -- -(methylmethacrylate) --.

In Column 46, Line 67, delete "edition. Osol." and insert -- edition, Osol, --.

In Column 47, Line 5, delete "articles." and insert -- articles, --.

In Column 47, Line 45, delete "September," and insert -- September; --.

CERTIFICATE OF CORRECTION (continued)
U.S. Pat. No. 12,209,120 B2

In Column 49, Line 22, delete "neplirosclerosis;" and insert -- nephrosclerosis; --.

In Column 52, Line 19, delete "Celsius." and insert -- Celsius, --.

In Column 56, Line 15, delete "library." and insert -- library, --.

In Column 58, Line 29, delete "form." and insert -- form, --.

In Column 58, Line 37, delete "Then." and insert -- Then, --.

In Column 59, Line 31, delete "clones." and insert -- clones, --.

In Column 64, Line 27, delete "Sac" and insert -- SacI --.

In Column 64, Line 27, delete "HindII" and insert -- HindIII --.

In Column 64, Line 28, after "NO: 50)" insert -- . --.

In Column 67, Lines 41-42, delete "-s-D-galactosides" and insert -- -β-D-galactosidase --.

In Column 68, Line 37, delete "Imidizale," and insert -- Imidazole, --.

In Column 71, Line 43, delete "Briefly." and insert -- Briefly, --.

In Column 71, Line 47, delete "acetate." and insert -- acetate, --.

In Column 72, Line 29, delete "(I" and insert -- (1 --.

In Column 73, Line 25, delete "(gtyttrtgngtnacyterca)" and insert -- (gtyttrtgngtnacytcrca) --.

In Column 78, Line 46, delete "scFv." and insert -- scFv, --.

In Column 79, Line 9, delete "scFv." and insert -- scFv, --.

In Column 79, Line 9, delete "scFv." and insert -- scFv, --.

In Column 79, Line 10, delete "scFv." and insert -- scFv, --.